United States Patent
Chen et al.

(10) Patent No.: US 11,896,619 B2
(45) Date of Patent: Feb. 13, 2024

(54) COMPOSITIONS AND METHODS FOR IMMUNOTHERAPY OF NPM1C-POSITIVE CANCER

(71) Applicant: Massachusetts Institute of Technology, Cambridge, MA (US)

(72) Inventors: Jianzhu Chen, Lexington, MA (US); Guozhu Xie, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 240 days.

(21) Appl. No.: 17/144,834

(22) Filed: Jan. 8, 2021

(65) Prior Publication Data

US 2021/0283178 A1 Sep. 16, 2021

Related U.S. Application Data

(60) Provisional application No. 62/987,612, filed on Mar. 10, 2020.

(51) Int. Cl.
| | | |
|---|---|---|
| A61K 35/17 | (2015.01) | |
| A61P 35/04 | (2006.01) | |
| C07K 16/28 | (2006.01) | |
| C07K 16/30 | (2006.01) | |

(52) U.S. Cl.
CPC ............. *A61K 35/17* (2013.01); *A61P 35/04* (2018.01); *C07K 16/2818* (2013.01); *C07K 16/3061* (2013.01)

(58) Field of Classification Search
CPC ..... A61K 35/17; A61P 35/04; C07K 16/2818; C07K 16/3061
See application file for complete search history.

(56) References Cited

U.S. PATENT DOCUMENTS

2014/0271635 A1 9/2014 Brogdon et al.

FOREIGN PATENT DOCUMENTS

| WO | WO-2007077028 A2 * | 7/2007 | ........... A61K 39/395 |
|---|---|---|---|
| WO | WO-2008099188 A1 * | 8/2008 | ................ A61P 1/04 |
| WO | WO-2012/044999 A2 | 4/2012 | |
| WO | WO-2018161017 A1 * | 9/2018 | ........... A61K 31/505 |
| WO | WO-2019/004831 A1 | 1/2019 | |
| WO | WO-2019036688 A1 * | 2/2019 | ......... A61K 39/0011 |
| WO | WO-2020/081537 A1 | 4/2020 | |

OTHER PUBLICATIONS

Leukaemia Care (2019) Relapse in Acute Myeloid Leukaemia (AML) A guide for patients; printed Oct. 2019, p. 1-32 (Year: 2019).*

(Continued)

*Primary Examiner* — Scarlett Y Goon
*Assistant Examiner* — Audrey L Buttice
(74) *Attorney, Agent, or Firm* — Foley & Lardner LLP

(57) ABSTRACT

The present disclosure relates to compounds (e.g., antibodies, antigen-binding fragments thereof, bispecific molecules, or chimeric antigen receptor polypeptides) that bind to a neoepitope of mutant nucleophosmin (NPM1c) in complex with, or presented by, a class I major histocompatibility complex (MHC class I) protein, or cells expressing such compounds, and their use in methods for treating, or ameliorating one or more symptoms of, cancer.

82 Claims, 28 Drawing Sheets

Specification includes a Sequence Listing.

(56) References Cited

OTHER PUBLICATIONS

Emmons, K. M., et al (Mar. 2017) Realizing the Potential of Cancer Prevention—The Role of Implementation Science N Engl J Med 376(10); 986-990 (Year: 2017).*
Cuzick, J. (Aug. 2017) Preventive therapy for cancer Lancet Oncol 18; e472-e482 (Year: 2017).*
Hummer, A.M., et al (2022) Advances in computational structure-based antibody design Current Opinion in Structural Biology 74(102379); 1-7 (Year: 2022).*
Chailyan, A., et al (2011) The association of heavy and light chain variable domains in antibodies: implications for antigen specificity FEBS Journal 278; 2858-2866 (Year: 2011).*
Rabia, L.A. et al (2018) Understanding and overcoming trade-offs between antibody affinity, specificity, stability and solubility Biochem Eng J 137; 365-374 (Year: 2018).*
Ramos, C.A., et al (2016) CAR-T Cell Therapy for Lymphoma Annu Rev Med 67; 165-183 (Year: 2016).*
Rojas, G. (2022) Understanding and Modulating Antibody Fine Specificity: Lessons from Combinatorial Biology Antibodies 11(48); 1-22 (Year: 2022).*
Herrmann, A.C., et al (2019) A novel T-cell engaging Bi-specific antibody targeting the leukemia antigen PR1/HLA-A2 Frontiers in Immunology 9(3153); 1-12 (Year: 2019).*
Hill, W.I (2012) Improving ScFv stability through framework engineering. Master's Thesis, University of Saskatchewan. 105 pages (Year: 2012).*
U.S. Appl. No. 17/910,776, filed Mar. 10, 2021, Chen et al.
Cohen et al., "Recombinant antibodies with MHC-restricted, peptide-specific, T-cell receptor-like antigen presentation and TCR-peptide-MHC interactions," Journal of Molecular Recognition, Sep. 1, 2003, 16(5):324-332.
Greiner et al., "Mutated regions of nucleophosmin 1 elicit both CD4 and CD8 T-cell responses in patients with acute myeloid leukemia," Blood, Aug. 9, 2012, 120(6):1282-1289.
He et al., "TCR-like antibodies in cancer immunotherapy," Journal of Hematology & Oncology, Sep. 14, 2019, 12(1):99, 13 pages.
International Search Report and Written Opinion in PCT/US2021/012701 dated Aug. 9, 2021.
Van der Lee et al., "Mutated nucleophosmin 1 as immunotherapy target in acute myeloid leukemia," The Journal of Clinical Investigation, Feb. 1, 2019, 129(2):774-785.
Xie et al., "CAR-T cells targeting a nucleophosmin neoepitope exhibit potent specific activity in mouse models of acute myeloid leukemia," Nature Biomedical Engineering, Oct. 12, 2020, 5(5):399-413.
Alexandrov, L. B. et al., "Signatures of mutational processes in human cancer," Nature, vol. 500: 415 (2013).
Amir, A. L et al., "PRAME-specific Allo-HLA-restricted T cells with potent antitumor reactivity useful for therapeutic T-cell receptor gene transfer," Clin Cancer Res., vol. 17 5615 (2011).
Bendle, G. M. et al., "Lethal graft-versus-host disease in mouse models of T cell receptor gene therapy," Nat Med., vol. 16:565 (2010).
Blankenstein, T., et al., "Targeting cancer-specific mutations by T cell receptor gene therapy," Curr Opin Immunol., vol. 33:112 (2015).
Chao, G. et al., "Isolating and engineering human antibodies using yeast surface display," Nat Protoc., vol. 1:755 (2006).
Choo, J. A., et al., "The immunodominant influenza A virus M158-66 cytotoxic T lymphocyte epitope exhibits degenerate class I major histocompatibility complex restriction in humans," J Virol., vol. 88:10613 (2014).
Coulie, P. G., et al., "Tumour antigens recognized by T lymphocytes: at the core of cancer immunotherapy," Nat Rev Cancer, vol. 14:135 (2014).
Dombret, H. et al., "An update of current treatments for adult acute myeloid leukemia," Blood, vol. 127 53 (2016).
Dubrovsky, L. et al., "T cell receptor mimic antibodies for cancer therapy," Oncoimmunology, vol. 5 e1049803 (2016).
Gill, S. et al., "Preclinical targeting of human acute myeloid leukemia and myeloablation using chimeric antigen receptor-modified T cells," Blood, vol. 123: 2343 (2014).
Zhang, J. et al., "The Emerging World of TCR-T Cell Trials Against Cancer: A Systematic Review," Technol Cancer Res Treat, vol. 18:13 pages (2019).
Hermanson, D. L. et al., "Induced Pluripotent Stem Cell-Derived Natural Killer Cells for Treatment of Ovarian Cancer," Stem Cells, vol. 34:93 (2016).
Kandoth, C. et al., "Mutational landscape and significance across 12 major cancer types," Nature, vol. 502: 333 (2013).
Kenderian, S. S. et al., "CD33-specific chimeric antigen receptor T cells exhibit potent preclinical activity against human acute myeloid leukemia," Leukemia, vol. 29:1637 (2015).
Kochenderfer, J. N., et al., "Recent advances in CAR T-cell toxicity: Mechanisms, manifestations and management," Blood Rev., vol. 34:45 (2019).
Leskov, I. et al., "Rapid generation of human B-cell lymphomas via combined expression of Myc and Bcl2 and their use as a preclinical model for biological therapies," Oncogene, vol. 32: 1066 (2013).
Watanabe, K., et al., "Expanding the Therapeutic Window for CAR T Cell Therapy in Solid Tumors: The Knowns and unknowns of CAR T Cell Biology," Front Immunol., vol. 9: 2486 (2018).
Li, Y., et al., "Human iPSC-Derived Natural Killer Cells Engineered with Chimeric Antigen Receptors Enhance Anti-tumor Activity," Cell Stem Cell, vol. 23:181 (2018).
Lorente, E., et al., "Allele-dependent processing pathways generate the endogenous human leukocyte antigen (HLA) class I peptide repertoire in transporters associated with antigen processing (TAP)-deficient cells," J Biol Chem., vol. 286: 38054 (2011).
Matsueda, S. et al., "Identification of prostate-specific G-protein coupled receptor as a tumor antigen recognized by CD8(+) T cells for cancer immunotherapy," Plos One, vol. 7: e45756 (2012).
Morris, E. C. et al., "Optimizing T-cell receptor gene therapy for hematologic malignancies," Blood, vol. 127:3305 (2016).
Ossenkoppele, G. J., et al., "Risk factors for relapse after allogeneic transplantation in acute myeloid leukemia," Haematologica, vol. 101:20 (2016).
Pallasch, C. P. et al., "Sensitizing protective tumor microenvironments to antibody-mediated therapy," Cell, vol. 156:590 (2014).
Papaemmanuil, E. et al., "Genomic Classification and Prognosis in Acute Myeloid Leukemia," N Engl J Med., vol. 374:2209 (2016).
Provasi, E. et al., "Editing T cell specificity towards leukemia by zinc finger nucleases and lentiviral gene transfer," Nat Med., vol. 18: 807 (2012).
Quentmeier, H. et al., "Cell line OCI/AML3 bears exon-12 NPM gene mutation-A and cytoplasmic expression of nucleophosmin," Leukemia, vol. 19:1760 (2005).
Salmikangas, P., et al., "Chimeric Antigen Receptor T-Cells (CAR T-Cells) for Cancer Immunotherapy—Moving Target for Industry?," Pharm Res., vol. 35: 152 (2018).
Schumacher, T. N. et al., "Neoantigens in cancer immunotherapy," Science, vol. 348 69 (2015).
Srivastava, S. et al., "Chimeric Antigen Receptor T Cell Therapy: Challenges to Bench-to-Bedside Efficacy," J Immunol., vol. 200:459 (2018).
Thomas, D. et al., "Biology and relevance of human acute myeloid leukemia stem cells," Blood, vol. 129: 1577 (2017).
Uhlen, M. et al., "Proteomics. Tissue-based map of the human proteome," Science, vol. 347 126041-9:12 pages (2015).
Watanabe, K. et al., "Target antigen density governs the efficacy of anti-CD20-CD28-CD3 zeta chimeric antigen receptor-modified effector CD8+ T cells," J Immunol., vol. 194:911 (2015).
Van Deventer, J. A., et al., "A switchable yeast display/secretion system," Protein Eng Des Sel., vol. 28:317 (2015).
van Loenen, M. M. et al., "Mixed T cell receptor dimers harbor potentially harmful neoreactivity," Proc Natl Acad Sci U S A., vol. 107:10972 (2010).
Vivier, E. et al., "Innate or adaptive immunity? The example of natural killer cells," Science vol. 331:44 (2011).

(56) References Cited

OTHER PUBLICATIONS

Greiner, J. et al., "Mutated regions of nucleophosmin 1 elicit both CD4 and CD8 T-cell responses in patients with acute myeloid leukemia," Myeloid Neoplasia, Blood, vol. 120 (6):1282-1289 (2012).

Ley, T. et al., "Genomic and Epigenomic Landscapes of Adult De Novo Acute Myeloid Leukemia," N Engl J Med., vol. 368(22): 2059-2074 (2013).

van der Lee, D. et al., "Mutated nucleophosmin 1 as immunotherapy target in acute myeloid leukemia," The Journal of Clinical Investigation, vol. 129(2): 774-785 (2019).

Xie, G., "CAR-T cells targeting a nucleophosmin neoepitope exhibit potent specific activity in mouse models of acute myeloid leukaemia," Nature Biomedicial Engineering, 19 pages (2020).

Berrien-Elliott et al., "Chimeric Antigen Receptor Modified Memory-like (CAR-ML) NK Cells Exhibit Potent Responses to NK-Resistant Tumors," Blood, Nov. 13, 2019, 134(Suppl.1):869.

Colamartino et al., "Efficient and Robust NK-Cell Transduction With Baboon Envelope Pseudotyped Lentivector," Frontiers in Immunology, Dec. 16, 2019, 10:2873.

Dong et al., "Engineered Memory-like NK Cars Targeting a Neoepitope Derived from Intracellular NPM1c Exhibit Potent Activity and Specificity Against Acute Myeloid Leukemia," Blood, Nov. 5, 2020, 136(Suppl.1):703.

Romee et al., "Cytokine-induced memory-like natural killer cells exhibit enhanced responses against myeloid leukemia," Science Translational Medicine, Sep. 21, 2016, 8(357):357ra123.

Yang et al., "Precision therapy for acute myeloid leukemia," Journal of Hematology and Oncology, Jan. 5, 2018, 11(1):3.

\* cited by examiner

Continued as Figure 1B-2

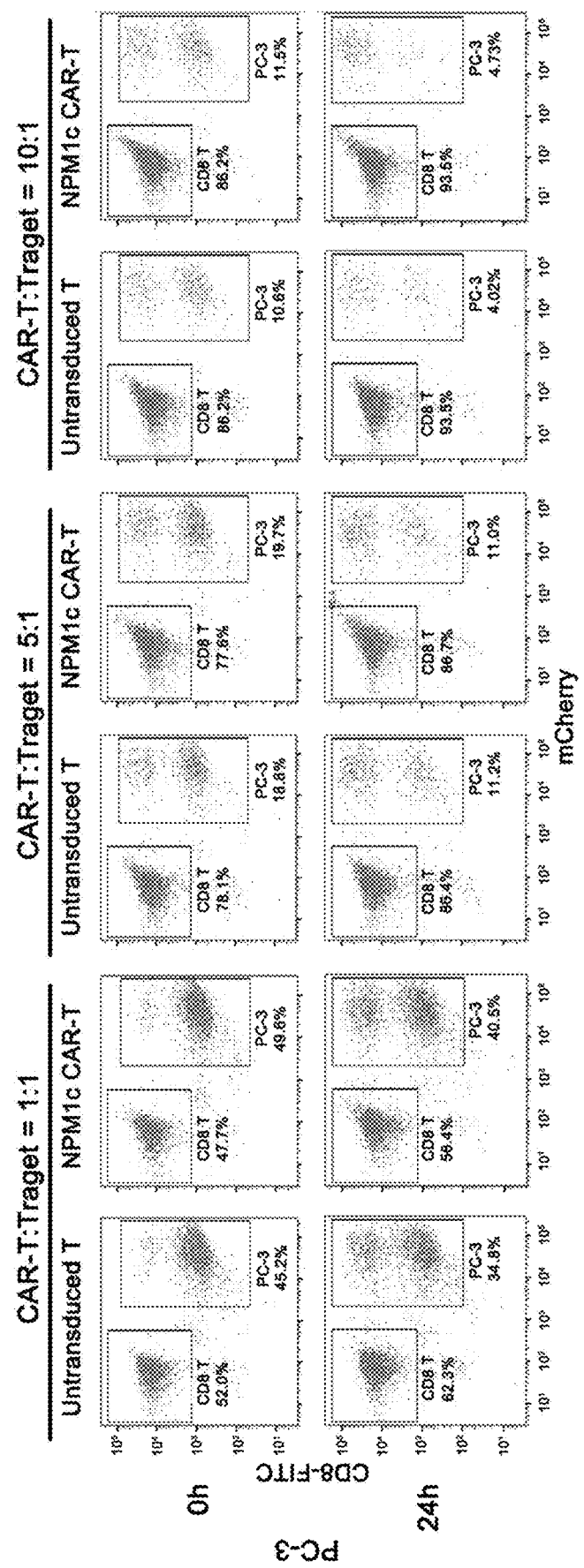
Figure 4A (contd)

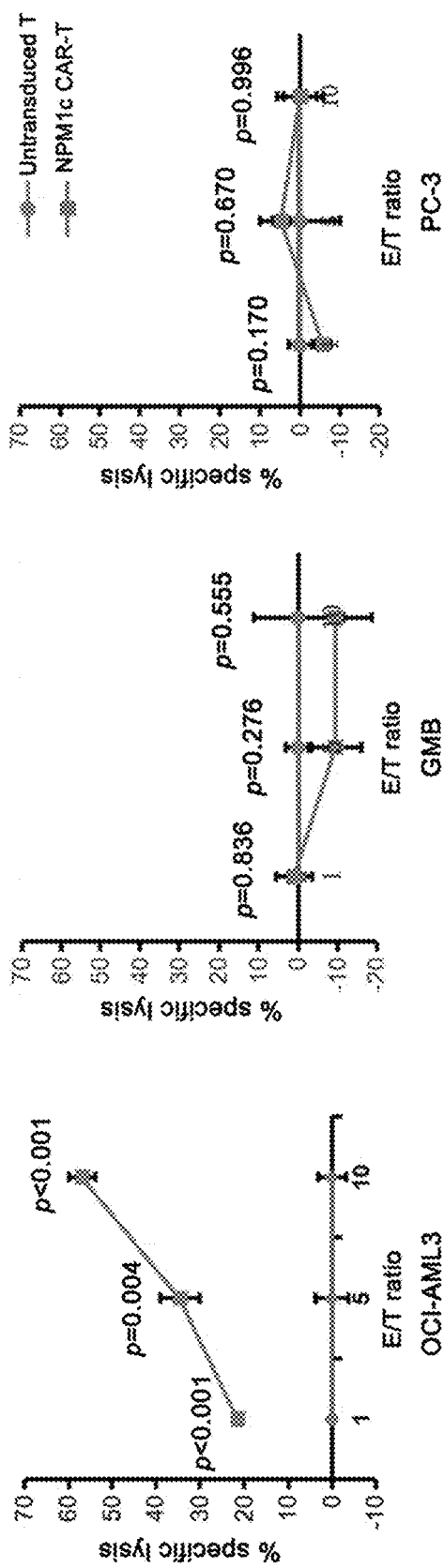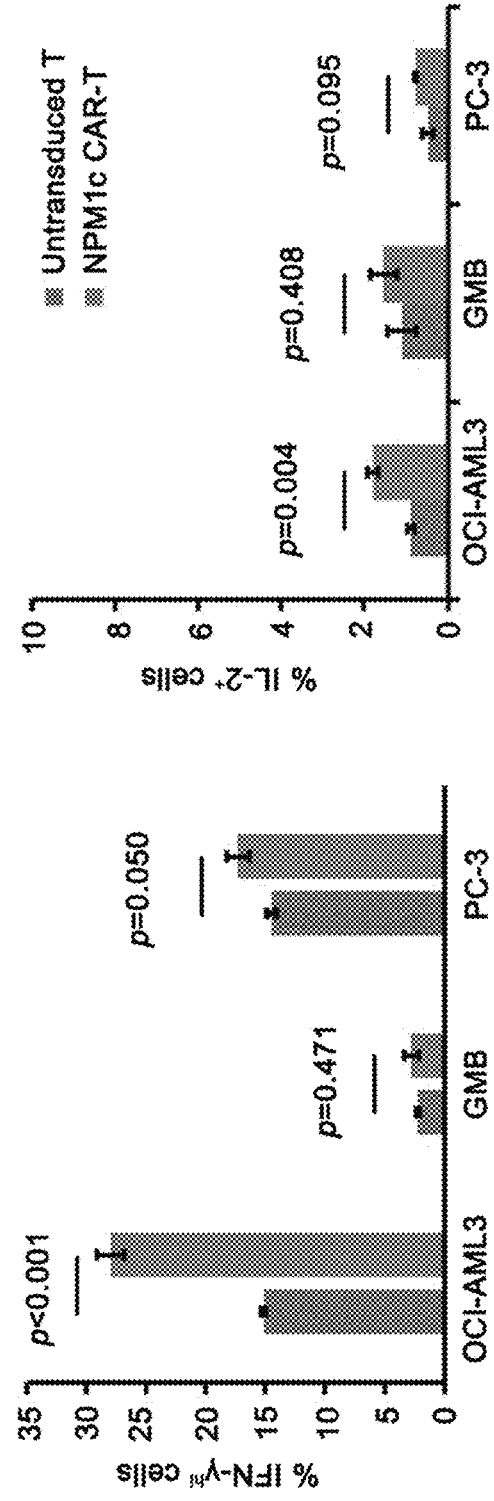
Figure 4B
Figure 4C

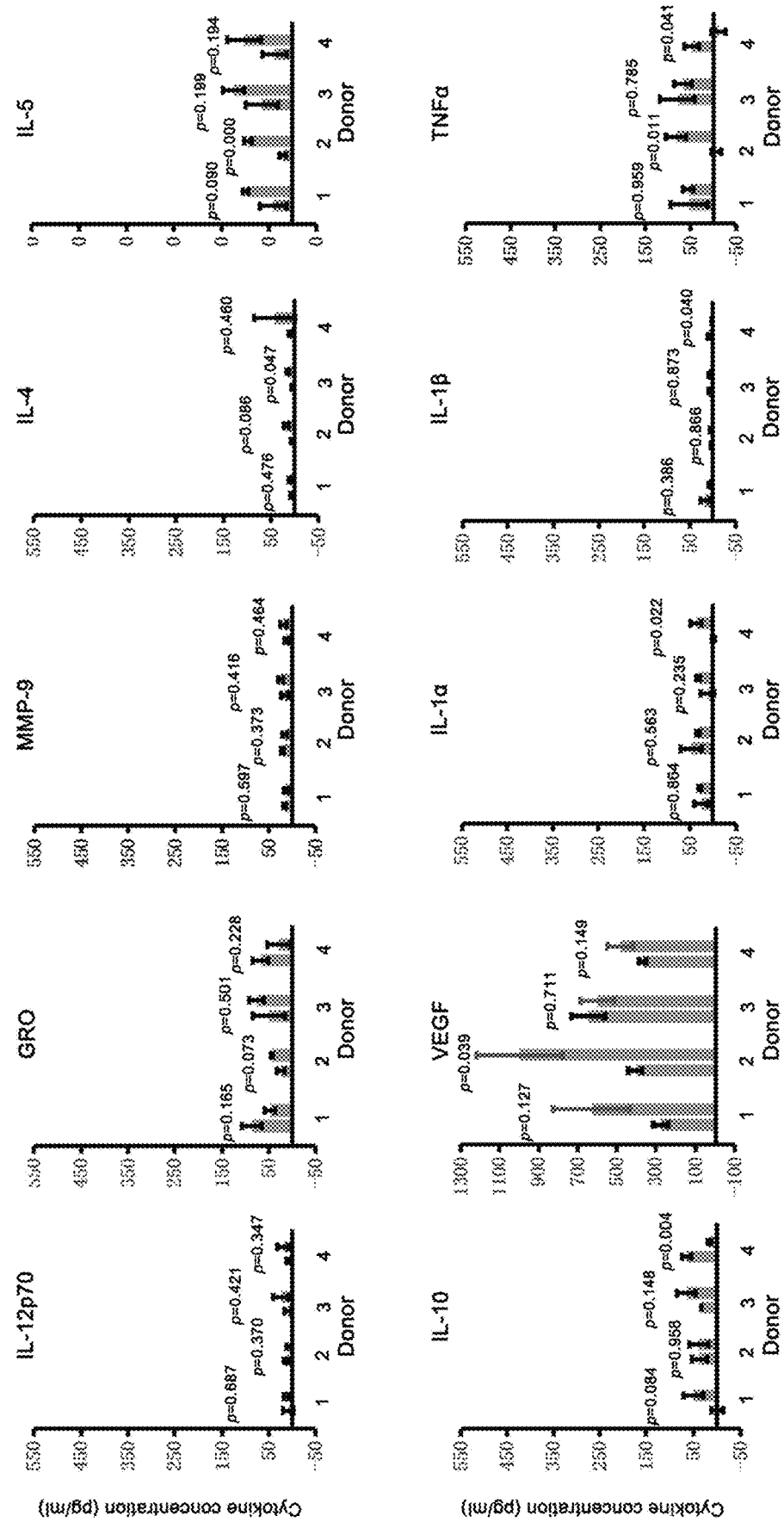
Figure 4D (contd)

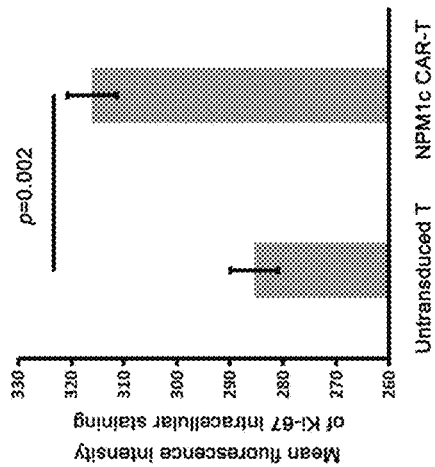
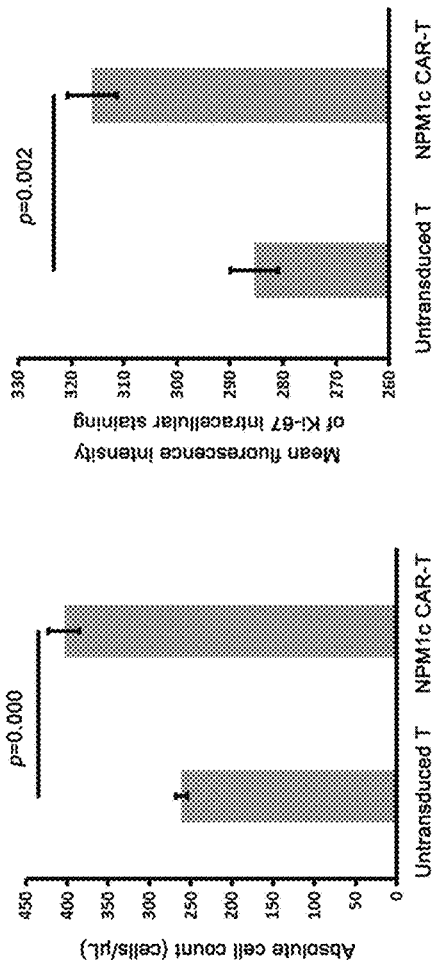
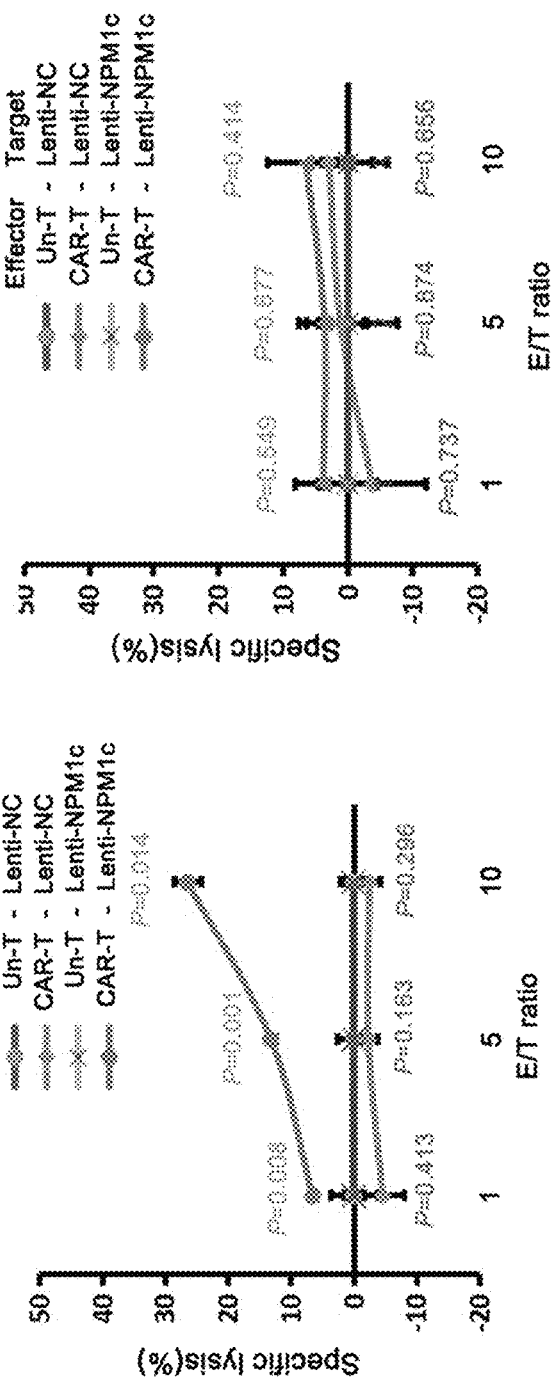

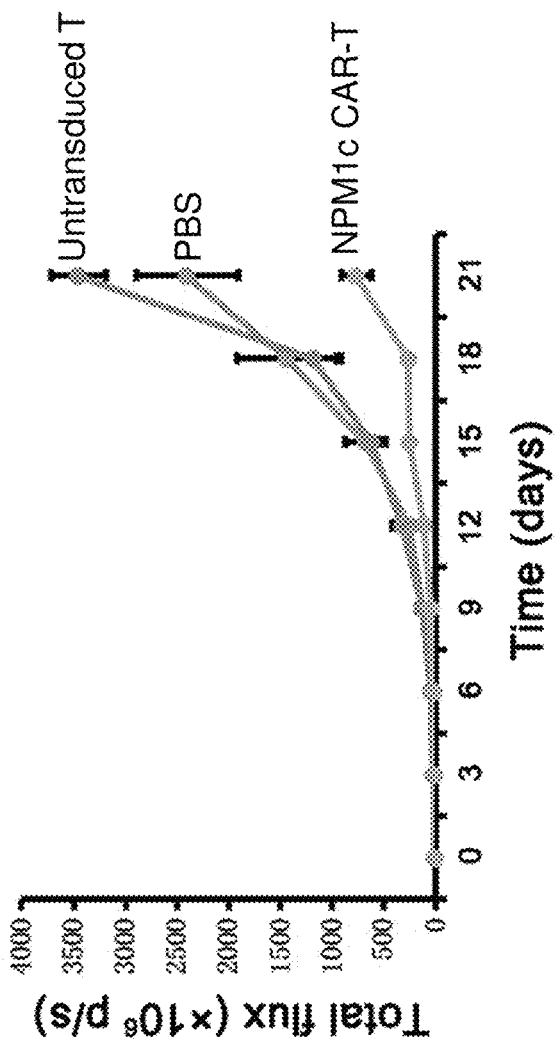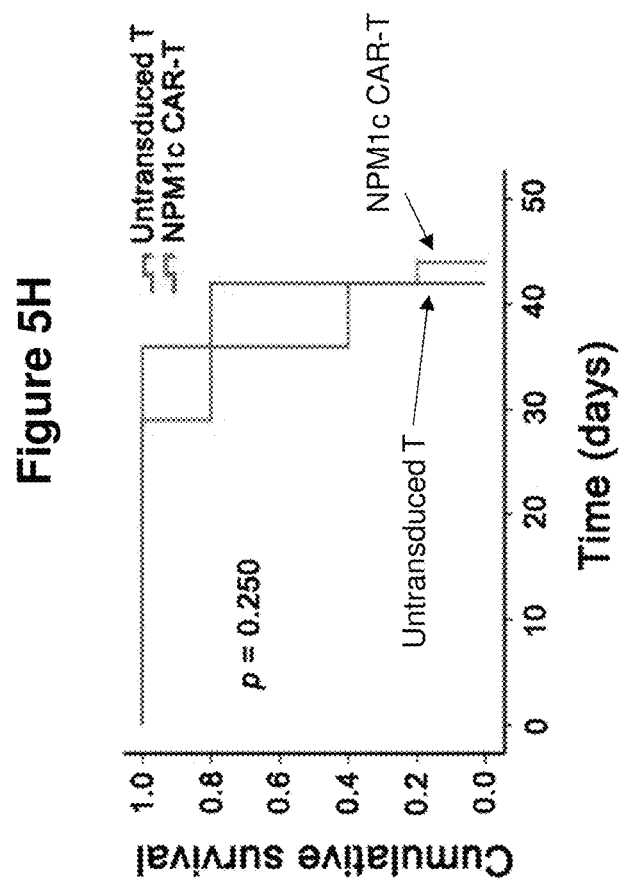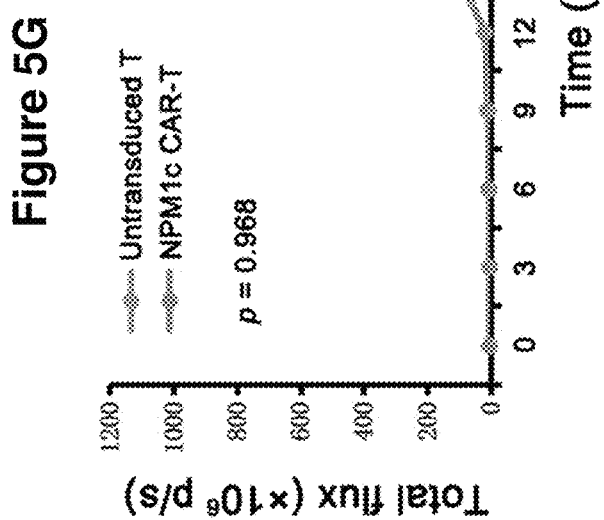
Figure 5F
Figure 5G
Figure 5H

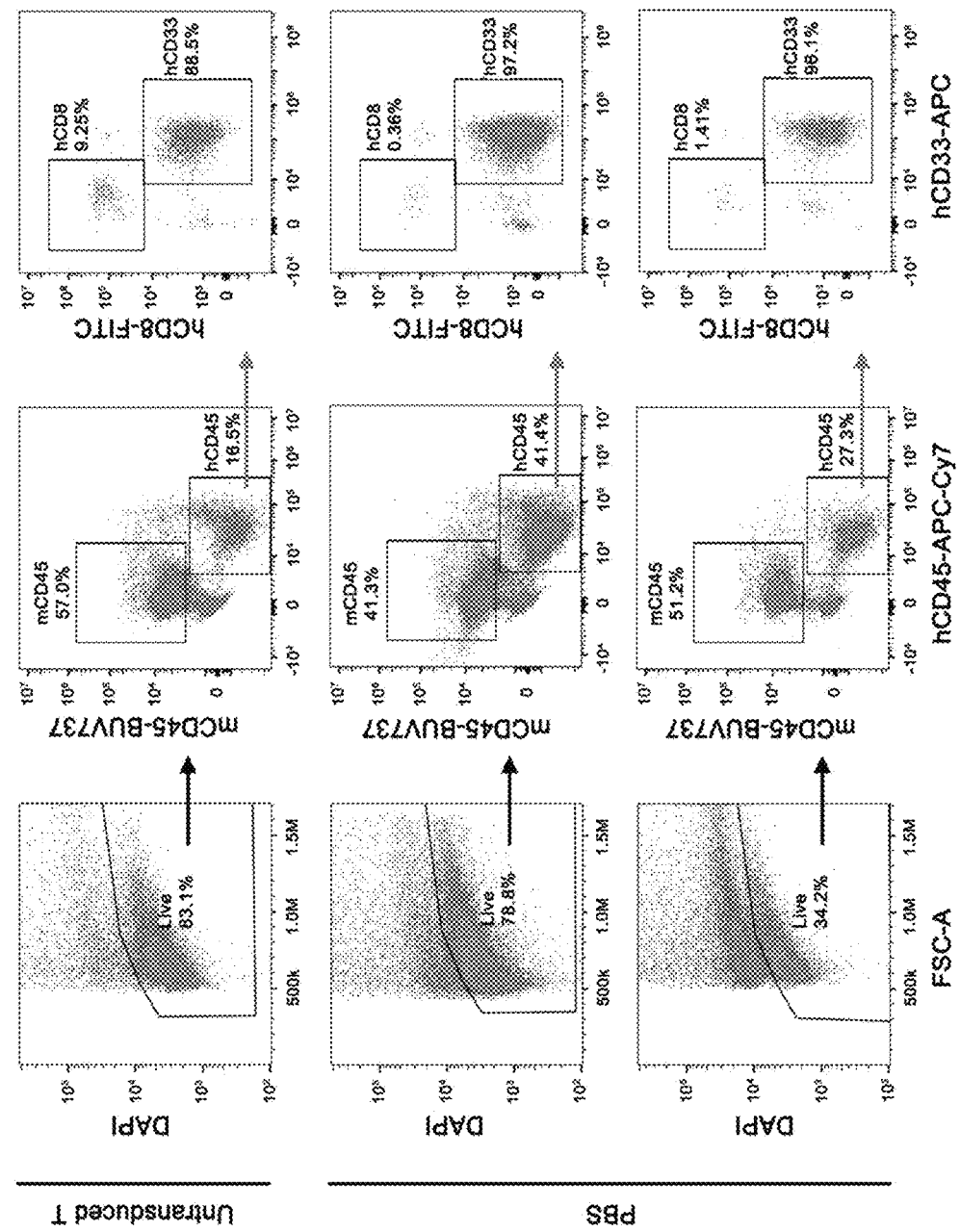
Figure 6I contd.

SEQUENCE LISTING

<160> NUMBER OF SEQ ID NOS: 96

<210> SEQ ID NO 1
<211> LENGTH: 9
<212> TYPE: PRT
<213> ORGANISM: Artificial Sequence
<220> FEATURE:
<223> OTHER INFORMATION: Synthetic: Leukemia-specific neoantigen epitope of NPM1c

<400> SEQUENCE: 1

Ala Ile Gln Asp Leu Cys Leu Ala Val
1               5

<210> SEQ ID NO 2
<211> LENGTH: 249
<212> TYPE: PRT
<213> ORGANISM: Artificial Sequence
<220> FEATURE:
<223> OTHER INFORMATION: Synthetic: YG1 scFv amino acid sequence

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Ser Gly Ile Leu Gly
            100                 105                 110

```
Thr Thr Ala Ala Ser Gly Ser Gly Gly Ser Ser Gly Ala Glu
            115                 120             125

Val Gln Leu Val Glu Ser Gly Gly Leu Val Gln Pro Gly Gly Ser
130             135                 140

Leu Arg Leu Ser Cys Ala Ala Ser Gly Phe Thr Phe Ser Ser Tyr Ala
145                 150                 155                 160

Met Ser Trp Val Arg Gln Ala Pro Gly Lys Gly Leu Glu Trp Val Ser
                165                 170                 175

Ala Ile Ser Gly Ser Gly Gly Ser Thr Tyr Tyr Ala Asp Ser Val Lys
                180                 185                 190

Gly Arg Phe Thr Ile Ser Arg Asp Asn Ser Lys Asn Thr Leu Tyr Leu
                195                 200                 205

Gln Met Asn Ser Leu Arg Ala Glu Asp Thr Ala Val Tyr Tyr Cys Ala
    210                 215                 220

Arg Leu Gly Tyr Pro Thr Thr Thr Leu Leu Pro Phe Asp Tyr Trp Gly
225                 230                 235                 240

Gln Gly Thr Leu Val Thr Val Ser Ser
                245

<210> SEQ ID NO 3
<211> LENGTH: 116
<212> TYPE: PRT
<213> ORGANISM: Artificial Sequence
<220> FEATURE:
<223> OTHER INFORMATION: Synthetic: YG1 scFv VL amino acid sequence

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Ser Gly Ile Leu Gly
            100                 105                 110

Thr Thr Ala Ala
        115

<210> SEQ ID NO 4
<211> LENGTH: 10
<212> TYPE: PRT
<213> ORGANISM: Artificial Sequence
<220> FEATURE:
<223> OTHER INFORMATION: Synthetic: YG1 scFv linker amino acid sequence

<400> SEQUENCE: 4

Ser Gly Ser Ser Gly Gly Ser Ser Gly
1               5                   10

<210> SEQ ID NO 5
<211> LENGTH: 123
<212> TYPE: PRT
<213> ORGANISM: Artificial Sequence
```

```
<220> FEATURE:
<223> OTHER INFORMATION: Synthetic: YG1 scFv VH amino acid sequence

<400> SEQUENCE: 5

Ala Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Ala Met Ser Trp Val Arg Gln Ala Pro Gly Lys Gly Leu Glu Trp
        35                  40                  45

Val Ser Ala Ile Ser Gly Ser Gly Gly Ser Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Leu Gly Tyr Pro Thr Thr Thr Leu Leu Pro Phe Asp Tyr
            100                 105                 110

Trp Gly Gln Gly Thr Leu Val Thr Val Ser Ser
        115                 120

<210> SEQ ID NO 6
<211> LENGTH: 6
<212> TYPE: PRT
<213> ORGANISM: Artificial Sequence
<220> FEATURE:
<223> OTHER INFORMATION: Synthetic: YG1 scFv VL CDR1 amino acid sequence
      (IMGT)

<400> SEQUENCE: 6

Gln Ser Ile Ser Ser Tyr
1               5

<210> SEQ ID NO 7
<211> LENGTH: 3
<212> TYPE: PRT
<213> ORGANISM: Artificial Sequence
<220> FEATURE:
<223> OTHER INFORMATION: Synthetic: YG1 scFv VL CDR2 amino acid sequence
      (IMGT)

<400> SEQUENCE: 7

Ala Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: Synthetic: YG1 scFv VL CDR3 amino acid sequence
      (IMGT)

<400> SEQUENCE: 8

Gln Gln Ser Tyr Ser Thr Pro Leu Thr
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic: YG1 scFv VH CDR1 amino acid sequence
      (IMGT)
```

<400> SEQUENCE: 9

Gly Phe Thr Phe Ser Ser Tyr Ala
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic: YG1 scFv VH CDR2 amino acid sequence
      (IMGT)

<400> SEQUENCE: 10

Ile Ser Gly Ser Gly Gly Ser Thr
1               5

<210> SEQ ID NO 11
<211> LENGTH: 15
<212> TYPE: PRT
<213> ORGANISM: Artificial Sequence
<220> FEATURE:
<223> OTHER INFORMATION: Synthetic: YG1 scFv VH CDR3 amino acid sequence
      (IMGT)

<400> SEQUENCE: 11

Ala Arg Leu Gly Tyr Pro Thr Thr Thr Leu Leu Pro Phe Asp Tyr
1               5                   10                  15

<210> SEQ ID NO 12
<211> LENGTH: 747
<212> TYPE: DNA
<213> ORGANISM: Artificial Sequence
<220> FEATURE:
<223> OTHER INFORMATION: Synthetic: YG1 scFv nucleic acid sequence

<400> SEQUENCE: 12
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta ccccgctcac gttcggccaa     300
gggaccaagg tggaaatcaa atccggaatt ctaggtacta ctgccgctag tggtagtagt     360
ggtggcagta gcagtggtgc cgaggtgcag ctggtggagt ctgggggagg cttggtacag     420
cctggggggt ccctgagact ctcctgtgca gcctctggat tcacctttag cagctatgcc     480
atgagctggg tccgccaggc tccagggaag gggctggagt gggtctcagc tattagtggt     540
agtggtggta gcacatacta cgcagactcc gtgaagggcc ggttcaccat ctccagagac     600
aattccaaga cacgctgta tctgcaaatg aacagcctga gaccgagga cacggccgtg      660
tattactgtg cgaggctggg ttaccctact actaccctac tacccttga ttactggggc      720
caaggtaccc tggtcactgt ctccagt                                         747

<210> SEQ ID NO 13
<211> LENGTH: 348
<212> TYPE: DNA
<213> ORGANISM: Artificial Sequence
<220> FEATURE:
<223> OTHER INFORMATION: Synthetic: YG1 scFv VL nucleic acid sequence

<400> SEQUENCE: 13

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccgctcac gttcggccaa   300
gggaccaagg tggaaatcaa atccggaatt ctaggtacta ctgccgct                348
```

<210> SEQ ID NO 14
<211> LENGTH: 30
<212> TYPE: DNA
<213> ORGANISM: Artificial Sequence
<220> FEATURE:
<223> OTHER INFORMATION: Synthetic: YG1 scFv linker nucleic acid
      sequence

<400> SEQUENCE: 14

```
agtggtagta gtggtggcag tagcagtggt                                     30
```

<210> SEQ ID NO 15
<211> LENGTH: 369
<212> TYPE: DNA
<213> ORGANISM: Artificial Sequence
<220> FEATURE:
<223> OTHER INFORMATION: Synthetic: YG1 scFv VH nucleic acid sequence

<400> SEQUENCE: 15

```
gccgaggtgc agctggtgga gtctggggga ggcttggtac agcctggggg gtccctgaga    60
ctctcctgtg cagcctctgg attcaccttt agcagctatg ccatgagctg ggtccgccag   120
gctccaggga aggggctgga gtgggtctca gctattagtg gtagtggtgg tagcacatac   180
tacgcagact ccgtgaaggg ccggttcacc atctccagag acaattccaa gaacacgctg   240
tatctgcaaa tgaacagcct gagagccgag gacacggccg tgtattactg tgcgaggctg   300
ggttacccta ctactaccct actacccttt gattactggg gccaaggtac cctggtcact   360
gtctccagt                                                           369
```

<210> SEQ ID NO 16
<211> LENGTH: 18
<212> TYPE: DNA
<213> ORGANISM: Artificial Sequence
<220> FEATURE:
<223> OTHER INFORMATION: Synthetic: YG1 scFv VL CDR1 nucleic acid
      sequence (IMGT)

<400> SEQUENCE: 16

```
cagagcatta gcagctat                                                  18
```

<210> SEQ ID NO 17
<211> LENGTH: 9
<212> TYPE: DNA
<213> ORGANISM: Artificial Sequence
<220> FEATURE:
<223> OTHER INFORMATION: Synthetic: YG1 scFv VL CDR2 nucleic acid
      sequence (IMGT)

<400> SEQUENCE: 17

```
gctgcatcc                                                            9
```

<210> SEQ ID NO 18
<211> LENGTH: 27

```
<212> TYPE: DNA
<213> ORGANISM: Artificial Sequence
<220> FEATURE:
<223> OTHER INFORMATION: Synthetic: YG1 scFv VL CDR3 nucleic acid
      sequence (IMGT)

<400> SEQUENCE: 18
caacagagtt acagtacccc gctcacg                                        27

<210> SEQ ID NO 19
<211> LENGTH: 24
<212> TYPE: DNA
<213> ORGANISM: Artificial Sequence
<220> FEATURE:
<223> OTHER INFORMATION: Synthetic: YG1 scFv VH CDR1 nucleic acid
      sequence (IMGT)

<400> SEQUENCE: 19
ggattcacct ttagcagcta tgcc                                           24

<210> SEQ ID NO 20
<211> LENGTH: 24
<212> TYPE: DNA
<213> ORGANISM: Artificial Sequence
<220> FEATURE:
<223> OTHER INFORMATION: Synthetic: YG1 scFv VH CDR2 nucleic acid
      sequence (IMGT)

<400> SEQUENCE: 20
attagtggta gtggtggtag caca                                           24

<210> SEQ ID NO 21
<211> LENGTH: 45
<212> TYPE: DNA
<213> ORGANISM: Artificial Sequence
<220> FEATURE:
<223> OTHER INFORMATION: Synthetic: YG1 scFv VH CDR3 nucleic acid
      sequence (IMGT)

<400> SEQUENCE: 21
gcgaggctgg gttaccctac tactaccota ctacccttg attac                     45

<210> SEQ ID NO 22
<211> LENGTH: 751
<212> TYPE: PRT
<213> ORGANISM: Artificial Sequence
<220> FEATURE:
<223> OTHER INFORMATION: Synthetic: NPM1c CAR amino acid sequence (with
      YG1 scFv)

<400> SEQUENCE: 22

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Ser Ile Ser Ser Tyr Leu Asn Trp Tyr Gln Gln Lys Pro Gly Lys Ala
    50                  55                  60

Pro Lys Leu Leu Ile Tyr Ala Ala Ser Ser Leu Gln Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Ser
```

-continued

```
            100                 105                 110
Tyr Ser Thr Pro Leu Thr Phe Gly Gln Gly Thr Lys Val Glu Ile Lys
            115                 120                 125

Ser Gly Ile Leu Gly Thr Thr Ala Ala Ser Gly Ser Ser Gly Gly Ser
    130                 135                 140

Ser Ser Gly Ala Glu Val Gln Leu Val Glu Ser Gly Gly Gly Leu Val
145                 150                 155                 160

Gln Pro Gly Gly Ser Leu Arg Leu Ser Cys Ala Ala Ser Gly Phe Thr
                165                 170                 175

Phe Ser Ser Tyr Ala Met Ser Trp Val Arg Gln Ala Pro Gly Lys Gly
            180                 185                 190

Leu Glu Trp Val Ser Ala Ile Ser Gly Ser Gly Gly Ser Thr Tyr Tyr
        195                 200                 205

Ala Asp Ser Val Lys Gly Arg Phe Thr Ile Ser Arg Asp Asn Ser Lys
    210                 215                 220

Asn Thr Leu Tyr Leu Gln Met Asn Ser Leu Arg Ala Glu Asp Thr Ala
225                 230                 235                 240

Val Tyr Tyr Cys Ala Arg Leu Gly Tyr Pro Thr Thr Leu Leu Pro
                245                 250                 255

Phe Asp Tyr Trp Gly Gln Gly Thr Leu Val Thr Val Ser Ser Thr Thr
                260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
        290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg Ala Thr Asn
                485                 490                 495

Phe Ser Leu Leu Lys Gln Ala Gly Asp Val Glu Glu Asn Pro Gly Pro
            500                 505                 510

Met Val Ser Lys Gly Glu Glu Leu Phe Thr Gly Val Val Pro Ile Leu
        515                 520                 525
```

Val Glu Leu Asp Gly Asp Val Asn Gly His Lys Phe Ser Val Ser Gly
            530                 535                 540

Glu Gly Glu Gly Asp Ala Thr Tyr Gly Lys Leu Thr Leu Lys Phe Ile
545                 550                 555                 560

Cys Thr Thr Gly Lys Leu Pro Val Pro Trp Pro Thr Leu Val Thr Thr
                565                 570                 575

Leu Thr Tyr Gly Val Gln Cys Phe Ser Arg Tyr Pro Asp His Met Lys
            580                 585                 590

Gln His Asp Phe Phe Lys Ser Ala Met Pro Glu Gly Tyr Val Gln Glu
        595                 600                 605

Arg Thr Ile Phe Phe Lys Asp Asp Gly Asn Tyr Lys Thr Arg Ala Glu
        610                 615                 620

Val Lys Phe Glu Gly Asp Thr Leu Val Asn Arg Ile Glu Leu Lys Gly
625                 630                 635                 640

Ile Asp Phe Lys Glu Asp Gly Asn Ile Leu Gly His Lys Leu Glu Tyr
                645                 650                 655

Asn Tyr Asn Ser His Asn Val Tyr Ile Met Ala Asp Lys Gln Lys Asn
            660                 665                 670

Gly Ile Lys Val Asn Phe Lys Ile Arg His Asn Ile Glu Asp Gly Ser
        675                 680                 685

Val Gln Leu Ala Asp His Tyr Gln Gln Asn Thr Pro Ile Gly Asp Gly
        690                 695                 700

Pro Val Leu Leu Pro Asp Asn His Tyr Leu Ser Thr Gln Ser Ala Leu
705                 710                 715                 720

Ser Lys Asp Pro Asn Glu Lys Arg Asp His Met Val Leu Leu Glu Phe
                725                 730                 735

Val Thr Ala Ala Gly Ile Thr Leu Gly Met Asp Glu Leu Tyr Lys
            740                 745                 750

<210> SEQ ID NO 23
<211> LENGTH: 21
<212> TYPE: PRT
<213> ORGANISM: Artificial Sequence
<220> FEATURE:
<223> OTHER INFORMATION: Synthetic: Amino acid sequence of the leading
      sequence in the NPM1c CAR

<400> SEQUENCE: 23

Met Ala Leu Pro Val Thr Ala Leu Leu Leu Pro Leu Ala Leu Leu Leu
1               5                   10                  15

His Ala Ala Arg Pro
            20

<210> SEQ ID NO 24
<211> LENGTH: 249
<212> TYPE: PRT
<213> ORGANISM: Artificial Sequence
<220> FEATURE:
<223> OTHER INFORMATION: Synthetic: Amino acid sequence of the YG1 scFv
      in the NPM1c CAR

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

```
Tyr Ala Ala Ser Ser Leu Gln Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Ser Thr Pro Leu
                 85                  90                  95
Thr Phe Gly Gln Gly Thr Lys Val Glu Ile Lys Ser Gly Ile Leu Gly
            100                 105                 110
Thr Thr Ala Ala Ser Gly Ser Ser Gly Gly Ser Ser Ser Gly Ala Glu
        115                 120                 125
Val Gln Leu Val Glu Ser Gly Gly Leu Val Gln Pro Gly Gly Ser
    130                 135                 140
Leu Arg Leu Ser Cys Ala Ala Ser Gly Phe Thr Phe Ser Ser Tyr Ala
145                 150                 155                 160
Met Ser Trp Val Arg Gln Ala Pro Gly Lys Gly Leu Glu Trp Val Ser
                165                 170                 175
Ala Ile Ser Gly Ser Gly Gly Ser Thr Tyr Tyr Ala Asp Ser Val Lys
            180                 185                 190
Gly Arg Phe Thr Ile Ser Arg Asp Asn Ser Lys Asn Thr Leu Tyr Leu
        195                 200                 205
Gln Met Asn Ser Leu Arg Ala Glu Asp Thr Ala Val Tyr Tyr Cys Ala
    210                 215                 220
Arg Leu Gly Tyr Pro Thr Thr Thr Leu Leu Pro Phe Asp Tyr Trp Gly
225                 230                 235                 240

Gln Gly Thr Leu Val Thr Val Ser Ser
                245

<210> SEQ ID NO 25
<211> LENGTH: 69
<212> TYPE: PRT
<213> ORGANISM: Artificial Sequence
<220> FEATURE:
<223> OTHER INFORMATION: Synthetic: Amino acid sequence of the CD8 hinge
      and transmembrane regions in the NPM1c CAR

<400> SEQUENCE: 25

Thr Thr Thr Pro Ala Pro Arg Pro Pro Thr Pro Ala Pro Thr Ile Ala
 1               5                  10                  15
Ser Gln Pro Leu Ser Leu Arg Pro Glu Ala Cys Arg Pro Ala Ala Gly
                20                  25                  30
Gly Ala Val His Thr Arg Gly Leu Asp Phe Ala Cys Asp Ile Tyr Ile
            35                  40                  45
Trp Ala Pro Leu Ala Gly Thr Cys Gly Val Leu Leu Leu Ser Leu Val
        50                  55                  60
Ile Thr Leu Tyr Cys
 65

<210> SEQ ID NO 26
<211> LENGTH: 42
<212> TYPE: PRT
<213> ORGANISM: Artificial Sequence
<220> FEATURE:
<223> OTHER INFORMATION: Synthetic: Amino acid sequence of the 4-1BB
      signaling domain in the NPM1c CAR

<400> SEQUENCE: 26

Lys Arg Gly Arg Lys Lys Leu Leu Tyr Ile Phe Lys Gln Pro Phe Met
 1               5                  10                  15
```

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 27
<211> LENGTH: 112
<212> TYPE: PRT
<213> ORGANISM: Artificial Sequence
<220> FEATURE:
<223> OTHER INFORMATION: Synthetic: Amino acid sequence of the CD3-zeta
      signaling domain in the NPM1c CAR

<400> SEQUENCE: 27

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 28
<211> LENGTH: 19
<212> TYPE: PRT
<213> ORGANISM: Artificial Sequence
<220> FEATURE:
<223> OTHER INFORMATION: Synthetic: Amino acid sequence of the P2A
      self-cleaving peptide in the NPM1c CAR

<400> SEQUENCE: 28

Ala Thr Asn Phe Ser Leu Leu Lys Gln Ala Gly Asp Val Glu Glu Asn
1               5                   10                  15

Pro Gly Pro

<210> SEQ ID NO 29
<211> LENGTH: 239
<212> TYPE: PRT
<213> ORGANISM: Artificial Sequence
<220> FEATURE:
<223> OTHER INFORMATION: Synthetic: Amino acid sequence of the EGFP
      region in the NPM1c CAR

<400> SEQUENCE: 29

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys

```
                65                  70                  75                  80
Gln His Asp Phe Phe Lys Ser Ala Met Pro Glu Gly Tyr Val Gln Glu
                            85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 30
<211> LENGTH: 2265
<212> TYPE: DNA
<213> ORGANISM: Artificial Sequence
<220> FEATURE:
<223> OTHER INFORMATION: Synthetic: NPM1c CAR nucleic acid sequence
      (with YG1 scFv)

<400> SEQUENCE: 30
atggccctcc ctgtcaccgc cctgctgctt ccgctggctc ttctgctcca cgccgctcgg     60
cccgacatcc agatgaccca gtctccatcc tccctgtctg catctgtagg agacagagtc    120
accatcactt gccgggcaag tcagagcatt agcagctatt taaattggta tcagcagaaa    180
ccagggaaag cccctaagct cctgatctat gctgcatcca gtttgcaaag tggggtccca    240
tcaaggttca gtggcagtgg atctgggaca gatttcactc tcaccatcag cagtctgcaa    300
cctgaagatt ttgcaactta ctactgtcaa cagagttaca gtaccccgct cacgttcggc    360
caagggacca aggtggaaat caaatccgga attctaggta ctactgccgc tagtggtagt    420
agtggtggca gtagcagtgg tgccgaggtg cagctggtgg agtctggggg aggcttggta    480
cagcctgggg ggtccctgag actctcctgt gcagcctctg gattcacctt tagcagctat    540
gccatgagct gggtccgcca ggctccaggg aaggggctgg agtgggtctc agctattagt    600
ggtagtggtg gtagcacata ctacgcagac tccgtgaagg gccggttcac catctccaga    660
gacaattcca agaacacgct gtatctgcaa atgaacagcc tgagagccga ggacacggcc    720
gtgtattact gtgcgaggct gggttaccct actactaccc tactaccctt tgattactgg    780
ggccaaggta ccctggtcac tgtctccagt accactaccc cagcaccgag gccacccacc    840
ccggctccta ccatcgcctc ccagcctctg tccctgcgtc cggaggcatg tagacccgca    900
gctggtgggg ccgtgcatac ccggggtctt gacttcgcct gcgatatcta catttgggcc    960
cctctggctg gtacttgcgg ggtcctgctg ctttcactcg tgatcactct ttactgtaag   1020
cgcggtcgga agaagctgct gtacatcttt aagcaacccc tcatgaggcc tgtgcagact   1080
```

```
actcaagagg aggacggctg ttcatgccgg ttcccagagg aggaggaagg cggctgcgaa    1140
ctgcgcgtga aattcagccg cagcgcagat gctccagcct acaagcaggg gcagaaccag    1200
ctctacaacg aactcaatct tggtcggaga gaggagtacg acgtgctgga caagcggaga    1260
ggacgggacc cagaaatggg cgggaagccg cgcagaaaga atccccaaga gggcctgtac    1320
aacgagctcc aaaaggataa gatggcagaa gcctatagcg agattggtat gaaaggggaa    1380
cgcagaagag gcaaaggcca cgacggactg taccagggac tcagcaccgc caccaaggac    1440
acctatgacg ctcttcacat gcaggccctg ccgcctcggg gatccggcgc aacaaacttc    1500
tctctgctga acaagccgg agatgtcgaa gagaatcctg accgatggt gagcaagggc    1560 gaggagctgt tcaccggggt ggtgcccatc ctggtcgagc tggacggcga cgtaaacggc    1620
cacaagttca gcgtgtccgg cgagggcgag ggcgatgcca cctacggcaa gctgaccctg    1680
aagttcatct gcaccaccgg caagctgccc gtgcctggc ccaccctcgt gaccaccctg    1740
acctacggcg tgcagtgctt cagccgctac cccgaccaca tgaagcagca cgacttcttc    1800
aagtccgcca tgcccgaagg ctacgtccag gagcgcacca tcttcttcaa ggacgacggc    1860
aactacaaga cccgcgccga ggtgaagttc gagggcgaca ccctggtgaa ccgcatcgag    1920
ctgaagggca tcgacttcaa ggaggacggc aacatcctgg gcacaagct ggagtacaac    1980 tacaacagcc acaacgtcta tatcatggcc gacaagcaga gaacggcat caaggtgaac    2040 ttcaagatcc gccacaacat cgaggacggc agcgtgcagc tcgccgacca ctaccagcag    2100 aacacccca tcggcgacgg ccccgtgctg ctgcccgaca accactacct gagcacccag    2160
tccgccctga gcaagacccc caacgagaag cgcgatcaca tggtcctgct ggagttcgtg    2220
accgccgccg ggatcactct cggcatggac gagctgtaca agtga                    2265

<210> SEQ ID NO 31
<211> LENGTH: 63
<212> TYPE: DNA
<213> ORGANISM: Artificial Sequence
<220> FEATURE:
<223> OTHER INFORMATION: Synthetic: Nucleic acid sequence of the leading
      sequence in the
      NPM1c CAR

<400> SEQUENCE: 31
atggccctcc ctgtcaccgc cctgctgctt ccgctggctc ttctgctcca cgccgctcgg    60
ccc                                                                   63

<210> SEQ ID NO 32
<211> LENGTH: 747
<212> TYPE: DNA
<213> ORGANISM: Artificial Sequence
<220> FEATURE:
<223> OTHER INFORMATION: Synthetic: Nucleic acid sequence of the YG1
      scFv in the NPM1c CAR

<400> SEQUENCE: 32
gacatccaga tgacccagtc tccatcctcc ctgtctgcat ctgtaggaga cagagtcacc    60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccgctcac gttcggccaa    300
gggaccaagg tggaaatcaa atccggaatt ctaggtacta ctgccgctag tggtagtagt    360
```

```
ggtggcagta gcagtggtgc cgaggtgcag ctggtggagt ctggggagg cttggtacag      420 cctgggggt ccctgagact ctcctgtgca gcctctggat tcacctttag cagctatgcc      480
atgagctggg tccgccaggc tccagggaag gggctggagt gggtctcagc tattagtggt      540
agtggtggta gcacatacta cgcagactcc gtgaagggcc ggttcaccat ctccagagac     600
aattccaaga acacgctgta tctgcaaatg aacagcctga gagccgagga cacggccgtg     660
tattactgtg cgaggctggg ttaccctact actaccctac tacccttga ttactggggc      720 caaggtaccc tggtcactgt ctccagt                                         747

<210> SEQ ID NO 33
<211> LENGTH: 207
<212> TYPE: DNA
<213> ORGANISM: Artificial Sequence
<220> FEATURE:
<223> OTHER INFORMATION: Synthetic: Nucleic acid sequence of the CD8
      hinge and transmembrane regions in the NPM1c CAR

<400> SEQUENCE: 33
accactaccc cagcaccgag gccacccacc ccggctccta ccatcgcctc ccagcctctg      60
tccctgcgtc cggaggcatg tagacccgca gctggtgggg ccgtgcatac ccggggtctt    120
gacttcgcct gcgatatcta catttgggcc cctctggctg gtacttgcgg ggtcctgctg    180
ctttcactcg tgatcactct ttactgt                                         207

<210> SEQ ID NO 34
<211> LENGTH: 126
<212> TYPE: DNA
<213> ORGANISM: Artificial Sequence
<220> FEATURE:
<223> OTHER INFORMATION: Synthetic: Nucleic acid sequence of the 4-1BB
      signaling domain in the NPM1c CAR

<400> SEQUENCE: 34
aagcgcggtc ggaagaagct gctgtacatc tttaagcaac ccttcatgag gcctgtgcag     60
actactcaag aggaggacgg ctgttcatgc cggttcccag aggaggagga aggcggctgc    120
gaactg                                                                126

<210> SEQ ID NO 35
<211> LENGTH: 336
<212> TYPE: DNA
<213> ORGANISM: Artificial Sequence
<220> FEATURE:
<223> OTHER INFORMATION: Synthetic: Nucleic acid sequence of the
      CD3-zeta signaling domain in the NPM1c CAR

<400> SEQUENCE: 35
cgcgtgaaat tcagccgcag cgcagatgct ccagcctaca gcaggggca gaaccagctc      60 tacaacgaac tcaatcttgg tcggagagag gagtacgacg tgctggacaa gcggagagga    120
cgggacccag aaatgggcgg gaagccgcgc agaaagaatc cccaagaggg cctgtacaac    180
gagctccaaa aggataagat ggcagaagcc tatagcgaga ttggtatgaa aggggaacgc    240
agaagaggca aggccacga cggactgtac cagggactca gcaccgccac caaggacacc    300
tatgacgctc ttcacatgca ggccctgccg cctcgg                              336

<210> SEQ ID NO 36
<211> LENGTH: 57
<212> TYPE: DNA
<213> ORGANISM: Artificial Sequence
<220> FEATURE:
```

<223> OTHER INFORMATION: Synthetic: Nucleic acid sequence of the P2A
      self-cleaving peptide in the NPM1c CAR

<400> SEQUENCE: 36

```
gcaacaaact tctctctgct gaaacaagcc ggagatgtcg aagagaatcc tggaccg         57
```

<210> SEQ ID NO 37
<211> LENGTH: 720
<212> TYPE: DNA
<213> ORGANISM: Artificial Sequence
<220> FEATURE:
<223> OTHER INFORMATION: Synthetic: Nucleic acid sequence of the EGFP
      region in the NPM1c CAR

<400> SEQUENCE: 37

```
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtga    720
```

<210> SEQ ID NO 38
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: Human IgG1

<400> SEQUENCE: 38

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

```
                    130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                    165                 170                 175

Glu Gln Tyr Asn Ser Thr Tyr Arg Val Val Ser Val Leu Thr Val Leu
                    180                 185                 190

His Gln Asp Trp Leu Asn Gly Lys Glu Tyr Lys Cys Lys Val Ser Asn
                    195                 200                 205

Lys Ala Leu Pro Ala Pro Ile Glu Lys Thr Ile Ser Lys Ala Lys Gly
                    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
                    275                 280                 285

Leu Tyr Ser Lys Leu Thr Val Asp Lys Ser Arg Trp Gln Gln Gly Asn
                    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                    325                 330

<210> SEQ ID NO 39
<211> LENGTH: 326
<212> TYPE: PRT
<213> ORGANISM: Homo sapiens
<220> FEATURE:
<221> NAME/KEY: misc_feature
<222> LOCATION: (1)..(326)
<223> OTHER INFORMATION: Human IgG4 (terminal K absent)

<400> SEQUENCE: 39

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly
            325

<210> SEQ ID NO 40
<211> LENGTH: 326
<212> TYPE: PRT
<213> ORGANISM: Homo sapiens
<220> FEATURE:
<221> NAME/KEY: misc_feature
<222> LOCATION: (1)..(326)
<223> OTHER INFORMATION: Human IgG4 single mutant (S228P) (terminal K
      absent)

<400> SEQUENCE: 40

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175
```

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
            325

<210> SEQ ID NO 41
<211> LENGTH: 326
<212> TYPE: PRT
<213> ORGANISM: Homo sapiens
<220> FEATURE:
<221> NAME/KEY: misc_feature
<222> LOCATION: (1)..(326)
<223> OTHER INFORMATION: Human IgG4 double mutant (S228P) (L235E)
      (terminal K absent)

<400> SEQUENCE: 41

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
        100                 105                 110

Glu Phe Glu Gly Gly Pro Ser Val Phe Leu Phe Pro Pro Lys Pro Lys
    115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
        180                 185                 190
```

-continued

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 42
<211> LENGTH: 326
<212> TYPE: PRT
<213> ORGANISM: Homo sapiens
<220> FEATURE:
<221> NAME/KEY: misc_feature
<222> LOCATION: (1)..(326)
<223> OTHER INFORMATION: Human IgG4 double mutant (S228P) (L235A)
      (terminal K absent)

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

```
Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 43
<211> LENGTH: 297
<212> TYPE: PRT
<213> ORGANISM: Artificial Sequence
<220> FEATURE:
<223> OTHER INFORMATION: Synthetic: CD20 amino acid sequence

<400> SEQUENCE: 43

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240
```

```
Glu Ile Lys Glu Glu Val Val Gly Leu Thr Glu Thr Ser Ser Gln Pro
            245                 250                 255

Lys Asn Glu Glu Asp Ile Glu Ile Ile Pro Ile Gln Glu Glu Glu
        260                 265                 270

Glu Glu Thr Glu Thr Asn Phe Pro Gly Pro Gln Asp Gln Glu Ser
    275                 280                 285

Ser Pro Ile Glu Asn Asp Ser Ser Pro
    290                 295

<210> SEQ ID NO 44
<211> LENGTH: 8
<212> TYPE: PRT
<213> ORGANISM: Artificial Sequence
<220> FEATURE:
<223> OTHER INFORMATION: Synthetic: FLAG

<400> SEQUENCE: 44

Asp Tyr Lys Asp Asp Asp Asp Lys
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic: polyhistidine (6-His)

<400> SEQUENCE: 45

His His His His His His
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic: hemagglutinin (HA)

<400> SEQUENCE: 46

Tyr Pro Tyr Asp Val Pro Asp Tyr Ala
1               5

<210> SEQ ID NO 47
<211> LENGTH: 10
<212> TYPE: PRT
<213> ORGANISM: Artificial Sequence
<220> FEATURE:
<223> OTHER INFORMATION: Synthetic: HCDR1.1 (anti-CD3) amino acid
      sequence

<400> SEQUENCE: 47

Gly Tyr Thr Phe Thr Arg Tyr Thr Met His
1               5                   10

<210> SEQ ID NO 48
<211> LENGTH: 5
<212> TYPE: PRT
<213> ORGANISM: Artificial Sequence
<220> FEATURE:
<223> OTHER INFORMATION: Synthetic: HCDR1.2 (anti-CD3) amino acid
      sequence

<400> SEQUENCE: 48

Arg Tyr Thr Met His
1               5
```

```
<210> SEQ ID NO 49
<211> LENGTH: 17
<212> TYPE: PRT
<213> ORGANISM: Artificial Sequence
<220> FEATURE:
<223> OTHER INFORMATION: Synthetic: HCDR2 (anti-CD3) amino acid sequence

<400> SEQUENCE: 49

Tyr Ile Asn Pro Ser Arg Gly Tyr Thr Asn Tyr Asn Gln Lys Phe Lys
1               5                   10                  15
Asp

<210> SEQ ID NO 50
<211> LENGTH: 10
<212> TYPE: PRT
<213> ORGANISM: Artificial Sequence
<220> FEATURE:
<223> OTHER INFORMATION: Synthetic: HCDR3 (anti-CD3) amino acid sequence

<400> SEQUENCE: 50

Tyr Tyr Asp Asp His Tyr Cys Leu Asp Tyr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic: LCDR1 (anti-CD3) amino acid sequence

<400> SEQUENCE: 51

Arg Ala Ser Ser Ser Val Ser Tyr Met Asn
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Synthetic: LCDR2 (anti-CD3) amino acid sequence

<400> SEQUENCE: 52

Asp Thr Ser Lys Val Ala Ser
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic: LCDR3 (anti-CD3) amino acid sequence

<400> SEQUENCE: 53

Gln Gln Trp Ser Ser Asn Pro Leu Thr
1               5

<210> SEQ ID NO 54
<211> LENGTH: 294
<212> TYPE: PRT
<213> ORGANISM: Homo sapiens
<220> FEATURE:
<221> NAME/KEY: misc_feature
<222> LOCATION: (1)..(294)
<223> OTHER INFORMATION: Human wild type nucleophosmin (amino acid
      sequence)
```

-continued

```
<400> SEQUENCE: 54

Met Glu Asp Ser Met Asp Met Asp Met Ser Pro Leu Arg Pro Gln Asn
1               5                   10                  15

Tyr Leu Phe Gly Cys Glu Leu Lys Ala Asp Lys Asp Tyr His Phe Lys
            20                  25                  30

Val Asp Asn Asp Glu Asn Glu His Gln Leu Ser Leu Arg Thr Val Ser
        35                  40                  45

Leu Gly Ala Gly Ala Lys Asp Glu Leu His Ile Val Glu Ala Glu Ala
    50                  55                  60

Met Asn Tyr Glu Gly Ser Pro Ile Lys Val Thr Leu Ala Thr Leu Lys
65                  70                  75                  80

Met Ser Val Gln Pro Thr Val Ser Leu Gly Gly Phe Glu Ile Thr Pro
                85                  90                  95

Pro Val Val Leu Arg Leu Lys Cys Gly Ser Gly Pro Val His Ile Ser
            100                 105                 110

Gly Gln His Leu Val Ala Val Glu Glu Asp Ala Glu Ser Glu Asp Glu
        115                 120                 125

Glu Glu Glu Asp Val Lys Leu Leu Ser Ile Ser Gly Lys Arg Ser Ala
130                 135                 140

Pro Gly Gly Gly Ser Lys Val Pro Gln Lys Lys Val Lys Leu Ala Ala
145                 150                 155                 160

Asp Glu Asp Asp Asp Asp Asp Glu Glu Asp Asp Glu Asp Asp
                165                 170                 175

Asp Asp Asp Asp Phe Asp Asp Glu Glu Ala Glu Glu Lys Ala Pro Val
            180                 185                 190

Lys Lys Ser Ile Arg Asp Thr Pro Ala Lys Asn Ala Gln Lys Ser Asn
            195                 200                 205

Gln Asn Gly Lys Asp Ser Lys Pro Ser Ser Thr Pro Arg Ser Lys Gly
        210                 215                 220

Gln Glu Ser Phe Lys Lys Gln Glu Lys Thr Pro Lys Thr Pro Lys Gly
225                 230                 235                 240

Pro Ser Ser Val Glu Asp Ile Lys Ala Lys Met Gln Ala Ser Ile Glu
                245                 250                 255

Lys Gly Gly Ser Leu Pro Lys Val Glu Ala Lys Phe Ile Asn Tyr Val
            260                 265                 270

Lys Asn Cys Phe Arg Met Thr Asp Gln Glu Ala Ile Gln Asp Leu Trp
        275                 280                 285

Gln Trp Arg Lys Ser Leu
    290

<210> SEQ ID NO 55
<211> LENGTH: 17
<212> TYPE: PRT
<213> ORGANISM: Homo sapiens
<220> FEATURE:
<221> NAME/KEY: misc_feature
<222> LOCATION: (1)..(17)
<223> OTHER INFORMATION: C-terminus of human wild type nucleophosmin
      (amino acid sequence)

<400> SEQUENCE: 55

Met Thr Asp Gln Glu Ala Ile Gln Asp Leu Trp Gln Trp Arg Lys Ser
1               5                   10                  15

Leu

<210> SEQ ID NO 56
```

```
<211> LENGTH: 298
<212> TYPE: PRT
<213> ORGANISM: Homo sapiens
<220> FEATURE:
<221> NAME/KEY: misc_feature
<222> LOCATION: (1)..(298)
<223> OTHER INFORMATION: Human nucleophosmin encoded by mutant NPM1c
      gene (amino acid sequence)

<400> SEQUENCE: 56

Met Glu Asp Ser Met Asp Met Asp Met Ser Pro Leu Arg Pro Gln Asn
1               5                   10                  15

Tyr Leu Phe Gly Cys Glu Leu Lys Ala Asp Lys Asp Tyr His Phe Lys
            20                  25                  30

Val Asp Asn Asp Glu Asn Glu His Gln Leu Ser Leu Arg Thr Val Ser
        35                  40                  45

Leu Gly Ala Gly Ala Lys Asp Glu Leu His Ile Val Glu Ala Glu Ala
    50                  55                  60

Met Asn Tyr Glu Gly Ser Pro Ile Lys Val Thr Leu Ala Thr Leu Lys
65                  70                  75                  80

Met Ser Val Gln Pro Thr Val Ser Leu Gly Gly Phe Glu Ile Thr Pro
                85                  90                  95

Pro Val Leu Arg Leu Lys Cys Gly Ser Gly Pro Val His Ile Ser
            100                 105                 110

Gly Gln His Leu Val Ala Val Glu Glu Asp Ala Glu Ser Glu Asp Glu
        115                 120                 125

Glu Glu Glu Asp Val Lys Leu Leu Ser Ile Ser Gly Lys Arg Ser Ala
    130                 135                 140

Pro Gly Gly Gly Ser Lys Val Pro Gln Lys Lys Val Lys Leu Ala Ala
145                 150                 155                 160

Asp Glu Asp Asp Asp Asp Asp Glu Glu Asp Asp Glu Asp Asp
                165                 170                 175

Asp Asp Asp Asp Phe Asp Glu Glu Ala Glu Glu Lys Ala Pro Val
                180                 185                 190

Lys Lys Ser Ile Arg Asp Thr Pro Ala Lys Asn Ala Gln Lys Ser Asn
            195                 200                 205

Gln Asn Gly Lys Asp Ser Lys Pro Ser Ser Thr Pro Arg Ser Lys Gly
    210                 215                 220

Gln Glu Ser Phe Lys Lys Gln Glu Lys Thr Pro Lys Thr Pro Lys Gly
225                 230                 235                 240

Pro Ser Ser Val Glu Asp Ile Lys Ala Lys Met Gln Ala Ser Ile Glu
                245                 250                 255

Lys Gly Gly Ser Leu Pro Lys Val Glu Ala Lys Phe Ile Asn Tyr Val
            260                 265                 270

Lys Asn Cys Phe Arg Met Thr Asp Gln Glu Ala Ile Gln Asp Leu Cys
        275                 280                 285

Leu Ala Val Glu Glu Val Ser Leu Arg Lys
    290                 295

<210> SEQ ID NO 57
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: C-terminus of human nucleophosmin encoded by
      mutant NPM1c gene (amino acid sequence)
```

```
<400> SEQUENCE: 57

Met Thr Asp Gln Glu Ala Ile Gln Asp Leu Cys Leu Ala Val Glu Glu
1               5                   10                  15

Val Ser Leu Arg Lys
            20

<210> SEQ ID NO 58
<211> LENGTH: 5
<212> TYPE: PRT
<213> ORGANISM: Artificial Sequence
<220> FEATURE:
<223> OTHER INFORMATION: Synthetic: Linker

<400> SEQUENCE: 58

Gly Gly Gly Gly Ser
1               5

<210> SEQ ID NO 59
<211> LENGTH: 10
<212> TYPE: PRT
<213> ORGANISM: Artificial Sequence
<220> FEATURE:
<223> OTHER INFORMATION: Synthetic: Linker

<400> SEQUENCE: 59

Gly Gly Gly Gly Ser Gly Gly Gly Gly Ser
1               5                   10

<210> SEQ ID NO 60
<211> LENGTH: 15
<212> TYPE: PRT
<213> ORGANISM: Artificial Sequence
<220> FEATURE:
<223> OTHER INFORMATION: Synthetic: Linker

<400> SEQUENCE: 60

Gly Gly Gly Gly Ser Gly Gly Gly Gly Ser Gly Gly Gly Gly Ser
1               5                   10                  15

<210> SEQ ID NO 61
<211> LENGTH: 20
<212> TYPE: PRT
<213> ORGANISM: Artificial Sequence
<220> FEATURE:
<223> OTHER INFORMATION: Synthetic: Linker

<400> SEQUENCE: 61

Gly Gly Gly Gly Ser Gly Gly Gly Gly Ser Gly Gly Gly Gly Ser Gly
1               5                   10                  15

Gly Gly Gly Ser
            20

<210> SEQ ID NO 62
<211> LENGTH: 9
<212> TYPE: PRT
<213> ORGANISM: Artificial Sequence
<220> FEATURE:
<223> OTHER INFORMATION: Synthetic: NY-ESO-1 neoepitope (SLL)

<400> SEQUENCE: 62

Ser Leu Leu Met Trp Ile Thr Gln Cys
1               5

<210> SEQ ID NO 63
<211> LENGTH: 9
```

```
<212> TYPE: PRT
<213> ORGANISM: Influenza virus
<220> FEATURE:
<221> NAME/KEY: misc_feature
<222> LOCATION: (1)..(9)
<223> OTHER INFORMATION: influenza virus M1 protein neoepitope (GIL)

<400> SEQUENCE: 63

Gly Ile Leu Gly Phe Val Phe Thr Leu
1               5

<210> SEQ ID NO 64
<211> LENGTH: 22
<212> TYPE: DNA
<213> ORGANISM: Artificial Sequence
<220> FEATURE:
<223> OTHER INFORMATION: Synthetic: Forward primer

<400> SEQUENCE: 64
gtcagtaatt gcggttctca cc                                              22

<210> SEQ ID NO 65
<211> LENGTH: 20
<212> TYPE: DNA
<213> ORGANISM: Artificial Sequence
<220> FEATURE:
<223> OTHER INFORMATION: Synthetic: Reverse primer

<400> SEQUENCE: 65
gtacagtggg aacaaagtcg                                                 20

<210> SEQ ID NO 66
<211> LENGTH: 24
<212> TYPE: DNA
<213> ORGANISM: Artificial Sequence
<220> FEATURE:
<223> OTHER INFORMATION: Synthetic: Forward primer

<400> SEQUENCE: 66
ccggggtaga acctaaaagt tccg                                            24

<210> SEQ ID NO 67
<211> LENGTH: 21
<212> TYPE: DNA
<213> ORGANISM: Artificial Sequence
<220> FEATURE:
<223> OTHER INFORMATION: Synthetic: Reverse primer

<400> SEQUENCE: 67
tttgttctgc acgcgtggat c                                               21

<210> SEQ ID NO 68
<211> LENGTH: 24
<212> TYPE: DNA
<213> ORGANISM: Artificial Sequence
<220> FEATURE:
<223> OTHER INFORMATION: Synthetic: Forward primer

<400> SEQUENCE: 68
gggtaattaa tcagcgaagc gatg                                            24

<210> SEQ ID NO 69
<211> LENGTH: 25
<212> TYPE: DNA
<213> ORGANISM: Artificial Sequence
<220> FEATURE:
<223> OTHER INFORMATION: Synthetic: Forward primer
```

-continued

<400> SEQUENCE: 69
gttaggccag cttggcactt gatgt                                     25

<210> SEQ ID NO 70
<211> LENGTH: 24
<212> TYPE: DNA
<213> ORGANISM: Artificial Sequence
<220> FEATURE:
<223> OTHER INFORMATION: Synthetic: Reverse primer

<400> SEQUENCE: 70
aggcacaatc agcattggta gctg                                      24

<210> SEQ ID NO 71
<211> LENGTH: 9
<212> TYPE: PRT
<213> ORGANISM: Artificial Sequence
<220> FEATURE:
<223> OTHER INFORMATION: Synthetic: NPM1c neoepitope

<400> SEQUENCE: 71

Ala Ile Gln Asp Leu Cys Val Ala Val
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic: NPM1c neoepitope

<400> SEQUENCE: 72

Cys Leu Ala Val Glu Glu Val Ser Leu
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic: NPM1c neoepitope

<400> SEQUENCE: 73

Val Glu Glu Val Ser Leu Arg Lys
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic: NPM1c neoepitope

<400> SEQUENCE: 74

Ala Val Glu Glu Val Ser Leu Arg
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic: NPM1c neoepitope

<400> SEQUENCE: 75

```
Ala Val Glu Glu Val Ser Leu Arg Lys
1               5
```

<210> SEQ ID NO 76
<211> LENGTH: 11
<212> TYPE: PRT
<213> ORGANISM: Artificial Sequence
<220> FEATURE:
<223> OTHER INFORMATION: Synthetic: NPM1c neoepitope

<400> SEQUENCE: 76

```
Cys Leu Ala Val Glu Glu Val Ser Leu Arg Lys
1               5                   10
```

<210> SEQ ID NO 77
<211> LENGTH: 9
<212> TYPE: PRT
<213> ORGANISM: Artificial Sequence
<220> FEATURE:
<223> OTHER INFORMATION: Synthetic: AIQ X1 substitution

<400> SEQUENCE: 77

```
Val Ile Gln Asp Leu Cys Leu Ala Val
1               5
```

<210> SEQ ID NO 78
<211> LENGTH: 9
<212> TYPE: PRT
<213> ORGANISM: Artificial Sequence
<220> FEATURE:
<223> OTHER INFORMATION: Synthetic: AIQ X1 substitution

<400> SEQUENCE: 78

```
Leu Ile Gln Asp Leu Cys Leu Ala Val
1               5
```

<210> SEQ ID NO 79
<211> LENGTH: 9
<212> TYPE: PRT
<213> ORGANISM: Artificial Sequence
<220> FEATURE:
<223> OTHER INFORMATION: Synthetic: AIQ X1 substitution

<400> SEQUENCE: 79

```
Ile Ile Gln Asp Leu Cys Leu Ala Val
1               5
```

<210> SEQ ID NO 80
<211> LENGTH: 9
<212> TYPE: PRT
<213> ORGANISM: Artificial Sequence
<220> FEATURE:
<223> OTHER INFORMATION: Synthetic: AIQ X3 substitution

<400> SEQUENCE: 80

```
Ala Ile Asn Asp Leu Cys Leu Ala Val
1               5
```

<210> SEQ ID NO 81
<211> LENGTH: 9
<212> TYPE: PRT
<213> ORGANISM: Artificial Sequence
<220> FEATURE:
<223> OTHER INFORMATION: Synthetic: AIQ X4 substitution

<400> SEQUENCE: 81

```
Ala Ile Gln Glu Leu Cys Leu Ala Val
```

```
<210> SEQ ID NO 82
<211> LENGTH: 9
<212> TYPE: PRT
<213> ORGANISM: Artificial Sequence
<220> FEATURE:
<223> OTHER INFORMATION: Synthetic: AIQ X5 substitution

<400> SEQUENCE: 82

Ala Ile Gln Asp Ile Cys Leu Ala Val
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic: AIQ X5 substitution

<400> SEQUENCE: 83

Ala Ile Gln Asp Val Cys Leu Ala Val
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic: AIQ X5 substitution

<400> SEQUENCE: 84

Ala Ile Gln Asp Met Cys Leu Ala Val
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic: AIQ X5 substitution

<400> SEQUENCE: 85

Ala Ile Gln Asp Ala Cys Leu Ala Val
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic: AIQ X5 substitution

<400> SEQUENCE: 86

Ala Ile Gln Asp Phe Cys Leu Ala Val
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic: AIQ X6 substitution

<400> SEQUENCE: 87

Ala Ile Gln Asp Leu Ser Leu Ala Val
1               5
```

<210> SEQ ID NO 88
<211> LENGTH: 9
<212> TYPE: PRT
<213> ORGANISM: Artificial Sequence
<220> FEATURE:
<223> OTHER INFORMATION: Synthetic: AIQ X6 substitution

<400> SEQUENCE: 88

Ala Ile Gln Asp Leu Ala Leu Ala Val
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic: AIQ X7 substitution

<400> SEQUENCE: 89

Ala Ile Gln Asp Leu Cys Ile Ala Val
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic: AIQ X7 substitution

<400> SEQUENCE: 90

Ala Ile Gln Asp Leu Cys Val Ala Val
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic: AIQ X7 substitution

<400> SEQUENCE: 91

Ala Ile Gln Asp Leu Cys Met Ala Val
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic: AIQ X7 substitution

<400> SEQUENCE: 92

Ala Ile Gln Asp Leu Cys Ala Ala Val
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic: AIQ X7 substitution

<400> SEQUENCE: 93

Ala Ile Gln Asp Leu Cys Phe Ala Val
1               5

```
<210> SEQ ID NO 94
<211> LENGTH: 9
<212> TYPE: PRT
<213> ORGANISM: Artificial Sequence
<220> FEATURE:
<223> OTHER INFORMATION: Synthetic: AIQ X8 substitution

<400> SEQUENCE: 94

Ala Ile Gln Asp Leu Cys Leu Val Val
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic: AIQ X8 substitution

<400> SEQUENCE: 95

Ala Ile Gln Asp Leu Cys Leu Leu Val
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic: AIQ X8 substitution

<400> SEQUENCE: 96

Ala Ile Gln Asp Leu Cys Leu Ile Val
1               5
```

COMPOSITIONS AND METHODS FOR IMMUNOTHERAPY OF NPM1C-POSITIVE CANCER

CROSS-REFERENCE TO RELATED APPLICATIONS

This application claims the benefit of U.S. Provisional Patent Application Ser. No. 62/987,612, filed Mar. 10, 2020. The entire contents of which is incorporated herein by reference.

GOVERNMENT LICENSE RIGHTS STATEMENT

This invention was made with Government support under Grant No. CA197605 awarded by the National Institutes of Health (NIH). The Government has certain rights in the invention.

STATEMENT REGARDING SEQUENCE LISTING

The instant application contains a Sequence Listing which has been submitted in ASCII format via EFS-Web and is hereby incorporated by reference in its entirety. Said ASCII copy, created on Apr. 19, 2021, is named "MITN-057_Sequence-Listing.txt" and is 66306 bytes in size.

BACKGROUND

Cell-based immunotherapies are in development for treatment of cancer. Approaches using adoptive cell transfer of T cells, monocyte-derived cells (e.g., macrophages, dendritic cells) and natural killer (NK) cells are being explored as cancer treatments (see, e.g., Andreesen, R. et al (1990) Cancer Res 50:7450-7456; Ruggeri, L. et al (2002) Science 295:2097-2100; Rezvani, K. (2019) Bone Marrow Transplantation 54:785-788). Specifically, adoptive cell therapy (ACT), in which ex vivo activated/expanded T cells are administered to patients, is one of the cancer treatments currently being tested. (Rosenberg et al. (2008) Nat Rev Cancer 8(4): 299; Dudley et al. (2002) Science 298(5594): 850; June et al. (2007) J Clin Invest 117(5): 1204; Stephan et al. (2007) Nat Med 13(12): 1440; Yee et al. (2002) Proc Natl Acad Sci USA 99(25): 16168). These approaches involve the use of autologous T cells taken from patients that are activated/expanded ex vivo and then reinfused to combat tumors, such as metastatic tumors. Strategies that enhance the persistence, in vivo expansion, and effector functions of ACT T cells have been used to increase the frequency of objective responses. (Rosenberg S A et al. (2008) Nat Rev Cancer 8(4): 299; June C H et al. (2007) J Clin Invest 117(5): 1204). One way to enhance the function of ACT T cells is via genetic engineering of the cells themselves, for example by introducing chimeric receptors or costimulatory molecules (see e.g., Stephan et al. (2007) Nat Med 13(12): 1440; Morgan et al. (2006) Science 314(5796): 126; Gade et al. (2005) Cancer Res 65(19): 9080).

Chimeric antigen receptor (CAR) T cell therapy has emerged as one of the strategies for the treatment of cancer. Chimeric antigen receptors (CARs) are genetically-engineered, artificial transmembrane receptors that confer a defined specificity for an antigen (e.g., ligand) onto an immune effector cell (e.g., a T cell, natural killer cell or other immune cell), which results in activation of the effector cell upon recognition and binding to the antigen. Typically, these chimeric receptors are used to impart the antigen specificity of a monoclonal antibody onto a T cell, referred to in the art as CAR T cells. Expression of the engineered chimeric antigen receptor on the surface of CAR T cells confers on the T cells the ability to lyse any target cells with surface expression of the particular antigen recognized by the chimeric receptor.

However, current CARs targeting lineage-restricted or tumor-associated antigens (TAAs) can be accompanied by severe toxicity due to low antigen expression in normal tissues (see Coulie et al., NAT REV CANCER 14: 135 (2014); Srivastava & Riddell, J IMMUNOL 200: 459 (2018)). Furthermore, because TAAs are not required for tumor cell survival, loss of TAA expression is the major cause of development of tumor resistance to CAR-T therapies (see Srivastava & Riddell, J IMMUNOL 200: 459 (2018)). Neoantigens are derived from tumor-specific gene mutations, and their formation and expression are restricted to malignant cells (see Blankenstein et al., CURR OPIN IMMUNOL 33 112 (2015); Schumacher et al. SCIENCE 348: 69 (2015); van der Lee et al., J CLIN INVEST 129: 774 (2019)). The majority of neoantigens, however, are encoded by patient-specific passenger mutations that could be lost due to immune editing, resulting in tumor immune evasion (see Verdegaal et al., NATURE 536: 91 (2016)). In addition, current CARs are mainly designed to bind to antigens on the surface of target cells. Actually, most proteins from mutated genes are expressed inside the cell, making them unavailable as targets for conventional CARs (see Uhlen et al., SCIENCE 347: 1260419 (2015)).

Application of cancer immunotherapies to Acute Myeloid Leukemia (AML) has been limited. AML is a rapidly-progressing hematopoietic malignancy, characterized by accumulation of malignant myeloid precursor cells that are arrested in their differentiation in the bone marrow (see van der Lee et al., J CLIN INVEST 129: 774 (2019); Thomas et al., BLOOD 129: 1577 (2017)). Current standard therapy for AML still relies on intensive chemotherapy and autologous or allogeneic hematopoietic stem cell transplantation (alloSCT) (see Dombret & Gardin, BLOOD 127: 53 (2016); Dohner et al., N Engl J Med 373: 1136 (2015)). Although most patients can respond to standard therapy and achieve complete remission, relapses occur in about 50% of these patients (see Ossenkoppele et al., HAEMATOLOGICA 101 20 (2016)). Patients with relapsed or refractory AML after intensive chemotherapy or alloSCT usually have a very poor prognosis (see van der Lee et al., J CLIN INVEST 129: 774 (2019)), and thus there is a strong need to develop new, effective and less toxic therapies for these patients.

SUMMARY OF THE INVENTION

In some aspects, the disclosure provides an antibody, or antigen binding fragment thereof, that specifically binds to an antigen comprising an NPM1c neoepitope in complex with a class I major histocompatibility complex (MHC class I) protein.

In some aspects, the antibody, or antigen binding fragment thereof, does not bind to, or substantially does not bind to: (a) the MHC class I protein alone, and/or (b) a control peptide in complex with the MHC class I protein, optionally wherein the control peptide is an NY-ESO-1 epitope or influenza virus M1 epitope.

In some aspects, the antibody, or antigen binding fragment thereof, does not bind to, or substantially does not bind to: (a) the MHC class I protein alone, and (b) a control peptide in complex with the MHC class I protein, optionally wherein the control peptide is an NY-ESO-1 epitope or influenza virus M1 epitope.

In some aspects, the antibody, or antigen binding fragment thereof, does not bind to, or substantially does not bind to: (a) the MHC class I protein alone, (b) a control peptide in complex with the MHC class I protein, optionally wherein the control peptide is an NY-ESO-1 epitope or influenza virus M1 epitope, and/or (c) the NPM1c neoepitope alone.

In some aspects, the antibody, or antigen binding fragment thereof, does not bind to, or substantially does not bind to: (a) the MHC class I protein alone, (b) a control peptide in complex with the MHC class I protein, optionally wherein the control peptide is an NY-ESO-1 epitope or influenza virus M1 epitope, and (c) the NPM1c neoepitope alone.

In any of the foregoing or related aspects, the NPM1c neoepitope comprises an amino acid sequence $X_1X_2X_3X_4X_5X_6X_7X_8X_9$, wherein $X_1$ is selected from A, V, L or I, wherein $X_2$ is selected from A, T, S, V, L, I, M or Q, wherein $X_3$ is selected from Q or N, wherein $X_4$ is selected from D or E, wherein $X_5$ is selected from L, I, V, M, A or F, wherein $X_6$ is selected from C, S, or A, wherein $X_7$ is selected from L, I, V, M, A, or F, wherein $X_8$ is selected from A, V, L or I, and wherein $X_9$ is selected from L, I, V, M or A. In some aspects, the NPM1c neoepitope comprises an amino acid sequence $X_1X_2X_3X_4X_5X_6X_7X_8X_9$, wherein $X_1$ is selected from A or V, wherein $X_2$ is selected from V, I, or L, wherein $X_3$ is selected from Q or N, wherein $X_4$ is selected from D or E, wherein $X_5$ is selected from L or I, wherein $X_6$ is selected from C or S, wherein $X_7$ is selected from V, L or I, wherein $X_8$ is selected from A or V, and wherein $X_9$ is selected from V, I, or L. In some aspects, the NPM1c neoepitope comprises an amino acid sequence $X_1X_2X_3X_4X_5X_6X_7X_8X_9$, wherein $X_1$ is A, wherein $X_2$ is selected from V, I, or L, wherein $X_3$ is Q, wherein $X_4$ is D, wherein $X_5$ is L, wherein $X_6$ is C, wherein $X_7$ is L, wherein $X_8$ is A, and wherein $X_9$ is selected from V, I, or L. In some aspects, the NPM1c neoepitope is within a peptide of 10, 15, 20, 30, 40, 50 or 100 amino acid residues in length.

In any of the foregoing or related aspects, the NPM1c neoepitope comprises an amino acid sequence selected from: AIQDLCLAV (SEQ ID NO:1) or AIQDLCVAV (SEQ ID NO: 71). In some aspects, the NPM1c neoepitope comprises an amino acid sequence selected from: CLAVEEVSL (SEQ ID NO:72), VEEVSLRK (SEQ ID NO:73), AVEEVSLR (SEQ ID NO:74), AVEEVSLRK (SEQ ID NO:75), CLAVEEVSLRK (SEQ ID NO:76). In some aspects, the NPM1c neoepitope comprises the amino acid sequence AIQDLCLAV (SEQ ID NO:1).

In any of the foregoing or related aspects, the NPM1c neoepitope is 7, 8, 9, 10, 11, 12, 13, 14, or 15 amino acid residues in length.

In any of the foregoing or related aspects, the MHC class I protein is an HLA-A*02 protein or is encoded by the HLA-A*02 allele group. In some aspects, the MHC class I protein is encoded by the HLA-A*02:01 allele.

In any of the foregoing or related aspects, the disclosure provides an antibody, or antigen binding fragment thereof, comprising:
(i) a heavy chain variable region (VH) comprising VH complementarity determining region (CDR)1, VH CDR2 and VH CDR3, said VH CDR1, VH CDR2 and VH CDR3 being the CDRs of a VH that has an amino acid sequence of SEQ ID NO:5, wherein the CDRs are as defined by IMGT; and/or
(ii) a light chain variable region (VL) comprising VL complementarity determining region (CDR)1, VL CDR2 and VL CDR3, said VL CDR1, VL CDR2 and VL CDR3 being the CDRs of a VL that has an amino acid sequence of SEQ ID NO:3, wherein the CDRs are as defined by IMGT.

In any of the foregoing or related aspects, the disclosure provides an antibody, or antigen binding fragment thereof, comprising a heavy chain variable region (VH) comprising VH complementarity determining region (CDR)1, VH CDR2 and VH CDR3, wherein the VH CDR1 has the amino acid sequence GFTFSSYA (SEQ ID NO:9), the VH CDR2 has the amino acid sequence ISGSGGST (SEQ ID NO:10), and the VH CDR3 has the amino acid sequence ARLGYPTTTLLPFDY (SEQ ID NO:11).

In any of the foregoing or related aspects, the disclosure provides an antibody, or antigen binding fragment thereof, further comprising a light chain variable region (VL) comprising VL complementarity determining region (CDR)1, VL CDR2 and VL CDR3, wherein the VL CDR1 has the amino acid sequence QSISSY (SEQ ID NO:6), the VL CD2 has the amino acid sequence AAS (SEQ ID NO:7), and the VL CD3 has the amino acid sequence QQSYSTPLT (SEQ ID NO:8).

In any of the foregoing or related aspects, the disclosure provides an antibody, or antigen binding fragment thereof, comprising a heavy chain variable region (VH) and a light chain variable region (VL), wherein the VH comprises an amino acid sequence which is at least 90% identical, or at least 95% identical, to the amino acid sequence of SEQ ID NO:5, and/or wherein the VL comprises an amino acid sequence which is at least 90% identical, or at least 95% identical, to the amino acid sequence of SEQ ID NO:3.

In any of the foregoing or related aspects, the disclosure provides an antibody, or antigen binding fragment thereof, comprising a heavy chain variable region (VH) and a light chain variable region (VL), wherein the VH comprises the amino acid sequence of SEQ ID NO:5, and/or wherein the VL comprises the amino acid sequence of SEQ ID NO:3.

In any of the foregoing or related aspects, the disclosure provides an antibody, or antigen binding fragment thereof, which is a human, humanized or chimeric antibody.

In any of the foregoing or related aspects, the disclosure provides an antibody, or antigen binding fragment thereof, which is a single chain Fv (scFv), an Fv fragment, a Fab fragment, a Fab' fragment, a F(ab')2 fragment, or a single chain antibody molecule.

In any of the foregoing or related aspects, the disclosure provides an antibody, or antigen binding fragment thereof, which is an scFv. In some aspects, the scFv is a human scFv. In some aspects, the scFv comprises a linker. In some aspects, the linker is a peptide linker. In some aspects, the peptide linker is a Gly-Ser linker. In some aspects, the Gly-Ser linker is selected from the group consisting of (Gly4Ser) (SEQ ID NO:58), (Gly4Ser)2 (SEQ ID NO:59), (Gly4Ser)3 (SEQ ID NO:60), and (Gly4Ser)4 (SEQ ID NO:61). In some aspects, the Gly-Ser linker comprises the amino acid sequence SGSSGGSSSG (SEQ ID NO:4).

In any of the foregoing or related aspects, the scFv has an amino acid sequence which is at least 80% identical, at least 85% identical, at least 90% identical, or at least 95% identical, to the amino acid sequence of SEQ ID NO:2; optionally wherein the scFv comprises: (a) a heavy chain variable region (VH) comprising VH complementarity determining region (CDR)1, VH CDR2 and VH CDR3, wherein the VH CDR1 has the amino acid sequence GFTFSSYA (SEQ ID NO:9), the VH CDR2 has the amino acid sequence ISGSGGST (SEQ ID NO:10), and the VH CDR3 has the amino acid sequence ARLGYPTTTLLPFDY (SEQ ID NO:11); and/or (b) a light chain variable region (VL) comprising VL complementarity determining region (CDR)1, VL CDR2 and VL CDR3, wherein the VL CDR1 has the amino acid sequence QSISSY (SEQ ID NO:6), the VL CD2 has the amino acid sequence AAS (SEQ ID NO:7), and the VL CD3 has the amino acid sequence QQSYSTPLT (SEQ ID NO:8).

In any of the foregoing or related aspects, the scFv has an amino acid sequence of SEQ ID NO:2.

In any of the foregoing or related aspects, the disclosure provides an antibody, or antigen binding fragment thereof, which is an antibody. In some aspects, the antibody is selected from the group consisting of an IgG1, an IgG2, an IgG3, an IgG4, an IgM, an IgA1, an IgA2, an IgD, and an IgE antibody isotypes. In some aspects, the antibody is of an IgG1 isotype or IgG4 isotype. In some aspects, the antibody comprises a wild type IgG1 heavy chain constant region or wild type IgG4 heavy chain constant region. In some aspects, the antibody comprises a mutant IgG1 heavy chain constant region or mutant IgG4 heavy chain constant region.

In any of the foregoing or related aspects, the antibody comprises a mutant IgG4 heavy chain constant region, wherein the mutant IgG4 heavy chain constant region comprises any one of the following substitutions: S228P, L235E, L235A, or a combination thereof, according to EU numbering.

In any of the foregoing or related aspects, the antibody comprises an Fc domain comprising at least one mutation.

In any of the foregoing or related aspects, the antigen is on the surface of a cancer cell. In some aspects, the cancer is Acute Myeloid Leukemia (AML).

In any of the foregoing or related aspects, the antibody, or antigen binding fragment thereof, binds to an antigen comprising an NPM1c neoepitope in complex with a class I major histocompatibility complex (MHC class I) protein with an equilibrium dissociation constant (Kd) of 100 nM or less, 50 nM or less, 20 nM or less, 10 nM or less, from 0.5 nM to 100 nM, or from 1 nM to 15 nM.

In any of the foregoing or related aspects, the disclosure provides an antibody, or antigen binding fragment thereof, which is a bispecific antibody, or antigen binding fragment thereof, which further specifically binds to a second antigen on an immune effector cell. In some aspects, the effector cell is a T cell, a natural killer cell or a macrophage. In some aspects, the second antigen is CD3. In some aspects, the CD3 is a human CD3 expressed on T cells. In some aspects, the second antigen is NKp46. In some aspects, the NKp46 is a human NKp46 expressed on NK cells. In some aspects, the second antigen is CD16A. In some aspects, the CD16A is a human CD16A expressed on NK-cells. In some aspects, the second antigen is CD40, CD47, 4-1BB, TGF-β, LAG-3, PD-1, TIM-3, CTLA-4, OX40, NKp30, NKG2A, NKG2D or DNAM-1.

In any of the foregoing or related aspects, the disclosure provides an antibody, or antigen binding fragment thereof, which is purified.

In some aspects, the disclosure provides an isolated nucleic acid, wherein the nucleic acid comprises a nucleic acid sequence encoding the antibody, or antigen binding fragment thereof, described herein.

In any of the foregoing or related aspects, the isolated nucleic acid comprises the nucleotide sequence of SEQ ID NO:12. In some aspects, the isolated nucleic acid comprises a nucleotide sequence having at least about 80%, 81%, 82%, 83%, 84%, 85%, 86%, 87%, 88%, 89%, 90%, 91%, 92%, 93%, 94%, 95%, 96%, 97%, 98%, or 99% identity to the nucleotide sequence set forth in SEQ ID NO:12.

In some aspects, the disclosure provides an expression vector comprising a nucleic acid described herein. In some aspects, the disclosure provides a cell transformed with an expression vector comprising a nucleic acid described herein.

In some aspects, the disclosure provides a method for producing an antibody, or antigen binding fragment thereof, described herein, the method comprising maintaining the cell transformed with an expression vector comprising a nucleic acid described herein under conditions permitting expression of the antibody, or antigen binding fragment thereof. In some aspects, the method further comprising purifying the antibody, or antigen binding fragment thereof.

In some aspects, the disclosure provides a pharmaceutical composition comprising a therapeutically effective amount of an antibody, or antigen binding fragment thereof, described herein, and a pharmaceutically acceptable carrier.

In some aspects, the disclosure provides a chimeric antigen receptor (CAR) polypeptide comprising an intracellular domain, a transmembrane domain and an extracellular binding domain, wherein the extracellular binding domain specifically binds to an antigen comprising an NPM1c neoepitope in complex with a class I major histocompatibility complex (MHC class I) protein.

In some aspects, the disclosure provides a chimeric antigen receptor (CAR) polypeptide comprising an intracellular domain, a transmembrane domain and an extracellular binding domain, wherein the extracellular binding domain comprises an antibody, or antigen binding fragment thereof, described herein.

In any of the foregoing or related aspects, the transmembrane domain comprises the transmembrane domain of CD3-zeta, CD8, CD28, NKG2D, CD16, NKp44 or NKp46. In some aspects, the intracellular domain comprises one or more costimulatory domains of one or more costimulatory molecules selected from the group consisting of: CD27, CD28, 4-1BB, OX40, CD30, CD40, PD-1, ICOS, 2B4, DAP10, CD137 and DAP12.

In any of the foregoing or related aspects, the disclosure provides a CAR polypeptide wherein the intracellular domain comprises a CD3-zeta signaling domain and a 4-1BB costimulatory domain; wherein the transmembrane domain comprises a CD8 transmembrane domain, and wherein the CAR polypeptide further comprises a CD8 hinge region.

In any of the foregoing or related aspects, the disclosure provides a CAR polypeptide wherein the intracellular domain comprises a CD3-zeta signaling domain comprising the amino acid sequence set forth in SEQ ID NO: 27, and a 4-1BB costimulatory domain comprising the amino acid sequence set forth in SEQ ID NO: 26; wherein the CAR polypeptide comprises a CD8 transmembrane domain and a CD8 hinge region, wherein the CD8 transmembrane domain and the CD8 hinge region comprise the amino acid sequence set forth in SEQ ID NO: 25; and wherein the extracellular binding domain comprises the antibody, or antigen binding fragment thereof, and a leading sequence comprising the amino acid sequence set forth in SEQ ID NO: 23.

In any of the foregoing or related aspects, the antibody, or antigen binding fragment thereof, in the extracellular binding domain is an scFv comprising the amino acid sequence set forth in SEQ ID NO:24, or an amino acid sequence which is at least 70% identical, at least 75% identical, at least 80% identical, at least 85% identical, at least 90% identical, or at least 95% identical, to the amino acid sequence of SEQ ID NO:24.

In any of the foregoing or related aspects, the intracellular domain further comprises a self-cleaving peptide sequence and a cytokine, wherein cleavage of the self-cleaving peptide releases the cytokine. In some aspects, the cytokine is IL-12, IL-7, IL-13, IL-15, TNF-α, IFN-γ, or CCL19.

In any of the foregoing or related aspects, the disclosure provides a CAR polypeptide which comprises the amino acid sequence set forth in SEQ ID NO: 22, or an amino acid sequence which is at least 70% identical, at least 75% identical, at least 80% identical, at least 85% identical, at least 90% identical, or at least 95% identical, to the amino acid sequence of SEQ ID NO:22.

In some aspects, the disclosure provides an isolated nucleic acid encoding a CAR polypeptide described herein. In some aspects, the isolated nucleic acid comprises the nucleotide sequence of SEQ ID NO:30, or a nucleotide sequence which is at least 70% identical, at least 75% identical, at least 80% identical, at least 85% identical, at least 90% identical, or at least 95% identical, to the nucleotide sequence of SEQ ID NO:30. In some aspects, the disclosure provides an expression vector comprising an isolated nucleic acid encoding a CAR polypeptide described herein, wherein the expression vector is a viral expression vector or a non-viral expression vector. In some aspects, the disclosure provides an expression vector comprising an isolated nucleic acid encoding a CAR polypeptide described herein, wherein the expression vector is a viral expression vector, and wherein the viral expression vector is a lentiviral expression vector.

In some aspects, the disclosure provides a cell transformed with an expression vector comprising an isolated nucleic acid encoding a CAR polypeptide described herein. In some aspects, the disclosure provides a cell expressing a CAR polypeptide described herein. In some aspects, the cell is an immune effector cell, wherein expression of the CAR polypeptide targets the immune effector cell to a cancer cell expressing an antigen comprising an NPM1c neoepitope in complex with a class I major histocompatibility complex (MHC class I) protein. In some aspects, the MHC class I protein is an HLA-A*2 protein or is encoded by the HLA-A*02 allele group. In some aspects, the immune effector cell does not substantially target and/or induce killing of a cancer cell expressing wild type NPM1. In some aspects, the immune effector cell does not substantially target a cancer cell expressing wild type NPM1. In some aspects, the immune effector cell does not substantially induce killing of a cancer cell expressing wild type NPM1. In some aspects, the cell is a T cell. In some aspects, the T cell is a human CD8$^+$ T cell. In some aspects, the cell is a Natural Killer (NK) cell. In some aspects, the cell is a macrophage. In some aspects, the cancer cell is an acute myeloid leukemia (AML) cell.

In some aspects, the disclosure provides a pharmaceutical composition, comprising a cell transformed with an expression vector comprising an isolated nucleic acid encoding a CAR polypeptide described herein, and a pharmaceutically acceptable carrier. In some aspects, the disclosure provides a pharmaceutical composition, comprising a cell expressing a CAR polypeptide described herein, and a pharmaceutically acceptable carrier.

In some aspects, the disclosure provides a method for producing a cell expressing a CAR polypeptide described herein, wherein the method comprises: (i) purifying a cell from peripheral blood mononuclear cells (PMBC) of a subject, (ii) optionally, activating the cell with an anti-CD3 antibody or an antigen binding fragment thereof and/or an anti-CD28 antibody or an antigen-binding fragment thereof, (iii) transducing the cell with an expression vector comprising an isolated nucleic acid encoding a CAR polypeptide described herein, (iv) isolating the cell expressing the CAR polypeptide, and (v) optionally, expanding the isolated cell.

In some aspects, the disclosure provides a method for producing a cell expressing a CAR polypeptide described herein, wherein the method comprises: (i) inducing a pluripotent stem cell (iPSC) to differentiate into an immune effector cell, (ii) transducing the immune effector cell with an expression vector comprising an isolated nucleic acid encoding a CAR polypeptide described herein, (iii) isolating the immune effector cell expressing the CAR polypeptide, and (iv) optionally, expanding the isolated immune effector cell.

In any of the foregoing or related aspects, the immune effector cell is a NK cell. In some aspects, the immune effector cell is a macrophage. In some aspects, the immune effector cell is a T cell.

In some aspects, the disclosure provides a method of treating a cancer in a subject in need thereof, wherein the cell surface of cells comprising the cancer displays an NPM1c neoepitope in complex with a class I major histocompatibility complex (MHC class I) protein, the method comprising administering to the subject an antibody, or antigen binding fragment thereof, described herein, a cell described herein, or a pharmaceutical composition described herein, in an amount sufficient to treat the cancer. In some aspects, the cancer is acute myeloid leukemia (AML). In some aspects, the method of treating cancer is a method of reducing cancer burden or a method of increasing survival in the subject.

In some aspects, the disclosure provides a method of treating acute myeloid leukemia (AML) in a subject in need thereof, the method comprising administering to the subject an antibody, or antigen binding fragment thereof, described herein, a cell described herein, or a pharmaceutical composition described herein, in an amount sufficient to treat AML. In some aspects, the AML is a relapsed AML or a refractory AML.

In some aspects, the disclosure provides a method of preventing relapse of AML in a subject in remission from AML, the method comprising administering to the subject an antibody, or antigen binding fragment thereof, described herein, a cell described herein, or a pharmaceutical composition described herein.

In any of the foregoing or related aspects, the disclosure provides a method further comprising, before the administering step, detecting whether the subject expresses NPM1c or whether the subject has an NPM1c mutation in the NPM1 gene, and if the subject expresses NPM1c or has an NPM1c mutation proceeding with the administering step.

In any of the foregoing or related aspects, the disclosure provides a method wherein the administering is intravenous, intrathecal, intraosseous, or into the spinal cord.

In any of the foregoing or related aspects, the method further comprises administering one or more additional therapeutic agents or procedures. In some aspects, the additional therapeutic agent is an inhibitor of an immune checkpoint molecule; optionally the immune checkpoint molecule is TIM-3, PD-1, PD-L1 or CTLA-4; optionally the inhibitor is an antibody.

In some aspects, the disclosure provides use of an antibody, or antigen binding fragment thereof, described herein, a CAR polypeptide described herein, a cell described herein, or a pharmaceutical composition described herein, in the manufacture of a medicament for treating a cancer in a subject, wherein the cell surface of cells comprising the cancer displays an NPM1c neoepitope in complex with a class I major histocompatibility complex (MHC class I) protein; optionally wherein the use is in combination with one or more additional therapeutic agents or procedures.

In any of the foregoing or related aspects, the subject is a human.

In some aspects, the disclosure provides a kit comprising one or more containers comprising: (i) an antibody, or antigen binding fragment thereof, described herein, a CAR polypeptide described herein, a cell described herein, or a pharmaceutical composition described herein; (ii) optionally, one or more additional therapeutic agents, and (iii) instructions for use in treating cancer in a subject.

In another aspect, described herein are antibodies or antigen binding fragments thereof that specifically bind to an antigen comprising a neoepitope in complex with (or presented by) an MHC (e.g., MHC class I) protein (e.g., HLA-A2). In certain embodiments of this aspect, the antibodies or antigen binding fragments thereof that specifically bind to an antigen comprising a neoepitope in complex with (or presented by) an MHC (e.g., MHC class I) protein (e.g., HLA-A2) are generated by: (i) isolating antibody clones that bind to the antigen using yeast surface display antibody (e.g., scFv) library or phage display antibody (e.g., scFv) library, and (ii) selecting antibody clones that specifically bind to the antigen, using yeast surface display antibody (e.g., scFv) library or phage display antibody (e.g., scFv) library, by subjecting the antibody clones to multiple rounds (two, three, four or more rounds) of positive selection (selecting yeast or phage clones binding the antigen) and multiple rounds (two, three, four or more rounds) of negative selection (e.g., selecting out yeast or phage clones binding an MHC protein alone and/or an MHC protein in complex with a control peptide (i.e., a peptide different from the neoepitope)); wherein the selected antibody clones bind the antigen and do not bind, or substantially do not bind, the MHC protein alone and/or the MHC protein in complex with a control peptide. In certain embodiments of this aspect, the antigen is a dimeric neoepitope-MHC complex. In certain embodiments of this aspect, the neoepitope-MHC complex is NPM1c:HLA-A2.

BRIEF DESCRIPTION OF THE DRAWINGS

FIGS. 1A-1D show isolation of human scFv specific for AIQ-HLA-A2 complex by yeast surface display.

FIG. 1A depicts a schematic of epitope peptide-HLA-A2 complex, scFv displayed on the yeast surface, and the binding of peptide-HLA-A2 complex to scFv on yeast cell surface. The schematic was adapted from Chao et al., *NAT PROTOC* 1: 755 (2006).

FIGS. 1B-1 and 1B-2 depict strategies and steps that were used to isolate yeast cells displaying scFvs that specifically recognize AIQ-HLA-A2 complex. Round of selection is indicated at the left (rounds 1-5 shown in FIG. 1B-1 and rounds 6-9 shown in FIG. 1B-2). "Antigen" indicates peptide-HLA-A2 complexes or HLA-A2 alone used in positive or negative selection. In the first two rounds of selection, yeast cells were selected by magnetic cell sorting (MACS). In the rest of rounds of selection, yeast cells were sorted by flow cytometry based on staining with FITC labeled anti-c-Myc antibody plus PE-labeled anti-mouse IgG or APC-labeled streptavidin. The gates for sorted cells are indicated. FACS plots are labeled from #1 to #7.

FIGS. 1C-1 and 1C-2 show flow cytometric data (FACS) on live cells. Sorted yeast cells from rounds 4 to 9 were expanded and then stained with FITC labeled anti-c-Myc antibody and biotin-labeled HLA-A2, GIL-HLA-A2, SLL-HLA-A2 or AIQ-HLA-A2, followed by APC-labeled streptavidin and flow cytometry gating on live cells (DAPI negative). Data for rounds 4 and 5 is shown in FIG. 1C-1 and for rounds 6-9 in FIG. 1C-2. FACS plots are labeled from #1 to #29.

FIG. 1D shows flow cytometric data. Yeast cells expressing either YG1 or YG2 clones were stained and analyzed as in FIG. 1C. The percentages in FIGS. 1B, 1C and 1D indicate percentages of cells in the gated regions.

FIG. 2A depicts a schematic diagram of switchable yeast display/secretion vector for expressing scFv-Fc fusion protein. In this switchable system, scFv-Fc can be secreted or displayed on the yeast cells depending on whether OmeY is added to the culture or not (Van Deventer et al., *PROTEIN ENG DES SEL* 28: 317 (2015)).

FIG. 2B shows SDS-PAGE analysis of purified YG1 scFv-Fc protein. Lane 1: protein ladder, lane 2: scFv-Fc protein (1 μg), nonreduced, lane 3: scFv-Fc protein, reduced (1 μg). Gel was stained using Coomassie Blue.

FIG. 2C shows flow cytometric data of HLA-A2 expression by OCI-AML3, T2, GMB, PC-3, and OCI-AML2 cells. Dark shade histograms: stained with anti-HLA-A2, and light shade histograms: stained with isotype control antibody.

FIG. 2D shows flow cytometric data of AIQ-HLA-A2 expression by OCI-AML3, T2, GMB, and PC-3 cells. Dark shade histograms: stained with YG1 scFv-Fc and anti-HA, and light shade histograms: stained with BSA followed by anti-HA. Representative data from triplicates is shown.

FIG. 2E shows kinetic analysis of the interactions between YG1 scFv-Fc and AIQ-HLA-A2, SLL-HLA-A2 or HLA-A2 by biolayer interferometry. The streptavidin biosensor tips of the ForteBio Octet RED 96 were coated with biotinylated YG1 scFv-Fc protein. The tips were dipped in increasing concentrations (indicated at the bottom of binding curve) of AIQ-HLA-A2, SLL-HLA-A2, or HLA-A2 to measure their binding to scFv-Fc (Association) and subsequently moved to wells containing buffer to measure dissociation rate (Dissociation). Shown are representative data from three separate experiments.

FIG. 3A depicts a schematic of CAR vector consisting of scFv (YG1 or CD19), the CD8a extracellular hinge and transmembrane domain, the 4-1BB co-stimulatory domain, and the CD3ζ activation domain, followed by self-cleavage P2A and EGFP.

FIG. 3B depicts a schematic of NPM1c CAR-T cell recognition of AIQ-HLA-A2 complex on AML cells.

FIG. 3C shows flow cytometric data of CAR expression by untransduced and transduced T cells. Transduced T cells were enriched by sorting for GFP+ cells, expanded and stained with AF647-labeled anti-human IgG heavy and light chain antibody that recognizes scFv. Untransduced T cells were activated and expanded without sorting. Shown are GFP versus anti-human IgG staining profiles of live cells (DAPI-).

FIG. 3D depicts flow cytometric data showing that NPM1c CAR-T cells recognize AIQ-HLA-A2 complex. Untransduced and transduced T cells were incubated with biotinylated AIQ-HLA-A2 or SLL-HLA-A2 or HLA-A2 complex, followed by streptavidin-APC staining. Shown are GFP versus streptavidin-APC staining profiles of live (DAPI-) untransduced T cells, NPM1c CAR-T cells, and CD19 CAR-T cells. Data in FIGS. 3C and 3D are representative from at least three independent experiments. The percentages indicate the percentages of cells in the gated regions.

FIGS. 4A-4J show that NPM1c CAR-T cells (comprising YG1 scFv) specifically kill HLA-A2+ NPM1c+ human AML cells in vitro.

FIGS. 4A-4B show that NPM1c CAR-T cells kill target cells in vitro. NPM1c CAR-T cells were co-cultured with OCI-AML3, GMB and PC-3 tumor cells at the indicated effector:target (E:T) ratios for 24 hours. The cell mixtures were stained for CD8 plus CD33, CD19, or mCherry, followed by flow cytometry. The percentages of CAR-T cells were quantified by CD8 staining and the percentages of OCI-AML3 cells by CD33, GMB cells by CD19, and PC-3 by mCherry. The percentages of specific lysis of tumor cells were calculated (see Materials and Methods section in the Examples for formula). Shown are examples of CD8 versus CD33, CD19, or mCherry staining profiles (FIG. 4A) and percentages of specific lysis (FIG. 4B) at different E:T ratios. Percentages of cells in the gated regions are indicated. The p values indicate comparison between NPM1c CAR-T cells and untransduced T cells at the same E:T ratio.

FIG. 4C shows comparison of IFN-γ and IL-2 expression between CAR-T cells and untransduced T cells. NPM1c CAR-T cells and untransduced T cells were co-cultured with OCI-AML3, GMB or PC-3 in the presence of monensin and brefeldin A for 12 hrs. Cells were stained for CD3 and then permeabilized and stained for intracellular IFN-γ or IL-2, followed by flow cytometry. Percentages of IFN-γ+ or IL-2+ NPM1c CAR-T cells and untransduced T cells are shown. P values are indicated.

FIG. 4D shows NPM1c CAR-T cells are stimulated to secrete multiple cytokines by NPM1c+HLA-A2+ target cells. NPM1c CAR-T cells or untransduced T cells were co-cultured with NPM1c+HLA-A2+ OCI-AML3 cells for 16 hours. Culture supernatants were collected and assayed for 20 different cytokines simultaneously using a Quantibody Human Cytokine Array. Each cytokine contained quadruplicate antibody spots. T cells from 4 different healthy donors were separately analyzed; n=4 replicate antibody spots; graph bars and error bars represent the mean±s.e.; p values are indicated.

FIGS. 4E-4F show NPM1c CAR-T cells proliferate in response to NPM1c+HLA-A2+ target cells. NPM1c CAR-T cells or untransduced T cells were co-cultured with OCI-AML3 cells for 5 days. The absolute cell number of CAR-T cells or untransduced T cells was determined by flow cytometry using precision count beads. Ki-67 expression by NPM1c CAR-T cells or untransduced T cells were assayed by intracellular staining followed by flow cytometry. FIG. 4E provides comparison of the numbers of NPM1c CAR-T cells and untransduced T cells at day 5. FIG. 4F provides comparison of mean fluorescence intensity (MFI) of intracellular Ki-67 staining between untransduced T cells and NPM1c CAR-T cells. The p values indicate comparison between NPM1c CAR-T cells and untransduced T cells; n=5 biologically independent samples; graph bars and error bars represent the mean±s.e.

FIGS. 4G-4H show NPM1c CAR-T cells specifically kill HLA-A2+ NPM1c+ human tumor cells in vitro. OCI-AML2 (HLA-A2 positive) and PC-3 (HLA-A2 negative) cells were transduced with lentivirus expressing NPM1c (Lenti-NPM1c) or empty negative control (Lenti-NC). Transduced cells were sorted and expanded. Shown is comparison of specific killing of transduced or control OCI-AML2 cells (FIG. 4G) and PC-3 cells (FIG. 4H) by NPM1c CAR-T cells or untransduced T cells. NPM1c CAR-T cells or untransduced T cells were co-cultured with transduced or control OCI-AML2 or PC-3 target cells at the indicated E:T ratios for 24 hours. Target cell killing was measured by assaying the luciferase activity of the surviving target cells. The percentages of specific lysis of tumor cells at different E:T ratios was calculated. Target cells and T cells in each reaction are shown.

FIG. 4I shows flow cytometry analysis of YG1 scFv-FC binding to T2 cells pulsed with different concentrations of AIQ peptide (left panel) or SLL peptide (right panel).

FIG. 4J shows comparison of specific killing of T2 cells pulsed with different concentrations of AIQ (left panel) or SLL (right panel) peptide by NPM1c CAR-T cells or untransduced T cells. NPM1c CAR-T cells or untransduced T cells were co-cultured with peptide-pulsed T2 target cells at the indicated E:T ratios for 24 hours. Target cell killing was measured by assaying the luciferase activity of the surviving target cells. The p values indicate comparison between NPM1c CAR-T cells and untransduced T cells at the same E:T ratio; n=3 biologically independent samples; data points and error bars represent the mean±s.e.

FIGS. 5A-5H show that NPM1c CAR-T (with YG1 scFv) therapy reduces leukemia burden and prolongs survival in mice with NPM1c-positive AML cells but not NPM1c-negative AML cells.

FIG. 5A shows experimental design: NSG mice were injected with OCI-AML3 cells ($1 \times 10^6$) or GMB cells ($2 \times 10^6$) intravenously (D-4) and imaged for engraftment 4 days later (DO); mice were then injected intravenously with $1 \times 10^7$ NPM1c CAR-T cells, untransduced T cells, or CD19 CAR-T cells. The mice were monitored by bioluminescence imaging every 3 days to assess tumor burden and survival.

FIG. 5B shows comparison of OCI-AML3 leukemia burden as measured by bioluminescence imaging between mice treated with NPM1c CAR-T cells and untransduced T cells at the indicated days (DO to D18) post T cell injection (n=5). Shown is comparison of the total flux (luciferase signal from systemic OCI-AML3 leukemia cells) for each experimental group. The experiment was repeated twice with 4 or 5 mice per group.

FIG. 5C shows Kaplan Meier survival curves (n=9) of mice treated with either NPM1c CAR-T cells or untransduced T cells as in FIG. 5B. P value is indicated.

FIG. 5D shows comparison of GMB lymphoma burden as measured by bioluminescence imaging between mice treated with NPM1c CAR-T cells, untransduced T cells, and CD19 CAR-T cells at the indicated days (DO to D21) post T cell injection (n=3-5). Shown is comparison of the total flux (luciferase signal from systemic GMB cells) for each experimental group. The experiment was repeated twice with 3-5 mice per group. P value for total flux is: untransduced T vs NPM1c CAR-T p=0.992; CD19 CAR-T vs untransduced T p=0.003; CD19 CAR-T vs NPM1c CAR-T p=0.047.

FIG. 5E shows Kaplan Meier survival curves (n=3-5) of mice treated with either NPM1c CAR-T cells or untransduced T cells or CD19 CAR-T cells as in FIG. 5D. P values: untransduced T vs NPM1c CAR-T p=0.124; CD19 CAR-T vs untransduced T p=0.012; and CD19 CAR-T vs NPM1c CAR-T p=0.015.

FIG. 5F provides comparison of OCI-AML3 leukemia burden as measured by bioluminescence imaging in mice given NPM1c CAR-T cells, untransduced T cells or PBS at the indicated days (DO to D21) post T cell/PBS injection (n=3-4). Shown is a comparison of total flux (luciferase signal from systemic OCI-AML3 cells). P value is PBS vs untransduced T p=0.395; PBS vs NPM1c CAR-T p=0.018; and untransduced T vs NPM1c CAR-t p=0.011.

FIG. 5G provides comparison of OCI-AML2 leukemia burden as measured by bioluminescence imaging between mice treated with NPM1c CAR-T cells (n=5) and untransduced T cells (n=5) at the indicated days (D0 to D21) post T cell injection. Shown is a comparison of total flux (luciferase signal from systemic OCI-AML2 cells).

FIG. 5H provides Kaplan Meier survival curves of mice shown in FIG. 5G treated with either NPM1c CAR-T cells (n=5) or untransduced T cells (n=5). Data points and error bars represent the mean±s.e.; p value is indicated

FIG. 6A shows comparison of OCI-AML3 leukemia burden as measured by bioluminescence imaging between NSG mice injected with OCI-AML3 AML cells and then either untransduced T cells or NPM1c CAR-T cells. Shown is a comparison of total flux (luciferase signal from systemic OCI-AML3 cells). Mice (n=5) were imaged on the day of T cell injection (day 0) and 18 days later.

FIGS. 6B-6C show representative flow cytometry plots showing the gating strategy and expression profiles for cell populations obtained from mice represented in FIG. 6A. Blood, spleen, bone marrow and liver were harvested on day 18 and single cell suspensions were prepared and stained for mouse CD45 and human CD45, CD8, CD33, PD-1 and Tim-3, followed by flow cytometry. Shown are representative staining profiles and gating strategies for blood and spleen (FIG. 6B) and for bone marrow and liver (FIG. 6C), including mCD45 vs. hCD45 gating on live cells (DAPI$^-$); hCD33 vs. hCD8 gating on hCD45$^+$ cells; hPD-1 vs. hCD8 gating on hCD8$^+$ cells; and hTim-3 vs. hCD8 gating on hCD8$^+$ cells. The numbers indicate percentages of cells in the gated region.

FIG. 6D shows comparison of total numbers of hCD33$^+$ leukemic cells and hCD8$^+$ T cells in different tissues between mice given NPM1c CAR-T cells and untransduced T cells (where the bars on the left represent treatment with untransduced T cells and the bars on the right represent treatment with NPM1c CAR-T cells).

FIG. 6E shows comparison of percentages of hCD33$^+$ leukemic cells and hCD8$^+$ T cells among hCD45$^+$ cells in different tissues between mice given NPM1c CAR-T cells and untransduced T cells (where the bars on the left represent treatment with untransduced T cells and the bars on the right represent treatment with NPM1c CAR-T cells).

FIG. 6F shows ratios of percentages of hCD8$^+$ T cells over hCD33$^+$ leukemic cells in different tissues in mice given NPM1c CAR-T cells or untransduced T cells (where the bars on the left represent treatment with untransduced T cells and the bars on the right represent treatment with NPM1c CAR-T cells).

FIGS. 6G-6H show the percentages of PD1$^+$ T cells (FIG. 6G) or Tim-3$^+$ T cells (FIG. 6H) among human CD8$^+$ T cells in different tissues (where the bars on the left represent treatment with untransduced T cells and the bars on the right represent treatment with NPM1c CAR-T cells). P values are indicated in FIGS. 6A, 6D, 6E, 6F, 6G and 6H (n=5).

FIG. 6I shows NPM1c CAR T cells effectively eliminate leukemia cells in the bone marrow 30 days post CAR-T cell injection. NSG mice were engrafted with OCI-AML3 and 4 days later injected with NPM1c CAR-T cells, untransduced T cells or PBS (mice as shown in FIG. 5F). 30 days after T cell injection, cells were harvested from the bone marrow of surviving mice. Cells were stained for mouse CD45 and human CD45, CD8, and CD33, followed by flow cytometry. Shown are FSC versus DAPI staining profiles of total cells (left), hCD45 vs mCD45 staining profiles gaining on live (DAPI$^-$) cells (middle), and hCD33 vs hCD8 staining profiles of hCD45$^+$ cells (right). The numbers indicate percentages of cells in the gated regions.

FIG. 7A shows NPM1c CAR-T cells kill NPM1c$^+$HLA-A2$^+$ primary AML blasts from three donors in vitro. NPM1c CAR-T cells or untransduced T cells were incubated with AML blasts at the indicated ratio for 24 hours. The absolute numbers of AML blasts were quantified by staining for CD8 and CD33, followed by flow cytometry with precision count beads. The percentages of specific lysis of tumor cells at different E:T ratios were calculated; n=3 biological replicates; graph bars and error bars represent the mean±s.e.; p values are indicated.

FIG. 7B shows flow cytometry analysis of HLA-A2 expression by HSPCs. Human CD34$^+$ HSPCs were purified from two donor fetal livers using EasySep Human CD34 Positive Selection Kit. Dark histograms: stained with anti-HLA-A2, and light histograms: stained with isotype control antibody. Representative data from technical triplicates is shown.

FIG. 7C shows flow cytometry analysis of HSPCs for YG1 scFv-Fc binding. Dark shade histograms: stained with YG1 scFv-Fc and anti-HA, and light shade histograms: stained with BSA followed by anti-HA. Representative data from three separate experiments with technical triplicates is shown.

FIG. 7D shows NPM1c CAR-T cells do not kill HLA-A2±CD34$^+$ HSPCs. NPM1c CAR-T cells and untransduced T cells were incubated with HSPCs at the indicated E:T ratios for 24 hours. The cell mixtures were stained for CD8 plus CD34 and quantified by flow cytometry with precision count beads. Shown are examples of CD8 (T cells) versus CD34 (HSPCs) staining profiles at different E:T ratios. The percentages of cells in the gated regions are indicated.

FIG. 7E shows comparison of specific lysis at different E:T ratios between NMP1c CAR-T cells and untransduced T cells; p values indicate comparison between NPM1c CAR-T cells and untransduced T cells at the same E:T ratio; n=3 biological replicates; data points and error bars represent the mean±s.e.

FIG. 7F shows NPM1c CAR-T cell treatment reduces leukemia burden in primary HLA-A2$^+$ NPM1c$^+$ AML xenografts. NSGS mice were engrafted with human AML blasts. Two weeks later when AML blasts were detectable in the blood, mice were given NPM1c CAR-T cells or untransduced T cells. At the indicated days after T cell transfer, mice were bled and mononuclear cells were stained for mCD45, hCD45 and hCD8. Shown are representative hCD45 vs mCD45 staining profiles gating on hCD8$^-$ live cells. AML blasts were hCD45$^+$ hCD8$^-$. The numbers indicate percentages of cells in the gated regions.

FIG. 7G shows comparison of percentages of hCD45±CD8$^-$ AML blasts in the peripheral blood between mice given NPM1c CAR-T cells and untransduced T cells, wherein level of AML blasts was measured before T cell injection (day 0), and 9 and 18 days post T cell injection. Left bars represent treatment with untransduced T cells, right bars represent treatment with NPM1c CAR-T cells;

DETAILED DESCRIPTION

Figure 1A:
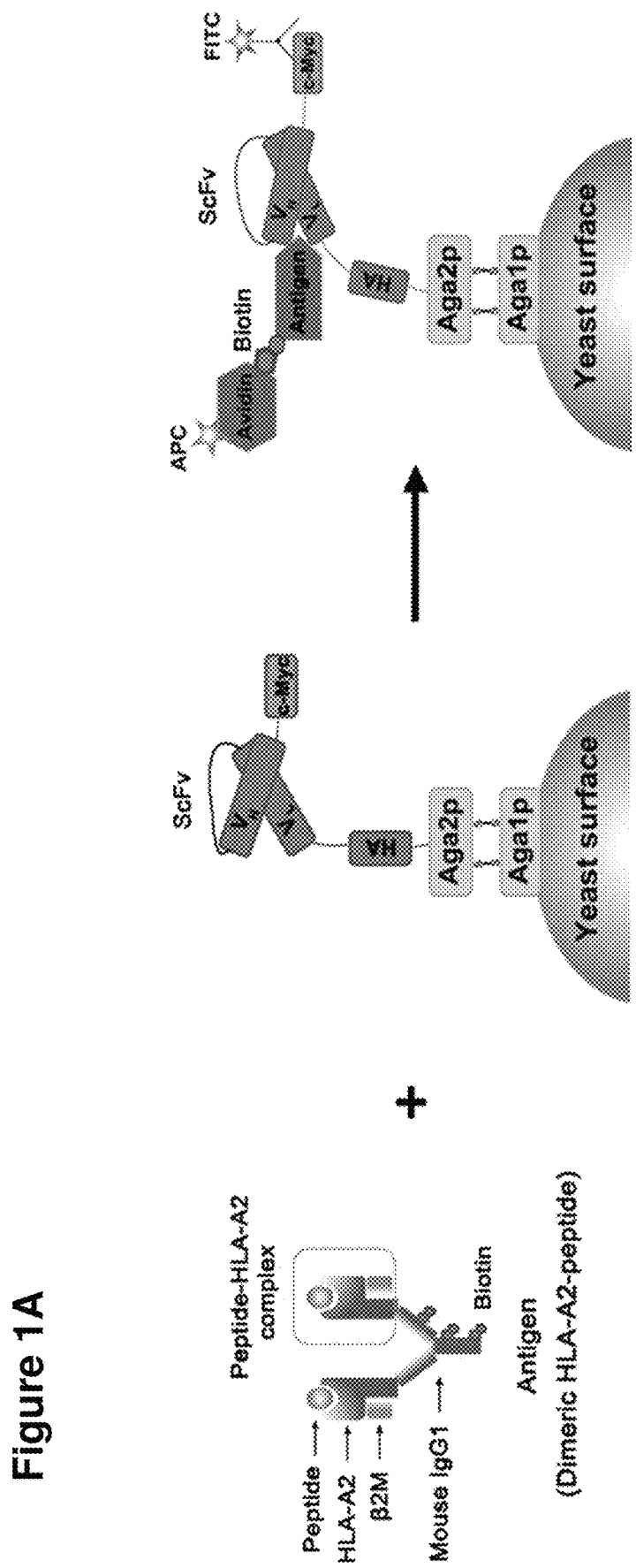

The present disclosure is based, at least in part, on the identification of a single chain variable antibody fragment (scFv) which specifically and with high affinity binds to an NPM1c neoepitope in complex with HLA-A2. The disclosure provides novel scFvs, antibodies and antigen binding fragments thereof that bind to such an NPM1c neoepitope in complex with HLA-A2. In addition, the disclosure provides bispecific binding molecules based on the scFvs of the disclosure which specifically bind to such an NPM1c neoepitope in complex with HLA-A2 and further binds to another target.

Further, the present disclosure provides chimeric antigen receptor (CAR) polypeptides comprising an extracellular binding domain that specifically binds to an antigen comprising an NPM1c neoepitope in complex with HLA-A2.

Further, the present disclosure provides T cells expressing a CAR polypeptide comprising an extracellular binding domain that specifically binds to an antigen comprising an NPM1c neoepitope in complex with HLA-A2. As described herein and shown in the Examples presented herein, the T cells expressing a CAR polypeptide comprising an extracellular binding domain that specifically binds to an antigen comprising an NPM1c neoepitope in complex with HLA-A2 specifically kill AML cells in vitro, and reduce leukemia burden and prolong survival in vivo, in an AML mouse model.

Accordingly, the antibodies and antigen binding fragments thereof, bispecific molecules, CAR polypeptides and T cells expressing CAR polypeptides described herein are useful for targeted immunotherapy to treat cancers that carry an NPM1c mutation. For example, the antibodies and antigen-binding fragments thereof, CAR polypeptides and T cells expressing CAR polypeptides disclosed herein are useful for targeted immunotherapy to treat acute myeloid leukemia (AML). In one aspect, provided herein are antibodies or antigen binding fragments thereof that specifically bind to an antigen comprising an NPM1c neoepitope when such epitope is in complex with (or presented by) a class I major histocompatibility complex (MHC class I) protein (e.g., HLA-A2). In one aspect, provided herein are antibodies or antigen binding fragments thereof that specifically bind to one or more of the neoepitopes having the following amino acid sequences: AIQDLCLAV (SEQ ID NO:1), AIQDLCVAV (SEQ ID NO: 71), CLAVEEVSL (SEQ ID NO: 72), VEEVSLRK (SEQ ID NO: 73), AVEEVSLR (SEQ ID NO: 74), AVEEVSLRK (SEQ ID NO: 75), CLAVEEVSLRK (SEQ ID NO: 76), when such epitope is in complex with a class I major histocompatibility complex (MHC class I) protein (e.g., HLA-A2). In one aspect, provided herein are antibodies or antigen binding fragments thereof that do not bind to, or substantially do not bind to, an MHC class I protein alone. In one aspect, provided herein are antibodies or antigen binding fragments thereof that do not bind to, or substantially do not bind to, a control peptide in complex with an MHC class I protein (e.g., wherein the control peptide is an NY-ESO-1 epitope (e.g., a peptide comprising SEQ ID NO:62) or influenza virus M1 epitope (e.g., a peptide comprising SEQ ID NO:63). In one aspect, provided herein are antibodies or antigen binding fragments thereof that do not bind to, or substantially do not bind to, an NPM1c neoepitope alone (without an MHC class I protein). In some aspects, the NPM1c neoepitope comprises the amino acid sequence AIQDLCLAV (SEQ ID NO:1), and the MHC class I protein is an HLA-A2 protein (e.g., a protein encoded by the HLA-A*02:01 allele). In some aspects, the antigen is on the surface of a cancer cell (e.g., where the cancer is NPM1c+, e.g., where the cancer is AML). In one aspect, provided herein are antibodies or antigen binding fragments thereof that specifically bind to an amino acid sequence comprising AIQDLCLAV (SEQ ID NO:1) in complex with an HLA-A2 protein (e.g., a protein encoded by the HLA-A*02:01 allele). Antibodies and antigen binding fragments thereof provided herein are described below.

In one aspect, provided herein are bispecific molecules comprising: (i) a first antigen-binding domain that specifically binds to an antigen comprising an NPM1c neoepitope in complex with a class I major histocompatibility complex (MHC class I) protein (e.g., HLA-A2), and (ii) a second antigen-biding domain that specifically binds to a second antigen. In some aspects, the second antigen is an antigen expressed on a T cell or a natural killer cell. In some aspects, the second antigen is CD3 (e.g., human CD3), NKp46 (e.g., human NKp46), or CD16A (e.g., human CD16A). In one aspect, provided herein are bispecific molecules comprising: (i) a first antigen-binding domain that specifically binds to an amino acid sequence comprising AIQDLCLAV (SEQ ID NO:1) in complex with an HLA-A2 protein (e.g., a protein encoded by the HLA-A*02:01 allele), and (ii) a second antigen-biding domain that specifically binds to a second antigen. Bispecific molecules provided herein are described below.

In one aspect, provided herein are pharmaceutical compositions comprising the antibodies or antigen binding fragments thereof described herein (and, optionally, a pharmaceutically acceptable carrier). In one aspect, provided herein are pharmaceutical compositions comprising the bispecific molecules described herein (and, optionally, a pharmaceutically acceptable carrier). Pharmaceutical compositions provided herein are described below.

In one aspect, provided herein are chimeric antigen receptor (CAR) polypeptides comprising an intracellular domain, a transmembrane domain and an extracellular domain, wherein the extracellular domain specifically binds to an antigen comprising an NPM1c neoepitope in complex with a class I major histocompatibility complex (MHC class I) protein (e.g., HLA-A2). In one aspect, provided herein are CAR polypeptides comprising an intracellular domain, a transmembrane domain and an extracellular domain, wherein the extracellular domain specifically binds to an amino acid sequence comprising AIQDLCLAV (SEQ ID NO:1) in complex with an HLA-A2 protein (e.g., a protein encoded by the HLA-A*02:01 allele). In one aspect, provided herein are CAR polypeptides comprising an intracellular domain, a transmembrane domain and an extracellular domain, wherein the extracellular domain comprises any antibody or antigen binding fragment thereof described herein. In one aspect, provided herein are CAR polypeptides comprising an intracellular domain, a transmembrane domain and an extracellular domain, wherein the extracellular domain comprises any bispecific molecule described herein. CAR polypeptides provided herein are described below.

In one aspect, provided herein are immune effector cells expressing a CAR polypeptide comprising an intracellular domain, a transmembrane domain and an extracellular domain, wherein the extracellular domain specifically binds to an antigen comprising an NPM1c neoepitope in complex with a class I major histocompatibility complex (MHC class I) protein (e.g., HLA-A2). In one aspect, provided herein are immune effector cells expressing a CAR polypeptide comprising an intracellular domain, a transmembrane domain and an extracellular domain, wherein the extracellular domain specifically binds to an amino acid sequence comprising AIQDLCLAV (SEQ ID NO:1) in complex with an HLA-A2 protein (e.g., a protein encoded by the HLA-A*02:01 allele). In one aspect, provided herein are immune effector cells expressing a CAR polypeptide comprising an intracellular domain, a transmembrane domain and an extracellular domain, wherein the extracellular domain comprises any antibody or antigen binding fragment thereof described herein. In one aspect, provided herein are immune effector cells expressing a CAR polypeptide comprising an intracellular domain, a transmembrane domain and an extracellular domain, wherein the extracellular domain comprises any bispecific molecule described herein. In one aspect, provided herein are immune effector cells expressing a CAR polypeptide described herein. In one aspect, an immune effector cell is a T cell (e.g., a CD8$^+$ T cell), a natural killer cell, or a macrophage. In one aspect, expression of the CAR polypeptide targets the immune effector cell to a cancer cell (e.g., wherein the cancer is AML) displaying on its surface an NPM1c neoepitope in complex with a class I major histocompatibility complex (MHC class I) protein (e.g., HLA-A2). In one aspect, expression of the CAR polypeptide targets the immune effector cell to a cancer cell (e.g., wherein the cancer is AML) displaying on its surface the amino acid sequence AIQDLCLAV (SEQ ID NO:1) in complex with an HLA-A2 protein (e.g., a protein encoded by the HLA-A*02:01 allele). Immune effector cells provided herein are described below.

In one aspect, provided herein are pharmaceutical compositions comprising any immune effector cell described herein (and, optionally, a pharmaceutically acceptable carrier).

In one aspect, provided herein are methods of treating cancer in a subject (e.g., a human), wherein the cell surface of cells comprising the cancer displays an NPM1c neoepitope in complex with a class I major histocompatibility complex (MHC class I) protein (e.g., HLA-A2), the method comprising administering to the subject any antibody or antigen-binding fragment described herein. In one aspect, provided herein are methods of treating cancer in a subject (e.g., a human), wherein the cell surface of cells comprising the cancer displays an NPM1c neoepitope in complex with a class I major histocompatibility complex (MHC class I) protein (e.g., HLA-A2), the method comprising administering to the subject any immune effector cell comprising a CAR polypeptide described herein. In one aspect, provided herein are methods of treating cancer in a subject (e.g., a human), wherein the cell surface of cells comprising the cancer displays an amino acid sequence comprising AIQDLCLAV (SEQ ID NO:1) in complex with an HLA-A2 protein (e.g., a protein encoded by the HLA-A*02:01 allele), the method comprising administering to the subject any antibody or antigen-binding fragment described herein. In one aspect, provided herein are methods of treating cancer in a subject (e.g., a human), wherein the cell surface of cells comprising the cancer displays an amino acid sequence comprising AIQDLCLAV (SEQ ID NO:1) in complex with an HLA-A2 protein (e.g., a protein encoded by the HLA-A*02:01 allele), the method comprising administering to the subject any immune effector cell comprising a CAR polypeptide described herein.

In some aspects, provided herein are methods of treating NPM1c-positive cancer in a subject (e.g., a human), the method comprising administering to the subject any antibody or antigen-binding fragment described herein. In some aspects, provided herein are methods of treating NPM1c-positive cancer in a subject (e.g., a human), the method comprising administering to the subject any immune effector cell comprising a CAR polypeptide described herein.

In one aspect, provided herein are methods of treating AML in a subject (e.g., a human), the method comprising administering to the subject any antibody or antigen-binding fragment described herein. In one aspect, provided herein are methods of treating AML in a subject (e.g., a human), the method comprising administering to the subject any immune effector cell comprising a CAR polypeptide described herein.

Methods of treatment using, uses of, and kits comprising, the antibodies or antigen binding fragments thereof provided herein, CAR polypeptides provided herein, immune effector cells comprising CAR polypeptides provided herein, and pharmaceutical compositions comprising the same provided herein, are described below.

The present disclosure is also based, at least in part, on the identification of a scFv which specifically binds to a neoepitope (in particular, a cancer neoepitope) in complex with an MHC protein (in particular, MHC class I protein such as HLA-A2). The isolation of such specific and high affinity antibodies was surprising, since there are many challenges associated with the development of antibodies and antigen binding fragments thereof that specifically bind neoepitope-MHC complexes. In particular, the neoepitope peptides easily dissociate from MHC proteins, making it difficult to generate antibodies specific for the complex. Without being bound by any theory, it was discovered that the use of multiple rounds of positive and negative selection of yeast populations specifically binding neoepitope-MHC complex without binding the MHC protein alone or the MHC protein in complex with a control peptide, using a yeast surface display methodology resulted in the identification of scFvs which specifically bind the neoepitope-MHC complex. The selection steps are described in Example 1 and Appendix 1. Without being bound by any theory, the use of dimeric neoepitope-MHC complexes as the antigen may have also contributed to the successful isolation of specific scFvs of high affinity.

Accordingly, in one aspect, provided herein are antibodies or antigen binding fragments thereof that specifically bind to an antigen comprising a neoepitope (e.g., a cancer neoepitope) in complex with (or presented by) an MHC (e.g., MHC class I) protein (e.g., HLA-A2). In certain embodiments of this aspect, the antibodies or antigen binding fragments are generated using yeast surface display antibody (e.g., scFv) library or phage display antibody (e.g., scFv) library, and optionally enriched for specific binders to the neoepitope-MHC complex using multiple rounds (two, three, four or more rounds) of positive selection (selecting yeast or phage populations binding the antigen) and multiple rounds (two, three, four or more rounds) of negative selection (e.g., selecting out yeast or phage populations binding the MHC protein alone and/or the MHC protein in complex with a control peptide (i.e., a peptide different from the neoepitope)). In specific embodiments of this aspect, the antibodies or antigen binding fragments are generated using yeast surface display antibody (e.g., scFv) library or phage display antibody (e.g., scFv) library, and optionally enriched for specific binders to the neoepitope-MHC complex using multiple rounds (at least 3, at least 4 or at least 5 rounds) of positive selection (selecting yeast or phage populations binding the antigen) and multiple rounds (at least 2, at least 3, or at least 4) of negative selection (e.g., selecting out yeast or phage populations binding the MHC protein alone and/or the MHC protein in complex with a control peptide (e.g., at least 2 rounds selecting out yeast or phage populations binding the MHC protein alone, and at least 2 rounds selecting out yeast or phage populations binding the MHC protein in complex with a control peptide). In certain embodiments, the cell populations are expanded following a selection step (e.g., following a positive selection step or steps, following a negative selection step or steps, or following each selection step). In certain embodiments of this aspect, the antigen is a dimeric neoepitope-MHC complex (in particular, having two neoepitope:MHC molecules linked together, for example, via an IgG Fc, e.g., mouse or human IgG1). In certain embodiments, yeast display methodology and library is used. In certain embodiments, the positive selection includes selection (e.g., at least 1 or at least 2 rounds of selection) for yeast or phage populations that stain for both the antigen (neoepitope-MHC complex) and the antibody (e.g., scFv). In certain embodiments, the yeast or phage populations are selected by magnetic sorting (MACS) and/or flow cytometry sorting using labeled antigen and antibody/fragment (e.g., scFv) molecules. For example, the antigen is biotinylated by covalently attaching biotin to the antigen (which can be detected by a secondary agent such as streptavidin conjugated to a fluorophore) and/or bound to an IgG molecule (which is detected by a labeled antibody specific for the IgG), and the antibody (e.g., scFv) is bound to an epitope tag (e.g., hemagglutinin or c-Myc) (which is detected by a fluorescently labeled antibody to the epitope tag). In one embodiment, at least three, four, five, six, seven, eight or nine of the following selection steps are used to generate an antibody or antigen binding fragment thereof that specifically binds a neoepitope-MHC complex: (i) a positive selection of antibody-carrying clones/cells that bind to labeled neoepitope:MHC complex (e.g., by selecting via labeled neoepitope-MHC complex), (ii) a negative selection (selecting out) of antibody-carrying clones/cells that bind to control peptide-MHC complex (such as by selecting antibody-carrying clones/cells unbound by labeled control peptide-MHC complex), (iii) a positive selection of antibody-carrying clones that bind to neoepitope-MHC (e.g., by selecting antibody carrying clones/cells doubly positive stained for antibody (e.g., scFv) and neoepitope-MHC complex, (iv) a positive selection of antibody-carrying clones/cells that bind to labeled neoepitope:MHC complex (e.g., by selecting antibody-carrying clones/cells stained with labeled neoepitope-MHC complex, and optionally stained for the antibody), (v) a negative selection (selecting out) of antibody-carrying clones/cells that bind to control peptide-MHC complex or MHC complex alone (such as by selecting antibody-carrying clones/cells unbound by labeled control peptide-MHC complex or labeled MHC protein), (vi) a positive selection of antibody-carrying clones that bind to neoepitope-MHC (e.g., by selecting antibody carrying clones/cells stained for neoepitope-MHC complex or by selecting antibody carrying clones/cells doubly positive stained for antibody (e.g., scFv) expression and neoepitope-MHC complex, (vii) a negative selection (selecting out) of antibody-carrying clones/cells that bind to MHC complex alone (such as by selecting antibody-carrying clones/cells unbound by labeled MHC protein), (viii) a positive selection of antibody-carrying clones that bind to neoepitope-MHC (e.g., by selecting antibody carrying clones/cells doubly positive stained for antibody (e.g., scFv) and neoepitope-MHC complex, (ix) a negative selection (selecting out) of antibody-carrying clones/cells that bind to MHC complex alone (such as by selecting antibody-carrying clones/cells unbound by labeled MHC protein). In some embodiments, at least 5, 6, 7, 8 or 9 steps recited in the preceding sentence are used in the specific antibody or fragment selection process including at least two positive selection steps and at least two negative selection steps. In some embodiments, at least 6, 7, 8 or 9 steps are used in the specific antibody or fragment selection process including at least two (preferably, at least three) positive selection steps for neoeptope-MHC complex, at least one (preferably, at least two) negative selection steps to select out clones/cells binding control peptide-MHC-complex, and at least one (preferably, at least two) negative selections steps to select out clones/cells binding MHC protein alone. In specific embodiments of this aspect, MHC protein is an MHC class I protein (e.g., HLA-A2). In specific embodiments of this aspect, the neoepitope is an NPM1c neoepitope. In a specific embodiment, the neoepitope:MHC complex is NPM1c:MHC class I (e.g., NPM1c:HLA-A2). In some embodiments of this aspect, the neoepitope is any NPM1c epitope referenced in the disclosure (e.g., an epitope having the amino acid sequence of AIQDLCLAV (SEQ ID NO:1)). In a specific embodiment, the neoepitope:MHC complex is AIQDLCLAV:HLA-A2. In some embodiments, the antibody or antigen binding fragment specific for the neoepitope:MHC complex is obtained using any 4, 5, 6, 7, 8, or all selection steps noted in Appendix 1, below. In some embodiments, instead of an yeast surface display or phage surface display methodology and library, a bacterial display, eukaryotic viral display, mammalian cell display, or cell-free (e.g., ribosomal display) antibody screening technology is used. Yeast surface display methodology and libraries are known in the art (see, e.g., Chao et al., 2006, Nature Protocols 1(2):755-768). Phage display methodology and libraries are known in the art Merz et al. (1995) *J Neurosci Methods* 62(1-2):213-9; Di Niro et al. (2005) *Biochem J* 388(Pt 3):889-894; and Engberg et al. (1995) *Methods Mol Biol* 51:355-376.

Antibodies

In one aspect, provided herein are antibodies and antigen binding fragments thereof that bind (e.g., specifically bind) to an antigen comprising a neoepitope (e.g., a cancer neoepitope) in complex with (or presented by) an MHC protein (e.g., MHC class I protein). In certain embodiments, provided herein are antibodies and antigen binding fragments thereof that specifically bind to an antigen comprising a neoepitope (e.g., a cancer neoepitope) in complex with (or presented by) an MHC protein (e.g., MHC class I protein) obtained by one of the methods described herein (e.g., using multiple rounds of selection steps to identify specific binders by yeast surface display methodology, phage display methodology or the like; also optionally using dimeric neoepitope-MHC complexes as the antigen; e.g., via immunizing a subject with neoepitope-MHC complex or dimeric neoepitope-MHC complex as the antigen to elicit antibody production). In certain embodiments, provided herein are antibodies and antigen binding fragments thereof that specifically bind to an antigen comprising a cancer neoepitope in complex with (or presented by) an MHC class I protein (e.g., HLA-A2 or a protein encoded by the HLA-A*02 allele group) obtained by one of the methods described herein. In certain embodiments, provided herein are antibodies or antigen binding fragments thereof that do not bind to, or substantially do not bind to, the MHC protein alone. In one aspect, provided herein are antibodies or antigen binding fragments thereof that do not bind to, or substantially do not bind to, a control peptide in complex with the MHC protein.

In one aspect, provided herein are antibodies or antigen binding fragments thereof that do not bind to, or substantially do not bind to, the neoepitope alone (without an MHC protein).

Functional MHC Class I molecules comprise a heavy α chain and a β2-microglobulin chain. Peptide binding by MHC Class I molecules is accomplished by interaction of the peptide amino acid side chains with discrete pockets within the peptide-binding groove of the MHC molecule that is formed by the α1 and α2 domains of the heavy chain. Typically, for the human leukocyte antigen (HLA), the main binding energy is derived from the interaction of residues in position 2 and the C-terminus of the peptide and the B and F binding pockets of the MHC molecule, respectively, though side chains throughout the peptide can promote or diminish MHC binding capacity (see, e.g., Guo, et al (1992) *Nature* 360:364; Silver et al (1992) *Nature* 360:367; Gorga et al (1992) Proteins 12; 87; Madden (1995) *Annu Rev Immunol* 13:587; Madden et al (1993) Cell 75; 693; Madden et al (1992) *Cell* 70:1035; Bjorkman, et al (1987) *Nature* 329:512; Saper et al (1991) *J Mol Biol* 219:277). For a peptide with 9 amino acid residues, the C-terminal residue (position 9) interacts with the F binding pocket of the MHC molecule.

MHC molecules are extremely polymorphic, and thousands of allelic variants have been identified at the class I A and B loci. Most of the polymorphism occurs at the peptide binding pocket, such that MHC molecules have a range of peptide binding specificities. Despite the polymorphism, it is known in the art that HLA class I molecules can be clustered into groups (i.e., supertypes) based upon shared peptide binding specificity. Each group (supertype) is defined by a peptide consensus sequence that reflects the positions of the peptide that are "anchor residues" or residues that are important for MHC binding. For example, HLA Class I molecules of the A2-supertype (i.e., HLA-A2 or a protein encoded by the HLA-A*02 allele group) share specific binding for peptides with small and aliphatic residues (e.g., alanine, tyrosine, serine, valine, leucine, isoleucine, methionine, glutamine) at position 2 and aliphatic (e.g., leucine, isoleucine, valine, methionine) or small hydrophobic residues (e.g., alanine, valine) at the C-terminus of the peptide (see, e.g., Sidney, et al (2008) *BMC Immunology* 9:1).

In certain embodiments, provided herein are antibodies and antigen binding fragments thereof that bind (e.g., specifically bind) to an antigen comprising acute myeloid leukemia (AML)-associated mutant nucleophosmin protein neoepitope in complex with (or presented by) an MHC class I protein such as HLA-A2 (such as NPM1c:HLA-A2).

Genomic analysis of AML has shown a lower mutational load than most other adult cancers, with an average of 13 coding mutations per AML patient (see Ley et al., *N Engl J Med* 368: 2059 (2013); Alexandrov et al., *NATURE* 500: 415 (2013); Kandoth et al., *NATURE* 502 333 (2013)). However, somatic mutations in AML often occur in the same genes (see Ley et al., *N Engl J Med* 368: 2059 (2013); Papaemmanuil et al., *N Engl J Med* 374: 2209 (2016)) and neoantigens derived from these hotspot mutations therefore become attractive targets for tumor-specific immunotherapy (see van der Lee et al., *J CLIN INVEST* 129: 774 (2019)). Among the most commonly occurring mutations is a 4-nucleotide duplication in a critical driver gene encoding nucleophosmin (NPM1; encoded by NPM1), which occurs in 30-35% of all adult AML patients (see Ley et al., *N Engl J Med* 368: 2059 (2013); Papaemmanuil et al., *N Engl J Med* 374: 2209 (2016); Falini et al., *N Engl J Med* 352: 254 (2005)). Such mutations in NPM1 result in its aberrant cytoplasmic localization, and the mutant protein is referred to as NPM1c. The AML-associated NPM1c mutant protein generates a leukemic neoantigen that is HLA class I restricted and presented on leukemic blasts of patients with the HLA-A*02:01 allele and some other alleles. For example, NPM1c produces a leukemia-specific neoantigen epitope (AIQDLCLAV (SEQ ID NO: 1), abbreviated as AIQ) that is presented by the most common HLA-A*0201 allele (~50% of human population) (see Greiner et al., *BLOOD* 120: 1282 (2012)).

In some aspects, provided herein are antibodies and antigen binding fragment thereof that bind to an antigen comprising a NPM1c neoepitope in complex with (or presented by) an MHC Class I protein such as HLA-A2. The length of the NPM1c neoepitope is any length that is reasonable for a peptide that binds an MHC Class I molecule. In some aspects, the length of the NPM1c neoepitope is 5-20 amino acids, 6-19 amino acids, 7-18 amino acids, 8-17 amino acids, 8-16 amino acids, 8-15 amino acids, 8-15 amino acids, 8-14 amino acids, 8-13 amino acids, 8-12 amino acids, 9-12 amino acids, or 9-11 amino acids. In some aspects, the length of the NPM1c neoepitope is 20, 19, 18, 17, 16, 15, 14, 13, 12, 11, 10, 9, 8, 7, 6, or 5 amino acids. In some aspects, the length of the NPM1c neoepitope is 12 amino acids. In some embodiments, the length of the NPM1c neoepitope is 11 amino acids. In some aspects, the length of the NPM1c neoepitope is 10 amino acids. In some aspects, the length of the NPM1c neoepitope is 9 amino acids. In some aspects, the length of the NPM1c neoepitope is 8 amino acids. In some embodiments, the NPM1c neoepitope is a peptide of 20, 19, 18, 17, 16, 15, 14, 13, 12, 11, 10, 9, 8, 7, 6, or 5 consecutive amino acids within a polypeptide of 10, 15, 20, 30, 40, 50, or 100 amino acid residues in length.

In some aspects, the NPM1c neoepitope binds to a MHC Class I protein that is HLA-A2. In some aspects, the NPM1c neoepitope that binds HLA-A2 comprises an amino acid sequence wherein position 2 of the amino acid sequence is a small and aliphatic residue (e.g., alanine, tyrosine, serine, valine, leucine, isoleucine, methionine, glutamine), and wherein the C-terminal residue of the amino acid sequence is an aliphatic residue (e.g., leucine, isoleucine, valine, methionine) or a small hydrophobic residue (e.g., alanine, valine). In some aspects, the NPM1c neoepitope that binds HLA-A2 comprises an amino acid sequence wherein position 2 of the amino acid sequence is valine, isoleucine or leucine and the C-terminal residue of the amino acid sequence is valine, leucine, or isoleucine. In some aspects, wherein the NPM1c neoepitope is 8 amino acid residues in length, the C-terminal amino acid is position 8. In some aspects, wherein the NPM1c neoepitope is 9 amino acid residues in length, the C-terminal amino acid is position 9. In some aspects, wherein the NPM1c neoepitope is 10 amino acid residues in length, the C-terminal amino acid is position 10. In some aspects, wherein the NPM1c neoepitope is 11 amino acid residues in length, the C-terminal amino acid is position 11. In some aspects, wherein the NPM1c neoepitope is 12 amino acid residues in length, the C-terminal amino acid is position 12.

Neoepitopes derived from NPM1c that bind to HLA-A2 are known in the art. For example, Greiner (2012) *Blood* 120:1282 identified amino acid sequences for 9-mer NPM1c neoepitopes that bind HLA-A2, including: AIQDLCLAV (SEQ ID NO:1) and AIQDLCVAV (SEQ ID NO:71). As a further example, van der Lee (2019) *J Clin Invest* 129:774 identified amino acid sequences of NPM1c neoepitopes that bind HLA-A2 Class I molecules, including CLAVEEVSL (SEQ ID NO:72), as well as amino acid sequences of NPM1c neoepitopes that bind to MHC Class I molecules encoded by other HLA haplotypes, including VEEVSLRK (SEQ ID NO:73), AVEEVSLR (SEQ ID NO:74), AVEEVSLRK (SEQ ID NO:75), and CLAVEEVSLRK (SEQ ID NO:76).

In some aspects, provided herein are antibodies and antigen binding fragments thereof that bind (e.g., specifically bind) to an antigen comprising a neoepitope of a mutant nucleophosmin protein in complex with (or presented by) an MHC class I protein (such as NPM1c:HLA-A2), wherein the mutation in the nucleophosmin protein is due to a four-nucleotide duplication in the gene encoding nucleophosmin. In some aspects, provided herein are antibodies and antigen binding fragments thereof that bind (e.g., specifically bind) to an antigen comprising a cytoplasmic (located in the cytoplasm) mutant nucleophosmin protein neoepitope in complex with (or presented by) an MHC class I protein (such as NPM1c:HLA-A2). In some aspects, the neoepitope is an 8, 9, 10, 11, or 12 amino acid peptide derived from mutant nucleophosmin protein. In some aspects, the neoepitope is an 8, 9, 10, 11, or 12 amino acid peptide derived from 10, 15, 20, 25, 30, 35, 40, 45, 50, 55, 60, 65, 70, 75, 80, 85, 90, 95, or 100 amino acid residues of mutant nucleophosmin protein. In some aspects, the neoepitope is an 8, 9, 10, 11, or 12 amino acid peptide derived from 10, 15, 20, 25, 30, 35, 40, 45, 50, 55, 60, 65, 70, 75, 80, 85, 90, 95, or 100 amino acid residues at the C-terminus of mutant nucleophosmin protein. In some aspects, the mutant nucleophosmin protein comprises an amino acid sequence as set forth by SEQ ID NO:56. In some aspects, the mutant nucleophosmin protein comprises an amino acid sequence having one or more mutations (e.g., insertion, deletion, substitution) relative to the amino acid sequence of wild-type nucleophosmin (e.g., SEQ ID NO:54). In some aspects, the mutant nucleophosmin protein neoepitope is an 8, 9, 10, 11, or 12 amino acid peptide derived from a protein comprising the amino acid sequence of SEQ ID NO:56. In some aspects, the mutant nucleophosmin protein neoepitope is an 8, 9, 10, 11, or 12 amino acid peptide derived from a protein comprising an amino acid sequence having one or more mutations (e.g., insertion, deletion, substitution) relative to the amino acid sequence of wild-type nucleophosmin (e.g., SEQ ID NO:54). In some aspects, the mutant nucleophosmin protein neoepitope is an 8, 9, 10, 11, or 12 amino acid peptide derived from 10, 15, 20, 25, 30, 35, 40, 45, 50, 55, 60, 65, 70, 75, 80, 85, 90, 95, or 100 amino acid residues of the amino acid sequence set forth by SEQ ID NO:56. In some aspects, the mutant nucleophosmin protein neoepitope is an 8, 9, 10, 11, or 12 amino acid peptide derived from a protein having an amino acid sequence with one or more mutations (e.g., insertion, deletion, substitution) relative to the amino acid sequence of wild-type nucleophosmin (e.g., SEQ ID NO:54), wherein the one or more mutations are within a region of the protein that is 10, 15, 20, 25, 30, 35, 40, 45, 50, 55, 60, 65, 70, 75, 80, 85, 90, 95, or 100 amino acid residues in length, and wherein the neoepitope is derived from the region of the protein comprising the one or more mutations. In some aspects, the mutant nucleophosmin protein neoepitope is an 8, 9, 10, 11, or 12 amino acid peptide derived from the 10, 15, 20, 25, 30, 35, 40, 45, 50, 55, 60, 65, 70, 75, 80, 85, 90, 95, or 100 amino acid residues at the C-terminus of a protein with the amino acid sequence set forth by SEQ ID NO:56. In some aspects, the mutant nucleophosmin protein neoepitope is an 8, 9, 10, 11, or 12 amino acid peptide derived from a protein with an amino acid sequence having one or more mutations (e.g., insertion, deletion, substitution) relative to the amino acid sequence of wild-type nucleophosmin (e.g., SEQ ID NO:54), wherein the one or more mutations are within a region of the protein that is proximal the C-terminus (e.g., about 10, 15, 20, 25, 30, 35, 40, 45, 50, 55, 60, 65, 70, 75, 80, 85, 90, 95, or 100 amino acid residues from the C-terminus), and wherein the neoepitope is derived from the region of the protein comprising the one or more mutations. In some aspects, provided herein are antibodies or antigen binding fragments thereof that specifically bind to an antigen comprising a neoepitope of a protein comprising the amino acid sequence of SEQ ID NO:56 in complex with (or presented by) an MHC class I protein (e.g., HLA-A2 protein).

In some aspects, the mutant nucleophosmin protein comprises the C-terminal amino acid sequence MTDQEAIQDLCLAVEEVSLRK (SEQ ID NO:57). In some aspects, provided herein are antibodies and antigen binding fragments thereof that specifically bind to an antigen comprising a neoepitope of a NPM1c protein comprising the C-terminal amino acid sequence MTDQEAIQDLCLAVEEVSLRK (SEQ ID NO:57) in complex with (or presented by) an MHC class I protein (e.g., HLA-A2 protein). In some aspects, the neoepitope is an 8, 9, 10, 11, or 12 amino acid peptide derived from the C-terminal amino acid sequence MTDQEAIQDLCLAVEEVSLRK (SEQ ID NO:57) of the NPM1c protein. In some aspects, provided herein are antibodies and antigen binding fragments thereof that specifically bind to an antigen comprising an NPM1c neoepitope in complex with (or presented by) an HLA-A2 protein or a protein encoded by the HLA-A*02 allele group (i.e., NPM1c:HLA-A2). In some aspects, NPM1c is a human NPM1c.

In some aspects, provided herein are antibodies or antigen binding fragments thereof that bind to (e.g., specifically bind to) an antigen comprising a cytoplasmic mutant nucleophosmin protein neoepitope in complex with (or presented by) an MHC class I protein (e.g., an HLA-A2 protein or a protein encoded by the HLA-A*02 allele group), wherein the amino acid sequence of the neoepitope comprises: AIQDLCLAV (SEQ ID NO:1), AIQDLCVAV (SEQ ID NO:71), CLAVEEVSL (SEQ ID NO:72), VEEVSLRK (SEQ ID NO:73), AVEEVSLR (SEQ ID NO:74), AVEEVSLRK (SEQ ID NO:75) or CLAVEEVSLRK (SEQ ID NO:76). In some aspects, provided herein are antibodies and antigen binding fragments thereof that bind to an antigen comprising an amino acid sequence selected from AIQDLCLAV (SEQ ID NO:1), AIQDLCVAV (SEQ ID NO:71), CLAVEEVSL (SEQ ID NO:72), VEEVSLRK (SEQ ID NO:73), AVEEVSLR (SEQ ID NO:74), AVEEVSLRK (SEQ ID NO:75) and CLAVEEVSLRK (SEQ ID NO:76) presented by HLA-A2. In some aspects, provided herein are antibodies and antigen binding fragments thereof that bind to an antigen comprising an amino acid sequence AIQDLCLAV (SEQ ID NO:1) presented by HLA-A2.

In some aspects, the antibodies or antigen binding fragments thereof described herein do not bind to, or substantially do not bind to, an MHC class I protein alone and/or a control peptide in complex with an MHC class I protein (e.g., wherein the control peptide has the same number of amino acids as the neoepitope but is derived from a protein different from the protein from which the neoepitope is derived).

In some aspects, the antibodies or antigen binding fragments thereof described herein do not bind to, or substantially do not bind to, a cytoplasmic mutant nucleophosmin protein neoepitope alone (without an MHC class I protein such as HLA-A2).

In some aspects, the NPM1c neoepitope comprises the amino acid sequence AIQDLCLAV (SEQ ID NO:1), and the MHC class I protein is an HLA-A2 protein (e.g., a protein encoded by the HLA-A*02:01 allele). In some aspects, the NPM1c neoepitope comprises an amino acid sequence selected from AIQDLCVAV (SEQ ID NO:71), CLAVEEVSL (SEQ ID NO:72), VEEVSLRK (SEQ ID NO:73), AVEEVSLR (SEQ ID NO:74), AVEEVSLRK (SEQ ID NO:75) and CLAVEEVSLRK (SEQ ID NO:76), and the MHC class I protein is an HLA-A2 protein (e.g., a protein encoded by the HLA-A*02:01 allele).

In some aspects, provided herein are antibodies or antigen binding fragments thereof that specifically bind to an antigen comprising a neoepitope comprising the amino acid sequence AIQDLCLAV (SEQ ID NO:1) in complex with a class I major histocompatibility complex (MHC class I) protein, wherein any one, two, three, four, five or six amino acids of the amino acid sequence AIQDLCLAV (SEQ ID NO:1) are substituted. In some aspects, provided herein are antibodies or antigen binding fragments thereof that specifically bind to an antigen comprising a neoepitope comprising the amino acid sequence AIQDLCLAV in complex with a class I major histocompatibility complex (MHC class I) protein, wherein any one, two, three or four amino acids of the amino acid sequence AIQDLCLAV are substituted. In some aspects, the amino acid substitution is a conservative amino acid substitution. In some aspects, the amino acid substitution is a substitution with an amino acid residue of a similar size as the size of the existing residue in the AIQDLCLAV sequence (SEQ ID NO:1). In some aspects, the amino acid substitution does not affect (or does not substantially affect) the binding of the antibody or antigen binding fragment described herein to the antigen.

In some aspects, provided herein are antibodies or antigen binding fragments thereof that specifically bind to an antigen comprising a neoepitope comprising the amino acid sequence AIQDLCLAV in complex with a class I major histocompatibility complex (MHC class I) protein, wherein one, two, or more anchor residues of the amino acid sequence AIQDLCLAV (SEQ ID NO:1) are substituted (e.g., position 2 and/or position 9 of SEQ ID NO:1, e.g., underlined residues of AIQDLCLAV (SEQ ID NO:1)). In some aspects, the amino acid substitution does not affect (or does not substantially affect) the binding of the antibody or antigen binding fragment described herein to the antigen or the binding of the neoepitope to the class I major histocompatibility complex (MHC class I) protein (e.g., HLA-A2). In some aspects, the amino acid residue I in the second position of AIQDLCLAV (SEQ ID NO:1) is substituted with the amino acid residue L (leucine). In some embodiments, the amino acid residue I in the second position of AIQDLCLAV (SEQ ID NO:1) is substituted with the amino acid residue V (valine), M (methionine), tyrosine (T), serine (S), glutamine (Q) or A (alanine). In some embodiments, the amino acid residue V in the ninth position of AIQDLCLAV (SEQ ID NO:1) is substituted with the amino acid residue I (isoleucine), L (leucine), M (methionine), or A (alanine).

In some aspects, provided herein are antibodies or antigen binding fragments thereof that specifically bind to an antigen comprising a neoepitope comprising the amino acid sequence AIQDLCLAV in complex with a class I major histocompatibility complex (MHC class I) protein, wherein any one, two, three, four, five or six amino acids of the amino acid sequence AIQDLCLAV (SEQ ID NO:1) are substituted, and wherein the substitution is a conservative amino acid substitution. In some aspects, provided herein are antibodies or antigen binding fragments thereof that specifically bind to an antigen comprising a neoepitope comprising an amino acid sequence identified in Table 1 in complex with a MHC class I protein.

TABLE 1

Conservative substitution of AIQ neoepitope

| Sequence name | Sequence | | | | | | | | | SEQ ID NO |
|---|---|---|---|---|---|---|---|---|---|---|
| AIQ residues | $X_1$ | $X_2$ | $X_3$ | $X_4$ | $X_5$ | $X_6$ | $X_7$ | $X_8$ | $X_9$ | |
| AIQ neoepitope | A | I | Q | D | L | C | L | A | V | 1 |
| Conservative substitution of residue $X_1$ | V | I | Q | D | L | C | L | A | V | 77 |
| | L | I | Q | D | L | C | L | A | V | 78 |
| | I | I | Q | D | L | C | L | A | V | 79 |
| Conservative substitution of residue $X_3$ | A | I | N | D | L | C | L | A | V | 80 |
| Conservative substitution of residue $X_4$ | A | I | Q | E | L | C | L | A | V | 81 |
| Conservative substitution of residue $X_5$ | A | I | Q | D | I | C | L | A | V | 82 |
| | A | I | Q | D | V | C | L | A | V | 83 |
| | A | I | Q | D | M | C | L | A | V | 84 |
| | A | I | Q | D | A | C | L | A | V | 85 |
| | A | I | Q | D | F | C | L | A | V | 86 |
| Conservative substitution of residue $X_6$ | A | I | Q | D | L | S | L | A | V | 87 |
| | A | I | Q | D | L | A | L | A | V | 88 |
| Conservative substitution of residue $X_7$ | A | I | Q | D | L | C | I | A | V | 89 |
| | A | I | Q | D | L | C | V | A | V | 90 |
| | A | I | Q | D | L | C | M | A | V | 91 |
| | A | I | Q | D | L | C | A | A | V | 92 |
| | A | I | Q | D | L | C | F | A | V | 93 |
| Conservative substitution of residue $X_8$ | A | I | Q | D | L | C | L | V | V | 94 |
| | A | I | Q | D | L | C | L | L | V | 95 |
| | A | I | Q | D | L | C | L | I | V | 96 |

In some aspects, the disclosure provides an antibody or antigen binding fragment which specifically binds to the amino acid sequence AIQDLCLAV (SEQ ID NO:1) in complex with a class I major histocompatibility complex (MHC class I) protein, wherein any one, two, three, four, five or six amino acids of the amino acid sequence AIQDLCLAV (SEQ ID NO:1) are substituted, wherein the antibody or antigen binding fragment had the same or substantially the same binding affinity to the amino acid sequence AIQDLCLAV (SEQ ID NO:1) in complex with the MHC class I protein. In some aspects, the disclosure provides an antibody or antigen binding fragment thereof which specifically binds to the amino acid sequence AIQDLCLAV (SEQ ID NO:1) in complex with a class I major histocompatibility complex (MHC class I) protein, wherein any one, two, three, four, five or six amino acids of the amino acid sequence AIQDLCLAV (SEQ ID NO:1) are substituted, wherein the antibody or antigen binding fragment specifically binds with the same or better affinity than to the amino acid sequence AIQDLCLAV (SEQ ID NO:1) in complex with the MHC class I protein. In some aspects, the antibody or antigen binding fragment described herein binds to the amino acid sequence AIQDLCLAV (SEQ ID NO:1) in complex with a class I major histocompatibility complex (MHC class I) protein, wherein any one, two, three, four, five or six amino acids of the amino acid sequence AIQDLCLAV (SEQ ID NO:1) are substituted, wherein the antibody or antigen binding fragment has a $K_D$ of 0.1 to 100 nM (e.g., 0.1 to 50 nM, 0.1 to 25 nM, 1 0.1 to 15 nM). In some aspects, the antibody or antigen binding fragment described herein binds to the amino acid sequence AIQDLCLAV (SEQ ID NO:1) in complex with a class I major histocompatibility complex (MHC class I) protein, wherein any one, two, three, four, five or six amino acids of the amino acid sequence AIQDLCLAV (SEQ ID NO: 1) are substituted, wherein the antibody or antigen binding fragment binds with a $K_D$ of less than 100 nM (e.g., less than 50 nM, less than 25 nM, less than 15 nM, less than 7 nM, less than 6 nM, less than 5 nM, less than 4 nM, less than 3 nM, less than 2 nM, less than 1 nM, less than 0.9 nM, less than 0.8 nM, less than 0.7 nM, less than 0.6 nM, less than 0.5 nM, less than 0.4 nM, less than 0.3 nM, less than 0.2 nM, or less than 0.1 nM).

In some aspects, provided herein are antibodies and antigen binding fragments thereof that bind to an NPM1c epitope presented by an MHC class I protein such as HLA-A2 (NPM1c:HLA-A2) and have an anti-cancer or anti-tumor effect (e.g., an anti-cancer effect in vivo, optionally, wherein the cancer is AML).

In some aspects, the disclosure provides an antibody, or antigen binding fragment thereof, that specifically binds to an antigen comprising an NPM1c neoepitope in complex with a class I major histocompatibility complex (MHC class I) protein, wherein the antibody, or antigen binding fragment thereof, comprises a heavy chain variable region (VH) and a light chain variable region (VL). In some aspects, the neoepitope comprises an amino acid sequence comprising AIQDLCLAV (SEQ ID NO:1). In some aspects, the MHC class I protein is encoded by an HLA-A allele comprising the HLA-A*02 allele group. In some aspects, the HLA-A allele is HLA-A*02:01.

In some aspects, provided herein are anti-NPM1c:HLA-A2 antibodies and antigen binding fragments thereof having heavy chain variable regions and/or light chain variable regions described herein (e.g., having sequences of heavy chain variable regions and/or light chain variable regions of YG1 scFV, see, e.g., Sequences section and the Examples). In some aspects, provided herein are anti-NPM1c:HLA-A2 antibodies and antigen binding fragments thereof having one or more complementarity determining regions (CDRs) described herein (e.g., having CDRs of YG1 scFv, see, e.g., Sequences section and the Examples). In some aspects, the antibody, or antigen binding fragment thereof, that binds to NPM1c:HLA-A2 is an scFv. An exemplary amino acid sequence for an scFv that specifically binds to NPM1c:HLA-A2 is set forth in SEQ ID NO: 2. In some aspects, provided herein is an scFv having at least 75%, at least 80%, at least 85%, at least 90%, at least 95%, at least 98% or at least 99% amino acid sequence identity to the amino acid sequence set forth in SEQ ID NO: 2. In some aspects, provided herein is an scFv having at least 75%, 80%, at least 85%, at least 90%, at least 95%, at least 98% or at least 99% amino acid sequence identity to the amino acid sequence set forth in SEQ ID NO: 2, wherein at least 95% of the differences in identity with the amino acid sequence set forth in SEQ ID NO: 2 are in the framework regions (or not in the complementarity determining regions (CDRs)) of the scFv.

In some aspects, provided herein are anti-NPM1c:HLA-A2 antibodies and antigen binding fragments thereof comprising a heavy chain variable region (VH) having the amino acid sequence SEQ ID NO:5 (the amino acid sequence of the VH of YG1 scFv). In some aspects, provided herein are anti-NPM1c:HLA-A2 antibodies and antigen binding fragments thereof comprising a heavy chain variable region (VH) having at least 75%, at least 80%, at least 85%, at least 90%, at least 95%, at least 98% or at least 99% amino acid sequence identity to the amino acid sequence set forth in SEQ ID NO:5 (the amino acid sequence of the VH of YG1 scFv). In some aspects, provided herein is a VH having at least 75%, 80%, at least 85%, at least 90%, at least 95%, at least 98% or at least 99% amino acid sequence identity to the amino acid sequence set forth in SEQ ID NO: 5, wherein at least 95% of the differences in identity with the amino acid sequence set forth in SEQ ID NO: 5 are in the framework regions (or not in the complementarity determining regions (CDRs)) of the VH.

In some aspects, provided herein are anti-NPM1c:HLA-A2 antibodies and antigen binding fragments thereof comprising a light chain variable region (VL) having the amino acid sequence SEQ ID NO:3 (the amino acid sequence of the VL of YG1 scFv). In some aspects, provided herein are anti-NPM1c:HLA-A2 antibodies and antigen binding fragments thereof comprising a light chain variable region (VL) having at least 75%, at least 80%, at least 85%, at least 90%, at least 95%, at least 98% or at least 99% amino acid sequence identity to the amino acid sequence set forth in SEQ ID NO:3 (the amino acid sequence of the VL of YG1 scFv). In some aspects, provided herein is a VL having at least 75%, 80%, at least 85%, at least 90%, at least 95%, at least 98% or at least 99% amino acid sequence identity to the amino acid sequence set forth in SEQ ID NO: 3, wherein at least 95% or all of the differences in identity with the amino acid sequence set forth in SEQ ID NO: 3 are in the framework regions (or not in the complementarity determining regions (CDRs)) of the VL.

In some aspects, provided herein are anti-NPM1c:HLA-A2 antibodies and antigen binding fragments thereof comprising a heavy chain variable region (VH) having the amino acid sequence SEQ ID NO:5 (the amino acid sequence of the VH of YG1 scFv), and a light chain variable region (VL) having the amino acid sequence SEQ ID NO:3 (the amino acid sequence of the VL of YG1 scFv). In some aspects, provided herein are anti-NPM1c:HLA-A2 antibodies and antigen binding fragments thereof comprising a heavy chain variable region (VH) having at least 75%, at least 80%, at least 85%, at least 90%, at least 95%, at least 98% or at least 99% amino acid sequence identity to the amino acid sequence set forth in SEQ ID NO:5 (the amino acid sequence of the VH of YG1 scFv), and a light chain variable region (VL) having at least 75%, at least 80%, at least 85%, at least 90%, at least 95%, at least 98% or at least 99% amino acid sequence identity to the amino acid sequence set forth in SEQ ID NO:3 (the amino acid sequence of the VL of YG1 scFv). In some aspects, provided herein is a VH and a VL having at least 75%, 80%, at least 85%, at least 90%, at least 95%, at least 98% or at least 99% amino acid sequence identity to the amino acid sequence set forth in SEQ ID NO: 5 and SEQ ID NO:3, respectively, wherein at least 95% or all of difference in identity with the amino acid sequence set forth in SEQ ID NO:5 and SEQ ID NO:3 are in the framework regions (or not in the complementarity determining regions (CDRs)) of the VH and the VL.

CDRs of the antibodies or antigen binding fragments of the disclosure are defined in various ways in the art, including the Kabat, Chothia, AbM, Contact, and IMGT.

In some aspects, the CDRs of an antibody of the disclosure are defined according to the Kabat system, which is based on sequence variability (see, e.g., Kabat E A & Wu T T (1971) Ann NY Acad Sci 190: 382-391; Kabat E A et al, (1991) Sequences of Proteins of Immunological Interest, Fifth Edition, U.S. Department of Health and Human Services, NIH Publication No. 91-3242. The Kabat CDR positions are determined according to methods known in the art. In one aspect, the CDRs of the antibodies and fragments thereof described herein are determined using the Kabat system. In some aspects, provided herein are anti-NPM1c:HLA-A2 antibodies and antigen binding fragments thereof having one or more complementarity determining regions (CDRs) of YG1 scFv as determined using the Kabat system.

In some aspects, the CDRs of an antibody of the disclosure are defined according to the Chothia system, which is based on the location of immunoglobulin structural loop regions (see, e.g., Chothia C & Lesk A M, (1987), J Mol Biol 196: 901-917; Al-Lazikani B et al., (1997) J Mol Biol 273: 927-948; Chothia C et al, (1992) J Mol Biol 227: 799-817; Tramontano A et al, (1990) J Mol Biol 215(1): 175-82; and U.S. Pat. No. 7,709,226). The term "Chothia CDRs," and like terms are recognized in the art and refer to antibody CDR sequences as determined according to the method of Chothia and Lesk, 1987, J. Mol. Biol., 196:901-917, which is referred to herein as the "Chothia CDRs" (see also, e.g., U.S. Pat. No. 7,709,226 and Martin, A., "Protein Sequence and Structure Analysis of Antibody Variable Domains," in Antibody Engineering, Kontermann and Diibel, eds., Chapter 31, pp. 422-439, Springer-Verlag, Berlin (2001)). The Chothia CDR positions are determined according to methods known in the art. In some aspects, the CDRs of the antibodies and fragments thereof described herein are determined using the Chothia system. In some aspects, provided herein are anti-NPM1c:HLA-A2 antibodies and antigen binding fragments thereof having one or more complementarity determining regions (CDRs) of YG1 scFv as determined using the Chothia system.

In some aspects, the CDRs of an antibody of the disclosure are defined according to the AbM system, which is based on AbM hypervariable regions that represent a compromise between the Kabat CDRs and Chothia structural loops, and where CDRs are determined using OxfordMolecular's AbM antibody modeling software (Oxford Molecular Group, Inc.). The AbM CDR positions is determined according to methods known in the art. In one aspect, the CDRs of the antibodies and fragments thereof described herein are determined using the AbM system. In some aspects, provided herein are anti-NPM1c:HLA-A2 antibodies and antigen binding fragments thereof having one or more complementarity determining regions (CDRs) of YG1 scFv as determined using the AbM system.

In some aspects, the CDRs of an antibody of the disclosure are defined according to the IMGT system (see "IMGT®, the international ImMunoGeneTics information System® website imgt.org, founder and director: Marie-Paule Lefranc, Montpellier, France; see, e.g., Lefranc, M.-P., 1999, The Immunologist, 7: 132-136 and Lefranc, M.-P. et al., 1999, Nucleic Acids Res., 27:209-212, both of which are incorporated herein by reference in their entirety). The IMGT CDR positions are determined according to methods known in the art. In one aspect, the CDRs of the antibodies and fragments thereof described herein are determined using the IMGT system. In some aspects, provided herein are anti-NPM1c:HLA-A2 antibodies and antigen binding fragments thereof having one or more complementarity determining regions (CDRs) of YG1 scFv as determined using the IMGT system.

In some aspects, the CDRs of an antibody of the disclosure are defined according to the Contact system. The Contact definition is based on an analysis of the available complex crystal structures (bioinf.org.uk) (see MacCallum R M et al., (1996) J Mol Biol 5: 732-745; see also, e.g., Martin A. "Protein Sequence and Structure Analysis of Antibody Variable Domains," in Antibody Engineering, Kontermann and Diibel, eds., Chapter 31, pp. 422-439, Springer-Verlag, Berlin (2001)). The Contact CDR positions are determined according to methods known in the art. In one aspect, the CDRs of the antibodies and fragments thereof described herein are determined using the Contact system. In some aspects, provided herein are anti-NPM1c:HLA-A2 antibodies and antigen binding fragments thereof having one or more complementarity determining regions (CDRs) of YG1 scFv as determined using the Contact system.

In some aspects, provided herein are antibodies or fragments thereof that specifically bind to an NPM1c epitope presented by HLA-A2 and comprise one, two, or three VH CDRs and/or one, two, or three VL CDRs of YG1 scFv as defined according to any of the above-described systems. For example, in one embodiment, provided herein are antibodies or fragments thereof that specifically bind to an NPM1c epitope presented by HLA-A2 and comprise one, two, or all three VH CDRs and/or one, two, or all three VL CDRs of YG1 scFv as defined by IMGT.

As is known in the art, VHs and VLs contain CDRs surrounded by framework regions (the CDRs and FR sequences appear in the following sequence in the VH and VL: FR1-CDR1-FR2-CDR2-FR3-CDR3-FR4). Optionally, the framework regions are human framework regions.

In certain aspects, provided herein are anti-NPM1c:HLA-A2 antibodies and antigen binding fragments thereof comprising a heavy chain variable region (VH) having one, two or all three VH CDRs of a VH having the amino acid sequence SEQ ID NO:5 (the amino acid sequence of the VH of YG1 scFv). In some aspects, provided herein are anti-NPM1c:HLA-A2 antibodies and antigen binding fragments thereof comprising a heavy chain variable region (VH) having one, two, or all three VH CDRs of a VH having the amino acid sequence SEQ ID NO:5 as defined by IMGT.

In some aspects, provided herein are anti-NPM1c:HLA-A2 antibodies and antigen binding fragments thereof comprising a light chain variable region (VL) having one, two or all three VL CDRs of a VL having the amino acid sequence SEQ ID NO:3 (the amino acid sequence of the VL of YG1 scFv). In some aspects, provided herein are anti-NPM1c:HLA-A2 antibodies and antigen binding fragments thereof comprising a light chain variable region (VL) having one, two or all three VL CDRs of a VL having the amino acid sequence SEQ ID NO:3 (the amino acid sequence of the VL of YG1 scFv) as defined by IMGT.

In some aspects, provided herein are anti-NPM1c:HLA-A2 antibodies and antigen binding fragments thereof comprising a heavy chain variable region (VH) having one, two or all three VH CDRs of a VH having the amino acid sequence SEQ ID NO:5 (the amino acid sequence of the VH of YG1 scFv), and a light chain variable region (VL) having one, two or all three VL CDRs of a VL having the amino acid sequence SEQ ID NO:3 (the amino acid sequence of the VL of YG1 scFv).

In some aspects, provided herein are anti-NPM1c:HLA-A2 antibodies and antigen binding fragments thereof comprising a heavy chain variable region (VH) having VH CDR1 of amino acid sequence SEQ ID NO:9, VH CDR2 of amino acid sequence SEQ ID NO:10, and/or VH CDR3 of amino acid sequence SEQ ID NO:11. In some embodiments, provided herein are anti-NPM1c:HLA-A2 antibodies and antigen binding fragments thereof comprising a heavy chain variable region (VH) having VH CDR1 of amino acid sequence SEQ ID NO:9, VH CDR2 of amino acid sequence SEQ ID NO:10, and VH CDR3 of amino acid sequence SEQ ID NO:11, wherein one, two, three, four or five amino acids of SEQ ID NO:9, SEQ ID NO:10, or SEQ ID NO:11 have been substituted. In some embodiments, the amino acid substation is a conservative substitution. In some embodiments, the amino acid substitution is a substitution with an amino acid residue of a similar size. In certain embodiments, the amino acid substitution does not affect (or does not substantially affect) or improves the binding of the antibody or antigen binding fragment described herein to the antigen.

In some aspects, provided herein are anti-NPM1c:HLA-A2 antibodies and antigen binding fragments thereof comprising a light chain variable region (VL) having VL CDR1 of amino acid sequence SEQ ID NO:6, VL CDR2 of amino acid sequence SEQ ID NO:7, and/or VL CDR3 of amino acid sequence SEQ ID NO:8. In some embodiments provided herein are anti-NPM1c:HLA-A2 antibodies and antigen binding fragments thereof comprising a light chain variable region (VL) having VL CDR1 of amino acid sequence SEQ ID NO:6, VL CDR2 of amino acid sequence SEQ ID NO:7, and/or VL CDR3 of amino acid sequence SEQ ID NO:8, wherein one, two, three, four or five amino acids of SEQ ID NO:6, SEQ ID NO:7, or SEQ ID NO:8 have been substituted. In some embodiments, the amino acid substation is a conservative substitution. In some embodiments, the amino acid substitution is a substitution with an amino acid residue of a similar size. In certain embodiments, the amino acid substitution does not affect (or does not substantially affect) or improves the binding of the antibody or antigen binding fragment described herein to the antigen.

In some aspects, provided herein are anti-NPM1c:HLA-A2 antibodies and antigen binding fragments thereof comprising a heavy chain variable region (VH) having VH CDR1 of amino acid sequence SEQ ID NO:9, VH CDR2 of amino acid sequence SEQ ID NO:10, and VH CDR3 of amino acid sequence SEQ ID NO:11, and/or a light chain variable region (VL) having VL CDR1 of amino acid sequence SEQ ID NO:6, VL CDR2 of amino acid sequence SEQ ID NO:7, and VL CDR3 of amino acid sequence SEQ ID NO:8. In certain embodiments, provided herein are anti-NPM1c:HLA-A2 antibodies and antigen binding fragments thereof comprising a heavy chain variable region (VH) having VH CDR1 of amino acid sequence SEQ ID NO:9, VH CDR2 of amino acid sequence SEQ ID NO:10, and VH CDR3 of amino acid sequence SEQ ID NO:11, and a light chain variable region (VL) having VL CDR1 of amino acid sequence SEQ ID NO:6, VL CDR2 of amino acid sequence SEQ ID NO:7, and VL CDR3 of amino acid sequence SEQ ID NO:8. In some embodiments provided herein are anti-NPM1c:HLA-A2 antibodies and antigen binding fragments thereof comprising a VH and a VL described herein, wherein one, two, three, four or five amino acids of the VH and/or a VL CDRs have been substituted.

In some aspects, one or more CDRs in the VH and/or VL region of an antibody or fragment described herein may vary by one, two, three, four or five amino acids as long as specific binding to NPM1c:HLA-A2 is maintained.

In some aspects, an antibody or fragment provided herein has been affinity matured, i.e., has one or more alterations in one or more complementarity determining regions compared to the described antibody or fragment, wherein such one or more alterations result in an improvement in the affinity of the antibody or fragment to the antigen relative to the described antibody or fragment. In some aspects, the antibodies or fragments provided herein have a Kd to the antigen (e.g., NPM1c:HLA-A2) of less than 100 nM (e.g., less than 50 nM, less than 25 nM, less than 15 nM, less than 7 nM, less than 6 nM, less than 5 nM, less than 4 nM, less than 3 nM, less than 2 nM, less than 1 nM, less than 0.9 nM, less than 0.8 nM, less than 0.7 nM, less than 0.6 nM, less than 0.5 nM, less than 0.4 nM, less than 0.3 nM, less than 0.2 nM, or less than 0.1 nM). In some aspects, the antibodies or fragments provided herein have a Kd to the antigen (e.g., NPM1c:HLA-A2) of less than 15 nM, less than 10 nM, less than 7 nM, less than 5 nM or less than 1 nM (e.g., 0.01 to 15 nM, 0.01 to 10 nM, 0.01 to 7 nM, 0.01 to 5 nM, 0.01 to 1 nM, 0.1 to 15 nM, 0.1 to 10 nM, 0.1 to 7 nM, 0.1 to 5 nM, 0.1 to 1 nM, 1 to 15 nM, 1 to 10 nM, 1 to 7 nM, 1 to 5 nM, 5 to 15 nM, 5 to 10 nM, or 5 to 7 nM).

In some aspects, the isolated antibody or antigen-binding fragment thereof includes three light chain variable region complementarity determining regions (VL CDRs 1-3) and three heavy chain variable region complementarity determining regions (VH CDRs 1-3). In some aspects the VH CDR1 comprises amino acid sequence having at least 80% sequence identity, or at least 81% sequence identity, or at least 82% sequence identity, or at least 83% sequence identity, or at least 84% sequence identity, or at least 85% sequence identity, or at least 86% sequence identity, or at least 87% sequence identity, or at least 88% sequence identity, or at least 89% sequence identity, or at least 90% sequence identity, or at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity to the amino acid sequence set forth in SEQ ID NO:9. In some aspects, the VH CDR2 comprises an amino acid sequence having at least 80% sequence identity, or at least 81% sequence identity, or at least 82% sequence identity, or at least 83% sequence identity, or at least 84% sequence identity, or at least 85% sequence identity, or at least 86% sequence identity, or at least 87% sequence identity, or at least 88% sequence identity, or at least 89% sequence identity, or at least 90% sequence identity, or at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity to the amino acid sequence set forth in SEQ ID NO:10. In some aspects, the VH CDR3 comprises an amino acid sequence having at least 80% sequence identity, or at least 81% sequence identity, or at least 82% sequence identity, or at least 83% sequence identity, or at least 84% sequence identity, or at least 85% sequence identity, or at least 86% sequence identity, or at least 87% sequence identity, or at least 88% sequence identity, or at least 89% sequence identity, or at least 90% sequence identity, or at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity to the amino acid sequence set forth in SEQ ID NO:11.

In some aspects, the VL CDR1 comprises an amino acid sequence having at least 80% sequence identity, or at least 81% sequence identity, or at least 82% sequence identity, or at least 83% sequence identity, or at least 84% sequence identity, or at least 85% sequence identity, or at least 86% sequence identity, or at least 87% sequence identity, or at least 88% sequence identity, or at least 89% sequence identity, or at least 90% sequence identity, or at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity to the amino acid sequences set forth in SEQ ID NO:6. In some aspects, the VL CDR2 comprises an amino acid sequence having at least 80% sequence identity, or at least 81% sequence identity, or at least 82% sequence identity, or at least 83% sequence identity, or at least 84% sequence identity, or at least 85% sequence identity, or at least 86% sequence identity, or at least 87% sequence identity, or at least 88% sequence identity, or at least 89% sequence identity, or at least 90% sequence identity, or at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity to the amino acid sequence set forth in SEQ ID NO:7. In some aspects, the VL CDR3 comprises an amino acid sequence having at least 80% sequence identity, or at least 81% sequence identity, or at least 82% sequence identity, or at least 83% sequence identity, or at least 84% sequence identity, or at least 85% sequence identity, or at least 86% sequence identity, or at least 87% sequence identity, or at least 88% sequence identity, or at least 89% sequence identity, or at least 90% sequence identity, or at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity to the amino acid sequence set forth in SEQ ID NO:8.

In some aspects, the antibody or antigen binding fragment thereof described herein is an isolated antibody or fragment. In some aspects, the antibody or antigen binding fragment thereof described herein is a purified antibody or fragment. In some aspects, the antibody or antigen binding fragment thereof described herein is purified to greater than 95%, 97%, 98% or 99% purity, as determined by, e.g., an electrophoretic (e.g., by SDS-PAGE, isoelectric focusing or capillary electrophoresis) or chromatographic (e.g., by ion exchange or reverse phase HPLC) method (see, e.g., Flatman, et al., J. Chromotogr. 848:79-87 (2007)). In some aspects, the antibody or antigen binding fragment thereof described herein is an isolated antibody or fragment that specifically binds to NPM1c:HLA-A2. In some aspects, the antibody or antigen binding fragment thereof described herein is a purified antibody or fragment that specifically binds to NPM1c:HLA-A2. In some aspects, the NPM1c neoepitope is any one described herein. In some aspects, the NP1M1c neoepitope is AIQDLCLAV (SEQ ID NO: 1).

In some aspects, the antibody or antigen binding fragment thereof described herein has a binding affinity (Kd) to the antigen (e.g., NPM1c:MHC class I) of at least $10^{-7}$M. In certain embodiments, the antibody or antigen binding fragment thereof described herein has a binding affinity (Kd) to the NPM1c:MHC class I antigen (e.g., NPM1c:HLA-A2) of at least $10^{-7}$ M or higher, at least $10^{-8}$ M or higher, at least $10^{-9}$ M or higher, at least 500 nM or higher, at least 250 nM or higher, at least 100 nM or higher, at least 50 nM or higher, at least 25 nM or higher, at least 20 nM or higher, at least 15 nM or higher, or at least 10 nM or higher. In some aspects, the antibody or antigen binding fragment thereof described herein has a binding affinity (Kd) to the NPM1c:MHC class I antigen (e.g., NPM1c:HLA-A2) of at least about 25 nM or higher, at least about 15 nM or higher, or at least about 10 nM or higher. In some aspects, the antibody or antigen binding fragment thereof described herein has a binding affinity (Kd) to the NPM1c:HLA-A2 antigen has a binding affinity (Kd) to the NPM1c:MHC class I antigen (e.g., NPM1c:HLA-A2) between (or from and to) 0.1 nM and 500 nM, 0.1 nM and 100 nM, 0.5 nM and 100 nM, 0.1 nM and 50 nM, 0.5 nM and 50 nM, 0.1 nM and 25 nM, 0.5 nM and 25 nM. 0.1 nM and 15 nM, 0.5 nM and 15 nM, 0.1 nM and 10 nM, or 0.5 nM and 10 nM, or 1 nM to 100 nM (or any value in between). In some aspects, the antibody or antigen binding fragment thereof described herein has a binding affinity (Kd) to the NPM1c:MHC class I antigen (e.g., NPM1c:HLA-A2) between (or from and to) about 0.1 nM and about 100 nM or about 0.5 nM to about 100 nM. In some aspects, the antibody or antigen binding fragment thereof described herein has a binding affinity (Kd) to the NPM1c:MHC class I antigen (e.g., NPM1c:HLA-A2) between (or from and to) about 0.1 nM and about 50 nM or about 0.5 nM to about 50 nM.

In some aspects, the antibody or antigen binding fragment thereof described herein has a Kon for the NPM1c:MHC class I antigen (e.g., NPM1c:HLA-A2) of at least $0.5\pm0.02\times10^4$ $Ms^{-1}$ or higher. In some aspects, the antibody or antigen binding fragment thereof described herein has a Kon for the NPM1c:MHC class I antigen (e.g., NPM1c:HLA-A2) of at least $1\pm0.02\times10^4$ $Ms^{-1}$ or higher. In some aspects, the antibody or antigen binding fragment thereof described herein has a Kon for the NPM1c:MHC class I antigen (e.g., NPM1c:HLA-A2) of at least $2.5\pm0.02\times10^4$ $Ms^{-1}$ or higher. In some aspects, the antibody or antigen binding fragment thereof described herein has a Kon for the NPM1c:MHC class I antigen (e.g., NPM1c:HLA-A2) of at least $5\pm0.02\times10^4$ $Ms^{-1}$ or higher. In some aspects, the antibody or antigen binding fragment thereof described herein has a Kon for the NPM1c:MHC class I antigen (e.g., NPM1c:HLA-A2) between (or from and to) $0.5\pm0.02\times10^4$ $Ms^{-1}$ and $50\pm0.02\times10^4$ $Ms^{-1}$. In some aspects, the antibody or antigen binding fragment thereof described herein has a Kon for the NPM1c:MHC class I antigen (e.g., NPM1c:HLA-A2) between (or from and to) $1\pm0.02\times10^4$ $Ms^{-1}$ and $10\pm0.02\times10^4$ $Ms^{-1}$.

In some aspects, the antibody or antigen binding fragment thereof described herein has a Koff for the NPM1c:MHC class I antigen (e.g., NPM1c:HLA-A2) of less than $50\pm0.02\times10^{-4}$ $s^{-1}$. In some aspects, the antibody or antigen binding fragment thereof described herein has a Koff for the NPM1c:MHC class I antigen (e.g., NPM1c:HLA-A2) of less than $10\pm0.02\times10^{-4}$ $s^{-1}$. In some aspects, the antibody or antigen binding fragment thereof described herein has a Koff for the NPM1c:MHC class I antigen (e.g., NPM1c:HLA-A2) of less than $5\pm0.02\times10^{-4}$ $s^{-1}$. In some aspects, the antibody or antigen binding fragment thereof described herein has a Koff for the NPM1c:MHC class I antigen (e.g., NPM1c:HLA-A2) between (or from and to) $0.5\pm0.02\times10^{-4}$ $s^{-1}$ and $50\pm0.02\times10^{-4}$ $s^{-1}$. In some aspects, the antibody or antigen binding fragment thereof described herein has a Koff for the NPM1c:MHC class I antigen (e.g., NPM1c:HLA-A2) between (or from and to) $1\pm0.02\times10^{-4}$ $s^{-1}$ and $15\pm0.02\times10^{-4}$ $s^{-1}$.

In some aspects, the antibodies described herein are monoclonal antibodies or antigen binding fragments thereof. In some aspects, the antibodies described herein are humanized or human. In some aspects, provided herein is a human antibody or an antigen binding fragment of a human antibody. In some aspects, provided herein is a humanized antibody or an antigen binding fragment of a humanized antibody. In some aspects, provided herein is a chimeric antibody or an antigen binding fragment of a chimeric antibody (where a chimeric antibody is an antibody with a variable region of one species and a constant region of another species).

Antibodies provided herein include immunoglobulin molecules that specifically bind to the antigen (such as NPM1c: HLA-A2), and immunologically active fragments of such molecules which bind to the same or substantially the same epitope of the antigen as the antibody. In some aspects, the antigen bound by an antibody, or antigen binding fragment thereof, is presented by an MHC class I molecule (e.g., HLA-A2) on the surface of a cancer cell. In some embodiments, the cancer cell is an AML cell.

In some aspects, an anti-NPM1c:HLA-A2 antibody is a human or humanized antibody or immunoglobulin that comprises the 3 VH CDRs and/or 3 VL CDRs as described herein, human or human-derived framework regions, and human or human-derived constant regions. Non-limiting examples of human framework regions are described in the art, e.g., see Kabat et al. (1991) Sequences of Proteins of Immunological Interest Fifth Edition, U.S. Department of Health and Human Services, NIH Publication No. 91-3242; Sims et al. J. Immunol. 151:2296 (1993); Carter et al. Proc. Natl. Acad. Sci. USA, 89:4285 (1992); Presta et al. J. Immunol., 151:2623 (1993); Almagro and Fransson, Front. Biosci. 13: 1619-1633 (2008); Baca et al., J. Biol. Chem. 272: 10678-10684 (1997); Rosok et al., J. Biol. Chem. 271:22611-22618 (1996); Chothia et al., J. Mol. Biol. 278: 457-479 (1998). One or more amino acid substitutions can be made with the framework regions, preferably, in order to improve binding of the antibody described herein to NPM1c:HLA-A2.

In some aspects wherein the antibody is an immunoglobulin, the types of the antibody that can be used include, without limitation, IgG, IgE, IgM, IgD, IgA, IgY. The classes of the antibody that can be used include, without limitation IgG1, IgG2, IgG3, IgG4, IgA1, IgA2. In some aspects, the antibody is an IgG antibody. In some embodiments, the antibody is an IgG1 antibody or an IgG4 antibody. In some aspects, the antibody comprises a wild type IgG1 heavy chain constant region. In some aspects, the antibody comprises a wild type IgG4 heavy chain constant region. In some aspects, the antibody comprises a mutant IgG1 heavy chain constant region. In some aspects, the antibody comprises a mutant IgG4 heavy chain constant region. In some aspects, the mutant IgG4 heavy chain constant region comprises any one of the substitutions S228P, L235E, L235A, or a combination thereof, according to EU numbering. In some aspects, the antibody comprises an Fc domain comprising at least one mutation.

In some aspects, provided herein is a single chain antibody, e.g., a single chain Fv (scFv). In some aspects, the scFv is a human or humanized scFv. In some aspects, the scFv comprises a linker. In some aspects, the linker is a peptide linker. In some aspects, the peptide linker is a Gly-Ser linker. In some aspects, the Gly-Ser linker is selected from the group consisting of (Gly4Ser)1 (SEQ ID NO:58), (Gly4Ser)2 (SEQ ID NO: 59), (Gly4Ser)3 (SEQ ID NO: 60), and (Gly4Ser)4 (SEQ ID NO: 61). In some aspects, the Gly-Ser linker comprises the amino acid sequence SGSSGGSSSG (SEQ ID NO:4). In some aspects, provided herein is an antigen binding fragment of an antibody, where the fragment can be, without limitation an Fv fragment, a Fab fragment, a F(ab') fragment, a F(ab')2 fragment, or a disulfide-linked Fv (sdFv). In one embodiment, provided herein is an Fv fragment. In one embodiment, provided herein is a Fab fragment. In one embodiment, provided herein is a F(ab') fragment. In one embodiment, provided herein is a F(ab') 2 fragment.

In some aspects, an antibody or antigen binding fragment thereof described herein is capable of inducing cytotoxicity against the cancer cells being targeted by such antibody or fragment, where the cytotoxicity can be due antibody-dependent cell-mediated cytotoxicity (ADCC), antibody-dependent cellular phagocytosis (ADCP), complement-dependent cytotoxicity (CDC), or cytotoxicity of a toxin or drug bound to such antibody or fragment. In some embodiments, an antibody or antigen binding fragment thereof described herein has ADCC, ADCP and CDC. In some aspects, an antibody or antigen binding fragment thereof described herein has ADCC and ADCP. In some aspects, an antibody or antigen binding fragment thereof described herein has only ADCC or only CDC activity.

In one embodiment, an antibody or antigen binding fragment thereof described herein mediates antibody-dependent cell-mediated cytotoxicity (ADCC) and/or antibody-dependent cellular phagocytosis (ADCP). Methods of making an antibody that has ADCC and/or ADCP function are known in the art. Generally, the Fc region of the antibody mediates its binding to an Fc receptor on neutrophils, macrophages, NK cells, eosinophils and mast cells which leads to ADCC, and on macrophages, neutrophils and dendritic cells which leads to ADCP. In some aspects, provided herein are antibodies that have ADCC activity, wherein the Fc region of the antibody is of a human IgG or IgE type. In one embodiment, the Fc region of the contemplated antibody is of IgG1 isotype. In one embodiment, the Fc region of the contemplated antibody is of IgG2 isotype. In one embodiment, the Fc region of the contemplated antibody is of IgG3 isotype. The antibody can be bioengineered to increase its ADCC and/or ADCP activity (e.g., by mutation, cross-linking, di-sulfide bond formation, or oligosaccharide addition) (see, e.g., Natsume et al., 2009, Drug Des Devel Ther. 3:7-16, which is incorporated by reference herein). In one embodiment, CH2 and/or CH3 domains of the Fc region of the antibody are modified at their glycosylation sites to reduce or remove fucose residues in order to improve ADCC and/or ADCP activity (see, e.g., Liu et al., 2015, Ca Immunol. Res. 3:173-183; Satoh et al., 2006, Expert Opin Biol. Ther. 6:1161-1173; both of which are incorporated by reference herein). In one embodiment, the Fc region of a human IgG1 isotype is mutated with alanine substitution at position 333 of the CH2 domain. In one embodiment, the Fc region of a human IgG1 isotype is mutated at the following residues: S239D, I332E, and A330L (see, e.g., Lazar et al., 2006, PNAS 103:4005-4010, which is incorporated by reference herein). In one embodiment, the Fc region of a human IgG1 isotype is mutated at the following residues: S239D, I332E, and G236A (see, e.g., Richards et al., 2008, Mol. Cancer Ther. 7:2517-27). In one embodiment, an Fc region comprises an amino acid substitution at positions 298, 333 and/or 334 (EU numbering), which improve(s) ADCC activity.

In one embodiment, an antibody or antigen binding fragment thereof described herein mediates complement-dependent cytotoxicity (CDC). Methods of making an antibody that has CDC function are known in the art. In some aspects, provided herein are antibodies that have CDC activity, wherein the Fc region of the antibody is of a human IgG or IgM type. In one embodiment, the Fc region of the contemplated antibody is of IgG1 isotype. In one embodiment, the Fc region of the contemplated antibody is of IgG2 isotype. In one embodiment, the Fc region of the contemplated antibody is of IgG3 isotype. The antibody can be bioengineered to increase its CDC activity (e.g., mutated) (see, e.g., Moore et al., 2010, MAbs 2(2):181-189; Idusogie et al., 2001, J Immunol. 166(4):2571-5; Natsume et al., 2009, Drug Des Devel Ther. 3:7-16; all of which are incorporated by reference herein). In one embodiment, an antibody having an IgG Fc is bioengineered at its Fc region to change the N-glycan structure at its glycosylation site to the GO glycan type terminating in N-acetylglucosamine without fucose and sialic residues. In one embodiment, an Fc region modified as described in, e.g., U.S. Pat. No. 6,194,551, WO 99/51642 or Idusogie et al., J. Immunol. 164:4178-4184 (2000), to improve CDC activity.

In one embodiment, an antibody or antigen binding fragment thereof described herein is bound to a cytotoxic agent (e.g., a toxin or drug). The cytotoxic agent can be an agent that induces cell death or inhibits a vital cellular function. The cytotoxic agent can be, without limitation, a chemotherapeutic agent, a growth inhibitory agent, a radioactive isotope, or a toxin. In one embodiment, the antibody or antigen binding fragment described herein is bound (e.g., conjugated) to a toxin (e.g., diphtheria A chain, exotoxin A chain, ricin A chain, abrin A chain, modeccin A chain, dianthin protein, *Momordica charantia* inhibitor, crotin, gelonin, neomycin, tricothecene, phenomycin, mitogellin, restrictocin, *Sapaonaria officinalis* inhibitor, curcin, *Phytolaca americana* protein, *Aleurites fordii* protein, or alpha-sarcin). In one embodiment, the antibody or antigen binding fragment described herein is bound (e.g., conjugated) to a radioactive isotope (e.g., $P^{32}$, $I^{131}$, $I^{125}$, $At^{211}$, $Y^{90}$, $Re^{186}$, $Re^{188}$, $Sm^{153}$, $Bi^{212}$, or $Pb^{212}$). In one embodiment, the antibody or antigen binding fragment described herein is bound (e.g., conjugated) to a drug (e.g., an antimetabolite drug, an anti-folate drug, an anthracyclin (e.g., doxorubicin), a methothrexate, a taxane (e.g., docetaxel), a paclitaxel, an auristatin, a dolastatin, a maytansinoid, or a calicheamicin). Methods of making antibody-drug conjugates are known in the art (including drugs that can be used in such conjugates, and linkers that can be used to link the antibody to the drug) (see, e.g., Peters & Brown, 2015, Biosci. Rep. 35, e00225, doi:10.1042/BSR20150089).

Also encompassed by the present disclosure are antibodies or fragments thereof that bind the same epitope and/or antibodies or fragments thereof that compete for binding to human NMP1c:HLA-A2 with any antibodies and fragments described herein (e.g., antibody or antibody fragment comprising VH and VL amino acid sequences set forth by SEQ ID NOs: 5 and 3 respectively). Antibodies and fragments thereof that recognize the same epitope or compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the antibody under test inhibits specific binding of a reference antibody to a common antigen, such as NMP1c:HLA-A2. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen (e.g., NPM1c:HLA-A2) bound to a solid surface or cells bearing either of these, an unlabeled test antibody and a labeled reference antibody (e.g., antibody comprising VH and VL amino acid sequences set forth by SEQ ID NOs: 5 and 3 respectively). Competitive inhibition is measured by determining the amount of label bound to the solid surface or cells in the presence of the test antibody. Usually the test antibody is present in excess. Usually, when a competing antibody is present in excess, it will inhibit specific binding of a reference antibody to a common antigen by at least 50-55%, 55-60%, 60-65%, 65-70% 70-75% or more. Other techniques include, for example, epitope mapping methods, such as, x-ray analyses of crystals of antigen:antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

Methods to Identify Neoepitopes

In some embodiments, the present disclosure provides antibodies, or antigen binding fragments thereof, that specifically bind to an antigen comprising a neoeptope in complex with (or presented by) an MHC molecule. In some embodiments, the neoepitope is a tumor- or cancer-specific neoepitope. In some embodiments, the MHC molecule is a MHC class I molecule.

Tumor- or cancer-specific antigens from which neoepitopes are derived contain altered amino-acid sequences that result from non-silent somatic mutations. For example, mutation-derived neoepitopes arise from point mutations (e.g., nonsynonymous mutations leading to different amino acids in the protein); read-through mutations in which a stop codon is modified or deleted, leading to translation of a longer protein with a novel tumor-specific sequence at the C-terminus; splice site mutations that lead to the inclusion of an intron in the mature mRNA and thus a unique tumor-specific protein sequence; chromosomal rearrangements that give rise to a chimeric protein with tumor-specific sequences at the junction of 2 proteins (i.e., gene fusion); frameshift mutations or deletions that lead to a new open reading frame with a novel tumor-specific protein sequence; and translocations.

Methods for identification of tumor neoepitopes resulting from tumor- or cancer-specific mutations are known in the art (see, e.g., Richters, et al. (2019) *Genome Medicine* 11:56; Liu, et al (2017) *Cell* 168:600). Such methods generally involve identification of tumor-specific mutations (e.g., using deep nucleic acid or protein sequencing techniques), identification of patient human leukocyte antigen types and prediction of corresponding major histocompatibility complexes present in the tumor, identification of neoepitopes (e.g., using application of validated peptide-MHC binding prediction algorithms or analytical techniques to generate a set of candidate T cell epitopes that may bind to patient HLA alleles and are based on mutations present in tumors), optional demonstration of antigen-specific T cells against selected neoepitopes or demonstration that a candidate neoepitope is bound to HLA proteins on the tumor surface.

The deep nucleic acid techniques are known in the art. Any suitable method of sequence analysis is used. Such methods include, for example, sequence analysis using conventional Sanger sequencing based upon the chain-termination sequencing method (see, e.g., Sanger, et al (1977) *PNAS* 74:5463). As a further example, methods of sequence analysis include use of next generating sequencing (NGS). Methods of NGS are known in the art, and include sequencing technologies based upon pyrosequencing, Illumina HiSeq and MiSeq sequencing by synthesis, supported oligonucleotide ligation and detection (SOLiD), DNA nanoball sequencing, Ion Torrent sequencing, single-molecule real-time (SMRT) sequencing, Helicos sequencing, and Nanopore sequencing.

Nucleic acid sequencing is performed on whole tumor genomes, tumor exomes (protein-encoding DNA), a targeted portion of the genome (e.g., HLA gene loci) or tumor transcriptomes. In some aspects, the results of the sequencing is compared with known control sets or with sequencing analysis performed on normal tissue or matched normal tissue of the patient. One or more algorithms are used to identify different classes of somatic mutations present in the sequencing data. For example, in some embodiments, algorithms are used to detect variation arising from single nucleotide variants (see, e.g., Cornish, et al (2015) *Biomed Res Int* 2015:456479; Ghoneim, et al (2014) *BMC Res Notes* 7:864; Krøigård, et al (2016) *PLoS One* 11:e0151664) and/or to detect variation arising from indels (see, e.g., Mose, et al (2014) 30:2813-2815; Narzisi, et al (2014) *Nat Methods* 11:1033-1036). Additionally, in some embodiments, detection of fusion of two protein-coding sequences is performed by analysis of RNA sequencing data and/or whole genome sequencing data (see, e.g, Li, et al (2011) *Bioinformatics* 27:1708; Scolnick, et al (2015) *PLoS One* 10:30128916; Zhang, et al (2016) *Genome Res* 26:108; Kumar, et al (2016) *Wiley Interdiscip Rev RNA* 7:811). Once variants in tumor DNA or RNA are detected, the effect of each variant on the amino acid sequence of translated polypeptides is determined using computational tools known in the art. Additionally, multiple tools are available that aid in the prediction of cleavage sites in translated polypeptides and identification of peptides that are derived from MHC class I antigen processing. Non-limiting examples of such tools include, NetChop20S, NetChopCterm, and ProteaSMM (see, e.g., Nielsen, et al (2005) *Immunogenetics* 57:33; Tenzer, et al (2005) *Cell Mol Life Sci* 62:1025).

Methods of protein sequencing are also known in the art. In some aspects, trotein sequencing is performed on tumor proteomes. In some aspects, protein mass spectrometry is used to identify or validate the presence of mutated peptides bound to MHC proteins on tumor cells. Peptides are acid-eluted from tumor cells or from HLA molecules that are immunoprecipitated from tumor, and then identified using mass spectrometry.

In some aspects, once variant tumor-specific peptides are identified, prediction of their binding to MHC class I or II molecules requires knowledge of the patient's HLA haplotypes. MHC in humans is encoded by the HLA gene complex, which is located on chromosome 6p21.3. This locus is highly polymorphic, with over 12,000 established alleles. Because HLA genes are individualized, precise HLA haplotyping is required. Methods of HLA haplotyping are known in the art. For example, HLA haplotyping is performed using sequence specific PCR amplification and sequencing using Sanger sequencing- or NGS-based methods. Multiple algorithms are available for identification of HLA class I and II haplotypes based upon sequencing data, for example, Polysolver (Shukla, et al (2015) *Nat Biotech* 33:1152), HLAMiner (Warren, et al (2012) *Genome Med* 4:95), and OptiType (Szolek, et al (2014) *Bioinformatics* 30:3310).

In some aspects, computer algorithms are used to predict putative neoepitopes, i.e. peptide sequences, which are bound by the MHC molecules of class I or class II in the form of a peptide-presenting complex and then, in this form, recognized by the T-cell receptors of T-lymphocytes. Non-limiting examples of programs useful for identifying peptides which bind to MHC Class I include: SMM (Nielsen, et al (2007) *BMC Bioinformatics* 8:238), SMMPMBEC (Kim et al (2009) *BMC Bioinformatics* 10:394), Pickpocket (Zhang, et al 2009) *Bioinformatics* 25:1293), NetMHC (Andreatta, et al 2016) *Bioinformatics* 32:511), NetMHCpan (Jurtz et al (2017) *J Immunol* 199:3360), NetMHCcons (Karosiene, et al (2012) *Immunogenetics* 64:177), MHCflurry (O'Donnell, et al (2018) *Cell Syst* 7:129), and EDGE (Bulik-Sullivan et al (2018) *Nat Biotech*).

In some aspects, once putative neoepitopes are selected, they are further tested using in vitro and/or in vivo assays. In some aspects, the selected peptides are synthesized and screened in human HLA panels to determine binding to MHC molecules encoded by different HLA haplotypes.

Methods of Making Antibodies

The antibodies and fragments described herein can be produced by any method known in the art.

In some embodiments, the methods described herein can involve, e.g., phage display technologies, bacterial display, yeast surface display, eukaryotic viral display, mammalian cell display, and cell-free (e.g., ribosomal display) antibody screening techniques (see, e.g., Etz et al. (2001) *J Bacteriol* 183:6924-6935; Cornelis (2000) *Curr Opin Biotechnol* 11:450-454; Klemm et al. (2000) *Microbiology* 146:3025-3032; Kieke et al. (1997) *Protein Eng* 10:1303-1310; Yeung et al. (2002) *Biotechnol Prog* 18:212-220; Boder et al. (2000) *Methods Enzymology* 328:430-444; Grabherr et al. (2001) *Comb Chem High Throughput Screen* 4:185-192; Michael et al. (1995) *Gene Ther* 2:660-668; Pereboev et al. (2001) *J Virol* 75:7107-7113; Schaffitzel et al. (1999) *J Immunol Methods* 231:119-135; Chao et al., 2006, *Nature Protocols* 1(2):755-768; and Hanes et al. (2000) *Nat Biotechnol* 18:1287-1292).

Methods for identifying antibodies using various phage display methods are well known in the art. In phage display methods, functional antibody domains are displayed on the surface of phage particles which carry the polynucleotide sequences encoding them. Such phage can be utilized to display antigen-binding domains of antibodies, such as Fab, Fv, or disulfide-bond stabilized Fv antibody fragments, expressed from a repertoire or combinatorial antibody library (e.g., human or murine). Phage used in these methods are typically filamentous phage such as fd and M13. The antigen binding domains are expressed as a recombinantly fused protein to any of the phage coat proteins pIII, pVIII, or pIX. See, e.g., Shi et al. (2010) *JMB* 397:385-396. Examples of phage display methods that can be used to make the immunoglobulins, or fragments thereof, described herein include those disclosed in Brinkman et al. (1995) *J Immunol Methods* 182:41-50; Ames et al. (1995) *J Immunol Methods* 184:177-186; Kettleborough et al. (1994) *Eur J Immunol* 24:952-958; Persic et al. (1997) *Gene* 187:9-18; Burton et al. (1994) *Advances in Immunology* 57:191-280; and PCT publication nos. WO 90/02809, WO 91/10737, WO 92/01047, WO 92/18619, WO 93/11236, WO 95/15982, and WO 95/20401. Suitable methods are also described in, e.g., U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

In some embodiments, the phage display antibody libraries can be generated using mRNA collected from B cells from the immunized mammals. For example, a splenic cell sample comprising B cells can be isolated from mice immunized with a NPM1c:HLA-A2 complex as described above. mRNA can be isolated from the cells and converted to cDNA using standard molecular biology techniques. See, e.g., Sambrook et al. (1989) *"Molecular Cloning: A Laboratory Manual,* 2nd Edition," Cold Spring Harbor Laboratory Press, Cold Spring Harbor, N.Y.; Harlow and Lane (1988), supra; Benny K. C. Lo (2004), supra; and Borrebaek (1995), supra. The cDNA coding for the variable regions of the heavy chain and light chain polypeptides of immunoglobulins are used to construct the phage display library. Methods for generating such a library are described in, e.g., Merz et al. (1995) *J Neurosci Methods* 62(1-2):213-9; Di Niro et al. (2005) *Biochem J* 388(Pt 3):889-894; and Engberg et al. (1995) *Methods Mol Biol* 51:355-376.

Methods for identifying antibodies using yeast surface display methods are well known in the art. An example of the yeast surface display method that can be used to make antibodies and fragments described herein includes the method described in Chao et al., 2006, *Nature Protocols* 1(2):755-768.

In some embodiments, methods for making an antibody described herein can include immunizing a subject (e.g., a non-human mammal) with an appropriate immunogen. Suitable immunogens for generating any of the antibodies described herein are set forth herein. For example, to generate an antibody that binds to NPM1c:HLA-A2 a skilled artisan can immunize a suitable subject (e.g., a nonhuman mammal such as a rat, a mouse, a gerbil, a hamster, a dog, a cat, a pig, a goat, a llama, a horse, or a non-human primate) with the antigen comprising NPM1c:HLA-A2 complex, e.g., where the NPM1c neoepitope is AIQDLCLAV (SEQ ID NO: 1). A suitable subject (e.g., a non-human mammal) can be immunized with the appropriate antigen along with subsequent booster immunizations a number of times sufficient to elicit the production of an antibody by the mammal. The immunogen can be administered to a subject (e.g., a non-human mammal) with an adjuvant.

Methods for producing antibodies using hybridoma technology are well known in the art. In some embodiments, the methods include preparing a hybridoma cell line that secretes a monoclonal antibody that binds to the immunogen. For example, a suitable mammal such as a laboratory mouse is immunized with a NPM1c:HLA-A2 complex as described above. Antibody-producing cells (e.g., B cells of the spleen) of the immunized mammal can be isolated two to four days after at least one booster immunization of the immunogen and then grown briefly in culture before fusion with cells of a suitable myeloma cell line. The cells can be fused in the presence of a fusion promoter such as, e.g., vaccinia virus or polyethylene glycol. The hybrid cells obtained in the fusion are cloned, and cell clones secreting the desired antibodies are selected. For example, spleen cells of Balb/c mice immunized with a suitable immunogen can be fused with cells of the myeloma cell line PAI or the myeloma cell line Sp2/0-Ag 14. After the fusion, the cells are expanded in suitable culture medium, which is supplemented with a selection medium, for example HAT medium, at regular intervals in order to prevent normal myeloma cells from overgrowing the desired hybridoma cells. The obtained hybrid cells are then screened for secretion of the desired antibodies (e.g., an antibody that binds to NPM1c:HLA-A2).

In some embodiments, a skilled artisan can identify an antibody of interest from a nonimmune based library as described in, e.g., U.S. Pat. No. 6,300,064 (to Knappik et al.; Morphosys AG) and Schoonbroodt et al. (2005) *Nucleic Acids Res* 33(9):e81.

In some embodiments, a combination of selection and screening can be employed to identify an antibody of interest from, e.g., a population of hybridoma-derived antibodies or a phage display antibody library. Suitable methods are known in the art and are described in, e.g., Hoogenboom (1997) *Trends in Biotechnology* 15:62-70; Brinkman et al. (1995), supra; Ames et al. (1995), supra; Kettleborough et al. (1994), supra; Persic et al. (1997), supra; and Burton et al. (1994), supra. For example, a plurality of phagemid vectors, each encoding a fusion protein of a bacteriophage coat protein (e.g., pIII, pVIII, or pIX of M13 phage) and a different antigen-combining region are produced using standard molecular biology techniques and then introduced into a population of bacteria (e.g., *E. coli*). Expression of the bacteriophage in bacteria can, in some embodiments, require use of a helper phage. In some embodiments, no helper phage is required (see, e.g., Chasteen et al., (2006) *Nucleic Acids Res* 34(21):e145). Phage produced from the bacteria are recovered and then contacted to, e.g., a target antigen bound to a solid support (immobilized). Phage may also be contacted to antigen in solution, and the complex is subsequently bound to a solid support.

A subpopulation of antibodies screened using the above methods can be characterized for their specificity and binding affinity for a particular antigen (e.g., NPM1c:HLA-A2) using any immunological or biochemical based method known in the art. For example, specific binding of an antibody to NPM1c:HLA-A2, may be determined for example using immunological or biochemical based methods such as, but not limited to, an ELISA assay, SPR assays, immunoprecipitation assay, affinity chromatography, and equilibrium dialysis as described above. Immunoassays which can be used to analyze immunospecific binding and cross-reactivity of the antibodies include, but are not limited to, competitive and noncompetitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

Methods for producing chimeric antibodies are well known in the art (see, e.g., Morrison, 1985, *Science* 229: 1202-7; Oi and Morrison, 1986, *BioTechniques* 4:214-221; Gillies et al., 1989, *J Immunol. Methods* 125:191-202; and U.S. Pat. Nos. 5,807,715, 4,816,567, 4,816,397, and 6,331,415).

Methods for producing humanized antibodies are well known in the art (see, e.g., WO 91/09967; Padlan, 1991, *Mol Immunol* 28(4/5): 489-498; Studnicka et al, 1994, *Prot Engineering* 7(6): 805-814; Roguska et al, 1994, *PNAS* 91: 969-973; WO 93/17105; Tan et al, 2002, *J Immunol* 169:

1119-25; Caldas et al, 2000, Protein Eng. 13(5): 353-60; Morea et al, 2000, Methods 20(3): 267-79; Baca et al, 1997, J Biol Chem 272(16):10678-84; Roguska et al, 1996, Protein Eng 9(10): 895 904; Couto et al, 1995, Cancer Res. 55 (23 Supp): 5973 s-5977 s; Couto et al, 1995, Cancer Res 55(8): 1717-22; Sandhu, 1994, Gene 150(2):409-10; Pedersen et al, 1994, J Mol Biol 235(3): 959-73. For example, a humanized antibody can be made by CDR grafting.

Methods for producing human antibodies are well known in the art. For example, human antibodies can be made by phage display or yeast surface display methods using antibody libraries derived from human immunoglobulin sequences, as described above. See also U.S. Pat. Nos. 4,444,887, 4,716,111, and 5,885,793; and WO 98/46645, WO 98/50433, WO 98/24893, WO 98/16654, WO 96/34096, WO 96/33735, and WO 91/10741. Human antibodies can also be made using mouse-human hybridomas (see, e.g., Shinmoto et al, 2004, Cytotechnology 46: 19-23; Naganawa et al, 2005, Human Antibodies 14: 27-31).

Methods of making antibody fragments are well known in the art. For example, Fab and F(ab')2 fragments can be produced by proteolytic cleavage of immunoglobulin molecules using enzymes such as pepsin (to produce F(ab')2 fragments) or papain (to produce Fab fragments). Methods of making scFv fragments are also known in the art (see, e.g., Ahmad et al., 2012, Clinical and Developmental Immunology, doi: 10.1155/2012/980250; Wang et al., 2006, Anal. Chem. 78, 997-1004; Pansri et al., 2009, BMC Biotechnology 9:6; Chao et al., 2006, *Nature Protocols* 1(2):755-768). scFv having desired antigen-binding properties can be selected by phage display technology or yeast surface display technology. scFv can be constructed by fusing variable domains of heavy and light chains of immunoglobulins via short polypeptide linkers (using recombinant expression techniques). Methods of making single domain antibodies (e.g., antibodies lacking the light chains) are well known in the art (see, e.g., Riechmann & Muyldermans, 1999, J Immunol 231:25-38; Nuttall et al, 2000, Curr Pharm Biotechnol 1(3):253-263; Muyldermans, 2001, J Biotechnol 74(4): 277-302).

Methods for producing bispecific antibodies are well known in the art (see, e.g., Konterman, 2012, MAbs 4: 182-197; Gramer et al., 2013, MAbs 5:962-973).

In embodiments where the selected CDR amino acid sequences are short sequences (e.g., fewer than 10-15 amino acids in length), nucleic acids encoding the CDRs can be chemically synthesized as described in, e.g., Shiraishi et al. (2007) *Nucleic Acids Symposium Series* 51(1):129-130 and U.S. Pat. No. 6,995,259. For a given nucleic acid sequence encoding an acceptor antibody, the region of the nucleic acid sequence encoding the CDRs can be replaced with the chemically synthesized nucleic acids using standard molecular biology techniques. The 5' and 3' ends of the chemically synthesized nucleic acids can be synthesized to comprise sticky end restriction enzyme sites for use in cloning the nucleic acids into the nucleic acid encoding the variable region of the donor antibody.

In some embodiments, the antibodies described herein comprise an altered heavy chain constant region that has enhanced or reduced (or absent) effector function relative to its corresponding unaltered constant region. Effector functions involving the constant region of the antibodies described herein may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and proinflammatory responses. Modulation refers to an increase, decrease, or elimination of an effector function activity exhibited by a subject antibody containing an altered constant region as compared to the activity of the unaltered form of the constant region. An altered constant region with altered FcR binding affinity and/or ADCC activity and/or altered CDC activity is a polypeptide which has either an enhanced or diminished FcR binding activity and/or ADCC activity and/or CDC activity compared to the unaltered form of the constant region. An altered constant region which displays increased binding to an FcR binds at least one FcR with greater affinity than the unaltered polypeptide. An altered constant region which displays decreased binding to an FcR binds at least one FcR with lower affinity than the unaltered form of the constant region.

Methods of conferring CDC or ADCC activity on an antibody are well known in the art (see, e.g., Kellner et al., 2014, Methods 65: 105-113; WO 2012010562; Natsume et al., 2009, Drug Design, Development and Therapy 3(3):7-16). Such methods include, without limitation, Fc isotype shuffling, amino acid mutations in the Fc region conferring enhanced CDC and/or ADCC activity, and changes in the Fc region glycosylation profile conferring enhanced CDC and/or ADCC activity.

For example, an antibody described herein may contain an altered constant region exhibiting enhanced or reduced complement dependent cytotoxicity (CDC). Modulated CDC activity may be achieved by introducing one or more amino acid substitutions, insertions, or deletions in an Fc region of the antibody. See, e.g., U.S. Pat. No. 6,194,551. Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See, e.g., Caron et al. (1992) *J Exp Med* 176:1191-1195 and Shopes (1992) *Immunol* 148:2918-2922; PCT publication nos. WO 99/51642 and WO 94/29351; Duncan and Winter (1988) *Nature* 322:738-40; and U.S. Pat. Nos. 5,648,260 and 5,624,821.

Any of the antibodies described herein can be screened and/or tested for their ability to modulate any of the activities or functions ascribed to the antigen, e.g., NPM1c:HLA-A2, either in vitro or in vivo, using any immunological or biochemical-based methods known in the art.

The antibodies or antigen-binding fragments thereof described herein can be produced using a variety of techniques known in the art of molecular biology and protein chemistry. For example, a nucleic acid encoding one or both of the heavy and light chain polypeptides of an antibody can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of cloned heavy chain and light chain polypeptides from nucleic acids in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA* 78:2072) or Tn5 neo (Southern and Berg (1982) *Mol Appl Genet* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA,* 79:7147), cytomegalovirus, polyoma virus (Deans et al. (1984) *Proc Natl Acad Sci USA* 81:1292), or SV40 virus (Lusky and Botchan (1981) *Nature* 293:79).

The expression vectors can be introduced into cells in a manner suitable for subsequent expression of the nucleic acid. The method of introduction is largely dictated by the targeted cell type, discussed below. Exemplary methods include CaPO4 precipitation, liposome fusion, cationic liposomes, electroporation, viral infection, dextran-mediated transfection, polybrene-mediated transfection, protoplast fusion, and direct microinjection.

Appropriate host cells for the expression of antibodies or antigen-binding fragments thereof include yeast, bacteria, insect, plant, and mammalian cells. Of particular interest are bacteria such as *E. coli*, fungi such as *Saccharomyces cerevisiae* and *Pichia pastoris*, insect cells such as SF9, mammalian cell lines (e.g., human cell lines), as well as primary cell lines.

In some embodiments, an antibody or fragment thereof can be expressed in, and purified from, transgenic animals (e.g., transgenic mammals). For example, an antibody can be produced in transgenic non-human mammals (e.g., rodents) and isolated from milk as described in, e.g., Houdebine (2002) *Curr Opin Biotechnol* 13(6):625-629; van Kuik-Romeijn et al. (2000) *Transgenic Res* 9(2):155-159; and Pollock et al. (1999) *J Immunol Methods* 231(1-2):147-157.

The antibodies and fragments thereof can be produced from the cells by culturing a host cell transformed with the expression vector containing nucleic acid encoding the antibodies or fragments, under conditions, and for an amount of time, sufficient to allow expression of the proteins. Such conditions for protein expression will vary with the choice of the expression vector and the host cell, and will be easily ascertained by one skilled in the art through routine experimentation. For example, antibodies expressed in *E. coli* can be refolded from inclusion bodies (see, e.g., Hou et al. (1998) *Cytokine* 10:319-30). Bacterial expression systems and methods for their use are well known in the art (see Current Protocols in Molecular Biology, Wiley & Sons, and Molecular Cloning—A Laboratory Manual—$3^{rd}$ Ed., Cold Spring Harbor Laboratory Press, New York (2001)). The choice of codons, suitable expression vectors and suitable host cells will vary depending on a number of factors, and may be easily optimized as needed. An antibody (or fragment thereof) described herein can be expressed in mammalian cells or in other expression systems including but not limited to yeast, baculovirus, and in vitro expression systems (see, e.g., Kaszubska et al. (2000) *Protein Expression and Purification* 18:213-220).

Following expression, the antibodies and fragments thereof can be isolated. An antibody or fragment thereof can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G column). Ultrafiltration and diafiltration techniques, in conjunction with protein concentration, are also useful. See, e.g., Scopes (1994) "Protein Purification, 3rd edition," Springer-Verlag, New York City, N.Y. The degree of purification necessary will vary depending on the desired use. In some instances, no purification of the expressed antibody or fragments thereof will be necessary.

Methods for determining the yield or purity of a purified antibody or fragment thereof are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

The antibodies or antigen-binding fragments thereof can be modified following their expression and purification. The modifications can be covalent or noncovalent modifications. Such modifications can be introduced into the antibodies or fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments.

In some embodiments, the antibodies or antigen-binding fragments thereof can be conjugated to a heterologous moiety. The heterologous moiety can be, e.g., a heterologous polypeptide, a therapeutic or a cytotoxic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (e.g., FLAG (DYKDDDDK (SEQ ID NO: 44)), polyhistidine (6-His; HHHHHH (SEQ ID NO: 45), hemagglutinin (HA; YPYDVPDYA (SEQ ID NO: 46)), glutathione-S-transferase (GST), or maltose-binding protein (MBP)) for use in purifying the antibodies or fragments. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., 32P, 33P, 14C, 125I, 131I, 35S, and 3H. Suitable fluorescent labels include, without limitation, fluorescein, fluorescein isothiocyanate (FITC), green fluorescent protein (GFP), DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins (e.g., an antibody and a heterologous moiety) can be crosslinked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., mmaleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of the antibody. Alternatively, the radioactive label can be included as part of a larger molecule (e.g., 125I in meta-[125I]iodophenyl-N-hydroxysuccinimide ([125I]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the antibodies or antigen-binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some embodiments, the antibodies or fragments can be modified, e.g., with a moiety that improves the stabilization and/or retention of the antibodies in circulation, e.g., in blood, serum, or other tissues. For example, the antibody or fragment can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476 or HESylated (Fresenius Kabi, Germany; see, e.g., Pavisić et al. (2010) *Int J Pharm* 387(1-2):110-119). The stabilization moiety can improve the stability, or retention of, the antibody (or fragment) by at least about 1.5 (e.g., at about least 2, 5, 10, 15, 20, 25, 30, 40, or 50 or more) fold.

In some embodiments, the antibodies or antigen-binding fragments thereof described herein can be glycosylated. In some embodiments, an antibody or antigen-binding fragment thereof described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No. 6,933,368; Wright et al. (1991) *EMBO J* 10(10):2717-2723; and Co et al. (1993) *Mol Immunol* 30:1361.

Bispecific Molecules

In certain embodiments, provided herein are antigen-binding constructs that may be used for forming bispecific molecules. An antibody to an antigen comprising a mutant nucleophosmin protein neoepitope in complex with an MHC protein (e.g., anti-NPM1c:MHC class I antibody), or antigen-binding fragments thereof, can be derivatized or linked to another molecule, e.g., another peptide or protein (e.g., another antibody or ligand for a receptor) to generate a bispecific molecule that binds to at least two different binding sites or target molecules. For example, an anti-NPM1c:HLA-A2 antibody, or an antigen binding fragment thereof (e.g., scFv), may be linked to an antibody, or antigen binding fragment thereof (e.g., scFv) that binds specifically to an antigen expressed on a T-cell (e.g., CD3) or a natural killer cell. Multispecific molecules that bind to more than two different binding sites and/or target molecules may be created by derivatizing or linking an antibody, or antigen binding fragment thereof, as described herein to more than one other molecules; such multispecific molecules are also intended to be encompassed by the term "bispecific molecule" as used herein. To generate a bispecific molecule described herein, an antibody, or an antigen binding fragment thereof, as described herein can be linked (e.g., by chemical coupling or conjugation, genetic fusion, noncovalent association or otherwise) to one or more other molecules, such as another antibody, antibody fragment, peptide or binding mimetic, such that a bispecific molecule results.

Accordingly, in certain embodiments, provided herein are bispecific molecules comprising at least one first binding specificity an antigen comprising a mutant nucleophosmin protein neoepitope in complex with an MHC protein (such as NPM1c:HLA-A2) (i.e., the first antigen-binding domain of the bispecific molecule) and a second binding specificity for a second target epitope (i.e., the second antigen-binding domain of the bispecific molecule). In an embodiment described herein in which the bispecific molecule is multispecific, the molecule can further include a third binding specificity.

In certain embodiments, the specificity of the first antigen-binding domain of the bispecific molecule and the second antigen-binding domain of the bispecific molecule is the same. In certain embodiments, the specificities of the first antigen-binding domain of the bispecific molecule and the second antigen-binding domain of the bispecific molecule are different.

In one embodiment, the bispecific molecules described herein comprise at least one antibody, or an antibody fragment thereof, e.g., a Fab fragment, a Fab' fragment, a F(ab')$_2$ fragment, an Fv fragment, or a single chain Fv (scFv), or a single chain antibody molecule. The antibody may also be a light chain or heavy chain dimer, or any minimal fragment thereof such as a Fv or a single chain construct as described in Ladner et al. U.S. Pat. No. 4,946,778, the contents of which are hereby incorporated by reference herein in their entirety.

In certain embodiments, the bispecific molecule of the disclosure is a bispecific single-chain antibody. In one embodiment, at least one of the antigen-binding domains in the bispecific molecule of the disclosure is a single-chain fragment of the variable region of an antibody.

In certain embodiments, the antibodies or antigen binding fragments used in the bispecific molecules described herein are human (e.g., human monoclonal antibodies). Other antibodies which can be employed in the bispecific molecules described herein are murine, chimeric or humanized antibodies (e.g., murine, chimeric or humanized monoclonal antibodies).

The bispecific molecules described herein can be prepared by conjugating the constituent antigen-binding domains using methods known in the art. For example, each antigen-binding domain of the bispecific molecule can be generated separately and then conjugated to one another.

When the antigen-binding domains are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci. USA* 82:8648). Other methods include those described in Paulus (1985) *Behring Ins. Mitt. No.* 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.).

When the antigen-binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both antigen-binding domains can be encoded by the same vector and expressed and assembled in the same host cell. This method is particularly useful where the bispecific molecule comprises mAb & mAb, mAb & Fab, mAb & Fab', mAb & F(ab')$_2$, mAb & Fv, mAb & scFv, Fab & F(ab')$_2$, Fab & Fab, Fab' & Fab', F(ab')$_2$ & F(ab')$_2$, scFv & scFv, Fv & Fv, or ligand & Fab fusion protein. A bispecific antibody may comprise an antibody comprising an scFv at the C-terminus of each heavy chain. A bispecific molecule described herein can be a single chain molecule comprising one single chain antibody and a binding determinant, or a single chain bispecific molecule comprising two binding determinants. A bispecific antibody may comprise an antibody comprising an scFv at the N-terminus of each heavy chain. A bispecific antibody may comprise an antibody comprising an scFv at the N-terminus or C-terminus of each light chain. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed using art-recognized methods, such as enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of interest by employing a labeled reagent (e.g., an antibody) specific for the complex of interest.

In some embodiments, the bispecific molecule of the disclosure binds (e.g., specifically binds) to an antigen comprising a mutant nucleophosmin protein neoepiope in complex with an MHC class I protein (e.g., HLA-A2) and simultaneously binds (e.g., specifically binds) to one or more antigens on an immune effector cell, e.g., a T cell (e.g., CD3) or a natural killer cell (e.g., NKp46 or CD16A). In some embodiments, the bispecific molecule of the disclosure specifically binds to NPM1c:HLA-A2 and simultaneously specifically binds to one or more antigens on an immune effector cell. In some aspects, such binding allows re-targeting of immune effector cells to tumor cells (see, e.g., Chames et al., 2009, MAbs 1:539-547). Immune effector cells include but are not limited to T cells, natural killer cells, macrophages, neutrophils, dendritic cells and B lymphocytes. In some aspects, the immune effector cells targeted by a bispecific antibody described herein is a T cell (e.g., CD3), a natural killer cell (e.g., NKp46 or CD16A), or a macrophage. In some embodiments, the bispecific molecule comprises an antibody or antigen binding fragment thereof (e.g., scFv) that binds to NPM1c:HLA-A2, and an antibody or antigen binding fragment thereof (e.g., scFv) that binds to an antigen on an immune effector cell, e.g., a T cell (e.g., CD3), a natural killer cell (e.g., NKp46 or CD16A), or a macrophage.

In some embodiments, the bispecific molecule of the disclosure binds (e.g., specifically binds) to an antigen comprising a mutant nucleophosmin protein neoepitope (e.g., NPM1c neoepitope) in complex with an MHC class I protein (e.g., HLA-A2) and simultaneously binds (e.g., specifically binds) to one or more of the following antigens: CD3, NKp46, CD16A, CD40, CD47, 4-1BB, TGF-β, LAG-3, PD-1, TIM-3, CTLA-4, OX-40, NKp30, NKG2A, NKG2D or DNAM-1. In one embodiment, the bispecific molecule of the disclosure comprises a second binding specificity to CD3. In one embodiment, the bispecific molecule of the disclosure comprises a second binding specificity to NKp46. In one embodiment, the bispecific molecule of the disclosure comprises a second binding specificity to CD16A. In one embodiment, the bispecific molecule of the disclosure comprises a second binding specificity to CD40. In one embodiment, the bispecific molecule of the disclosure comprises a second binding specificity to CD47. In one embodiment, the bispecific molecule of the disclosure comprises a second binding specificity to 4-1BB. In one embodiment, the bispecific molecule of the disclosure comprises a second binding specificity to TGF-β. In one embodiment, the bispecific molecule of the disclosure comprises a second binding specificity to LAG-3. In one embodiment, the bispecific molecule of the disclosure comprises a second binding specificity to PD-1. In one embodiment, the bispecific molecule of the disclosure comprises a second binding specificity to TIM-3. In one embodiment, the bispecific molecule of the disclosure comprises a second binding specificity to CTLA-4. In one embodiment, the bispecific molecule of the disclosure comprises a second binding specificity to OX-40. In one embodiment, the bispecific molecule of the disclosure comprises a second binding specificity to NKp30. In one embodiment, the bispecific molecule of the disclosure comprises a second binding specificity to NKG2A. In one embodiment, the bispecific molecule of the disclosure comprises a second binding specificity to NKG2D. In one embodiment, the bispecific molecule of the disclosure comprises a second binding specificity to DNAM-1.

In some embodiments, the bispecific molecule may be a bispecific single chain antibody. The terms "bispecific single chain antibody" or "single chain bispecific antibody" refer to antibody constructs that result from joining at least two antibody variable regions in a single polypeptide chain devoid of the constant and/or Fc portion(s) present in full immunoglobulins. For example, each antigen-specific portion of the bispecific single chain antibody comprises an antibody VH region and an antibody $V_L$ region.

Advantageous variants of a bispecific single chain antibody are described below from N terminus to C terminus (where "CD3" is used as an example of the second specificity, but can be substituted by another antigen, e.g., NKp46, CD16A, CD40, CD47, 4-1BB, TGF-β, LAG-3, PD-1, TIM-3, CTLA-4, OX-40, NKp30, NKG2A, NKG2D or DNAM-1):

$V_L$(NPM1c:HLA-A2)-$V_H$(NPM1c:HLA-A2)-$V_H$(CD3)-$V_L$(CD3), $V_H$(NPM1c:HLA-A2)-$V_L$(NPM1c:HLA-A2)-$V_H$(CD3)-$V_L$(CD3), $V_L$(NPM1c:HLA-A2)-$V_H$(NPM1c:HLA-A2)-$V_L$(CD3)-$V_H$(CD3), $V_H$(NPM1c:HLA-A2)-$V_L$(NPM1c:HLA-A2)-$V_L$(CD3)-$V_H$(CD3), $V_H$(CD3)-$V_L$(CD3)-$V_H$(NPM1c:HLA-A2)-$V_L$(NPM1c:HLA-A2), $V_H$(CD3)-$V_L$(CD3)-$V_L$(NPM1c:HLA-A2)-$V_H$(NPM1c:HLA-A2), $V_L$(CD3)-$V_H$(CD3)-$V_H$(NPM1c:HLA-A2)-$V_L$(NPM1c:HLA-A2), or $V_L$(CD3)-$V_H$(CD3)-$V_L$(NPM1c:HLA-A2)-$V_H$(NPM1c:HLA-A2).

The antigen-binding domains of the bispecific molecule of the disclosure preferably have a specificity at least substantially identical to the binding specificity of the, e.g., antibody or immunoglobulin chain which they are derived from.

In certain embodiments, an antigen-binding domain of the bispecific molecule that binds to one or more antigens on an immune effector cell, e.g., a T cell (e.g., CD3) or a natural killer cell (e.g., NKp46 or CD16A) has a binding affinity (Kd) to the antigen of at least $10^{-4}$M, at least $10^{-5}$M, at least $10^{-6}$M, or at least at least $10^{-7}$M. In certain embodiments, an antigen-binding domain that binds to one or more antigens on an immune effector cell, e.g., a T cell (e.g., CD3) or a natural killer cell (e.g., NKp46 or CD16A) has a binding affinity (Kd) to the antigen not higher than $10^{-7}$M (e.g., between $10^{-4}$M and $10^{-7}$M, or between $10^{-5}$M and $10^{-7}$M). In certain embodiments, an antigen-binding domain of the bispecific molecule that binds to NPM1c:HLA-A2 antigen has a binding affinity (Kd) to the NPM1c:HLA-A2 antigen of at least $10^{-7}$ M or higher, at least $10^{-8}$M or higher, at least $10^{-9}$ M or higher, at least 500 nM or higher, at least 250 nM or higher, at least 100 nM or higher, at least 50 nM or higher, at least 25 nM or higher, at least 20 nM or higher, at least 15 nM or higher, or at least 10 nM or higher. In specific embodiments, an antigen-binding domain of the bispecific molecule that binds to NPM1c:HLA-A2 antigen has a binding affinity (Kd) to the NPM1c:HLA-A2 antigen of at least 20 nM or higher, at least 15 nM or higher, or at least 10 nM or higher. In certain embodiments, an antigen-binding domain of the bispecific molecule that binds to NPM1c:HLA-A2 antigen has a binding affinity (Kd) to the NPM1c:HLA-A2 antigen between (or from and to) 0.1 nM and 500 nM, 0.1 nM and 100 nM, 0.5 nM and 100 nM, 0.1 nM and 50 nM, 0.5 nM and 50 nM, 0.1 nM and 25 nM, 0.5 nM and 25 nM. 0.1 nM and 15 nM, 0.5 nM and 15 nM, 0.1 nM and 10 nM, or 0.5 nM and 10 nM, or 1 nM to 10 nM (or any value in between). Such antigen-binding domains can have a binding affinity of at least $10^{-5}$M, for example, not higher than $10^{-7}$M, for an antigen on an antigen on an immune effector cell (e.g., CD3 antigen) and, for example, $10^{-8}$ M or higher, 50 nM or higher, 25 nM or higher, 15 nM or higher, 10 nM or higher for the NPM1c:HLA-A2 antigen. In certain embodiments of the bispecific molecule of the disclosure: (a) said binding site of the first antigen-binding domain (binding to NPM1c:MHC class I) has an affinity of at least about $10^{-7}$M, at least about $10^{-8}$M, at least about $10^{-9}$M, at least about 500 nM, at least about 100 nM, at least about 50 nM, or at least about 25 nM, or at least about 15 nM; and/or (b) said binding site of the second antigen-binding domain has an affinity of less than about $10^{-7}$M, less than about $10^{-6}$M, or in the order of $10^{-5}$M. In some embodiments of the bispecific molecule of the disclosure: (a) said binding site of the first antigen-binding domain (binding to NPM1c:HLA-A2) has an affinity of at least about 100 nM or at least about 25 nM; and/or (b) said binding site of the second antigen-binding domain has an affinity of less than about $10^{-7}$M, less than about $10^{-6}$M, or in the order of $10^{-5}$M.

In accordance with certain embodiments referred to above, it is advantageous if the binding site recognizing an antigen comprising a mutant NPM1c neoepitope in complex with an MHC protein (e.g., NPM1c:HLA-A2 antigen) has a high affinity in order to capture the target cells to be destroyed with high efficiency. On the other hand, the binding affinity of the binding site recognizing an antigen on an immune effector cell (e.g., CD3 antigen) can be in the order of those of the natural receptor for the antigen (e.g., CD3 receptor) or of that usually found for the interaction of the immune effector cell receptor (e.g., T-cell receptor) with its ligand, that is an MHC-peptide complex on the target cell surface.

In one embodiment of the disclosure said first and/or second domain of the bispecific molecule of the disclosure mimic or correspond to a $V_H$ and $V_L$ region from a natural antibody. The antibody providing the binding site for the bispecific molecule of the disclosure can be, e.g., a monoclonal antibody, polyclonal antibody, chimeric antibody, humanized antibody, bispecific antibody, synthetic antibody, antibody fragment, such as Fab, Fv or scFv fragments etc., or a chemically modified derivative of any of these. Monoclonal antibodies can be prepared, for example, by the techniques as originally described in Kohler and Milstein, Nature 256 (1975), 495, and Galfre, Meth. Enzymol. 73 (1981), 3, which comprise the fusion of mouse myeloma cells to spleen cells derived from immunized mammals with modifications developed by the art. Furthermore, antibodies or fragments thereof to the aforementioned antigens can be obtained by using methods which are described, e.g., in Harlow and Lane "Antibodies, A Laboratory Manual", CSH Press, Cold Spring Harbor, 1988. Antibodies might be obtained from several species, including human. When derivatives of said antibodies are obtained by the phage display technique, surface plasmon resonance as employed in the BIAcore system can be used to increase the efficiency of phage antibodies which bind to the NPM1c:HLA-A2 or the second antigen (Schier, Human Antibodies Hybridomas 7 (1996), 97 105; Malmborg, J. Immunol. Methods 183 (1995), 7 13). The production of chimeric antibodies is described, for example, in WO 89/09622. Methods for the production of humanized antibodies are described in, e.g., EP-A1 0 239 400 and WO 90/07861. A further source of antibodies to be utilized in accordance with the present disclosure are so-called xenogenic antibodies. The general principle for the production of xenogenic antibodies such as human antibodies in mice is described in, e.g., WO 91/10741, WO 94/02602, WO 96/34096 and WO 96/33735.

Another source of antibodies to be utilized in accordance with the present disclosure are human antibodies isolated and engineered using yeast surface display, e.g., as described in Chao et al., 2006, Nature Protocols 1(2):755-768.

In one embodiment, the NPM1c:HLA-A2 specific domain of the bispecific molecule described herein comprises at least one $V_H$ CDR3 comprising or being the amino acid sequence set forth as SEQ ID NO:11 (ARLGYPTT-TLLPFDY), at least one $V_H$ CDR2 comprising or being the amino acid sequence set forth as SEQ ID NO:10 (IS-GSGGST), and/or at least one VH CDR1 comprising or being the amino acid sequence set forth as SEQ ID NO:9 (GFTFSSYA).

The bispecific molecule of the disclosure may also comprise one or more $V_L$ region CDR(s) of the NPM1c:HLA-A2 specific domain. Such $V_L$ regions CDR(s) of the NPM1c:HLA-A2 specific domain may comprise at least one $V_L$ CDR3 comprising or being the amino acid sequence set forth as SEQ ID NO:8 (QQSYSTPLT), at least one $V_L$ CDR2 comprising or being the amino acid sequence of SEQ ID NO:7 (AAS), and/or at least one $V_L$ CDR1 comprising or being the amino acid sequence set forth as SEQ ID NO:6 (QSISSY).

In one embodiment, the bispecific molecule comprises CDR1, CDR2 and CDR3 of the $V_H$ and/or $V_L$ of an antibody specifically binding to NPM1c:HLA-A2 in one construct (e.g., the CDRs described herein).

In one embodiment, the anti-NPM1c:HLA-A2 CDRs referred to herein are in accordance with the IMGT numbering system. The IMGT numbering scheme is a widely adopted standard for numbering the residues in an antibody in a consistent manner (see "IMGT®, the international ImMunoGeneTics information System® website imgt.org, founder and director: Marie-Paule Lefranc, Montpellier, France; see, e.g., Lefranc, M.-P., 1999, The Immunologist, 7:132-136 and Lefranc, M.-P. et al., 1999, Nucleic Acids Res., 27:209-212, both of which are incorporated herein by reference in their entirety).

In certain embodiments, the bispecific molecule (e.g., a bispecific antibody or fragment) of the disclosure binds to NPM1c:HLA-A2 and CD3 simultaneously. In some embodiments, the bispecific molecule comprises a single-chain variable (scFv) fragment that binds to NPM1c:HLA-A2, and an antibody or antigen binding fragment thereof (e.g., scFv) that binds to CD3.

As used herein, "human CD3" denotes an antigen that is expressed on human T cells as part of the multimolecular T cell receptor complex, the CD3 consisting of five different chains: CD3-epsilon, CD3-gamma, CD3-delta, CD3-eta and CD3 zeta.

Clustering of CD3 on T cells, e.g., by anti-CD3 antibodies leads to T cell activation similar to the binding of an antigen but independent from the clonal specificity of the T cell subset. Thus, a bispecific molecule specifically binding with one of its antigen-binding domains to the human CD3 can be capable of binding to the human CD3 complex expressed on human T cells and capable of inducing elimination/lysis of target cells, wherein such target cells carry/display an antigen (e.g., NPM1c:HLA-A2) which is bound by the other, non-CD3-binding portion of the bispecific molecule. Binding of the CD3 complex by CD3-specific binders (e.g., a bispecific molecule disclosed herein) leads to activation of T cells as known in the art; see e.g. WO 99/54440 or WO 2004/106381. In one embodiment, a bispecific molecule of the disclosure is advantageously able to eliminate/lyse target cells in vivo and/or in vitro. Corresponding target cells can be cells expressing or displaying on its surface a tumor antigen, e.g., NPM1c:HLA-A2, which is recognized by another antigen-binding domain of the bispecific molecule (i.e. the non-CD3-binding portion of the bispecific molecule). In one embodiment, the additional specificity is for NPM1c:HLA-A2.

In one embodiment of the disclosure, the $V_H$ and $V_L$ regions of the CD3 specific domain of the bispecific molecule are derived from an CD3 specific antibody selected from the group consisting of: OKT-3, $X_{35}$-3, VIT3, BMA030 (BW264/56), CLB-T3/3, CRIS7, YTH12.5, F111409, CLB-T3.4.2, TR-66, WT31, WT32, SPv-T3b, 11D8, XIII-141, XII146, XIII-87, 12F6, T3/RW2-8C8, T3/RW24B6, OKT3D, M-T301, SMC2 and F101.01. Each of these antibodies is well described in the art (see e.g., U.S. Pat. Nos. 8,007,796 and 884,088).

In one embodiment, the CD3 specific domain of the bispecific molecule described herein comprises at least one $V_H$ CDR3 comprising the amino acid sequence set forth as SEQ ID NO:50 (YYDDHYCLDY), at least one $V_H$ CDR2 comprising the amino acid sequence set forth as SEQ ID NO:49 (YINPSRGYTNYNQKFKD), and/or at least one $V_H$ CDR1 comprising the amino acid sequence set forth as SEQ ID NO:47 (GYTFTRYTMH) or SEQ ID NO:48 (RYTMH).

In some aspects, the bispecific molecule of the disclosure comprises one or more $V_L$ region CDR(s) of the CD3 specific domain. Such $V_L$ regions CDR(s) of the CD3 specific domain comprises at least one $V_L$ CDR3 comprising the amino acid sequence set forth as SEQ ID NO:53 (QQWSSNPLT), at least one $V_L$ CDR2 comprising the amino acid sequence of SEQ ID NO:52 (DTSKVAS), and/or at least one $V_L$ CDR1 comprising the amino acid sequence set forth as SEQ ID NO:51 (RASSSVSYMN).

In one embodiment, the bispecific molecule comprises CDR1, CDR2 and CDR3 of the $V_H$ and/or $V_L$ of an antibody specifically binding to CD3 in one construct (e.g., the CDRs described herein).

In one embodiment, said NPM1c:HLA-A2 specific domain of the bispecific molecule comprises at least one $V_H$ CDR3 region comprising the amino acid sequence set forth in SEQ ID NO:11 (ARLGYPTTTLLPFDY), and said CD3 specific domain of the bispecific molecule comprises at least one $V_H$ CDR2 region comprising the amino acid sequence set forth as SEQ ID NO: 49 (YINPSRGYTNYNQKFKD) and/or at least one $V_H$ CDR1 region comprising the amino acid sequence set forth in SEQ ID NO: 47 (GYTFTRYTMH) or SEQ ID NO:48 (RYTMH). In some embodiments, such bispecific molecule further comprises $V_L$ CDR(s) of the respective antigen-binding antibodies. For example, said NPM1c:HLA-A2 specific domain of the bispecific molecule comprises at least one $V_L$ CDR3 region comprising the amino acid sequence set forth in SEQ ID NO:8 (QQSYSTPLT), at least one $V_L$ CDR2 region comprising the amino acid sequence of SEQ ID NO:7 (AAS), and/or said CD3 specific domain comprises at least one $V_L$ CDR1 region comprising the amino acid sequence set forth as SEQ ID NO:51 (RASSSVSYMN). In one embodiment, the above-referenced CDRs (e.g., CDR1, CDR2, CDR3) are comprised in one single bispecific molecule.

In one embodiment of the disclosure, the NPM1c:HLA-A2 and CD3 bispecific molecule comprises CDR1, CDR2 and CDR3 of both the heavy and light chain of an anti-CD3 antibody. In one embodiment of the disclosure, the NPM1c:HLA-A2 and CD3 bispecific molecule comprises CDR1, CDR2 and CDR3 of both the heavy and light chain of an anti-NPM1c:HLA-A2 antibody. In some embodiments of the disclosure, the NPM1c:HLA-A2 and CD3 bispecific molecule of the disclosure comprises CDR1, CDR2 and CDR3 of both the heavy and light chain of an anti-CD3 antibody and CDR1, CDR2 and CDR3 of both the heavy and light chain of an anti-NPM1c:HLA-A2 antibody.

In one embodiment, the anti-CD3 CDRs referred to herein are in accordance with the Kabat numbering system. The Kabat numbering scheme is a widely adopted standard for numbering the residues in an antibody in a consistent manner (Kabat et al., Sequences of Proteins of Immunological Interest, 1991, which is incorporated herein by reference in its entirety).

In one embodiment of the disclosure, the NPM1c:HLA-A2 and CD3 bispecific molecule comprises:
 (a) NPM1c:HLA-A2 heavy chain variable region ($V_H$) comprising the amino acid sequence set forth SEQ ID NO:5; and/or NPM1c:HLA-A2 light chain variable region ($V_L$) comprising the amino acid sequence set forth in SEQ ID NO:3;
 and
 (b) CD3 heavy chain variable region (VH) and/or light chain variable region (VL) from a CD3 specific antibody (e.g., an antibody selected from the group consisting of: OKT-3, $X_{35}$-3, VIT3, BMA030 (BW264/56), CLB-T3/3, CRIS7, YTH12.5, F111-409, TR-66, WT31, WT32, SPv-T3b, 11D8, XIII-141, XIII-46, XIII-87, 12F6, T3/RW2-8C8, T3/RW2-4B6, OKT3D, M-T301, SMC2 and F101.01).

In one embodiment of the disclosure, the NPM1c:HLA-A2 and CD3 bispecific molecule comprises:
 (a) NPM1c:HLA-A2 heavy chain variable region ($V_H$) comprising the amino acid sequence set forth SEQ ID NO:5; and NPM1c:HLA-A2 light chain variable region (VL) comprising the amino acid sequence set forth in SEQ ID NO:3;
 and
 (b) CD3 heavy chain variable region (VH) and light chain variable region (VL) from a CD3 specific antibody (e.g., an antibody selected from the group consisting of: OKT-3, $X_{35}$-3, VIT3, BMA030 (BW264/56), CLB-T3/3, CRIS7, YTH12.5, F111-409, TR-66, WT31, WT32, SPv-T3b, 11D8, XIII-141, XIII-46, XIII-87, 12F6, T3/RW2-8C8, T3/RW2-4B6, OKT3D, M-T301, SMC2 and F101.01).

Natural killer (NK) cell activity is regulated by a complex mechanism that involves both activating and inhibitory signals. Several distinct NK cell receptors have been identified that play an important role in the NK cell mediated recognition and killing of HLA Class I deficient target cells. One receptor, although not specific to NK cells, is FcγRIIIA (CD16A) which is responsible for NK cell mediated cytotoxicity (ADCC). Another NK cell receptor is NKp46, a member of the Ig superfamily. It is specific to NK cells and its cross-linking, induced by specific mAbs, leads to a strong NK cell activation resulting in increased intracellular Ca++ levels, triggering of cytotoxicity, and lymphokine release.

In some aspects, the bispecific molecule (e.g., a bispecific antibody or fragment) of the disclosure binds to NPM1c:HLA-A2 and NKp46 simultaneously. In some embodiments, the bispecific molecule of the disclosure binds to NPM1c:HLA-A2 expressed or displayed on tumor cells and NKp46 expressed on NK cells simultaneously. In some embodiments, the bispecific molecule comprises a single-chain variable (scFv) fragment recognizing NPM1c:HLA-A2, and an antibody or antigen binding fragment thereof (e.g., scFv) that binds to NKp46. Antibodies and/or antigen binding fragments that specifically bind to NKp46 are known in the art (see e.g., WO 15/197593, WO 17/114694).

In some embodiments, the bispecific molecule (e.g., a bispecific antibody or fragment) of the disclosure binds to NPM1c:HLA-A2 and CD16A simultaneously. In some embodiments, the bispecific molecule of the disclosure binds to NPM1c:HLA-A2 expressed or displayed on tumor cells and CD16A expressed on NK cells simultaneously. In some embodiments, the bispecific molecule comprises a single-chain variable (scFv) fragment recognizing NPM1c:HLA-A2, and an antibody or antigen binding fragment thereof (e.g., scFv) that binds to CD16A. Antibodies and/or antigen binding fragments that specifically bind to CD16A are known in the art (see e.g., Stein et al., (2012) *Antibodies* 1:88-123, and references cited therein).

In some embodiments, binding of a bispecific molecule provided by the disclosure to an NK cell activates the NK cell. In some embodiments, binding of a bispecific molecule provided by the disclosure to an NK cell induces NK cell anti-tumor activity. In some embodiments, binding of a bispecific antibody provided by the disclosure to an NK cell induces antibody-dependent cell-mediated cytotoxicity (ADCC).

Accordingly, in some embodiments, the disclosure provides a bispecific antigen-binding polypeptide, comprising:
 (i) a first antigen-binding domain that specifically binds to an NPM1c neoepitope in complex with a class I major histocompatibility complex (MHC class I) protein (e.g., HLA-A2); and
 (ii) a second antigen-binding domain that specifically binds to one of the following: CD3, NKp46, CD16A, CD40, CD47, 4-1BB, TGF-β, LAG-3, PD-1, TIM-3, CTLA-4, OX-40, NKp30, NKG2A, NKG2D or DNAM-1.

In some embodiments, the disclosure provides a bispecific antigen-binding polypeptide, comprising:
 (i) a first antigen-binding domain that specifically binds to an NPM1c neoepitope in complex with a class I major histocompatibility complex (MHC class I) protein (e.g., HLA-A2); and
 (ii) a second antigen-binding domain that specifically binds to CD3 (e.g., human CD3). In some embodiments, the second antigen-binding domain specifically binds to human CD3 expressed on T cells.

In some embodiments, the disclosure provides a bispecific antigen-binding polypeptide, comprising:
 (i) a first antigen-binding domain that specifically binds to an NPM1c neoepitope in complex with a class I major histocompatibility complex (MHC class I) protein (e.g., HLA-A2); and
 (ii) a second antigen-binding domain that specifically binds to NKp46 (e.g., human NKp46). In some embodiments, the second antigen-binding domain specifically binds to human NKp46 expressed on natural killer (NK) cells.

In some embodiments, the disclosure provides a bispecific antigen-binding polypeptide, comprising:
 (i) a first antigen-binding domain that specifically binds to an NPM1c neoepitope in complex with a class I major histocompatibility complex (MHC class I) protein (e.g., HLA-A2); and
 (ii) a second antigen-binding domain that specifically binds to CD16A (e.g., human CD16A). In some embodiments, the second antigen-binding domain specifically binds to human CD16A expressed on NK cells.

In some embodiments, the NPM1c neoepitope comprises an amino acid sequence selected from the following: AIQDLCVAV (SEQ ID NO:71), CLAVEEVSL (SEQ ID NO:72), VEEVSLRK (SEQ ID NO:73), AVEEVSLR (SEQ ID NO:74), AVEEVSLRK (SEQ ID NO:75) and CLAVEEVSLRK (SEQ ID NO:76). In one embodiment, the NPM1c neoepitope comprises the amino acid sequence AIQDLCLAV (SEQ ID NO:1).

In some embodiments, the MHC class I protein is encoded by an HLA-A allele comprising the HLA-A*02 allele group. In some embodiments, the HLA-A allele is HLA-A*02:01.

In some embodiments, the first antigen-binding domain comprises a heavy chain variable region (VH) and/or a light chain variable region (VL), wherein the VH comprises the amino acid sequence set forth in SEQ ID NO:5 and the VL comprises the amino acid sequence set forth in SEQ ID NO:3.

In some embodiments, the first antigen-binding domain comprises a heavy chain variable region (VH) and/or a light chain variable region (VL), wherein the VH comprises the amino acid sequence which is at least 90%, at least 95%, at least 98% or at least 99% identical to the amino acid sequence set forth in SEQ ID NO:5 and the VL comprises the amino acid sequence which is at least 90%, at least 95%, at least 98% or at least 99% identical to the amino acid sequence set forth in SEQ ID NO:3.

In some embodiments, the first antigen-binding domain comprises a heavy chain variable region (VH) and a light chain variable region (VL), wherein the VH comprises the amino acid sequence set forth in SEQ ID NO:5 and the VL comprises the amino acid sequence set forth in SEQ ID NO:3. In some embodiments, the first antigen-binding domain comprises a heavy chain variable region (VH) and a light chain variable region (VL), wherein the VH comprises the amino acid sequence which is at least 90%, at least 95%, at least 98% or at least 99% identical to the amino acid sequence set forth in SEQ ID NO:5 and the VL comprises the amino acid sequence which is at least 90%, at least 95%, at least 98% or at least 99% identical to the amino acid sequence set forth in SEQ ID NO:3.

In some embodiments, the first antigen-binding domain comprises VH CDR1, VH CDR2 and VH CDR3 sequences set forth in SEQ ID NOs: 9, 10 and 11, respectively, and/or VL CDR1, VL CDR2 and VL CDR3 sequences set forth in SEQ ID NOs: 6, 7 and 8, respectively.

In some embodiments, the first antigen-binding domain comprises VH CDR1, VH CDR2 and VH CDR3 sequences set forth in SEQ ID NOs: 9, 10 and 11, respectively, and VL CDR1, VL CDR2 and VL CDR3 sequences set forth in SEQ ID NOs: 6, 7 and 8, respectively.

In some embodiments, the first antigen-binding domain comprises an scFv, an Fab, or an F(ab') 2, and wherein the second antigen-binding domain comprises an scFv, and Fab, or an F(ab') 2.

Antibodies to be employed in accordance with the disclosure or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, *Molecular Cloning: A Laboratory Manual*, Cold Spring Harbor Laboratory (1989) N.Y. The modification referred to are preferably carried out at the nucleic acid level.

Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992). Traditionally, the recombinant production of bispecific antibodies is based on the co-expression of two immunoglobulin heavy-chain/light-chain pairs, where the two heavy chain/light-chain pairs have different specificities (Milstein and Cuello, (1983) *Nature* 305:537-539). Antibody variable domains with the desired binding specificities (antibody-antigen combining sites) can be fused to immunoglobulin constant domain sequences. The fusion of the heavy chain variable region is preferably with an immunoglobulin heavy-chain constant domain, including at least part of the hinge, CH2, and CH3 regions. For further details of illustrative currently known methods for generating bispecific antibodies see, e.g., Suresh et al., (1986) *Methods Enzymol.* 121:210; PCT Publication No. WO 96/27011; Brennan et al., (1985) *Science* 229:81; Shalaby et al., *J. Exp. Med.* (1992) 175:217-225; Kostelny et al., (1992) *J. Immunol.* 148(5):1547-1553; Hollinger et al., (1993) *Proc. Natl. Acad. Sci. USA* 90:6444-6448; Gruber et al., (1994) *J. Immunol.* 152:5368; and Tutt et al., (1991) *J. Immunol.* 147:60. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) *J Immunol* 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) Proc Natl Acad Sci USA 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) J Immunol 152:5368. Alternatively, the antibodies can be "linear antibodies" as described in, e.g., Zapata et al. (1995) Protein Eng. 8(10):1057-1062. Briefly, these antibodies comprise a pair of tandem Fd segments (VH-CH1-VH-CH1) which form a pair of antigen binding regions. Linear antibodies can be bispecific or monospecific.

The disclosure also embraces variant forms of multi-specific antibodies such as the dual variable domain immunoglobulin (DVD-Ig) molecules described in Wu et al. (2007) Nat Biotechnol 25(11): 1290-1297. The DVD-Ig molecules are designed such that two different light chain variable domains (VL) from two different parent antibodies are linked in tandem directly or via a short linker by recombinant DNA techniques, followed by the light chain constant domain. Similarly, the heavy chain comprises two different heavy chain variable domains (VH) linked in tandem, followed by the constant domain CH1 and Fc region. Methods for making DVD-Ig molecules from two parent antibodies are further described in, e.g., PCT Publication Nos. WO 08/024188 and WO 07/024715. In some embodiments, the bispecific antibody is a Fabs-in-Tandem immunoglobulin, in which the light chain variable region with a second specificity is fused to the heavy chain variable region of a whole antibody. Such antibodies are described in, e.g., International Patent Application Publication No. WO 2015/103072.

Chimeric Antigen Receptors

In one aspect, provided herein are chimeric antigen receptors (CARs) comprising an extracellular domain, wherein the extracellular domain comprises any antibody, or antigen binding fragment thereof, or a bispecific molecule described herein. In certain embodiments, chimeric antigen receptors (CARs) provided herein comprise an extracellular domain that binds a neoantigen (e.g., a cancer or tumor neoantigen). A cancer neoantigen is an antigen that is present solely in cancer cells due to mutations that occur in such cancer cells. The cancer antigen may be expressed intracellularly and presented by an MHC class I protein on the surface of the cancer cell. For example, the cancer neoantigen targeted by a CAR contemplated herein may be NPM1c:HLA-A2. In certain embodiments, the antibodies or antigen binding fragments (e.g., scFv) of the disclosure can be used to make chimeric antigen receptors (CARs). In one embodiment, an antibody or antigen binding fragment thereof (e.g., an scFv) that binds NPM1c:HLA-A2 is used to generate a chimeric antigen receptor (CAR) polypeptide. In certain embodiments, provided herein are chimeric antigen receptors (CARs) comprising an extracellular binding domain, wherein the extracellular binding domain comprises any antibody, or antigen binding fragment thereof, or a bispecific molecule described herein, wherein such antibody, antigen binding fragment thereof, or bispecific molecule binds to a mutant nucleophosmin protein neoepitope (such as NPM1c neoepitope) in complex with (or presented by) a class I major histocompatibility complex (MHC class I) protein (e.g., HLA-2).

CARs are genetically-engineered, artificial membrane-bound proteins that, when expressed in an immune effector cell, direct such immune effector cell to an antigen, and generally stimulate the immune effector cell to kill the cell displaying the antigen. Thus, the chimeric antigen receptors (CARs) can be used to impart a desired antigenic specificity to immune effector cells, such as an anti-tumor specificity (in particular, the antigenic specificity of is imparted by the extracellular domain of the CAR).

CARs generally comprise an extracellular domain that binds one or more antigens displayed on a cell, a transmembrane domain, and an intracellular domain that transmits an activation signal to the immune effector cell upon binding of the extracellular domain to the one or more antigens. In certain embodiments, CARs contain three domains: 1) an extracellular domain typically comprising a signal peptide, a ligand or antigen recognition region (e.g. scFv), and a flexible spacer; 2) a transmembrane (TM) domain; 3) an intracellular domain (also known as a cytoplasmic domain) typically comprising one or more signaling domains. The extracellular domain of the CAR resides outside of the cell and exposed to the extracellular space, whereby it is accessible for interaction with its ligand/antigen. The TM domain allows the CAR to be anchored into the cell membrane of the effector cell. The intracellular domain of a CAR may comprise one or more cytoplasmic domains derived from signal transducing proteins different from the protein from which the extracellular domain is derived. The intracellular domain aids in effector cell activation upon binding of the CAR to its ligand/antigen. In some embodiments, effector cell activation comprises induction of cytokine and chemokine production, as well as activation of the cytolytic activity of the effector cell. In some embodiments, the CARs redirect cytotoxicity toward tumor cells.

Engagement of the antigen binding domain of the CAR with its target antigen on the surface of a target cell results in clustering of the CAR and delivers an activation stimulus to the CAR-containing cell. In some embodiments, the main characteristic of CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific co-receptors. Although scFv-based CARs engineered to contain a signaling domain from CD3ζ or FcRγ have been shown to deliver a potent signal for T cell activation and effector function, they may not be sufficient to elicit signals that promote T cell survival and expansion in the absence of a concomitant co-stimulatory signal. A new generation of CARs containing a binding domain, a hinge, a transmembrane and the signaling domain derived from CD3ζ or FcRγ together with one or more co-stimulatory signaling domains (e.g., intracellular co-stimulatory domains derived from CD28, CD137, CD134 and CD278) has been shown to more effectively direct antitumor activity as well as increased cytokine secretion, lytic activity, survival and proliferation in CAR expressing T cells in vitro, in animal models and cancer patients (Milone et al., Molecular Therapy, 2009; 17: 1453-1464; Zhong et al., Molecular Therapy, 2010; 18: 413-420; Carpenito et al., PNAS, 2009; 106:3360-3365).

In some aspects, provided herein are CARs that include an extracellular (antigen-binding) domain, a transmembrane domain, and an intracellular (cytoplasmic) domain that includes a cytoplasmic sequence of CD3ζ sequence sufficient to stimulate a T cell when the antigen-binding domain binds to the antigen, and optionally, a cytoplasmic sequence of one or more (e.g., two, three, or four) co-stimulatory proteins (e.g., a cytoplasmic sequence of one or more of B7-H3, BTLA, CD2, CD7, CD27, CD28, CD30, CD40, CD40L, CD80, CD160, CD244, ICOS, LAGS, LFA-1, LIGHT, NKG2C, 4-1BB, OX40, PD-1, PD-L1, TIM3, 2B4, DAP10, CD137, DAP12, and a ligand that specifically binds to CD83) that provides for co-stimulation of the T cell when the antigen-binding domain binds to the antigen. In some embodiments, a CAR can further include a linker. Additional aspects of CARs and CAR-expressing immune effector cells, including exemplary extracellular (antigen-binding) domains, linkers, transmembrane domains, and intracellular (cytoplasmic) domains, are described in, e.g., Kakarla et al., *Cancer J.* 20:151-155, 2014; Srivastava et al., *Trends Immunol.* 36:494-502, 2015; Nishio et al., *Oncoimmunology* 4(2): e988098, 2015; Ghorashian et al., *Br. J. Haematol.* 169:463-478, 2015; Levine, *Cancer Gene Ther.* 22:79-84, 2015; Jensen et al., *Curr. Opin. Immunol.* 33:9-15, 2015; Singh et al., *Cancer Gene Ther.* 22:95-100, 2015; Li et al., *Zhongguo Shi Yan Xue Ye Xue Za Zhi* 22:1753-1756, 2014; Gill et al., *Immunol. Rev.* 263:68-89, 2015; Magee et al., *Discov. Med.* 18:265-271, 2014; Gargett et al., *Front. Pharmacol.* 5:235, 2014; Yuan et al., *Zhongguo Shi Yan Xue Ye Xue Za Zhi* 22:1137-1141, 2014; Pedgram et al., *Cancer J.* 20:127-133, 2014; Eshhar et al., *Cancer J.* 20:123-126, 2014; Ramos et al., *Cancer J.* 20:112-118, 2014; Maus et al., *Blood* 123: 2625-2635, 2014; Jena et al., *Curr. Hematol. Malig. Rep.*

9:50-56, 2014; Maher et al., *Curr. Gene Ther.* 14:35-43, 2014; Riches et al., *Discov. Med.* 16:295-302, 2013; Cheadle et al., *Immunol. Rev.* 257:83-90, 2014; Davila et al., *Int. J. Hematol.* 99:361-371, 2014; Xu et al., *Cancer Lett.* 343:172-178, 2014; Kochenderfer et al., *Nat. Rev. Clin. Oncol.* 10:267-276, 2013; Hosing et al., *Curr. Hematol. Malig. Rep.* 8:60-70, 2013; Hombach et al., *Curr. Mol. Med.* 13:1079-1088, 2013; Xu et al., *Leuk. Lymphoma* 54:255-260, 2013; Gilham et al., *Trends Mol. Med.* 18:377-384, 2012; Lipowska-Bhalla et al., *Cancer Immunol. Immunother.* 61:953-962, 2012; Chmielewski et al., *Cancer Immunol. Immunother.* 61:1269-1277, 2013; Jena et al., *Blood* 116:1035-1044, 2010; Dotti et al, *Immunology Reviews* 257(1): 107-126, 2013; Dai et al., *Journal of the National Cancer Institute* 108(7): djv439, 2016; Wang and Riviere, *Molecular Therapy-Oncolytics* 3: 16015, 2016; U.S. Patent Application Publication Nos. 2018/0057609; 2018/0037625; 2017/0362295; 2017/0137783; 2016/0152723; 2016/0206656, 2016/0199412, 2016/0208018, 2015/0232880, 2015/0225480; 2015/0224143; 2015/0224142; 2015/0190428; 2015/0196599; 2015/0152181; 2015/0140023; 2015/0118202; 2015/0110760; 2015/0099299; 2015/0093822; 2015/0093401; 2015/0051266; 2015/0050729; 2015/0024482; 2015/0023937; 2015/0017141; 2015/0017136; 2015/0017120; 2014/0370045; 2014/0370017; 2014/0369977; 2014/0349402; 2014/0328812; 2014/0322275; 2014/0322216; 2014/0322212; 2014/0322183; 2014/0314795; 2014/0308259; 2014/0301993; 2014/0296492; 2014/0294784; 2014/0286973; 2014/0274909; 2014/0274801; 2014/0271635; 2014/0271582; 2014/0271581; 2014/0271579; 2014/0255363; 2014/0242701; 2014/0242049; 2014/0227272; 2014/0219975; 2014/0170114; 2014/0134720; 2014/0134142; 2014/0120622; 2014/0120136; 2014/0106449; 2014/0106449; 2014/0099340; 2014/0086828; 2014/0065629; 2014/0050708; 2014/0024809; 2013/0344039; 2013/0323214; 2013/0315884; 2013/0309258; 2013/0288368; 2013/0287752; 2013/0287748; 2013/0280221; 2013/0280220; 2013/0266551; 2013/0216528; 2013/0202622; 2013/0071414; 2012/0321667; 2012/0302466; 2012/0301448; 2012/0301447; 2012/0060230; 2011/0213288; 2011/0158957; 2011/0104128; 2011/0038836; 2007/0036773; and 2004/0043401. Additional aspects of CARs and CAR-expressing immune effector cells, including exemplary extracellular (antigen-binding) domains, linkers, transmembrane domains, and intracellular (cytoplasmic) domains, are described in WO 2016/168595; WO 12/079000; 2015/0141347; 2015/0031624; 2015/0030597; 2014/0378389; 2014/0219978; 2014/0206620; 2014/0037628; 2013/0274203; 2013/0225668; 2013/0116167; 2012/0230962; 2012/0213783; 2012/0093842; 2012/0071420; 2012/0015888; 2011/0268754; 2010/0297093; 2010/0158881; 2010/0034834; 2010/0015113; 2009/0304657; 2004/0043401; 2014/0322253; 2015/0118208; 2015/0038684; 2014/0024601; 2012/0148552; 2011/0223129; 2009/0257994; 2008/0160607; 2008/0003683; 2013/0121960; 2011/0052554; and 2010/0178276.

In some aspects, provided herein are CARs that comprise an intracellular domain, a transmembrane domain and an extracellular domain, wherein the extracellular domain comprises any antibody, or antigen binding fragment thereof, or a bispecific molecule described herein. In some aspects, provided herein are chimeric antigen receptors (CARs) comprising an intracellular domain, a transmembrane domain and an extracellular binding domain, wherein the extracellular binding domain comprises any antibody, or antigen binding fragment thereof, or a bispecific molecule described herein, wherein such antibody, antigen binding fragment thereof, or bispecific molecule binds to an antigen comprising an NPM1c neoepitope in complex with (or presented by) a class I major histocompatibility complex (MHC class I) protein.

In some aspects, provided herein are chimeric antigen receptors (CARs) having the intracellular, transmembrane and/or extracellular domains of NPM1c CAR described in the Examples section (see, e.g., Example 3).

In some aspects, provided herein are CARs comprising an intracellular domain comprising one or more costimulatory domains of one or more costimulatory molecules selected from the group consisting of: CD27, CD28, 4-1BB, OX40, CD30, CD40, PD-1, ICOS, 2B4, DAP10, CD137 and DAP12. In specific embodiments, provided herein are CARs comprising an intracellular domain comprising a CD3-zeta signaling domain and, optionally, a 4-1BB costimulatory domain. In some aspects, provided herein are CARs comprising a transmembrane domain of CD3-zeta, CD8, CD28, NKG2D, CD16, NKp44 or NKp46. In specific embodiments, provided herein are CARs comprising a transmembrane domain comprising a CD8 transmembrane domain. In some aspects, provided herein are CARs comprising an extracellular domain comprising any antibody or antigen binding fragment thereof described herein (e.g., scFv). In specific embodiments, provided herein are CARs comprising an extracellular domain comprising any antibody or antigen binding fragment thereof described herein (e.g., scFv) that specifically binds to an antigen comprising a mutant nucleophosmin protein epitope (e.g., an NPM1c neoepitope) in complex with (or presented by) a class I major histocompatibility complex (MHC class I) protein (e.g., HLA-A2). In specific embodiments, provided herein are CARs comprising an extracellular domain comprising any antibody or antigen binding fragment thereof described herein (e.g., scFv) that specifically binds to an antigen comprising AIQDLCLAV (SEQ ID NO:1) neoepitope in complex with (or presented by) a class I major histocompatibility complex (MHC class I) protein (e.g., HLA-A2). In specific embodiments, provided herein are CARs comprising an extracellular domain comprising any antibody or antigen binding fragment thereof described herein (e.g., scFv) comprising a VH and a VL, wherein the VH comprises the amino acid sequence of SEQ ID NO:5 or an amino acid sequence that is at least 75%, 80%, 85%, 90%, 95%, 98% or 99% identical to SEQ ID NO:5, and wherein the VL comprises the amino acid sequence of SEQ ID NO:3 or an amino acid sequence that is at least 75%, 80%, 85%, 90%, 95%, 98% or 99% identical to SEQ ID NO:3. In specific embodiments, provided herein are CARs comprising an extracellular domain comprising any antibody or antigen binding fragment thereof described herein (e.g., scFv) comprising a VH comprising VH CDR1 having amino acid sequence of SEQ ID NO:9, VH CDR2 having amino acid sequence of SEQ ID NO:10, CDR3 having amino acid sequence of SEQ ID NO:11, and/or comprising a VL comprising VL CDR1 having amino acid sequence of SEQ ID NO:6, VL CDR2 having amino acid sequence of SEQ ID NO:7, and VL CDR3 having amino acid sequence of SEQ ID NO:8. In specific embodiments, provided herein are CARs comprising an extracellular domain comprising any antibody or antigen binding fragment thereof described herein (e.g., scFv) comprising a VH comprising VH CDR1, VH CDR2 and VH CDR3 being the CDRs of a VH that has an amino acid sequence of SEQ ID NO:5, and/or comprising a VL comprising VL CDR1, VL CDR2 and VL CDR3 being the CDRs of a VL that has an amino acid sequence of SEQ ID NO:3. In specific embodiments, provided herein are CARs comprising an extracellular domain comprising an scFv that has the amino acid sequence of SEQ ID NO:2, or an scFv that has amino acid sequence that is at least 75%, 80%, 85%, 90%, 95%, 98% or 99% identical to SEQ ID NO:2.

Examples of extracellular, transmembrane and intracellular domains of CARs provided herein are described below.

Antibody Antigen Binding Domains, Including Extracellular (Antigen Binding) Domains of CARs Non-limiting examples of an antigen binding domains include: a monoclonal antibody (e.g., IgG1, IgG2, IgG3, IgG4, IgM, IgE, and IgD) (e.g., a fully human or a chimeric (e.g., a humanized) antibody), an antigen binding fragment of an antibody (e.g., Fab, Fab', or F(ab')$_2$ fragments) (e.g., a fragment of a fully human or a chimeric (e.g., humanized) antibody), a diabody, a triabody, a tetrabody, a minibody, a scFv, scFv-Fc, (scFv)$_2$, scFab, bis-scFv, hc-IgG, a BiTE, a single domain antibody (e.g., a V-NAR domain or a VhH domain), IgNAR, and a multispecific (e.g., bispecific antibody) antibody. In one embodiment, the antigen binding domain comprises an scFv. Methods of making these antigen-binding domains are known in the art.

In some embodiments, an antigen binding domain includes at least one (e.g., one, two, three, four, five, or six) CDR (e.g., any of the three CDRs from an immunoglobulin light chain variable domain and/or any of the three CDRs from an immunoglobulin heavy chain variable domain) of an antibody that is capable of specifically binding to the target antigen, such as immunoglobulin molecules (e.g., light or heavy chain immunoglobulin molecules) and immunologically-active (antigen-binding) fragments of immunoglobulin molecules.

In some embodiments, an antigen binding domain is a single-chain antibody (e.g., a V-NAR domain or a V$_H$H domain, or any of the single-chain antibodies as described herein). In some embodiments, an antigen binding domain is a whole antibody molecule (e.g., a human, humanized, or chimeric antibody) or a multimeric antibody (e.g., a bi-specific antibody).

In some embodiments, antigen-binding domains include antibody fragments and multi-specific (e.g., bi-specific) antibodies or antibody fragments. Examples of antibodies and antigen-binding fragments thereof include but are not limited to: single-chain Fvs (scFvs), Fab fragments, Fab' fragments, F(ab')$_2$, disulfide-linked Fvs (sdFvs), Fvs, and fragments containing either a VL or a VH domain.

Additional antigen binding domains provided herein are polyclonal, monoclonal, multi-specific (multimeric, e.g., bi-specific), human antibodies, chimeric antibodies (e.g., human-mouse chimera), single-chain antibodies, intracellularly-made antibodies (i.e., intrabodies), and antigen-binding fragments thereof. The antibodies or antigen-binding fragments thereof can be of any type (e.g., IgG, IgE, IgM, IgD, IgA, and IgY), class (e.g., IgG$_1$, IgG2, IgG3, IgG4, IgA$_1$, and IgA2), or subclass. In some embodiments, the antigen binding domain is an IgG$_1$ antibody or antigen-binding fragment thereof. In some examples, the antigen binding domain is an IgG4 antibody or antigen-binding fragment thereof. In some embodiments, the antigen binding domain is an immunoglobulin comprising a heavy and light chain.

Additional examples of antigen binding domains are antigen-binding fragments of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4), an antigen-binding fragment of an IgA (e.g., an antigen-binding fragment of IgA1 or IgA2) (e.g., an antigen-binding fragment of a human or humanized IgA, e.g., a human or humanized IgA1 or IgA2), an antigen-binding fragment of an IgD (e.g., an antigen-binding fragment of a human or humanized IgD), an antigen-binding fragment of an IgE (e.g., an antigen-binding fragment of a human or humanized IgE), or an antigen-binding fragment of an IgM (e.g., an antigen-binding fragment of a human or humanized IgM).

In some embodiments, an antigen binding domain can bind to a particular antigen (e.g., a tumor-associated antigen) with an affinity ($K_D$) about or higher than $1\times10^{-7}$ M (e.g., about or higher than $1\times10^{-8}$ M, about or higher than $1\times10^{-9}$ M, about or higher than 500 nM, about or higher than 100 nM, about or higher than 25 nM, about or higher than 15 nM, about or higher than 7 nM, about or higher than 5 nM, or about or higher than 1 nM), e.g., in saline or in phosphate buffered saline.

As can be appreciated by those in the art, the choice of the antigen binding domain to include in the CAR depends upon the type and number of ligands that define the surface of a cell (e.g., cancer cell or tumor) to be targeted in a subject in need thereof. For example, the antigen binding domain may be chosen to recognize a tumor specific antigen (TSA), such as a cancer neoantigen. For example, the tumor specific antigen may be an NMP1c neoantigen in complex with (or presented by) a MHC Class I protein (e.g., HLA-A2), such as NPM1c:HLA-A2. In some embodiments, the NMP1c neoantigen comprises the amino acid sequence AIQDLCLAV (SEQ ID NO:1)

In some embodiments, the CAR molecule comprises an antigen binding domain that recognizes a tumor antigen of an acute myeloid leukemia. In some embodiments, the tumor antigen is a tumor-specific antigen (TSA), such as an acute myeloid leukemia neoantigen. A TSA is unique to tumor cells and does not occur on other cells in the body. In one embodiment, the tumor antigen is a tumor specific antigen. In certain embodiments, the tumor-specific antigen is determined by sequencing a patient's tumor cells and identifying mutated proteins only found in the tumor. These antigens are referred to as "neoantigens." Once a neoantigen has been identified, therapeutic antibodies can be produced against it and used in the methods described herein. In one embodiment, the neoantigen is an NPM1c neoantigen. In one embodiment, the NPM1c neoantigen is in complex with (or presented by) a MHC Class I protein (e.g., HLA-A2), such as NPM1c:HLA-A2.

Tumor antigens, (e.g. tumor-associated antigens (TAAs) and tumor-specific antigens (TSAs)) that may be targeted by CAR effector cells (e.g., CART cells), include, but are not limited to NPM1c:HLA-A2. In one embodiment, the tumor specific antigen is NPM1c:HLA-A2.

Linkers Between Domains of CARs

Provided herein are CARs that can optionally include a linker: (1) between the extracellular (antigen binding) domain and the transmembrane domain, and/or (2) between the transmembrane domain and the intracellular (cytoplasmic) domain. In some embodiments, the linker can be a polypeptide linker. For example, the linker can have a length of between about 1 amino acid and about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, about 8 amino acids, about 6 amino acids, about 4 amino acids, or about 2 amino acids; about 2 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, about 8 amino acids, about 6 amino acids, or about 4 amino acids; about 4 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, about 8 amino acids, or about 6 amino acids; about 6 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, about 12 amino acids, about 10 amino acids, or about 8 amino acids; about 8 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, about 12 amino acids, or about 10 amino acids; about 10 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, about 14 amino acids, or about 12 amino acids; about 12 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, about 18 amino acids, about 16 amino acids, or about 14 amino acids; about 14 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, about 20 amino acids, or about 18 amino acids; about 18 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, about 25 amino acids, or about 20 amino acids; about 20 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, about 30 amino acids, or about 25 amino acids; about 25 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, about 35 amino acids, or about 30 amino acids; about 30 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, about 40 amino acids, or about 35 amino acids; about 35 amino acids to about 500 amino acids, about 400 amino acids, about 300 amino acids, about 200 amino acids, about 100 amino acids, about 90 amino acids, about 80 amino acids, about 70 amino acids, about 60 amino acids, about 50 amino acids, or about 40 amino acids; about 40 amino acids to about 500 amino acids, about 400 amino acids, about 300 amino acids, about 200 amino acids, about 100 amino acids, about 90 amino acids, about 80 amino acids, about 70 amino acids, about 60 amino acids, or about 50 amino acids; about 50 amino acids to about 500 amino acids, about 400 amino acids, about 300 amino acids, about 200 amino acids, about 100 amino acids, about 90 amino acids, about 80 amino acids, about 70 amino acids, or about 60 amino acids; about 60 amino acids to about 500 amino acids, about 400 amino acids, about 300 amino acids, about 200 amino acids, about 150 amino acids, about 100 amino acids, about 90 amino acids, about 80 amino acids, or about 70 amino acids; about 70 amino acids to about 500 amino acids, about 400 amino acids, about 300 amino acids, about 200 amino acids, about 100 amino acids, about 90 amino acids, or about 80 amino acids; about 80 amino acids to about 500 amino acids, about 400 amino acids, about 300 amino acids, about 200 amino acids, about 100 amino acids, or about 90 amino acids; about 90 amino acids to about 500 amino acids, about 400 amino acids, about 300 amino acids, about 200 amino acids, or about 100 amino acids; about 100 amino acids to about 500 amino acids, about 400 amino acids, about 300 amino acids, or about 200 amino acids; about 200 amino acids to about 500 amino acids, about 400 amino acids, or about 300 amino acids; about 300 amino acids to about 500 amino acids or about 400 amino acids; or about 400 amino acids to about 500 amino acids.

Transmembrane Domains of CARs

The CARs provided herein also include a transmembrane domain. In some embodiments, the transmembrane domain may be derived from a natural source. In some embodiments, the transmembrane domain may be derived from any membrane-bound or transmembrane protein. Non-limiting examples of transmembrane domains that may be used in CARs described herein may be derived from (e.g., comprise at least the transmembrane sequence or a part of the transmembrane sequence of) the alpha, beta, or zeta chain of the T-cell receptor, CD28, CD3 epsilon, CD33, CD37, CD64, CD80, CD45, CD4, CD5, CD8, CD9, CD16, CD22, CD86, CD 134, CD137, or CD 154. In one embodiment, the transmembrane domain is from a CD4 molecule. In one embodiment, the transmembrane domain is from a CD8 molecule.

In some embodiments, the transmembrane domain may be synthetic. For example, in some embodiments where the transmembrane domain is from a synthetic source, the transmembrane domain may include (e.g., predominantly include) hydrophobic residues (e.g., leucine and valine). In some embodiments, the synthetic transmembrane domain will include at least one (e.g., at least two, at least three, at least four, at least five, or at least six) triplet of phenylalanine, tryptophan, and valine at the end of a synthetic transmembrane domain. In some embodiments, the transmembrane domain of a CAR can include a CD8 hinge domain.

In some embodiments, the transmembrane domain is naturally associated with a sequence in the cytoplasmic domain. In some embodiments, the transmembrane domain can be modified by one or more (e.g., two, three, four, five, six, seven, eight, nine, or ten) amino acid substitutions to avoid the binding of the domain to other transmembrane domains (e.g., the transmembrane domains of the same or different surface membrane proteins) to minimize interactions with other members of the receptor complex.

In some embodiments, the transmembrane domain of CARs provided herein comprises the transmembrane domain of CD3-zeta, CD8, CD28, NKG2D, CD16, NKp44, or NKp46. In specific embodiments, the transmembrane domain of CARs provided herein comprises the transmembrane domain of CD3-zeta, CD8 or CD28. In some of these embodiments, the intracellular domain of the CAR comprises a costimulatory domain of a costimulatory molecule selected from the group consisting of: CD27, CD28, 4-1BB, OX40, CD30, CD40, PD-1, ICOS, and any combination thereof.

Intracellular (Cytoplasmic) Domains of CARs

The intracellular domain can be any polypeptide domain known to function to transmit a signal causing, for example, activation of an immune effector cell such as a T cell, a NK cell or a macrophage. Such a domain or motif may transmit a primary antigen-binding signal that is necessary for the activation of a T lymphocyte in response to the binding of the extracellular domain of the CAR to the target antigen. Examples of intracellular domains include, without limitation, ILR chain, CD28, 4-1BB and CD3ζ.

Typically, the intracellular domain comprises an ITAM (immunoreceptor tyrosine-based activation motif).

In one embodiment, the intracellular domain is or comprises a CD3ζ signaling sequence (e.g., an ITAM-containing portion thereof). In one embodiment, the intracellular domain comprises a lymphocyte receptor chain. In one embodiment, the intracellular domain comprises a TCR/CDR3 complex protein. In one embodiment, the intracellular domain comprises an Fc receptor subunit. In one embodiment, the intracellular domain comprises an IL-2 receptor subunit.

The intracellular domain of CARs provided herein can include two distinct classes of cytoplasmic signaling sequences: signaling sequences that initiate antigen-dependent activation through the TCR (primary cytoplasmic signaling sequences) (e.g., a CD3ζ cytoplasmic signaling sequence) and a cytoplasmic sequence of one or more of co-stimulatory proteins that act in an antigen-independent manner to provide a secondary or co-stimulatory signal (secondary cytoplasmic signaling sequences).

In certain embodiments, provided herein are CARs that comprise an intracellular signaling domain that includes a cytoplasmic sequence of CD3ζ sufficient to stimulate a T cell when the antigen binding domain binds to the antigen, and optionally, a cytoplasmic sequence of one or more of co-stimulatory proteins (e.g., a cytoplasmic sequence of one or more of CD27, CD28, 4-1BB, OX40, CD30, CD40L, CD40, PD-1, PD-L1, ICOS, LFA-1, CD2, CD7, CD160, LIGHT, BTLA, TIM3, CD244, CD80, LAGS, NKG2C, B7-H3, 2B4, DAP10, CD137, DAP12, a ligand that specifically binds to CD83, and any of the ITAM sequences described herein or known in the art) that provides for co-stimulation of the T cell. In some embodiments, the entire intracellular signaling domain of a co-stimulatory protein is included in the intracellular domain of a CAR. In some embodiments, the intracellular domain includes a truncated portion of an intracellular signaling domain of a co-stimulatory protein (e.g., a truncated portion of the intracellular signaling domain that transduces an effector function signal in the CAR-expressing immune effector cell). Non-limiting examples of intracellular signaling domains that can be included in an intracellular domain include the cytoplasmic sequences of the T cell receptor (TCR) and co-receptors that act in concert to initiate signal transduction following antigen receptor engagement, as well as any variant of these sequences including at least one (e.g., one, two, three, four, five, six, seven, eight, nine, or ten) substitution and have the same or about the same functional capability.

In some embodiments, the intracellular domain of a CAR can be designed to include the CD3ζ signaling domain by itself or combined with any other desired cytoplasmic signaling sequence(s) useful in the context of a CAR. In some embodiments, the cytoplasmic domain of a CAR can include a CD3ζ chain portion and a costimulatory cytoplasmic signaling sequence. The costimulatory cytoplasmic signaling sequence refers to a portion of a CAR including a cytoplasmic signaling sequence of a costimulatory protein (e.g., CD27, CD28, 4-IBB (CD 137), OX40, CD30, CD40, PD-1, ICOS, lymphocyte function-associated antigen-1 (LFA-1), CD2, CD7, LIGHT, NKG2C, B7-H3, and a ligand that specifically binds with CD83).

In some embodiments, the cytoplasmic signaling sequences within the intracellular domain of a CAR are positioned in a random order. In some embodiments, the cytoplasmic signaling sequences within the intracellular domain of a CAR are linked to each other in a specific order. In some embodiments, a linker (e.g., any of the linkers described herein) can be used to form a linkage between different cytoplasmic signaling sequences.

In some embodiments, the intracellular domain is designed to include the cytoplasmic signaling sequence of CD3ζ and the cytoplasmic signaling sequence of the costimulatory protein CD28. In some embodiments, the intracellular domain is designed to include the cytoplasmic signaling sequence of CD3ζ and the cytoplasmic signaling sequence of costimulatory protein 4-IBB. In some embodiments, the intracellular domain is designed to include the cytoplasmic signaling sequence of CD3ζ and the cytoplasmic signaling sequences of costimulatory proteins CD28 and 4-1BB. In some embodiments, the intracellular domain does not include the cytoplasmic signaling sequences of 4-1BB.

In some embodiments, the CAR comprises one or more co-stimulatory domains derived from a protein such as CD28, CD137 (also known as 4-1BB), CD134 (also known as OX40) and CD278 (also known as ICOS). In some embodiments, the CAR does not comprise a co-stimulatory domain derived from CD137.

In certain embodiments, the intracellular domain further comprises a cytokine. In some embodiments, the intracellular domain further comprises a self-cleaving domain (e.g., the P2A self-cleaving peptide) and a cytokine, wherein the cleavage of the self-cleaving domain releases the cytokine. In some embodiments, the self-cleaving domain (e.g., the P2A self-cleaving peptide) and the cytokine are positioned at the C-terminal end of the CAR protein and its intracellular domain. In some embodiments, the cytokine is one or more of the following: IL-12, IL-7, IL-13, IL-15, IL-4, IL-10, TNF-α, IFN-γ, TGF-β and CCL19. In one embodiment, the cytokine is IL-12. In one embodiment, the cytokine is IL-7. In one embodiment, the cytokine is IL-13. In one embodiment, the cytokine is IL-15. In one embodiment, the cytokine is IL-4. In one embodiment, the cytokine is IL-10. In one embodiment, the cytokine is TNF-α. In one embodiment, the cytokine is IFN-γ. In one embodiment, the cytokine is TGF-β. In one embodiment, the cytokine is CCL19. Immune effector cells modified to express a cytokine are known in the art (see, e.g., Adachi et al, 2018, Nature Biotechnology, doi:10.1038/nbt.4086; Liu et al., 2019, J. Immunol., doi:10.4049/jimmunol.1800033; Krenciute et al., 2017, Cancer Immunol. Res. 597):571-581, doi:10.1158/2326-6066, CIR-16-0376; Liu et al., 2018, Leukemia 32:520-531). In certain embodiments, the modification of immune effector cells described herein to express a cytokine is the same as that described in Adachi et al, 2018, Nature Biotechnology, doi:10.1038/nbt.4086; Liu et al., 2019, J. Immunol., doi:10.4049/jimmunol.1800033; Krenciute et al., 2017, Cancer Immunol. Res. 597):571-581, doi:10.1158/2326-6066, CIR-16-0376; or Liu et al., 2018, *Leukemia* 32:520-531, or in accordance with the methods described therein.

CAR-Expressing Immune Effector Cells

In one aspect, provided herein are immune effector cells comprising any chimeric antigen receptor (CAR) described herein. In certain embodiments, provided herein are immune effector cells transformed with a nucleic acid encoding any chimeric antigen receptor (CAR) described herein. In certain embodiments, provided herein are immune effector cells expressing any chimeric antigen receptor (CAR) described herein.

Immune effector cells that can be used for carrying or expressing a CAR include, without limitation, T cells, natural killer (NK) cells and macrophages. In one embodiment, the immune effector cell is a T cell (e.g., a cytotoxic T cell). In one embodiment, the immune effector cell is an NK cell. In one embodiment, the immune effector cell is a macrophage.

In some aspects, the immune effector cells provided herein have been isolated from, or expanded from, peripheral blood, cord blood, or lymph.

In some aspects, the immune effector cells provided herein are autologous to a subject to whom they are to be administered (after their modification to express a CAR described herein). In certain embodiments, the immune effector cells provided herein are allogeneic to a subject to whom they are to be administered (after their modification to express a CAR described herein). Where allogeneic immune effector cells are used to prepare CAR-expressing immune effector cells, immune effector cells can be selected that will reduce the possibility of graft-versus-host disease in the subject or the immune effector cells can be co-administered with one or more immunosuppressive agents. In some embodiments, an immune effector cell is obtained from a subject, optionally expanded, and transformed with a polynucleotide expressing a CAR described herein, and optionally further expanded.

In some aspects, immune effector cells are derived from a patient with a disease or condition (such as cancer, e.g., AML) and genetically modified in vitro to express at least one CAR with specificity for any antigen described herein (e.g., neoantigen). For example, the antigen can be a cancer neoantigen presented by an MHC class I protein (such as an antigen comprising a mutant nucleophosmin protein neoepitope in complex with an MHC class I protein, e.g., NPM1c:HLA-A2). In some of these embodiments, the immune effector cells genetically modified to express a CAR with specificity for be a cancer neoantigen presented by an MHC class I protein (e.g., NPM1c:HLA-A2) is then administered to treat cancer in the patient (e.g., NPM1c-positive cancer, e.g., AML). In some embodiments, the immune effector cells perform at least one effector function (e.g. induction of cytokines) that is stimulated or induced by the specific binding of the ligand or antigen to the CAR and that is useful for treatment of the same patient's disease or condition. In some embodiments, the effector cell is a T cell (e.g. a cytotoxic T cell) that exerts its effector function (e.g. a cytotoxic T cell response) on a target cell when brought in contact or in proximity to the target or target cell (e.g. a cancer cell) (see e.g., Chang and Chen (2017) *Trends Mol Med* 23(5):430-450).

The stimulation of an immune effector cell comprising a CAR (e.g., by binding of the extracellular domain of the CAR to a cancer neoantigen) can result in the activation of one or more anti-cancer activities of the CAR immune effector cell. For example, in some embodiments, stimulation of a CAR immune effector cell can result in an increase in the cytolytic activity or helper activity of the CAR immune effector cell, including the secretion of cytokines.

In some embodiments, CAR effector cells (e.g., CAR T cells) comprise a CAR molecule that binds to any antigen described herein (e.g., NPM1c:HLA-A2). In some embodiments, the immune effector cell comprising a CAR molecule (e.g., CAR T cell) useful in the methods disclosed herein expresses a CAR comprising an extracellular domain that binds an NPM1c neoepitope in complex with (or presented by) an MHC class I protein (e.g., HLA-A2), such as NPM1c: HLA-A2. In some embodiments, the immune effector cell comprising a CAR molecule (e.g., CAR T cell) useful in the methods disclosed herein expresses a CAR comprising an NPM1c:HLA-A2 binding domain.

Prolonged exposure of T cells to their cognate antigen can result in exhaustion of effector functions, enabling the persistence of infected or transformed cells. Recently developed strategies to stimulate or rejuvenate host effector function using agents that induce an immune checkpoint blockade have resulted in success towards the treatment of several cancers. Emerging evidence suggests that T cell exhaustion may also represent a significant impediment in sustaining long-lived antitumor activity by chimeric antigen receptor-expressing T cells (CAR T cells). The differentiation status of the patient-harvested T cells prior to CAR transduction and the conditioning regimen a patient undergoes before reintroducing the CAR T cells (e.g., addition or exclusion of alkylating agents, fludarabine, total-body irradiation) can profoundly affect the persistence and cytotoxic potential of CAR T cells. In vitro culture conditions that stimulate (via anti-CD3/CD28 or stimulator cells) and expand (via cytokines, such as IL-2) T cell populations can also alter the differentiation status and effector function of CART cells (Ghoneim et al., (2016) *Trends in Molecular Medicine* 22(12): 1000-1011).

Methods of Making CAR-Expressing Immune Effector Cells

Provided herein are methods that can be used to generate any of the immune effector cells described herein comprising any CAR described herein.

In some embodiments, a subject's immune effector cells (e.g., T cells) are genetically modified with a chimeric antigen receptor (Sadelain et al., *Cancer Discov.* 3:388-398, 2013). For example, an immune effector cell (e.g., a T cell) is provided and recombinant nucleic acid encoding a chimeric antigen receptor is introduced into the patient-derived immune effector cell (e.g., a T cell) to generate a CAR cell. In some embodiments, immune effector cells (e.g., T cells) not derived from the subject are genetically modified with a chimeric antigen receptor. For example, in some embodiments, immune effector cells (e.g., T cells) are allogeneic cells that have been engineered to be used as an "off the shelf" adoptive cell therapy, such as Universal Chimeric Antigen Receptor T cells (UCARTs), as developed by Cellectis.

A variety of different methods known in the art can be used to introduce any of the nucleic acids encoding a CAR described herein or expression vectors comprising a nucleic acid encoding a CAR described herein into an immune effector cell (e.g., a T cell). Non-limiting examples of methods for introducing nucleic acid into an immune effector cell (e.g., a T cell) include: lipofection, transfection (e.g., calcium phosphate transfection, transfection using highly branched organic compounds, transfection using cationic polymers, dendrimer-based transfection, optical transfection, particle-based transfection (e.g., nanoparticle transfection), or transfection using liposomes (e.g., cationic liposomes)), microinjection, electroporation, cell squeezing, sonoporation, protoplast fusion, impalefection, hydrodynamic delivery, gene gun, magnetofection, viral transfection, and nucleofection. Furthermore, the CRISPR/Cas9 genome editing technology known in the art can be used to introduce CAR nucleic acids into immune effector cells (e.g., T cells) and/or to introduce other genetic modifications (e.g., as described below) into immune effector cells (e.g., T cells) to enhance CAR T cell activity (for use of CRISPR/Cas9 technology in connection with CAR T cells, see e.g., U.S. Pat. Nos. 9,890,393; 9,855,297; US 2017/0175128; US 2016/0184362; US 2016/0272999; WO 2015/161276; WO 2014/191128; CN 106755088; CN 106591363; CN 106480097; CN 106399375; CN 104894068).

In some aspects, a method for producing an immune effector cell described herein comprises: (i) obtaining cells from peripheral blood, cord blood or lymph (e.g., from peripheral blood mononuclear cells (PMBC)), (ii) optionally, purifying the obtained cells, (iii) optionally, expanding the cells, (iv) optionally, activating the cells (e.g., with an anti-CD3 antibody or an antigen binding fragment thereof and/or an anti-CD28 antibody or an antigen-binding fragment thereof), (v) optionally, expanding the activated cells, (vi) transducing the cells with an expression vector comprising a CAR described herein, (vii) isolating the cells expressing the CAR, and (viii) optionally, expanding the isolated cells.

In some aspects, a method for producing an immune effector cell described herein comprises: (i) obtaining a pluripotent stem cell (iPSC) (ii) inducing iPSC to differentiate into an immune effector cell (e.g., into a NK cell, a macrophage or a T cell (such as CD8$^+$ T cell)), (iii) optionally, expanding the immune effector cells, (iv) transducing the immune effector cells with an expression vector comprising a CAR described herein, (v) isolating the immune effector cells expressing the CAR, and (vi) optionally, expanding the isolated cells.

Compositions

In one aspect, provided herein are compositions (e.g., pharmaceutical compositions) comprising the antibodies or antigen binding fragments thereof disclosed herein. The antibody or fragment in the pharmaceutical composition can be purified.

In one aspect, provided herein are compositions (e.g., pharmaceutical compositions) comprising the bispecific molecules (e.g., the bispecific antibodies) disclosed herein. The bispecific molecule in the pharmaceutical composition can be purified.

In one aspect, provided herein are compositions (e.g., pharmaceutical compositions) comprising any immune effector cell (e.g., CAR polypeptide expressing immune effector cell) disclosed herein.

Pharmaceutical compositions may comprise a pharmaceutically acceptable carrier. Appropriate pharmaceutically acceptable carriers, including but not limited to excipients and stabilizers, are known in the art (see, e.g., Remington's Pharmaceutical Sciences (1990) Mack Publishing Co., Easton, Pa.).

Pharmaceutical compositions can be sterile compositions that comprise cells, tethering means (e.g., lipid nanoparticles) and/or proteins or peptides, preferably in a pharmaceutically-acceptable carrier (e.g., one or more compatible solid or liquid filler, diluents or encapsulating substances that are suitable for administration to a human or other subject contemplated herein). The carrier can be an organic or inorganic ingredient, natural or synthetic, with which the cells, tethering means (e.g., lipid nanoparticles) and/or proteins or peptides are combined to facilitate administration. The components of the pharmaceutical compositions are commingled in a manner that precludes interaction that would substantially impair their desired pharmaceutical efficiency.

Pharmaceutically acceptable carriers may include, without limitation, a buffer, an emulsifying agent, a suspending agent, a dispersing agent, an isotonic agent, a wetting agent, a chelating agent, a sequestering agent, a pH buffering agent, a solubility enhance, an antimicrobial agent, an anesthetic, and/or an antioxidant.

Various excipients for formulating pharmaceutical compositions and techniques for preparing the composition are known in the art (see Remington: *The Science and Practice of Pharmacy*, 21st Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition. Excipients may include, for example: antiadherents, antioxidants, binders, coatings, compression aids, disintegrants, dyes (colors), emollients, emulsifiers, fillers (diluents), film formers or coatings, glidants (flow enhancers), lubricants, preservatives, printing inks, sorbents, suspending or dispersing agents, sweeteners, and waters of hydration. Exemplary excipients include, but are not limited to: saline, butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, sucrose, dextrose, magnesium stearate, malt, maltitol, mannitol, methionine, methylcellulose, methyl paraben, microcrystalline cellulose, polyethylene glycol, glycerol, ethanol, polyvinyl pyrrolidone, povidone, starch (e.g., pregelatinized starch), propylene, propyl paraben, retinyl palmitate, shellac, silica gel, silicon dioxide, sodium carboxymethyl cellulose, sodium citrate, sodium stearate, sodium starch glycolate, sorbitol, starch (corn), stearic acid, talc, base cream, titanium dioxide, vitamin A, vitamin E, vitamin C, and xylitol.

In some embodiments, the pharmaceutical compositions disclosed herein may include at least one pharmaceutically acceptable salt. Examples of pharmaceutically acceptable salts that may be included in a composition of the disclosure include, but are not limited to, acid addition salts, alkali or alkaline earth metal salts, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like The pharmaceutical compositions can be formulated such that they are suitable for administration to a subject (e.g., a human). A pharmaceutical composition may be formulated for any route of administration.

The pharmaceutical compositions, when it is desirable to deliver them systemically, may be formulated for parenteral administration by injection, e.g., by bolus injection or continuous infusion. Such formulations can be prepared as liquid solutions, suspensions, emulsions or solid forms suitable making into a solution or suspension prior to injection. Formulations for injection may be presented in unit dosage form, e.g., in ampoules or in multi-dose containers. Pharmaceutical parenteral formulations include aqueous solutions of the ingredients. Aqueous injection suspensions may contain substances which increase the viscosity of the suspension, such as sodium carboxymethyl cellulose, sorbitol, or dextran. Alternatively, suspensions of ingredients may be prepared as oil-based suspensions. Suitable lipophilic solvents or vehicles include fatty oils such as sesame oil, or synthetic fatty acid esters, such as ethyl oleate or triglycerides, or liposomes. If administered parenterally, suitable pharmaceutically acceptable carriers may include, without limitation, physiological saline or phosphate buffered saline (PBS), or solutions containing, e.g., polyethylene glycol, polypropylene glycol or glucose.

The antibody or antigen binding fragment, bispecific molecule or CAR-expressing immune effector cell described herein can be used or present in a therapeutically effective amount in the pharmaceutical composition disclosed herein. The therapeutically effective amount can be determined by standard clinical techniques.

The pharmaceutically acceptable compositions contemplated herein may include, in addition to the antibody or antigen binding fragment, bispecific molecule or CAR-expressing immune effector cell described herein, an additional anti-cancer agent (e.g., any one, two, three or more anti-cancer agents described herein).

Therapeutic Methods and Uses

In one aspect, the disclosure provides for treating cancer (e.g., inhibiting cancer proliferation, inhibiting cancer progression) in a subject in need thereof comprising administering to the subject any antibody or antigen binding fragment described herein, any bispecific molecule described herein, any immune effector cell comprising a CAR polypeptide described herein, or any pharmaceutical composition described herein. In certain embodiments, the disclosure provides for treating an NPM1c-positive cancer. As used herein a "NPM1c-positive cancer" refers to a cancer comprising tumor cells with a mutation in the NPM1 gene (e.g., a 4 nt duplicative mutation in NPM1), wherein the mutation in NPM1 results in increased cytoplasmic localization of NPM1 protein when compared to cells expressing wild-type NPM1. Methods of measuring gene expression in a cancer to determine the presence of a particular genetic mutation (e.g., 4 nt duplicative mutation in NPM1) are known in the art, and comprise analysis of a malignant tumor sample collected from a subject (e.g., blood, bone marrow, tumor, and/or tissue sample). In some aspects, methods to detect small duplications, insertions, or deletions in a gene are performed using real time quantitative polymerase chain reaction (RT-PCR), droplet digital PCR, Sanger sequencing, and next-generation sequencing (e.g., whole-genome sequencing, e.g., whole-exome sequencing). In some aspects, a NPM1c-positive cancer is detected to have a mutation in the NPM1 gene (e.g., a 4 base pair frameshift insertion in exon 12 of the gene, a mutation encoding C-terminal 11 amino acids in an alternative reading frame, or an NPM1 mutation resulting in expression of a protein comprising the following C-terminal amino acid sequence: MTDQEAIQDLCLAVEEVSLRK (SEQ ID NO:57)). In some embodiments, a NPM1c-positive cancer comprises tumor cells with increased cytoplasmic localization of NPM1 protein. Methods of assessing NPM1 cellular localization are known in the art, for example, using a labeled anti-NPM1 antibody and assessing localization by microscopy or flow cytometry. In some embodiments, tumor cells isolated from a NPM1c-positive cancer have increased cytoplasmic localization of NPM1 protein when compared to cells isolated from a healthy non-cancerous tissue sample.

In some embodiments, the disclosure provides methods for treating NPM1c-positive cancer (e.g., inhibiting proliferation or progression of the cancer) in a subject in need thereof comprising administering to the subject an antibody or antigen binding fragment described herein, a bispecific molecule described herein, an immune effector cell comprising a CAR polypeptide described herein, or a pharmaceutical composition described herein.

In one aspect, the disclosure provides for treating AML (e.g., inhibiting proliferation or progression of AML) in a subject in need thereof comprising administering to the subject any antibody or antigen binding fragment described herein, any bispecific molecule described herein, any immune effector cell comprising a CAR polypeptide described herein, or any pharmaceutical composition described herein. In some embodiments, the patient harbors a mutation in the nucleophosmin 1 gene. In some embodiments, the AML comprises NPM1c-positive tumor cells or tumor cells that express a mutation in the nucleophosmin 1 gene. In certain embodiments, the disclosure provides for treating an NPM1c-positive AML.

In certain embodiments, the antibodies or antigen binding fragments thereof (e.g., scFv), bispecific molecules, CAR polypeptides, immune effector cells comprising CAR polypeptides, or pharmaceutical compositions of the disclosure can be used in the development of targeted immunotherapy for treating cancer. In some embodiments, the cancer is an NPM1c-positive cancer.

In certain embodiments, the antibodies or antigen binding fragments thereof (e.g., scFv), bispecific molecules, CAR polypeptides, immune effector cells comprising CAR polypeptides, or pharmaceutical compositions of the disclosure can be used for the treatment of AML. In some embodiments, the AML is NPM1c-positive.

In certain embodiments, the antibodies or antigen binding fragments thereof (e.g., scFv), bispecific molecules, CAR polypeptides, immune effector cells comprising CAR polypeptides, or pharmaceutical compositions of the disclosure can be used as cytotoxic agents to kill AML cells. In some embodiments, the AML cells, or a subpopulation thereof, are NPM1c-positive.

In some embodiments, the disclosure provides methods for treating a NPM1c-positive cancer (e.g., AML) in a subject carrying an allele encoding HLA-A2 (i.e., HLA-A*02:01 allele). In some embodiments, the NPM1c-positive cancer (e.g., AML) comprises tumor cells with expression of HLA-A2. Methods of determining HLA expression are known in the art, and includes flow cytometry, immunohistochemistry, and western blot using labeled antibodies that recognize HLA-A2. HLA expression may also be determined by RT-PCR and RNA sequencing.

In certain embodiments, the disclosure provides for treating cancer (e.g., NPM1c-positive cancer, e.g., AML) in a subject in need thereof, wherein the cell surface of cells comprising the cancer displays an NPM1c neoepitope in complex with an MHC class I protein (e.g., HLA-A2), the treating comprising administering to the subject any antibody or antigen binding fragment described herein, any bispecific molecule described herein, any immune effector cell comprising a CAR polypeptide described herein, or any pharmaceutical composition described herein.

In certain embodiments, the disclosure provides for treating cancer (e.g., NPM1c-positive cancer, e.g., AML) in a subject in need thereof, wherein the cell surface of cells comprising the cancer displays AIQDLCLAV (SEQ ID NO:1) neoepitope in complex with an MHC class I protein (e.g., HLA-A2 or a protein encoded by the HLA-A*02 allele group, such a protein encoded by the HLA-A*02:01 allele), the treating comprising administering to the subject any antibody or antigen binding fragment described herein, any bispecific molecule described herein, any immune effector cell comprising a CAR polypeptide described herein, or any pharmaceutical composition described herein.

In certain embodiments, the disclosure provides for reducing cancer burden or increasing survival in a subject with cancer (e.g., wherein the cancer is NPM1c-positive, e.g., wherein the cancer is AML) comprising administering to the subject any antibody or antigen binding fragment described herein, any bispecific molecule described herein, any immune effector cell comprising a CAR polypeptide described herein, or any pharmaceutical composition described herein. In certain embodiments, the cell surface of cells comprising the cancer displays an NPM1c neoepitope (e.g., SEQ ID NO:1) in complex with an MHC class I protein (e.g., HLA-A2).

In certain embodiments, the disclosure provides for preventing cancer in a subject in remission from cancer comprising administering to the subject any antibody or antigen binding fragment described herein, any bispecific molecule described herein, any immune effector cell comprising a CAR polypeptide described herein, or any pharmaceutical composition described herein.

In one embodiment, the cancer is a relapsed cancer. In one embodiment, the cancer is a refractory cancer. In one embodiment, the cancer is an advanced stage cancer. In one embodiment, the cancer is resistant to one or more other therapies (e.g., chemotherapy, radiotherapy, stem cell transplantation, or another immunotherapy).

In certain embodiments, the disclosure provides for preventing AML in a subject in need thereof comprising administering to the subject any antibody or antigen binding fragment described herein, any bispecific molecule described herein, any immune effector cell comprising a CAR polypeptide described herein, or any pharmaceutical composition described herein. In one embodiment, the disclosure provides for preventing AML in a subject in remission from AML.

In certain embodiments, the cancer to be treated is AML. In one embodiment, the cancer is relapsed AML. In one embodiment, the cancer is refractory AML. In one embodiment, the cancer is advanced AML. In one embodiment, the cancer is AML resistant to one or more other therapies (e.g., chemotherapy, radiotherapy, stem cell transplantation, or another immunotherapy).

The effectiveness of any therapy described herein can be assessed by evaluating a parameter (e.g., tumor burden) before and after administration of the therapy (e.g., to the subject being treated or an animal model of the cancer being treated). Any assay known in the art can be used to evaluate the therapeutic effectiveness of the therapies described herein.

Methods of Administration

The therapies described herein can be administered to a subject by any suitable means which include, but are not limited to, parenteral route of administration. In some embodiments, the composition is administered to the patient parenterally. Non-limiting examples of suitable routes of parenteral administration include intravenous, intramuscular, intraarterial, subcutaneous, intratumoral, intrathecal and intraperitoneal administration. In one embodiment, the therapies described herein are administered intravenously. In one embodiment, the therapies described herein are administered intraperitoneally. In one embodiment, the therapies described herein are administered intramuscularly. In one embodiment, the therapies described herein are administered subcutaneously. In certain embodiments, the administration is intravenous, intrathecal, intraosseous or into the spinal cord. In one embodiment, the therapies described herein are administered into the spinal cord or the spinal canal. In one embodiment, the therapies described herein are administered intrathecally. In one embodiment, the therapies described herein are administered intraosseously. In one embodiment, the therapies described herein are administered into the bone marrow.

The appropriate dosage will vary with the particular cancer being treated, the age, weight and physical condition of the subject being treated, the severity of the cancer, the route of administration, the duration of the treatment, the responsiveness of the subject being treated, the nature of the concurrent or combination therapy (if any), the specific route of administration and like factors within the knowledge and expertise of the health practitioner. In certain embodiments, a maximum tolerable dose is to be used, that is, the highest safe dose according to sound medical judgment. In preferred embodiments, the therapies are to be administered in effective amounts. An effective amount is a dosage of the composition sufficient to provide a medically desirable result.

For example, if the subject has a tumor, an effective amount may be that amount that reduces the tumor volume or load (as for example determined by imaging the tumor). Effective amounts may also be assessed by the presence and/or frequency of cancer cells in the blood or other body fluid or tissue (e.g., a biopsy). If the tumor is impacting the normal functioning of a tissue or organ, then the effective amount may be assessed by measuring the normal functioning of the tissue or organ.

In certain embodiments, the CAR-expressing immune effector cells are administered in an amount of about or at least $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times100^{10}$, $5\times100^{10}$, $1\times10^{11}$, or $5\times10^{11}$, $1\times10^{112}$, or $5\times10^{12}$ cells (or any value or range in between).

Various dosing schedules of the therapies described herein are contemplated including single administration or multiple administrations over a period of time. The methods of administration include, without limitation, bolus administration and infusions (e.g., continues or pulse infusions).

The therapeutic regimen for use in the methods described herein may include administration of a therapy twice a week, once every week, once every two weeks, once every three weeks, once every month or 4 weeks, once every six weeks, once every two months or eight weeks, or once every three months or twelve weeks. In certain embodiments, the subject receives a single dose of any therapy described herein. In certain embodiments, the subject receives from at least two, at least three, at least four, at least five, at least six, at least eight, or at least ten doses of any therapy described herein. In certain embodiments, a therapy described herein is administered daily, every other day, or two times a week. In certain embodiments, a therapy described herein is administered for a period of time, such as one week, two weeks, three weeks, four weeks, six weeks, two months, three months, four months, five months, six months, or one year.

In some embodiments, the initial treatment period (where the therapy is administered, e.g., a single time, twice a week, once a week, twice in two weeks, or once a month) is followed by a withdrawal period in which the antibody is not administered (for, e.g., a week, two weeks, three weeks, 1 month or four weeks, six weeks, two months or 8 weeks, three months, four months, five months, six months, or 1 year), and then followed by a second treatment period (where the therapy is administered, e.g., a single time, twice a week, once a week, twice in two weeks, or once a month). Such initial treatment and such second treatment periods can last, for example, two weeks, three weeks, four weeks, six weeks, two months, or three months (where the initial treatment period can be the same or different from the second treatment period).

Patient Populations

The subject being treated in accordance with the methods described herein include, but are not limited to, humans and non-human vertebrates. In certain embodiments, the subject being treated in accordance with the methods described herein is a mammal, such as a household pet (e.g., a dog, a cat, a rabbit, a ferret, etc.), a livestock or farm animal (e.g., a cow, a pig, a sheep, a goat, a pig, a chicken or another poultry), a horse (e.g., a thoroughbred horse), a monkey, a laboratory animal (e.g., a mouse, a rat, a rabbit, etc.), and the like. Subjects also include fish and other aquatic species. In a preferred embodiment, the subject being treated in accordance with the methods described herein is a human. In one embodiment, the disclosure can be practiced in any subject that is likely to benefit from targeted immunotherapy for the treatment of acute myeloid leukemia (AML). In some embodiments, the disclosure is for use in a subject that has a NPM1c-positive cancer (e.g., AML).

In some aspects, the therapeutic methods and uses of the disclosure can be practiced in any subject that has (e.g., has been diagnosed with) a cancer that may (or is likely to) benefit from any immunotherapy described herein. A subject having a cancer (e.g., NPM1c-positive cancer, e.g., AML) is a subject that has detectable cancer cells. The disclosure contemplates administration of any antibodies or antigen binding fragments thereof (e.g., scFv) described herein, any bispecific molecules described herein, and any immune effector cells expressing CAR polypeptide described herein to subjects having a cancer (e.g., NPM1c-positive cancer, e.g., AML).

In some aspects, the therapeutic methods and uses of the disclosure can be practiced in any subject that has cancer characterized by (e.g., known to have, expected to have, or detected to have) a mutation in the NPM1 gene (e.g., a 4 base pair frameshift insertion in exon 12 of the gene, a mutation encoding C-terminal 11 amino acids in an alternative reading frame, or an NPM1 mutation resulting in expression of a protein comprising the following C-terminal amino acid sequence: MTDQEAIQDLCLAVEEVSLRK (SEQ ID NO:57)). In certain embodiments, the therapeutic methods and uses of the disclosure can be practiced in any subject that has cancer characterized by expression (e.g., known to express, expected to express, or detected to express) of a mutant NPM1 protein (e.g., an NPM1c mutant protein having cytoplasmic localization, a protein having a mutation in the C-terminal domain, a mutant protein lacking a folded C-terminal domain, a protein comprising the following C-terminal amino acid sequence: MTDQEAIQDLCLAVEEVSLRK (SEQ ID NO:57), a protein set forth by SEQ ID NO:56, or NPM1c). The mutated C-terminal sequence of NPM1c is known in the art (see, e.g., van der Lee et al., 2019, *J. Clin. Invest.* 129(2):774-785, which is incorporated herein by reference in its entirety, see e.g., FIG. 1). In some aspects, the therapeutic methods and uses of the disclosure can be practiced in any subject that has cancer, wherein the cell surface of cells comprising the cancer displays (e.g., known to display, expected to display, or detected to display) a mutant nucleophosmin neoepitope (such as NPM1c neoepitope, e.g., AIQDLCLAV (SEQ ID NO:1)) in complex with a class I major histocompatibility complex (MHC class I) protein (e.g., HLA-A2). In some aspects, the therapeutic methods and uses of the disclosure are practiced in any subject that has cancer, wherein a class I major histocompatibility complex (MHC class I) protein (e.g., HLA-A2) displays or presents an NPM1c neoepitope (e.g., AIQDLCLAV (SEQ ID NO:1)) on the cell surface of cells comprising the cancer.

Optionally, the cancer cells of the prospective patient to be treated in accordance with the methods described herein are tested for a mutation in the NPM1 gene or NPM1 protein, or are tested to determine whether the cell surface of cells comprising the cancer display an antigen comprising an NPM1c neoepitope (e.g., AIQDLCLAV (SEQ ID NO:1)) in complex with a class I major histocompatibility complex (MHC class I) protein (e.g., HLA-A2). In some aspects, the patient is treated in accordance with the methods described herein if such a test is positive for a mutation in the NPM1 gene or a mutation in NPM1 protein, or is determined to display an antigen comprising an NPM1c neoepitope (e.g., AIQDLCLAV (SEQ ID NO:1)) in complex with a class I major histocompatibility complex (MHC class I) protein (e.g., HLA-A2) on the cell surface of cancer cells.

In some aspects, the therapeutic methods and uses of the disclosure can be practiced in a subject that has Acute Myeloid Leukemia (AML). In a specific embodiment, the therapeutic methods and uses of the disclosure are practiced in a subject that has been diagnosed with AML.

Tests for diagnosing the cancers to be treated by the methods described herein are known in the art and will be familiar to the ordinary medical practitioner. These laboratory tests include, without limitation, microscopic analyses, cultivation dependent tests (such as cultures), and nucleic acid detection tests. These include wet mounts, stain-enhanced microscopy, immune microscopy (e.g., FISH), hybridization microscopy, particle agglutination, enzyme-linked immunosorbent assays, urine screening tests, DNA probe hybridization, serologic tests, etc. The medical practitioner generally takes a full history and conducts a complete physical examination in addition to running the laboratory tests listed above.

Methods for the detection of AML include, but are not limited to, flow cytometry of PBMC for leukemic cells, followed by PCR and sequencing for NPM1c mutation. Clinical methods for AML diagnosis are known in the art. Risk factors for the development of AML include smoking, chemotherapy, radiation therapy, certain blood disorder, and age.

In one embodiment, the subject being treated has been diagnosed with an early stage cancer (e.g., AML). In one embodiment, the subject being treated has been diagnosed with an advanced stage cancer (e.g., AML).

In certain embodiments, the subject being treated has any stage of AML progression.

In some aspects, the subject being treated has previously undergone one or more other cancer therapies (e.g., chemotherapy, radiotherapy, or stem cell transplantation). In certain embodiments, the subject being treated has previously undergone one or more other cancer therapies (e.g., chemotherapy, radiotherapy, or stem cell transplantation), and the subject's cancer has relapsed. In certain embodiments, the subject being treated has previously undergone one or more other cancer therapies (e.g., chemotherapy, radiotherapy, or stem cell transplantation), and the subject has developed resistance to the one or more other cancer therapies. In certain embodiments, the subject being treated is in remission (e.g., in partial remission or in complete remission of cancer). In certain embodiments, the subject being treated is refractory to one or more other cancer therapies (e.g., chemotherapy, radiotherapy, or stem cell transplantation).

In other embodiments, contemplated herein is treating a subject that is at risk of developing cancer that may (or is likely to) benefit from any immunotherapy described herein in accordance with the therapeutic methods and uses of the disclosure. A subject at risk of developing a cancer (e.g., AML) is a subject that has a higher than normal probability of developing cancer. These subjects include, for instance, subjects having a genetic abnormality that has been demonstrated to be associated with a higher likelihood of developing a cancer, subjects having a familial disposition to cancer, subjects exposed to cancer causing agents (i.e., carcinogens) such as tobacco, asbestos, or other chemical toxins, and subjects previously treated for cancer and in apparent remission. The disclosure contemplates administration of antibodies or antigen binding fragments thereof (e.g., scFv) described herein, bispecific molecules described herein, and immune effector cells expressing CAR polypeptide described herein to subjects at risk of developing a cancer (e.g., AML).

In on embodiment, the subject being treated is an adult. In one embodiment, the subject is a human subject over 18 years of age. In one embodiment, the subject is a human subject over 21 years of age. In one embodiment, the subject is a human subject over 45 years of age. In one embodiment, the subject is a human subject over 65 years of age. In one embodiment, the subject is a human subject under 18 years of age. In one embodiment, the subject is a human subject under 45 years of age (or between 18 and 45 years of age, or between 21 and 45 years of age). In one embodiment, the subject is a human subject under 65 years of age (or between 18 and 65 years of age, between 21 and 65 years of age, or between 45 and 65 years of age).

Combination Therapies

In some aspects, the therapeutic methods and uses described herein further include treatment of the subject with additional agents that enhance therapeutic responses, such as enhance an anti-tumor response in the subject and/or that are cytotoxic to the tumor (e.g., chemotherapeutic agents).

In some aspects, a therapy described herein is administered to a subject in combination with one or more anti-cancer therapy, e.g., a chemotherapy, a radiation therapy, stem cell transplantation, a small molecule with an anti-cancer activity, another anti-cancer immunotherapy (e.g., another anti-cancer antibody or fragment thereof, or another T cell therapy), or any other anti-cancer therapy known in the art.

In some aspects, one or more of the antibodies, antigen binding antibody fragments, bispecific molecules, or compositions comprising the same, described herein are administered to a subject in combination with one or more anti-cancer therapy, e.g., a chemotherapy, a radiation therapy, stem cell transplantation, a small molecule with an anti-cancer activity, another anti-cancer immunotherapy (e.g., another anti-cancer antibody or fragment thereof, or another T cell therapy), or any other anti-cancer therapy known in the art.

In some aspects, one or more of the CAR-expressing immune effector cells, or compositions comprising the same, described herein are administered to a subject in combination with stem cell transplantation or another anti-cancer immunotherapy (e.g., another anti-cancer antibody or fragment thereof, or another T cell therapy). For administration with the immune effector cells comprising CARs, any combination therapies that would not negatively affect the viability of the immune effector cells are contemplated herein.

Suitable therapeutic agents for use in combination therapy include small molecule chemotherapeutic agents, including protein tyrosine kinase inhibitors, as well as biological anti-cancer agents, such as anti-cancer antibodies, including but not limited to those discussed further below.

In some aspects, combination therapy includes administering to the subject an immune checkpoint inhibitor to enhance anti-tumor immunity, such as a PD-1 inhibitor, a PD-L1 inhibitor, a PD-L2 inhibitor, or a CTLA-4 inhibitor. Other modulators of immune checkpoints may target TIM-3, OX-40, OX-40L or ICOS. In one embodiment, an agent that modulates an immune checkpoint is an antibody (e.g., an antagonistic antibody to PD-1, PD-L1, PD-L2, CTLA-4, TIM-3, or OX-40). In another embodiment, an agent that modulates an immune checkpoint is a protein or small molecule modulator. In another embodiment, the agent (such as an mRNA) encodes an antibody modulator of an immune checkpoint. In one embodiment, any therapy described herein is administered in combination with a TIM-3 inhibitor. In one embodiment, any therapy described herein is administered in combination with a PD-1 inhibitor. In one embodiment, any therapy described herein is administered in combination with a PD-L1 inhibitor. In one embodiment, any therapy described herein is administered in combination with a CTLA-4 inhibitor. Non-limiting examples of immune checkpoint inhibitors that can be used in combination therapy include pembrolizumab, alemtuzumab, nivolumab, pidilizumab, ofatumumab, rituximab, MEDI0680, PDR001, AMP-224, PF-06801591, BGB-A317, REGN2810, SHR-1210, TSR-042, affimer, avelumab (MSB0010718C), atezolizumab (MPDL3280A), durvalumab (MEDI4736), BMS936559, ipilimumab, tremelimumab, AGEN1884, MEDI6469 and MOXR0916.

In a specific embodiment, a therapy described herein is administered to a subject in combination with chemotherapy. Examples of types of chemotherapeutic agents that can be used in the combination therapy described herein include, without limitation, an alkylating agent, a nitrosourea agent, an antimetabolite, a platinum complex derivative, a topoisomerase inhibitor, an aromatase inhibitor, an alkaloid derived from a plant, a hormone antagonist, an antitumor antibiotic, and a P-glycoprotein inhibitor. Specific examples of chemotherapeutic drugs that can be used in the combination therapy described herein include, without limitation, taxol, paclitaxel, nab-paclitaxel, 5-fluorouracil (5-FU), gemcitabine, doxorubicin, daunorubicin, colchicin, mitoxantrone, tamoxifen, cyclophosphamide, mechlorethamine, melphalan, chlorambucil, busulfan, uramustine, mustargen, ifosamide, bendamustine, carmustine, lomustine, semustine, fotemustine, streptozocin, thiotepa, mitomycin, diaziquone, tetrazine, altretamine, dacarbazine, mitozolomide, temozolomide, procarbazine, hexamethylmelamine, altretamine, hexalen, trofosfamide, estramustine, treosulfan, mannosulfan, triaziquone, carboquone, nimustine, ranimustine, azathioprine, sulfanilamide, fluoropyrimidine, thiopurine, thioguanine, mercaptopurine, cladribine, capecitabine, pemetrexed, fludarabine, methotrexate, hydroxyurea, nelarabine or clofarabine, cytarabine, decitabine, pralatrexate, floxuridine, thioquanine, azacitidine, cladribine, pentostatin, mercaptopurine, imatinib, dactinomycin, cerubidine, bleomycin, actinomycin, luteomycin, epirubicin, idarubicin, plicamycin, vincristin, vinblastine, vinorelbine, vindesine, vinflunine, paclitaxel, docetaxel, etoposide, teniposide, periwinkle, *vinca*, taxane, irinotecan, topotecan, camptothecin, teniposide, pirarubicin, novobiocin, merbarone, aclarubicin, amsacrine, antiandrogen, antiestrogen, bicalutamide, medroxyprogesterone, fluoxymesterone, diethylstilbestrol, estrace, octreotide, megestrol, raloxifene, toremifene, fulvestrant, prednisone, flutamide, leuprolide, goserelin, aminoglutethimide, testolactone, anastrozole, letrozole, exemestane, vorozole, formestane, fadrozole, androstene, resveratrol, myosmine, catechin, apigenin eriodictyol isoliquiritigenin, mangostin, amiodarone, azithromycin, captopril, clarithromycin, cyclosporine, piperine, quercetine, quinidine, quinine, reserpine, ritonavir, tariquidar, verapamil, cisplatin, carboplatin, oxaliplatin, transplatin, nedaplatin, satraplatin, triplatin and carboplatin.

In a specific embodiment, a therapy described herein is administered to a subject in combination with one or more chemotherapies for treatment of AML. In some embodiments, the one or more chemotherapies is selected from: cytarabine, daunorubicin, idarubicin, cladribine, fludarabine, mitoxantrone, etoposide, 6-thioguanine, hydroxyurea, prednisone, dexamethasone, methotrexate, 6-mercaptopurine, azacytidine, and decitabine.

In a specific embodiment, a therapy described herein is administered to a subject in combination with radiation therapy.

In a specific embodiment, any therapy described herein is administered to a subject in combination with stem cell transplantation.

In certain embodiments, any therapy described herein can be administered before, during (i.e., concurrently) or after one or more additional anti-cancer therapy. In one embodiment, the subject being treated in accordance with the methods described herein has not previously received an anti-cancer therapy. In one embodiment, the subject being treated in accordance with the methods described herein has previously received an anti-cancer therapy (e.g., a chemotherapy, a radiation therapy, or a stem cell transplant).

Diagnostic Applications

In some embodiments, the antibody or antibody fragment compositions described herein are used in diagnostic applications. For example, labeled antibodies or antigen-binding fragments as described herein are used in assays to detect the presence or amount of the target antigen (e.g., NPM1c:HLA-A2) in a sample (e.g., a biological sample). In another example, labeled antibodies or antigen-binding fragments as described herein that bind to a target antigen (e.g., NPM1c neoepitope in complex with an MHC I, e.g., NPM1c:HLA-A2) are used as a positive control to identify additional compounds (e.g., small molecules, aptamers, or antibodies) that bind to the target antigen.

In some embodiments, the antibody or antibody fragment compositions described herein is used in in vitro assays for characterizing or identifying cells presenting NPM1c neoepitope in complex with an MHC I (e.g., NPM1c:HLA-A2), for example by flow cytometry or microscopy. In some embodiments, e.g., in which an antibody or antigen-binding fragment composition described herein binds to NPM1c neoepitope in complex with an MHC I (e.g., NPM1c:HLA-A2), the compositions are used to identify cells presenting the target antigen in a sample (e.g., a biological sample). Accordingly, the antibodies, or antigen-binding fragments thereof, as described herein, are used to diagnose, prognose, and/or determine progression of disease (e.g., cancer, e.g., cancer with mutation in NPM1 gene, e.g., AML with mutation in NPM1 gene) in a patient.

Kits

In one aspect, provided herein are kits comprising one or more containers comprising: (i) an antibody or antigen binding fragment thereof described herein, a bispecific molecule described herein, a CAR polypeptide described herein, an immune effector cell (e.g., a T cell or a NK cell) comprising a CAR polypeptide described herein, or a pharmaceutical composition described herein; (ii) optionally, one or more additional anti-cancer agents (e.g., a chemotherapeutic agent), and (iii) optionally, instructions for use in treating cancer in a subject.

In certain embodiments, the disclosure pertains to kits comprising antibodies or antigen-binding fragments thereof that bind to an antigen comprising an NPM1c neoepitope in complex with an MHC class I protein (e.g., NPM1c:HLA-A2) as disclosed herein, and instructions for use. A kit can include a single chain variable antibody fragment (scFv) which binds to an antigen comprising an NPM1c neoepitope in complex with an MHC class I protein (e.g., NPM1c:HLA-A2) as disclosed herein, and instructions for use. In certain embodiments, the disclosure pertains to kits comprising a chimeric antigen receptor (CAR) polypeptide that binds to an antigen comprising an NPM1c neoepitope in complex with an MHC class I protein (e.g., NPM1c:HLA-A2) as disclosed herein, and instructions for use. In certain embodiments, the disclosure pertains to kits comprising a bispecific molecule which binds to an antigen comprising an NPM1c neoepitope in complex with an MHC class I protein (e.g., NPM1c:HLA-A2) and a second antigen (e.g., CD3) as disclosed herein, and instructions for use.

In one embodiment, the kits may comprise, in the same or separate suitable containers, antibodies or antigen-binding fragments thereof that bind to an antigen comprising an NPM1c neoepitope in complex with an MHC class I protein (e.g., NPM1c:HLA-A2), and a pharmaceutically acceptable carrier (e.g., a buffer). In one embodiment, the kits may comprise, in the same or separate suitable containers, a single chain variable antibody fragment (scFv) which binds to an antigen comprising an NPM1c neoepitope in complex with an MHC class I protein (e.g., NPM1c:HLA-A2), and a pharmaceutically acceptable carrier (e.g., a buffer). In one embodiment, the kits may comprise, in the same or separate suitable containers, a bispecific molecule which binds to an antigen comprising an NPM1c neoepitope in complex with an MHC class I protein (e.g., NPM1c:HLA-A2) and a second antigen (e.g., CD3), and a pharmaceutically acceptable carrier (e.g., a buffer). In one embodiment, the kits may comprise, in the same or separate suitable containers, a chimeric antigen receptor (CAR) polypeptide that binds to an antigen comprising an NPM1c neoepitope in complex with an MHC class I protein (e.g., NPM1c:HLA-A2), and a pharmaceutically acceptable carrier (e.g., a buffer). In one embodiment, the kits may comprise, in the same or separate suitable containers, an immune effector cell comprising a CAR polypeptide which binds to an antigen comprising an NPM1c neoepitope in complex with an MHC class I protein (e.g., NPM1c:HLA-A2) and a second antigen (e.g., CD3), and a pharmaceutically acceptable carrier (e.g., a buffer).

The suitable containers may include, without limitation, a vial, well, test tube, flask, bottle, syringe, infusion bag, or other container means, into which the antibody or antigen-binding fragment thereof described herein (e.g., scFv), a bispecific molecule described herein, a chimeric antigen receptor (CAR) polypeptide described herein, or an immune effector cell comprising a CAR polypeptide described herein, may be placed (and in some instances, suitably aliquoted). Where an additional component is provided, the kit can contain additional containers into which this component may be placed. The containers may further include injection or blow-molded plastic containers in which the desired vials are retained. Containers and/or kits can include labeling with instructions for use and/or warnings.

The following examples are offered by way of illustration and not by way of limitation. Various other embodiments of the invention may be practiced, given the general description provided herein.

Definitions

As used herein, the term "NPM1c" refers to a mutant nucleophosmin protein (NPM1), resulting from a 4-nucleotide duplication in the NPM1 gene, which has cytoplasmic localization. Human nucleophosmin encoded by the wild-type NPM1 gene has an amino acid sequence as set forth by SEQ ID NO:54 (accession number NM_002520). An exemplary NPM1c protein that is encoded by the NPM1 gene with a 4-nucleotide duplication has an amino acid sequence as set forth by SEQ ID NO:56. Furthermore, the C-terminal amino acid sequence of said exemplary NPM1c protein comprises MTDQEAIQDLCLAVEEVSLRK (SEQ ID NO:57), with the portion of the sequence that is mutated relative to wild-type nucleophosmin protein highlighted in bold (see, e.g., van der Lee et al., 2019, JCI 129(2):774-785; Verhaak, R. et al (2005) *Blood* 106:3747). In some embodiments, a NPM1c neoepitope of the disclosure comprises a neoepitope derived from a NPM1c protein comprising the amino acid sequence MTDQEAIQDLCLAVEEVSLRK (SEQ ID NO:57). In some embodiments, a NPM1c neoepitope of the disclosure comprises a neoepitope derived from the portion of NPM1c having an amino acid sequence comprising MTDQEAIQDLCLAVEEVSLRK (SEQ ID NO:57).

As used herein, the term "NPM1c:HLA-A2" refers to a neoepitope of NPM1c in complex with an HLA-A2 protein. In some embodiments, the neoepitope of NPM1c comprises an amino acid sequence AIQDLCLAV (SEQ ID NO:1).

As used herein, the term "YG1" or "YG1 scFv" refers to an exemplary scFv comprising a full-length amino acid sequence set forth by SEQ ID NO:2, wherein the variable heavy chain (VH) and variable light chain (VL) have amino acid sequences as set forth by SEQ ID NOs: 5 and 3 respectively.

As used herein, the term "about," when used to modify a numerical value, indicates that deviations of up to 10% above and below the numerical value remain within the intended meaning of the recited value.

As used herein, the terms "VH" or "$V_H$" refer to the heavy chain variable region of an antibody.

As used herein, the terms "VL" or "$V_L$" refer to the light chain variable region of an antibody.

As used herein, the term "percent (%) amino acid sequence identity" or "percent sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity. Alignment for purposes of determining percent amino acid sequence identity can be achieved in various ways that are known in the art, for instance, using publicly available computer software such as BLASTp, BLAST-2, ALIGN (e.g., ALIGN-2) or Megalign (DNASTAR) software. To obtain gapped alignments for comparison purposes, Gapped BLAST can be utilized as described in Altschul et al., (1997) Nucleic Acids Res. 25(17):3389-3402. In addition, the percent identity between two amino acid sequences can be determined using the Needleman and Wunsch (J. Mol. Biol. (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "antibody" generally refers to an antibody comprising two light chain polypeptides and two heavy chain polypeptides (unless the context in which this term is used suggests otherwise). Antibodies include different antibody isotypes including IgM, IgG, IgA, IgD, and IgE antibodies. The term "antibody" includes, without limitation, a polyclonal antibody, a monoclonal antibody, a chimerized or chimeric antibody, a humanized antibody, a primatized antibody, a deimmunized antibody, and a fully human antibody. The antibody can be made in or derived from any of a variety of species, e.g., mammals such as humans, non-human primates (e.g., orangutan, baboons, or chimpanzees), horses, cattle, pigs, sheep, goats, llama, dogs, cats, rabbits, guinea pigs, gerbils, hamsters, rats, and mice. The antibody can be a purified or a recombinant antibody As used herein, the term "antibody fragment," "antigen binding fragment," or similar terms refer to a fragment of an antibody that retains the ability to bind to a target antigen. Such fragments include, without limitation, a single chain antibody, a single chain Fv fragment (scFv), a Fab fragment, a Fab' fragment, and a F(ab')$_2$ fragment. This term also includes, e.g., single domain antibodies such as camelid single domain antibodies. See, e.g., Muyldermans et al. (2001) *Trends Biochem Sci* 26:230-235; Nuttall et al. (2000) *Curr Pharm Biotech* 1:253-263; Reichmann et al. (1999) *J Immunol Meth* 231:25-38; PCT application publication nos. WO 94/04678 and WO 94/25591; and U.S. Pat. No. 6,005,079, all of which are incorporated herein by reference in their entireties. In some embodiments, the disclosure provides single domain antibodies comprising two VH domains with modifications such that single domain antibodies are formed. In addition, intrabodies, minibodies, triabodies, and diabodies are also included in the definition of antibody fragments and are compatible for use in the methods described herein. See, e.g., Todorovska et al. (2001) *J Immunol Methods* 248(1):47-66; Hudson and Kortt (1999) *J Immunol Methods* 231(1):177-189; Poljak (1994) *Structure* 2(12):1121-1123; Rondon and Marasco (1997) *Annual Review of Microbiology* 51:257-283, the disclosures of each of which are incorporated herein by reference in their entirety.

As used herein, the term an "amino acid substitution" or "substituted" (when such term is referred to a substituted amino acid) refers to the replacement of at least one existing amino acid residue in a predetermined amino acid sequence with a different amino acid residue. The term "amino acid insertion" refers to the incorporation of at least one additional amino acid into a predetermined amino acid sequence. While the insertion will usually consist of the insertion of one or two amino acid residues, larger "peptide insertions," can also be made. The replaced or inserted amino acid residue(s) may be naturally occurring or non-naturally occurring (modified). The term "amino acid deletion" refers to the removal of at least one amino acid residue from a predetermined amino acid sequence.

As used herein, a "conservative amino acid substitution" is one in which the amino acid residue is replaced with an amino acid residue having a similar side chain. Families of amino acid residues having similar side chains have been defined in the art, including:
(1) hydrophobic side chains: norleucine, Met, Ala, Val, Leu;
(2) neutral hydrophilic side chains: Cys, Ser, Thr, Asn, Gln;
(3) acidic side chains: Asp, Glu;
(4) basic side chains: His, Lys, Arg;
(5) side chains that influence chain orientation: Gly, Pro; and
(6) aromatic side chains: Trp, Tyr, Phe.

For example, a non-conservative amino acid substitution is a substitution of an amino acid residue with an amino acid residue with a substantially different side chain (i.e., an amino acid residue that is a member of a different family).

In some embodiments, a conservative amino acid substitution is made by considering the hydropathic index of the amino acid residue. Each amino acid is assigned a hydropathic index on the basic of its hydrophobicity and charge characteristics. They are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). The importance of the hydropathic amino acid index in conferring interactive function on a polypeptide is understood in the art (see, e.g., Kyte et al (1982) *J Mol Biol* 157:105-131). In some embodiments, a conservative amino acid substitution is made by replacing one amino acid residue with another amino acid residue having a the same or similar (e.g., within about +2, +1.5, +1, +0.5, −0.5, −1, −1.5, or −2) hydropathic index.

In some embodiments, a conservative amino acid substitution is made by considering the hydrophilicity of the amino acid residue. The following hydrophilicity values have been assigned: Arg (+3.0); Lys (+3.0±1); Asp (+3.0±1); Glut (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); and Trp (−3.4). In some embodiments, a conservative amino acid substitution is made by replacing one amino acid residue with another amino acid residue having a the same or similar (e.g., within about +2, +1.5, +1, +0.5, −0.5, −1, −1.5, or −2) hydrophilicity.

Exemplary amino acid substitutions are set forth in Table 2.

TABLE 2

Conservative amino acid substitutions

| Original Residue | Exemplary Substitution | Preferred Substitution |
|---|---|---|
| Ala | Val, Leu, Ile | Val |
| Arg | Lys, Gln, Asn | Lys |
| Asn | Gln | Gln |
| Asp | Gln | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Nle | Leu |
| Leu | Nle, Ile, Val, Met, Ala, Phe | Ile |
| Lys | Arg, Dbu, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Nle | Leu |

Nle = norleucine
Dbu = 2,4-diaminobutyric acid

As used herein, the term "isolated antibody" refers to an antibody which has been separated from a component of its natural environment. An isolated antibody is typically substantially free of other cellular material and/or chemicals. An isolated antibody is substantially free of other antibodies having different antigenic specificities (e.g., an isolated antibody that specifically binds to NMP1c:HLA-A2 is substantially free of antibodies that specifically bind antigens other than NMP1c:HLA-A2).

As used herein, the term "isolated nucleic acid molecule" refers to a nucleic acid molecule that has been separated from a component of its natural environment. An isolated nucleic acid molecule is present at a location that is different from its natural chromosomal location.

As used herein, the term "neoepitope" refers to a disease-specific antigen comprising a peptide that arises from disease-specific mutations, which are recognized as different from self and presented on the surface of cells affected by the disease but not normal cells. A "tumor neoepitope" or "cancer neoepitope" refers to a tumor- or cancer-specific antigen comprising a peptide that arises from tumor- or cancer-specific mutations, which are recognized as different from self and presented on the surface of tumor/cancer cells but not normal cells. Presentation of a tumor- or cancer-specific neoepitope occurs following intracellular processing and cleavage of a tumor- or cancer-specific antigen within a tumor cell, thereby producing one or more distinct peptides of 8-15 amino acids comprising the tumor- or cancer-specific mutations. The subset of these peptides that bind MHC class I or II molecules for presentation to CD8+ or CD4+ T cells, respectively, constitute tumor neoepitopes.

As used herein the term "$K_D$" or "Kd" or "$K_d$" has the same meaning as commonly understood by one of ordinary skill in the art, and refers to the equilibrium dissociation constant of a binding reaction between an antibody (or antigen binding fragment thereof) and an antigen. The value of $K_D$ is a numeric representation of the ratio of the antibody off-rate constant (koff) to the antibody on-rate constant (kon). The value of $K_D$ is inversely related to the binding affinity of an antibody to an antigen. The smaller the $K_D$ value the greater the affinity of the antibody for its antigen. Affinity can be measured by any method known in the art.

As used herein, the term "koff" or "$k_{off}$" has the same meaning as commonly understood by one of ordinary skill in the art, and refers to the off-rate constant for the dissociation of an antibody from an antibody/antigen complex. The value of koff is a numeric representation of the fraction of complexes that decay or dissociate per second, and is expressed in units $sec^{-1}$.

As used herein, the term "kon" or "$k_{on}$" has the same meaning as commonly understood by one of ordinary skill in the art, and refers to the on-rate constant for the association of an antibody with an antigen. The value of kon is a numeric representation of the number of antibody/antigen complexes formed per second in a 1 molar (1M) solution of antibody and antigen, and is expressed in units $M^{-1}sec^{-1}$.

As used herein, the terms "specific binding," "specifically binds," "selective binding," and "selectively binds," are intended to mean that an antibody or antigen-binding fragment thereof that exhibits appreciable affinity for a particular antigen or epitope (e.g., NPM1c:HLA-A2) and, generally, does not bind to, or substantially does not bind to, other antigens and epitopes (e.g., HLA-A2 alone, e.g., NPM1c neoepitope alone, e.g., non-NPM1c neoepitope in complex with HLA-A2). "Appreciable" or preferred binding includes binding with a $K_D$ of $10^{-7}$, $10^{-8}$, $10^{-9}$, or $10^{-10}$ M or better. The $K_D$ of an antibody antigen interaction (the affinity constant) indicates the concentration of antibody at which 50% of antibody and antigen molecules are bound together. Thus, at a suitable fixed antigen concentration, 50% of a higher (i.e., stronger) affinity antibody will bind antigen molecules at a lower antibody concentration than would be required to achieve the same percent binding with a lower affinity antibody. Thus a lower $K_D$ value indicates a higher (stronger) affinity. As used herein, "better" affinities are stronger affinities, and are of lower numeric value than their comparators, with a $K_D$ of $10^{-7}$M being of lower numeric value and therefore representing a better affinity than a $K_D$ of $10^{-6}$M. Affinities better (i.e., with a lower $K_D$ value and therefore stronger) than $10^{-7}$M, preferably better than $10^{-8}$ M, are generally preferred. Values intermediate to those set forth herein are also contemplated, and a preferred binding affinity can be indicated as a range of affinities, for example preferred binding affinities for antibodies that bind NPM1c:HLA-A2 disclosed herein are, $10^{-7}$ to $10^{-12}$M, more preferably $10^{-8}$ to $10^{-12}$ M.

An antibody that "does not bind to" or "substantially does not bind to" an antigen is one that will not appreciably bind to an off-target antigen (e.g., MHC class I protein alone, e.g., neoepitope alone e.g., a control peptide in complex with the MHC class I protein). For example, in one embodiment, an antibody that specifically binds to NPM1c:HLA-A2 will exhibit at least a two, and preferably three, or four or more orders of magnitude better binding affinity (i.e., binding exhibiting a two, three, or four or more orders of magnitude lower $K_D$ value) for NPM1c:HLA-A2 than, e.g., HLA-A2 alone, NPM1c neoepitope alone, and/or a non-NPM1c neoepitope in complex with HLA-A2. Specific or selective binding can be determined according to any art-recognized means for determining such binding, including, for example, according to Scatchard analysis, Biacore analysis, bio-layer interferometry, and/or competitive (competition) binding assays.

As used herein, the term "vector" has the same meaning as commonly understood by one of ordinary skill in the art, and refers to a nucleic acid molecule capable of transporting another nucleic acid molecule to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors used in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "HLA-A" has the same meaning as commonly understood by one of ordinary skill in the art, and refers to a group of human leukocyte antigens (HLA) that are encoded by the HLA-A locus in humans. HLA is a major histocompatibility complex (MHC) antigen specific to humans. HLA-A is one of three major types of human MHC class I cell surface receptors. The others are HLA-B and HLA-C. The HLA-A protein is a heterodimer, and is composed of a heavy α chain and smaller β chain. The α chain is encoded by a variant HLA-A gene, and the β chain (β2-microglobulin) is an invariant β2 microglobulin molecule. The β2 microglobulin protein is coded for by a separate region of the human genome. HLA-A*02 (A*02) is a human leukocyte antigen serotype within the HLA-A serotype group. The serotype is determined by the antibody recognition of the α2 domain of the HLA-A α-chain. For A*02, the α chain is encoded by the HLA-A*02 gene and the β chain is encoded by the B2M locus.

As used herein, the term "effective dose" or "effective amount" refers to an amount sufficient to achieve or at least partially achieve the desired therapeutic effect.

EXAMPLES

Most chimeric antigen receptor-T (CAR-T) cell therapies target tumor-associated antigens (TAAs), which could lead to on-target/off-tumor toxicity due to low level expression in normal tissues and tumor resistance due to loss of TAA expression by tumor cells. As described herein, a scFV targeting a neoepitope derived from an intracellular neoantigen resulting from a tumor-specific oncogenic driver gene mutation was identified in NPM1c, a four-nucleotide duplication in nucleophosmin, a driver oncogene mutation in ~35% of acute myeloid leukemia (AML). The mutations in NPM1 are clonal and essential for malignant transformation early in leukemogenesis. The mutation creates a neoepitope that is presented by the most common HLA-A2 allele. Specifically, NPM1c produces a leukemia-specific neoantigen epitope (AIQDLCLAV (SEQ ID NO: 1), abbreviated as AIQ) that is presented by the most common HLA-A*0201 allele (~50% of human population) (see Greiner et al., *BLOOD* 120: 1282 (2012)).

It was shown that NPM1c$^+$ AML patients with specific CD8 T cell responses to AIQ neoepitope had a dramatically better overall survival than NPM1c$^+$ AML patients without CD8 T cell response to the neoepitope (Greiner, J. et al., *BLOOD* 122:1087 (2013)). Moreover, Van der Lee et al. identified T cell receptors (TCR) recognizing a NPM1c neoepitope CLAVEEVSL (SEQ ID NO:72) presented by HLA-A2 and showed that T cells transduced with such TCRs are effective in killing NPM1c+ HLA-A2$^+$ AML (see van der Lee et al., *J CLIN INVEST* 129: 774 (2019)). However, a drawback of such therapy is the risk of TCR chain mispairing between exogenous and endogenous TCR α and β chains, resulting in potential toxicity and reduced efficacy (see van der Lee et al., *J CLIN INVEST* 129: 774 (2019); Bendle et al., *NAT MED* 16: 565, 1p (2010); van Loenen et al., *Proc Natl Acad Sci USA* 107: 10972 (2010)). Another major challenge for TCRs is their low binding affinity to tumor antigens (see Zhang. & Wang., Technol Cancer Res Treat 18 1078098716 (2019)).

As described herein, yeast surface display using a series of positive and negative selection steps was used to identify a human scFv that specifically binds to the NPM1c epitope-HLA-A2 complex (i.e., AIQ-HLA-A2), but not HLA-A2 alone or HLA-A2 loaded with control peptides or other antigenic peptides (e.g., HLA-A2 loaded with cancer-testis antigen NY-ESO-1 epitope SLLMWITQC (SEQ ID NO:62) or SLL-HLA-A2, e.g., HLA-A2 loaded with influenza virus M1 epitope GILGFVFTL (SEQ ID NO:63) or GIL-HLA-A2). Further, the affinity of the isolated scFv for AIQ-HLA-A2 complex was determined to be about 7 nM, which is 10-100-fold higher than the affinity of a typical TCR for its cognate peptide-MHC complex. An engineered CAR-T cells expressing the isolated scFv was found to exhibit potent cytotoxicity both in vitro and in vivo against NPM1c$^+$HLA-A2$^+$ leukemia cells, but not NPM1c$^-$HLA-A2$^+$ leukemia cells or HLA-A2$^-$ tumor cells. The results described herein show that NPM1c CAR-T cells are useful as a cancer-specific immunotherapy for treating NPM1c$^+$HLA-A2$^+$ cancers, such as AML, potentially with reduced on-target/off-tumor toxicity and tumor resistance.

As described herein the scFv (referred to as "YG1") was shown to bind to an NPM1c neoepitope (AIQDLCLAV; SEQ ID NO:1) in complex with HLA-A2 specifically and with high affinity (about 7 nM). A CAR polypeptide comprising the YG1 scFv (NPM1c CAR) that specifically binds to an NPM1c neoepitope (AIQDLCLAV; SEQ ID NO:1) in complex with HLA-A2 was generated and T cells (in particular, CD8$^+$ T cells) expressing the NPM1c CAR polypeptide specifically kill AML cells in vitro, reduce leukemia burden, and prolong survival in vivo, in an AML mouse model (injected with AML tumor cells). Specifically, engineered CAR-T cells expressing the YG1 scFv exhibit potent cytotoxicity both in vitro and in vivo against NPM1c+ HLA-A2$^+$ leukemia cells and primary AML blasts, but not NPM1c$^-$HLA-A2$^+$ leukemia cells or HLA-A2$^-$ tumor cells.

Thus, NPM1c CAR-T cells are expected to specifically target NPM1c$^+$HLA-A2$^+$ leukemia cells, regardless of the heterogeneity of tumor cell population, and thus reduce the development of tumor resistance. Moreover, due to the absence of NPM1c expression in healthy tissues, NPM1c CAR-T are expected to mediate antitumor immunity with no or minimal on-target/off-tumor toxicity. Indeed, engineered CAR-T cells expressing the YG1 scFv were found to not react to CD34$^+$ normal hematopoietic stem/progenitor cells.

In addition, compared to TCR and conventional CAR approaches, scFv targeting peptide-HLA complex is expected to have a unique advantage to arm NK cells. NK cells normally recognize and kill target cells that have no or low HLA expression (Vivier et al., *SCIENCE* 331: 44 (2011)). Without being bound by theory, leukemia cells that lack HLA expression or have low levels of HLA molecules may be preferentially killed by NK cells, as well as those leukemia cells that express high level of HLA, and thus more AIQ-HLA-A2 targets are efficiently killed by NPM1c CAR-NK cells. As antigen loss is an important mechanism of tumor resistance following CAR-T therapy (Shah & Fry, *NAT REV CLIN ONCOL* 16: 372 (2019)), NPM1c CAR-NK cells may be especially effective in reducing resistance to therapy and disease relapse. For example, based on the results disclosed herein, induced pluripotent stem cells (iPSC) may be differentiated into NK cells (see Hermanson., et al., *STEM CELLS* 34: 93 (2016)) to provide standardized, targeted "off-the-shelf" lymphocytes at clinical scale for anti-cancer immunotherapy (see Li et al., *CELL STEM CELL* 23: 181 (2018)). Therefore, also contemplated herein is incorporation of the NPM1c CAR into NK cells for improving anti-leukemia efficacy in HLA-A2$^+$ NPM1c$^+$ cancer patients (e.g., HLA-A2$^+$ NPM1c$^+$ AML patients).

Abbreviations

AIQ, AIQDLCLAV (SEQ ID NO:1); AML, acute myeloid leukemia; alloSCT, allogeneic hematopoietic stem cell transplantation; BLI, Bioluminescence imaging; CAR, chimeric antigen receptor; CAR-T, chimeric antigen receptor T cell; FACS, fluorescence-activated cell sorting; FBS, fetal bovine serum; GIL, GILGFVFTL (SEQ ID NO:63); HSCs, hematopoietic stem cells; MACS, magnetic-activated cell sorting; NPM1, nucleophosmin; NPM1c, mutant nucleophosmin; scFv, single-chain variable fragment; SLL, SLL-MWITQC (SEQ ID NO:62); TAAs, tumor-associated antigens; TCR, T-cell receptor; HSPCs, hematopoietic stem/progenitor cells.

Materials and Methods Used in Examples 1-7
Preparation of Peptide-HLA-A2 Complexes The CD8 T-cell epitope peptide (AIQDLCLAV (SEQ ID NO:1); abbreviated AIQ) from mutant NPM1c and control peptides from cancer-testis antigen NY-ESO-1 (SLL-MWITQC (SEQ ID NO:62), abbreviated as SLL) and influenza virus M1 protein (GILGFVFTL (SEQ ID NO:63), abbreviated as GIL) were synthesized and purified by Genscript. Recombinant human HLA-A2:Ig fusion protein (DimerX I) was obtained from BD Biosciences. Peptide-HLA-A2 complexes were prepared according to the manufacturer's protocol. Briefly, peptide was mixed with HLA-A2:Ig fusion protein at a molar ratio of 640:1, and the mixture was incubated at 37° C. overnight to allow for spontaneous complex assembly. The peptide-loaded HLA-A2:Ig fusion protein, referred to as peptide-HLA-A2, was stored at 4° C. for up to one week.

Yeast Media Formulations

SDCAA media: 20 g dextrose, 6.7 g Difco yeast nitrogen base, 5 g Bacto casamino acids, 10.2 g $Na_2HPO_4 \cdot 7H_2O$ and 8.56 g $NaH_2PO_4 \cdot H_2O$ were dissolved in deionized $H_2O$ to a volume of 1 liter and filter sterilized using 0.2 μm filter units.

SGCAA media: 20 g galactose, 6.7 g Difco yeast nitrogen base, 5 g Bacto casamino acids, 10.2 g $Na_2HPO_4 \cdot 7H_2O$ and 8.56 g $NaH_2PO_4 \cdot H_2O$ were dissolved in deionized $H_2O$ to a volume of 1 liter and filter sterilized using 0.2 μm filter units.

SDCAA plate: 10.2 g $Na_2HPO_4 \cdot 7H_2O$ and 8.56 g $NaH_2PO_4 \cdot H_2O$, 182 g sorbitol and 15 g bacto agar were dissolved in deionized $H_2O$ to a volume of 900 ml and autoclaved. In a separate beaker, 20 g dextrose, 6.7 g Difco yeast nitrogen base and 5 g bacto casamino acids were dissolved in deionized $H_2O$ to a volume of 100 ml and sterilized by filtration. The autoclaved mixture was cooled with stirring until below 50 1 C, combined with the filter-sterilized solution, mixed and poured into plates.

SG-2×SCAA media: SG (6.7 g Difco yeast nitrogen base, 20 g galactose, 10.2 g $Na_2HPO_4 \cdot 7H_2O$ and 8.56 g $NaH_2PO_4 \cdot H_2O$), 190 mg Arg, 400 mg Asp, 1,260 mg Glu, 130 mg Gly, 140 mg His, 290 mg Ile, 400 mg Leu, 440 mg Lys, 108 mg Met, 200 mg Phe, 220 mg Thr, 52 mg Tyr, 380 mg Val and 1 g BSA were dissolved in deionized $H_2O$ to a volume of 1 liter and sterilized by filtration.

Cell Line Culture

OCI-AML3, T2, and PC-3 cells were purchased from ATCC. OCI-AML2 cells were purchased from DSMZ. OCI-AML3 cells and OCI-AML2 were cultured in RPMI 1640 medium (Gibco) supplemented with 10% FBS (Life Tech and VWR) and 2 mM L-Glutamine (Thermo Fisher Scientific). GMB cells were generated by engrafting human hematopoietic stem cells (HSCs) transduced with the oncogenes c-Myc and Bcl2 into immunodeficient mice as previously described (see Leskov et al., ONCOGENE 32: 1066 (2013); Pallasch et al., CELL 156: 590 (2014)). GMB cells were cultured in DMEM medium (Gibco) supplemented with 110 mg/L pyruvate sodium, 1×Non-Essential Amino Acids, 1×2-mercaptoethanol and 10% FBS. T2 cells (174× CEM.T2) (ATCC® CRL☐1992™) were cultured in IMDM medium (Gibco) supplemented with 20% FBS. PC-3 cells were cultured with F-12K medium (ATCC) supplemented with 10% FBS. All of media were supplemented with 1% v/v Penicillin-Streptomycin solution (Life Technologies).

Isolation of Human scFv Specific for AIQ-HLA-A2 Complex

Figures 1, 1C:
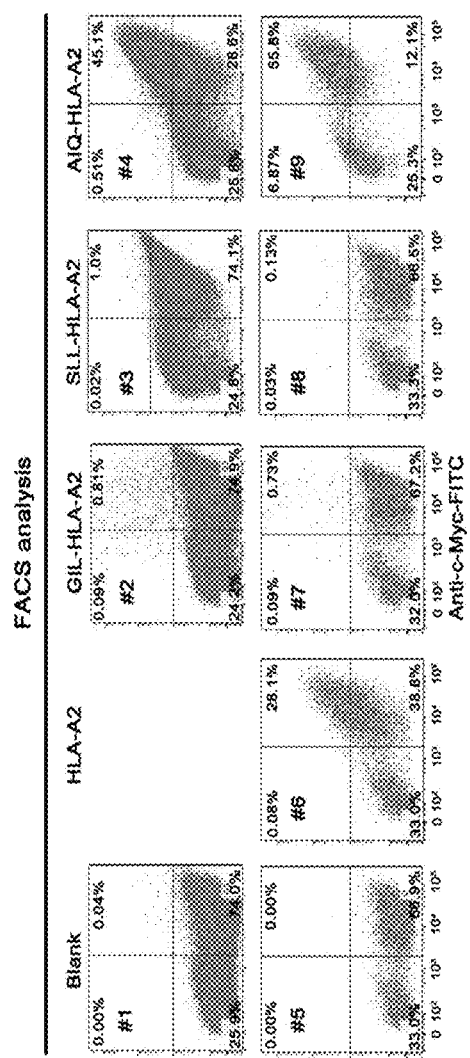
Figures 1, 1B:
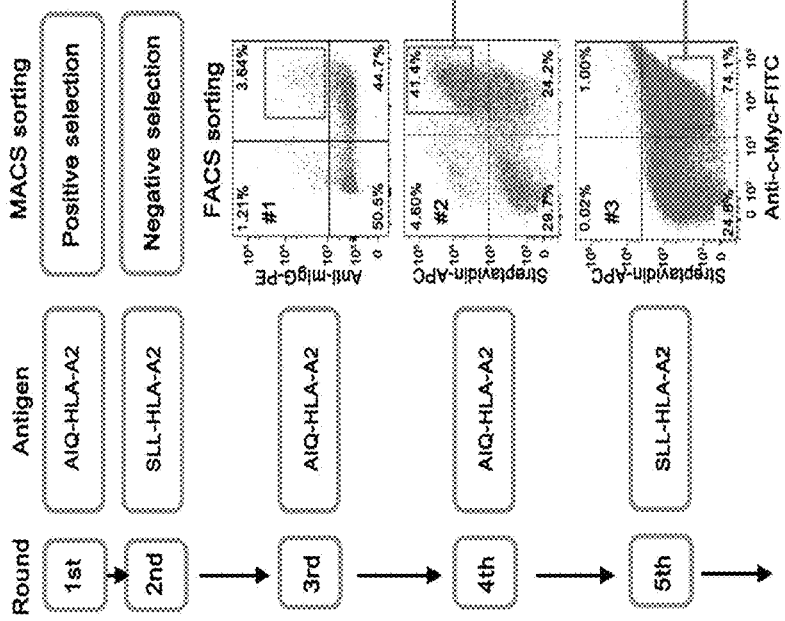
Figures 1, 1B, 1C, 2:
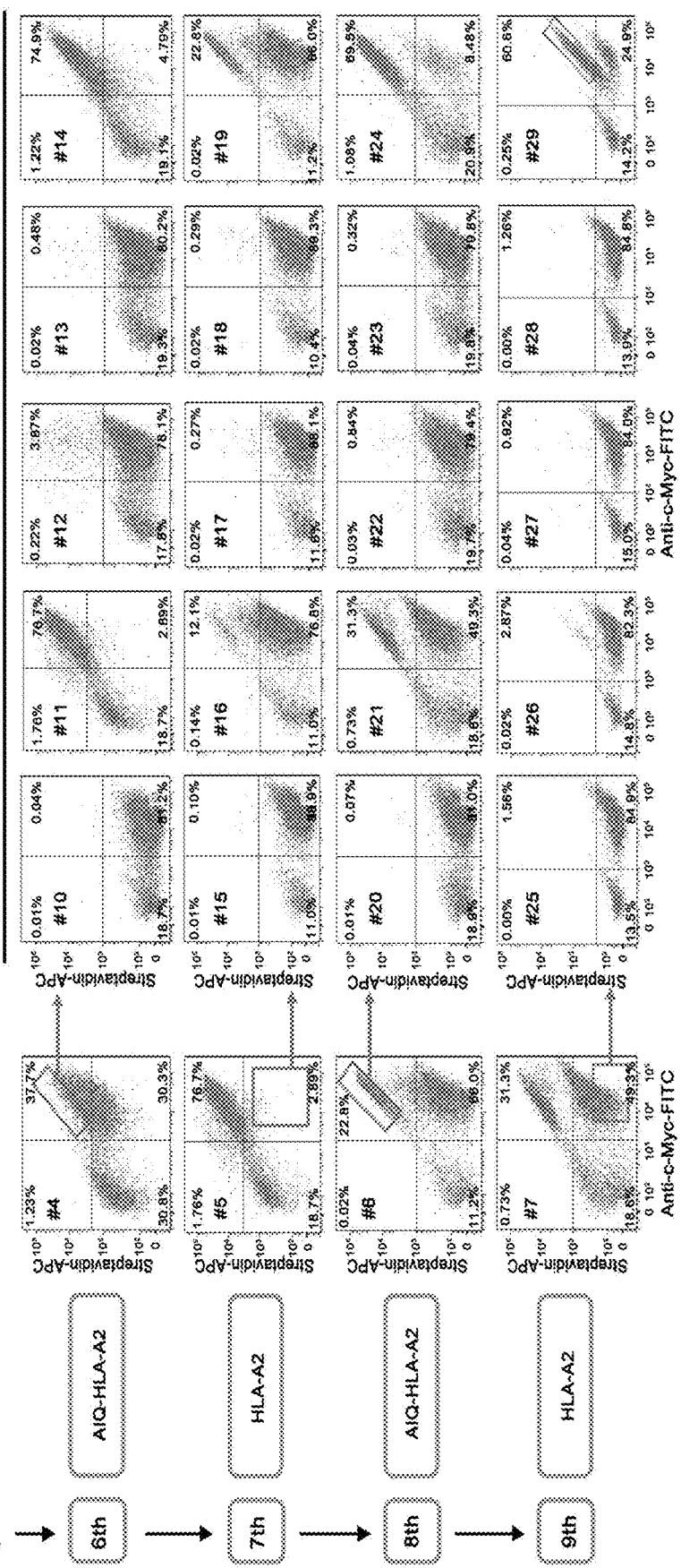

Human scFv that recognizes AIQ-HLA-A2 complex was isolated from a nonimmune human scFv library displayed on yeast surface using magnetic-activated cell sorting selection (MACS) followed by selection using fluorescence-activated cell sorting (FACS, Aria 2), as previously described (see Chao et al., NAT PROTOC 1: 755 (2006)). To enrich scFv specific for AIQ-HLA-A2 complex, SLL-HLA-A2 complex and HLA-A2 protein were used for negative selection. AIQ-HLA-A2, SLL-HLA-A2 and HLA-A2 were biotinylated prior to each round of selection. The selected yeast pool from each round was propagated in SDCAA media overnight and then induced to express scFv in SGCAA media. The numbers of induced yeast cells used for the subsequent round of selection were about ten-fold of the number of the selected yeast cells from the previous round of selection. The strategy for isolation of scFv recognizing AIQ-HLA-A2 complex is shown in FIG. 1A and FIG. 1B. After two rounds of MACS selection including positive selection with AIQ-HLA-A2, followed by negative selection with SLL-HLA-A2, the selected yeast pool was subject to multiple rounds of FACS selection (FIG. 1B). During each round of FACS selection, the selected yeast cell pool was assayed by flow cytometry for binding to HLA-A2, GIL-HLA-A2, SLL-HLA-A2 and AIQ-HLA-A2 (FIG. 1C).

Isolation of Plasmid DNA from the Selected Yeast Cells and Sequencing of scFvs

Plasmid DNA from the selected population of yeast cells was isolated using a Zymoprep kit (Zymo Research) according to the manufacturer's instructions. The numbers of yeast cells used for plasmid isolation was at least tenfold higher than the expected population diversity, so as to yield display plasmids from each of the different yeast clones in the selected population (see Chao et al., NAT PROTOC 1: 755 (2006)). Alpha-select Gold E. coli competent cells (Bioline) were transformed with 5 μL of plasmid DNA, plated onto LB Amp plates and incubated overnight at 37° C. Twenty five single colonies were randomly picked, inoculated in LB Amp media and grown overnight at 37° C., shaking at 200 rpm. Plasmid DNA was then prepared from these 25 cultures by miniprep (QIAGEN) and scFv was sequenced using following primers: forward, 5'-GTCAGTAAT-TGCGGTTCTCACC-3' (SEQ ID NO:64), and reverse, 5'-GTACAGTGGGAACAAAGTCG-3' (SEQ ID NO:65).

Characterization of scFv Clones

The RJY100 competent yeast cells were prepared using Frozen-EZ Yeast Transformation II kit (Zymo Research). The display plasmid for a single scFv clone of interest was transformed into competent yeast cells according to the manufacturer's protocol. Single clones were obtained by plating the transformed yeast cells on an SDCAA plate and incubating at 30° C. for more than 2 days until they formed visible colonies. 3-5 clones were randomly selected and inoculated separately in a 5-mL SDCAA culture and grown at 30° C., shaking at 250 rpm overnight. To induce scFv expression on yeast surface, $5 \times 10^7$ yeast cells from SDCAA culture were inoculated into 5-ml SGCAA media, and induced at 20° C., shaking at 250 rpm for at least 20 hrs. The resulting yeast cells were incubated with biotin-labeled HLA-A2, GIL-HLA-A2, SLL-HLA-A2 or AIQ-HLA-A2, followed by staining with streptavidin-APC (BioLegend) and FITC-labeled anti-c-Myc antibody (Abcam) on ice for 20 min in the dark. Stained yeast cells were analyzed by flow cytometry (LSR II HTS-1), collecting at least 20,000 events per sample.

Expression of Soluble scFv-Fc Protein

Soluble scFv-Fc protein was produced using a switchable yeast display/secretion system (see Van Deventer et al., PROTEIN ENG DES SEL 28: 317 (2015)). ScFv DNA was synthesized (Integrated DNA Technologies, IDT) and the Fc fragment was amplified by PCR using Q5 High-Fidelity 2×Master Mix (NEB). PCR primers were 5'-CCGGGGTAGAACCTAAAAGTTCCG-3' (SEQ ID NO:66) (forward) and 5'-TTTGTTCTGCACGCGTG-GATC-3' (SEQ ID NO:67) (reverse). The switchable yeast display/secretion vector backbone pCHA-FcSup-TAG was doubly digested with enzymes NheI and BamHI. After gel purification, the vector backbone, scFv DNA and Fc DNA fragments were assembled using Gibson Assembly Master Mix (New England BioLabs, NEB) according to the manufacturer's protocol. Two µL of the assembly reaction mixture was transformed into alpha-select Gold E. coli competent cells (Bioline). The transformed cells were shaken (200 rpm) at 37° C. for 60 min and then plated on LB ampicillin plate. Colonies were picked and grown in liquid LB media containing ampicillin for plasmid extraction. The resulting plasmids were sequenced and sequencing primers were 5'-GGGTAATTAATCAGCGAAGCGATG-3' (SEQ ID NO:68) (forward) and 5'-GTACAGTGG-GAACAAAGTCG-3' (SEQ ID NO:65) (reverse). The correct plasmid was transformed into the RJY100 competent yeast cells. The transformed yeast cells were grown to saturation at 30° C. in SD-SCAA media, shaking at 250 rpm overnight. The saturated cultures were pelleted and resuspended to $OD_{600}$ of 1.0 in 200 ml SG-2×SCAA induction media. The resuspended cultures were then grown for 4 days at 20° C. with shaking at 250 rpm. The yeast cells were pelleted at 10,000×g for 15 min and the supernatant was filtered using a 0.2 µM filter (Pall Corporation). The pH of filtrate was adjusted to pH 7.4 with 10×PBS, pH 7.4 (Gibco) to a final concentration of 1×. ScFv-Fc was purified by passing the filtrate twice through a pre-equilibrated protein A column containing 1 ml resin (Genscript) according to the manufacturer's protocol. The flow-through media were collected for measuring the binding efficiency to the resin by SDS-PAGE. Resin with bound scFV-Fc was washed three times using 10 mL Binding/Wash Buffer. ScFv-Fc was eluted from the resin using 10 mL Elution Buffer. The eluate containing scFv-Fc was immediately neutralized to pH 7.4 with Neutralization Buffer (1/10 volume of total eluate). Neutralized eluate was concentrated and buffer exchanged into 1×PBS using centrifugal filtration units (Millipore 30 kDa molecular weight cut-off). ScFv-Fc was quantified by A280 measurement on a Nanodrop spectrophotometer (Thermo Scientific), and the purity was assessed by SDS-PAGE using 5% stacking gel and 6% separating gel. Specific binding of the purified scFv-Fc protein to AIQ-HLA-A2 complex on the surface of target cells was assessed by flow cytometry using 5 nM protein to incubate with $5×10^5$ target cells in 200 ul PBS buffer for 30 min at room temperature, followed by staining with PE-labeled anti-HA-tag antibody.

ScFv-Fc Affinity Determination by Biolayer Interferometry

Biolayer Interferometry experiments were performed using the Octet RED96 instrument (ForteBio Inc.) at 25° C. The same buffer used for all steps comprised binding buffer with 0.05% Tween 20 and 0.1% BSA. The scFv-Fc fusion proteins were biotinylated using EZ-Link-NHS-PEG4-Biotin (Thermo Scientific). Streptavidin-coated biosensors (Streptavidin Dip and Read Biosensors, Fortebio Inc.) were loaded with 200 µL volume of 20 µg/mL biotinylated scFv-Fc protein until all sensors (except for the reference) reached a capture threshold of 0.5 nm. After a 60 s rinse and baseline steps in buffer alone, sensors were exposed to 1:2 dilution series (0 nM, 2.5 nM, 5 nM, 10 nM, 20 nM, 40 nM, and 80 nM) of the antigen (AIQ-HLA-A2 complex, SLL-HLA-A2 complex or HLA-A2). Association with antigen was monitored for 1,000 seconds and dissociation was carried out for 1,500 seconds in buffer alone. Data analysis was performed using ForteBio Data Analysis 8.2 (ForteBio). The data set was fit to a 1:1 binding model to determine $K_{on}$, $K_{off}$, and $K_D$.

CAR Vector Design

The sequence of CAR, consisting of the YG1 or CD19 scFv, the CD8a leader sequence, extracellular hinge domain and transmembrane domain, the 4-1BB co-stimulatory domain, and the CD3zeta activation domain, was custom-synthesized by Integrated DNA Technologies (IDT). The second fragment consisting of self-cleavage P2A followed by EGFP (P2A-GFP) was synthesized by the same way. The pHIV vector (plasmid #21373) was doubly digested with the enzymes XbaI and ClaI. After gel purification of the vector backbone, the pHIV backbone, CAR fragment and P2A-GFP fragment were assembled basing on their overlap region at 5' and 3' terminals using HiFi DNA Assembly Master Mix (New England BioLabs) according to the manufacturer's protocol. The resulting plasmids were sequenced using following sequencing primers: 5'-GT-TAGGCCAGCTTGGCACTTGATGT-3' (SEQ ID NO:69) (forward) and 5'-AGGCACAATCAGCATTGGTAGCTG-3' (SEQ ID NO:70) (reverse). The plasmid with the correct sequence was named pHIV-CAR-GFP.

Generation of CAR-Expressing Primary Human T Cells

Lentivirus was generated by transfecting 293T cells with pHIV-CAR-GFP, pCMV-VSVG, pCMV-Δ8.9, and pAdv plasmids. Culture supernatants were collected at 48 and 72 hrs and lentivirus particles were pelleted by ultracentrifugation at 25,000 rpm, 4° C. for 2 hrs. Lentivirus particles were suspended in 100 µL of serum-free DMEM media and frozen at −80° C. Human $CD8^+$ T cells were isolated from $HLA-A2^+$ donor peripheral blood mononuclear cells (PBMCs) using EasySep™ Human $CD8^+$ T Cell Isolation Kit (Stem Cell). The purity of the isolated T cells (>95%) was quantified using FACS with CD3ζ and CD8 stainings. The $CD8^+$ T cells were activated and expanded using T Cell TransAct™ (Miltenyi), and cultured in TexMACS Medium (Miltenyi) supplemented with 50 IU/mL IL-2 (Miltenyi), 3% fetal bovine serum (FBS) and 1% penicillin-streptomycin (Life Technologies). T cells were transduced with lentivirus (MOI=10) 4 days after TransAct™ stimulation. $GFP^+$ CAR-T cells were purified by FACS, and CAR expression on T cells was determined using Alexa Fluor® 647 AffiniPure F(ab')$_2$ Fragment Goat Anti-Human IgG (H+L) (Jackson ImmunoResearch). CAR-T cells were expanded in TexMACS Medium (Miltenyi) supplemented with 10 ng/mL recombinant human IL-7 (Peprotech), 5 ng/mL recombinant human IL-15 (Peprotech), 3% fetal bovine serum (FBS) and 1% v/v penicillin-streptomycin solution (Life Technologies) for 10 days before use.

Cytotoxicity of CAR-T Cells In Vitro

To assess the ability of CAR-T cells to kill target cells, $CD8^+$ CAR-T cells were incubated with target cells at indicated effector:target ratios. Immediately after mixing the cells (0 hr) and 24 hrs after incubation, cells were washed in PBS without serum and stained using Live/Dead Fixable Dead Cell Stain Kits (Invitrogen) according to the manufacturer's protocol. Cells were then stained with FITC-anti-human CD8, PE-anti human CD33 or PE-anti human CD19 antibody on ice for 30 min in the dark. Cells were washed with FACS buffer and analyzed by flow cytometry (LSRII HTS-1). Specific lysis of each sample was calculated using the following formula: lysis (%)={1−[(% target cells at 24 h/% target cells at 0 h) in CAR-T group/(% target cells at 24 h/% target cells at 0 h) in untransduced T group]}×100.

Intracellular Cytokine Staining

CAR transduced or untransduced human $CD8^+$ T cells were co-cultured with target cells in a 1:1 ratio, at $2×10^6$ cells/mL in 96-well round bottom plates in RPMI-1640 containing 10% FBS without any cytokines, in the presence of protein transport inhibitor monensin (BD Biosciences) and brefeldin A (BioLegend) at 37° C., 5% CO2 for 12 hrs. Cells were washed, stained with Live/Dead Fixable Aqua Dead Cell Stain, followed by surface staining for CD3, then fixed, permeabilized, and intracellularly stained with anti-IFN-γ-APC-Cy7 (BioLegend) and anti-IL-2-APC (BioLegend). Cells were analyzed by flow cytometry (LSR Fortessa HTS-2) and live $CD3^+$ lymphocytes were gated for further analysis.

CAR-T Cells Killing of Target Cells In Vivo

NOD-scid $IL2rg^{null}$(NSG) mice were purchased from the Jackson Laboratories and housed in the specific pathogen-free (SPF) vivarium at the Massachusetts Institute of Technology (MIT). All experiments with mice were approved by the Institutional Animal Care and Use Committee. Briefly, luciferase-expressing OCI-AML3 cells ($1 \times 10^6$), GMB cells ($2 \times 10^6$), or OCI-AML2 cells ($1 \times 10^6$) were injected in 200 µL of PBS into NSG mice by tail vein injection. After 4 days, $1 \times 10^7$ CAR-T cells that were sorted based on GFP expression, or activated but untransduced human T cells were injected into the tumor-bearing mice. Bioluminescence imaging (BLI) was performed every three days using a Xenogen IVIS-200 Spectrum camera.

To analyze T cells and tumor cells by flow cytometry, blood, spleen, bone marrow and liver were harvested 18 days post T cells injection. About 200 µL of blood was collected by heart-puncture into microcentrifuge tube containing 1 ml of PBS with 4 mM EDTA. Cells were pelleted by centrifugation at 1,500 rpm for 5 min and resuspended with 1 mL of ACK Lysis Buffer (Lonza Bioscience) by gently pipetting the mixture up and down and kept at room temperature for 5 min. The cells were centrifuged at 1,500 rpm for 5 min and then resuspended in FACS buffer. Prior to organ harvesting, liver was perfused with 5 mL PBS through superior mesenteric vein. Spleen and liver were mechanically disrupted by pressing them through a 70 µm strainer using a syringe plunger. The disrupted liver was digested with 2 mg/mL collagenase D (Sigma-Aldrich, USA) at 37° C. for 30 minutes. Bone marrow cells were collected from the bilateral femurs by flushing with 5 ml of cold PBS. Single-cell suspensions were prepared and lysed of red blood cells. Cells were washed with FACS buffer, centrifuged at 1,500 rpm, 4° C. for 5 min, resuspended with FACS buffer and counted with trypan blue staining.

For flow cytometry analysis, 5 millions of cells were aliquoted and mixed with 20 µL human serum to block Fc receptor for 5 min. Then, cells were stained with the following conjugated antibodies on ice for 30 min in the dark: anti-mCD45.1-BUV737 (BD Biosciences), anti-hCD45-APC-Cy7 (BioLegend), anti-hCD8-PE (BioLegend), anti-CD33-APC (BioLegend), anti-hPD1-PE-Cy7 (BioLegend) and anti-Tim-3-BV711 (BioLegend). Cells were washed with FACS buffer and resuspended in FACS buffer containing DAPI. Flow cytometry analysis was performed using LSR Fortessa HTS-2 flow cytometer (BD Biosciences), collecting 100,000 events per sample.

Statistical Analysis

Data are expressed as mean±s.e., from at least three independent experiments, unless otherwise stated. A two-tailed t-test was used to compare two independent groups. Tumor growth in vivo was compared using two-way repeated-measures ANOVA. The Kaplan-Meier method was used to analyze survival patterns in tumor-bearing mice and statistical differences were evaluated according to the Mantel-Cox log-rank test. A p value<0.05 was considered statistically significant. All of statistical analysis was performed using SPSS Statistics 22 software.

Cytotoxicity Assay by Measuring Luciferase Activity

Cytotoxicity assays of CAR-T cells were performed using luciferase-expressing target cell lines. T cells were incubated with target cells at indicated effector:target (E:T) ratios for 24 hr. Cells were then rinsed once in PBS, lysed in luciferase cell culture lysis reagent (Promega), and subsequently mixed with luciferase assay reagent (Promega). Luminescence of the lysates was analyzed using a plate spectrophotometer (Infinite M200PRO, TECAN). The luminescence of target cells alone was used as a baseline control. Specific lysis of each sample was calculated using the following formula: specific lysis (%)=100×{1−[(luminescence in CAR-T group/luminescence in target cells alone)/(luminescence in untransduced T group/luminescence in target cells alone)]}.

Quantibody Human Cytokines Array

Quantibody Human Cytokines Array1 (QAH-CYT-1) was purchased from Raybiotech. One glass slide is spotted with 16 wells of identical cytokine antibody arrays. Each well contained quadruplicate antibody spots for 20 human cytokines. 2×105 of NPM1c CAR-T cells or untransduced T cells that were derived from 4 healthy donors were co-cultured with 1×105 of NPM1c+HLA-A2+ OCI-AML3 cells in RPMI-1640 containing 10% FBS without any cytokines in 96-well round bottom plates at 37° C., 5% CO2 for 16 hours, and then 100 µl of cell-free supernatants were collected from each well for cytokine quantification. The array slides were treated and processed according to manufacturer instructions. Some of the slide wells were treated with pure antigens in order to calculate a standard curve. Fluorescence signals were detected by a laser scanner (Axon GenePix). Data extraction was done using the GAL file (www.RayBiotech.com) that is specific for this array along with the microarray analysis software (GenePix), and F488 total intensity from spots was analyzed by ELISA Calc software. A standard curve of known concentration of each cytokine was established, and the concentration of cytokine in the samples was then calculated by interpolation onto the standard curve.

Cytotoxicity Assay by Flow Cytometry with Precision Count Beads

Patient-derived primary AML samples were purchased from the Dana-Farber Cancer Institute. NPM1c CAR-T cells were incubated with primary AML cells at indicated effector:target ratios. After 24-hrs incubation, cells were washed in PBS without serum and stained using Live/Dead Fixable Dead Cell Stain Kits (Invitrogen) according to the manufacturer's protocol. Cells were then stained with FITC-anti-human CD8, PE-anti-human CD33 on ice for 30 min in the dark. Cells were washed with FACS buffer, resuspended with 180 ul FACS buffer and then 20 ul of precision count beads (BioLegend) were added into cell suspension according to manufacturer instructions, in a total volume of 200 ul. Cells were analyzed by flow cytometry (LSRII HTS-1). Absolute cell count of primary AML cells was calculated according to the formula in manufacturer instructions. Specific lysis of each sample was calculated using the following formula: specific lysis (%)=100×[1−(absolute cells count of primary AML cells in CAR-T group/absolute cells count of primary AML cells in untransduced T group)].

Human $HLA-A2^+$ $CD34^+$ hematopoietic stem/progenitor cells (HSPCs) were purified from fetal livers of two donors by EasySep Human CD34 Positive Selection Kit (StemCell Technologies) as previously described (see Chen, Q. et al (2013) *Stem Cells* 31:1160; Kaur, M. et al (2019) *J Immunol* 202:1885). NPM1c CAR-T cells were incubated with $CD34^+$ HSPCs at indicated effector:target ratios. After 24-hrs incubation, cells were washed in PBS without serum and stained using Live/Dead Fixable Dead Cell Stain Kits (Invitrogen) according to the manufacturer's protocol. Cells were then stained with FITC-anti-human CD8, PE-anti human CD34 on ice for 30 min in the dark. As described above, cells were washed with FACS buffer, resuspended with 180 ul FACS buffer and then 20 ul of precision count beads (BioLegend) were added into cell suspension according to manufacturer instructions, in a total volume of 200 ul. Cells were analyzed by flow cytometry (LSRII HTS-1). Absolute cell count of $CD34^+$ HSPCs was calculated according to the formula in manufacturer instructions. Specific lysis of each sample was calculated using the following formula: specific lysis (%)=100×[1−(absolute cells count of $CD34^+$ HSPCs in CAR-T group/absolute cells count of $CD34^+$ HSPCs in untransduced T group)]. The use of human tissue in this study was approved by the Institutional Review Board at Massachusetts Institute of Technology.

CAR-T Cell Killing of Primary HLA-A2$^+$ NPM1c$^+$ AML Xenografts

Patient-derived primary NPM1c$^+$HLA-A2$^+$ AML samples were purchased from the Dana-Farber Cancer Institute. The NSG-SGM3 (NSGS) mice with 10-week age were purchased from the Jackson Laboratories and housed in the specific pathogen-free (SPF) vivarium at the Massachusetts Institute of Technology (MIT). To improve engraftment efficiency of human primary AML in mice, NSGS mice were hydrodynamically injected with 100 µg DNA plasmids encoding human IL-3 and GM-CSF 24 hours before primary AML injection, as previously described (see Chen, et al (2009) PNAS 106:21783). NSGS mice were irradiated at 250 cGy, followed by tail vein injection with $1 \times 10^6$ of primary NPM1c$^+$HLA-A2$^+$ AML cells within 24 hours post irradiation. After 2 weeks, $1 \times 10^7$ CAR-T cells that were sorted based on GFP expression, or the same number of activated but untransduced human T cells were injected into the tumor-bearing mice. AML burden was quantified in the peripheral blood by tail vein bleeding and analyzed by flow cytometry (LSR Fortessa HTS-2, BD Biosciences) every 9 days. AML engraftment was defined as the percentage of circulating human CD45$^+$ CD8$^-$ cells.

Proliferation Assays

NPM1c CAR-T cells or untransduced T cells ($1 \times 10^5$) were co-cultured with $1 \times 10^5$ of NPM1c$^+$HLA-A2$^+$ OCI-AML3 cells in RPMI-1640 containing 10% FBS without any cytokines in 96-well round bottom plates at 37° C., 5% CO2 for 5 days. Cells were then harvested, stained with Live/Dead Fixable Aqua Dead Cell Stain (Invitrogen), FITC-anti-human CD8 (BioLegend), and PE-anti-human CD33 (BioLegend), and precision count beads (BioLegend) were added prior to flow cytometry analysis. Absolute cell count of CD8$^+$ T cells was calculated according to the formula in manufacturer instructions of precision count beads. For intracellular Ki-67 staining, cells were washed, stained with Live/Dead Fixable Aqua Dead Cell Stain, followed by surface staining for CD8, then fixed, permeabilized, and intracellularly stained with PE-anti-human Ki67 (BioLegend) according to the manufacturer's protocol. Cells were analyzed by flow cytometry (LSRII HTS-1) and live CD8$^+$ lymphocytes were gated for further analysis.

Western Blotting

Equal number of cells were washed with PBS and lysed in RIPA buffer supplemented with protease inhibitors. Total cell extracts were dissolved in SDS Loading Buffer, boiled for 5 minutes at 95° C., separated using 10% SDS-PAGE, and transferred to a PVDF membrane. After blocking the membrane with 5% non-fat milk TBS-T solution, the membrane was probed with antibodies specific for the mutant NPM1c (NB 110-61646SS; NovusBio) or GAPDH (#3683; Cell Signaling Technology).

Example 1: Isolation of Human scFv Specific for AIQ-HLA-A2 Complex by Yeast Surface Display Isolation of human scFv specific for AIQ-HLA-A2 complex formed the basis for developing tumor-specific CAR-T therapy for AML with NPM1c mutation. Yeast surface display (YSD) (see Chao et al., NAT PROTOC 1: 755 (2006)) was used to identify high-affinity scFv specific for AIQ-HLA-A2 complex. Because YSD allows quantitative discrimination between different scFv variants based on their binding to antigens on the yeast cell surface by flow cytometry, selection of high-affinity scFvs can be achieved during the screening process. Furthermore, because the yeast-display library was constructed using the entire repertoire of variable region gene fragments from human splenic B cells (i.e., from fully human antibody sequences), the isolated scFvs are already of human origin, have reduced immunogenicity, and therefore suitable for therapeutic development for human use. To isolate scFvs that specifically recognize AIQ-HLA-A2 complex, AIQ-HLA-A2 complex was used for positive selection, HLA-A2 only or HLA-A2 loaded with control epitope peptide (SLLMWITQC (SEQ ID NO:62), abbreviated as SLL-HLA-A2) derived from NY-ESO-1 were used for negative selection (FIG. 1A and FIG. 1B), and a YSD library used was estimated to have a diversity of $1 \times 10^7$ to $1 \times 10^9$ different clones.

A series of positive and negative selections were performed to isolate scFvs with specificity to the AIQ-HLA-A2 complex but not to HLA-A2 in the presence or absence of other antigenic peptides, such as cancer-testis antigen NY-ESO-1 epitope (SLLMWITQC (SEQ ID NO:62), abbreviated as SLL-HLA-A2) (FIG. 1A and FIG. 1B). Approximately $1 \times 10^{10}$ yeast cells (at least tenfold of the library diversity) were incubated with soluble biotin-labeled AIQ-HLA-A2 complex, followed by streptavidin-labeled magnetic beads and magnetic-activated cell sorting selection (MACS) purification (FIG. 1B, round 1). The positively selected yeast cells were expanded approximately 10-fold and incubated with soluble biotin-labeled SLL-HLA-A2 complex, followed by streptavidin-labeled magnetic beads and MACS negative selection (FIG. 1B, round 2). The unbound yeast cells were expanded and incubated with soluble biotin-labeled AIQ-HLA-A2 complex, followed by PE-labeled antibody specific for the mouse IgG (Fc portion of HLA-A2 dimer, FIG. 1A) and FITC-labeled anti-c-Myc antibody, which detects the c-Myc epitope at the C-terminal of scFv (FIG. 1A). As shown in FIG. 1B (round 3, plot #1), ~3.6% of yeast cells were positive for anti-mouse IgG and c-Myc epitope. The double positive yeast cells were isolated by fluorescence-activated cell sorting (FACS) (FIG. 1B, round 3).

To further enrich scFv specificity for AIQ-HAL-A2 complex, the sorted yeast cells were expanded and subjected to a series of positive (with biotin-labeled AIQ-HLA-A2) and negative (with biotin-labeled SLL-HLA-A2 or HLA-A2) selection, followed by staining with streptavidin-APC and FITC-labeled anti-c-Myc antibody and cell sorting. To assess the enrichment, the selected yeast cells were analyzed for non-specific binding to HLA-A2, GIL-HLA-A2 [HLA-A2 loaded with GILGFVFTL (SEQ ID NO:63) (abbreviated as GIL) peptide from influenza virus M1 (see Choo et al., J VIROL 88: 10613 (2014))], and SLL-HLA-A2, and specific binding to AIQ-HLA-A2 (FIG. 1C). For example, in round 6 (FIG. 1B), yeast cells displaying scFv with high affinity for AIQ-HLA-A2 complex were purified. However, most of the purified yeast cells bound to both HLA-A2 and AIQ-HLA-A2, but not GIL-HLA-A2 and SLL-HLA-A2 (FIG. 1C, plot #11-14), indicating that most of the selected scFvs can bind to HLA-A2 without peptide. To select yeast cells displaying scFv specific for AIQ-HLA-A2, yeast cells were stained with HLA-A2 and purified HLA-A2-negative yeast cells by cell sorting (FIG. 1B, round 7, plot #5). Around 12% of the selected yeast cells were positive for HLA-A2 and c-Myc (FIG. 1C, plot #16), 22.8% positive for AIQ-HLA-A2 and c-Myc (FIG. 1C, plot #19), and less than 1% positive for either GIL-HLA-A2 or SLL-HLA-A2 (FIG. 1C, plot #17 and 18), indicating an enrichment of scFv for AIQ-HLA-A2. With further positive and negative selection (FIG. 1B, rounds 8 and 9), yeast cells were selected that were mostly positive for AIQ-HLA-A2 and c-Myc (~60%, FIG. 1C, plot #29) but mostly negative for HLA-A2 (<3%, FIG. 1C, plot #26).

Figure 1D:
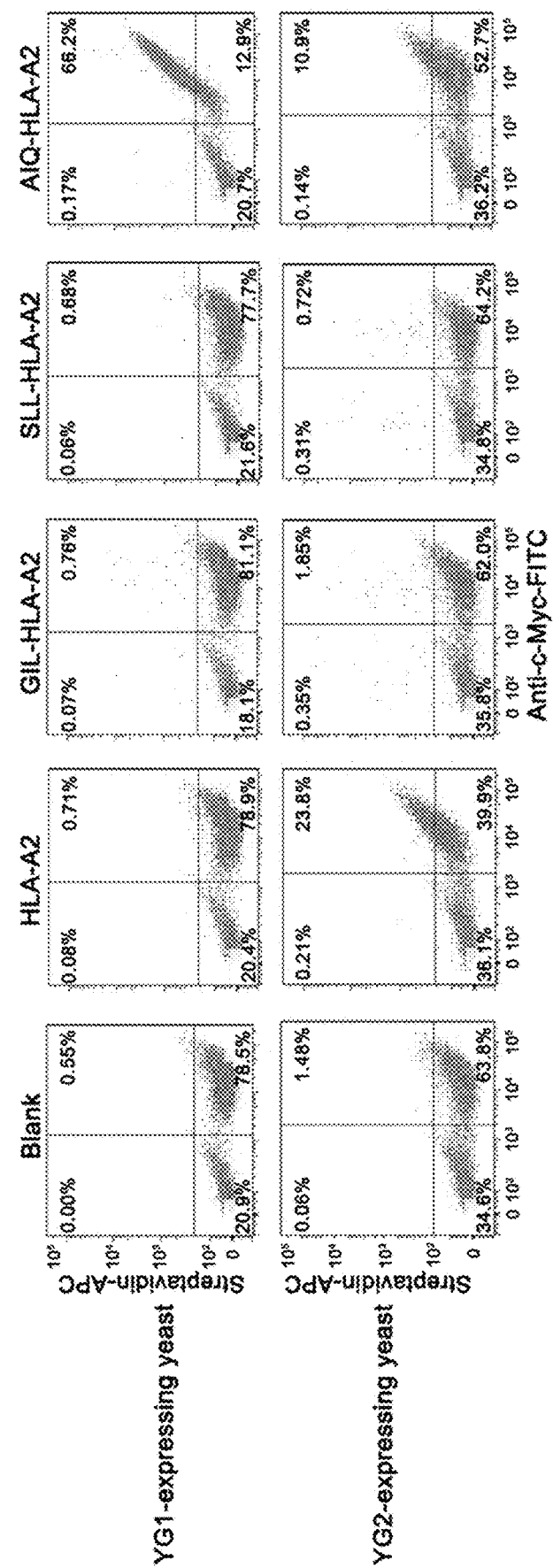

To identify the sequences of scFvs, plasmid DNA was extracted from the selected yeast cell pool and transformed into *E. coli*. Twenty-five single colonies were randomly picked for plasmid isolation and sequencing. Twenty-four of the 25 had the same scFv DNA sequence (referred to as YG1, see the Sequences section, below), and the remaining one had a different scFv DNA sequence (referred to as YG2). YG1 and YG2 were then transformed separately into RJY100 competent yeast cells and scFv expression was induced by culturing yeast cells in SGCAA media. Flow cytometry analysis showed that c-Myc-positive YG1-expressing yeast cells were also stained positive for AIQ-HLA-A2 complex but not HLA-A2, GIL-HLA-A2 or SLL-HLA-A2 complexes, while c-Myc-positive YG2-expressing yeast cells were weakly stained for both HLA-A2 and AIQ-HLA-A2 (FIG. 1D). These results show that scFv from YG1 is specific for AIQ-HLA-A2 complex.

Figure 2A:
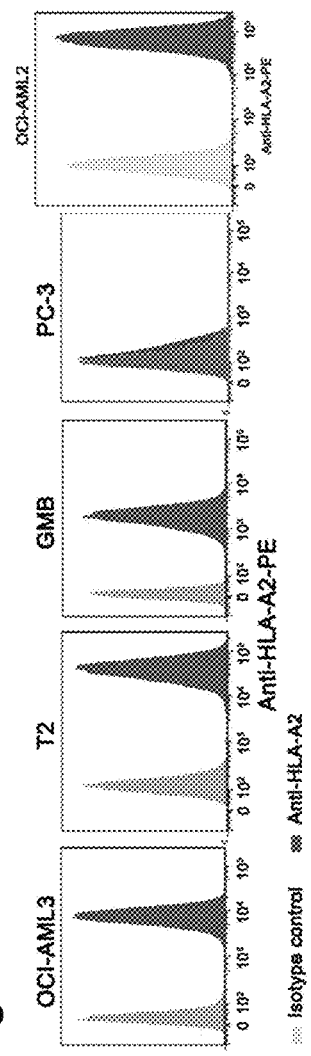
FIGS. 2A-2E show specific and high affinity binding of YG1 scFv-Fc to AIQ-HLA-A2 complex on AML cells.
Figure 2B:
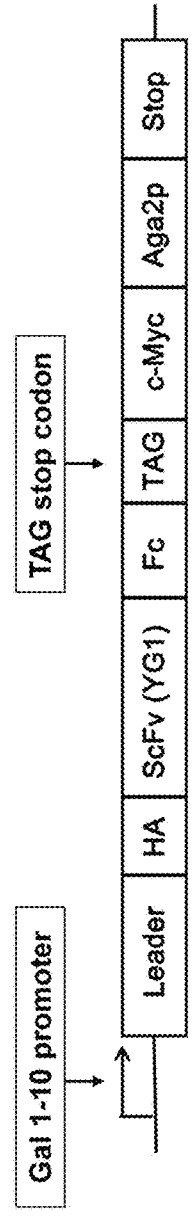

Example 2: Specific and High Affinity Binding of YG1 scFv-Fc to AIQ-HLA-A2 Complex To further characterize YG1 scFv, YG1 scFv-Fc fusion protein was produced using a switchable yeast display/secretion system (FIG. 2A). The fusion protein was purified using protein A-resin and analyzed by SDS-PAGE. Under the non-reducing condition, major bands were detected at approximately 60, 140 and 260 kDa, corresponding to the sizes of monomeric, dimeric, and tetrameric scFv-Fc protein products (FIG. 2B). Upon reduction, the intensity of the 60 kDa band was increased and the 260 kDa band was gone, consistent with the expected molecular weight of a monomeric scFv-Fc protein product. The persistence of the 140 kDa band is likely due to post-translational modification, such as glycosylation, of the fusion protein (see Van Deventer et al., *PROTEIN ENG DES SEL* 28: 317 (2015)).

Figure 2C:
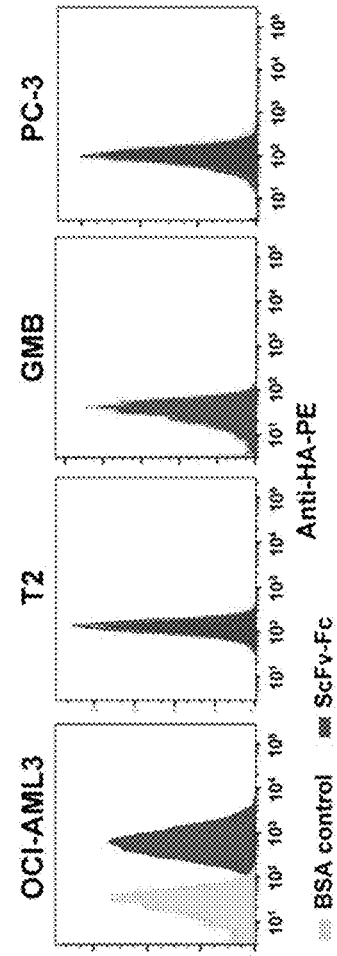
Figure 2D:
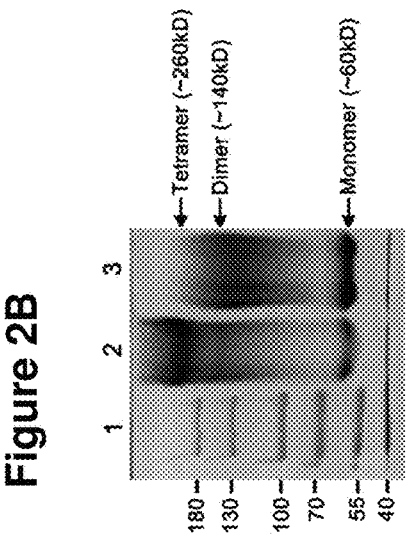

Flow cytometry was used to verify specific binding of the YG1 scFv-Fc protein to the AIQ-HLA-A2 complex in a panel of NPM1c and HLA-A2-positive and -negative cell lines, including OCI-AML3, a HLA-A2+ AML cell line with NPM1c mutation (see Quentmeier et al., *LEUKEMIA* 19: 1760 (2005)); OCI-AML2, a HLA-A2+ AML cell line with wildtype NPM1; T2, a HLA-A2+ lymphoblastic cell line with wildtype NPM1 (see Lorente et al., *J BIOL CHEM* 286: 38054 (2011)); GMB, a HLA-A2+ B cell leukemia/lymphoma line derived from overexpression of Myc and Bcl2 (Leskov et al., *ONCOGENE* 32: 1066 (2013)); and PC-3, a HLA-A2− prostate cancer cell line with wildtype NPM1 (see Matsueda et al., *PLOS ONE* 7: e45756 (2012)). When cells were stained for HLA-A2, OCI-AML3, OCI-AML2, T2 and GMB cells were positive and PC-3 cells were negative, as expected (FIG. 2C). When the cells were stained with YG1 scFv-Fc fusion protein followed with PE-labeled anti-HA antibody to detect HA epitope in the fusion protein (see FIG. 2A), almost all OCI-AML3 cells were positive but none of the T2, GMB or PC-3 cells were positive (FIG. 2D). Additionally, none of the OCI-AML2 cells were positive (data not shown). Thus, the YG1 scFv is capable of specific binding to AIQ-HLA-A2 complex on human HLA-A2+ AML cells with the NPM1c mutation.

Figure 2E:
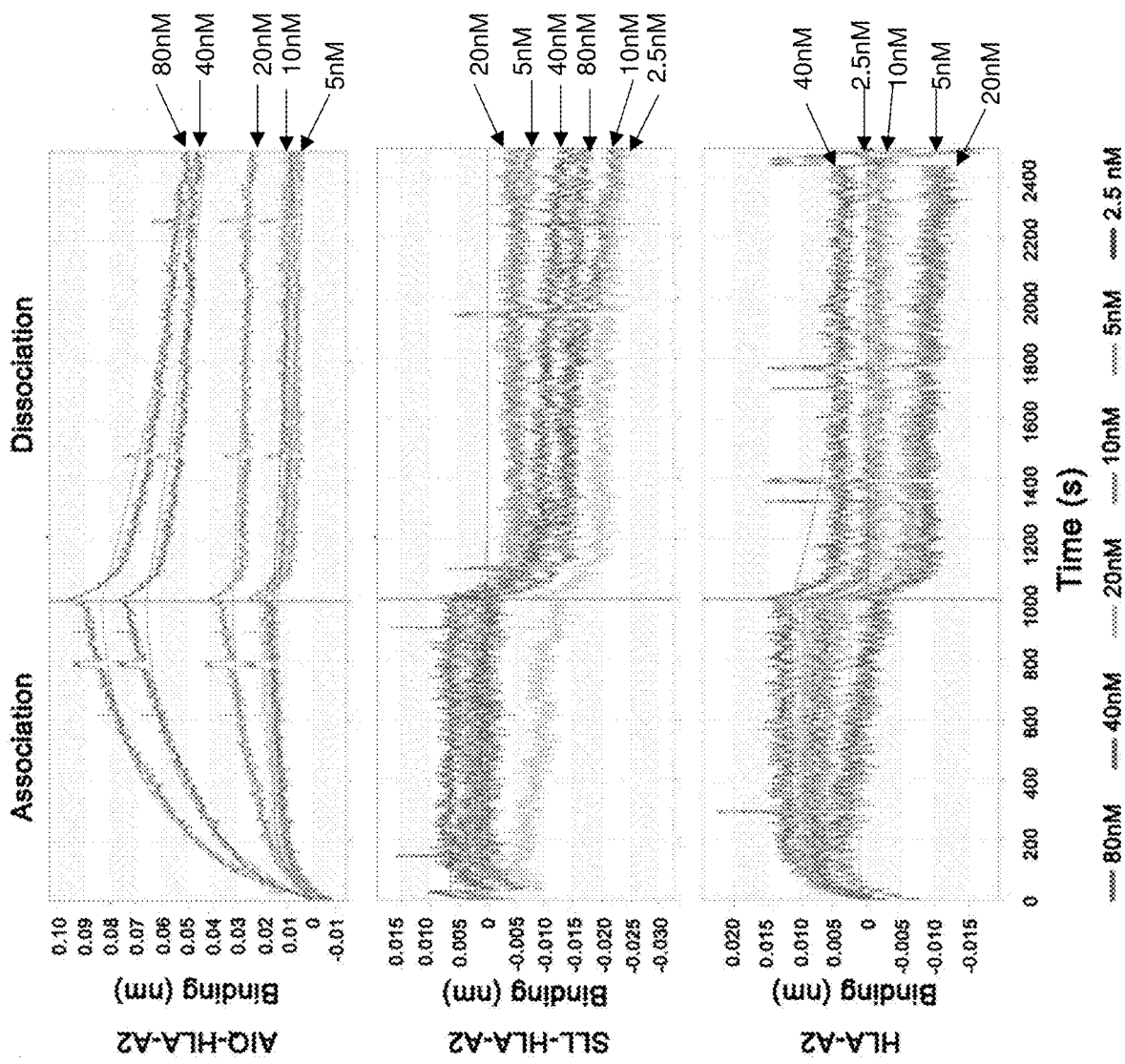

The affinity of the YG1 scFv-Fc to AIQ-HLA-A2 complex was measured using Biolayer Interferometry. Purified YG1 scFv-Fc fusion protein was biotinylated and captured on streptavidin (SA) biosensors. Upon addition of AIQ-HLA-A2, the binding amplitudes increased in a concentration dependent manner (FIG. 2E), whereas the binding amplitudes were not significantly changed upon addition of increasing concentrations of SLL-HLA-A2 or HLA-A2 complexes. Based on the association and dissociation kinetics, the association constant ($K_{on}$) of YG1 scFv-Fc with AIQ-HLA-A2 was $5.33\pm0.02\times10^4$ Ms$^{-1}$, the dissociation constant ($K_{off}$) was $3.77\pm0.02\times10^{-4}$ s$^{-1}$, and the equilibrium dissociation constant ($K_D$) was $7.07\pm0.08$ nM. Together, these results show that the YG1 scFv-Fc fusion protein binds to AIQ-HLA-A2 complex with high specificity and affinity.

Example 3: Generation of CAR-T Cells Specific to AIQ-HLA-A2 Complex

Figure 3A:
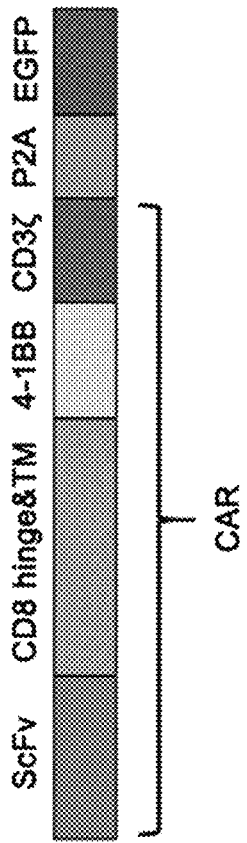
FIGS. 3A-3D show generation of NPM1c-CAR-T cells (comprising YG1 scFv) specific to AIQ-HLA-A2 complex.
Figure 3B:
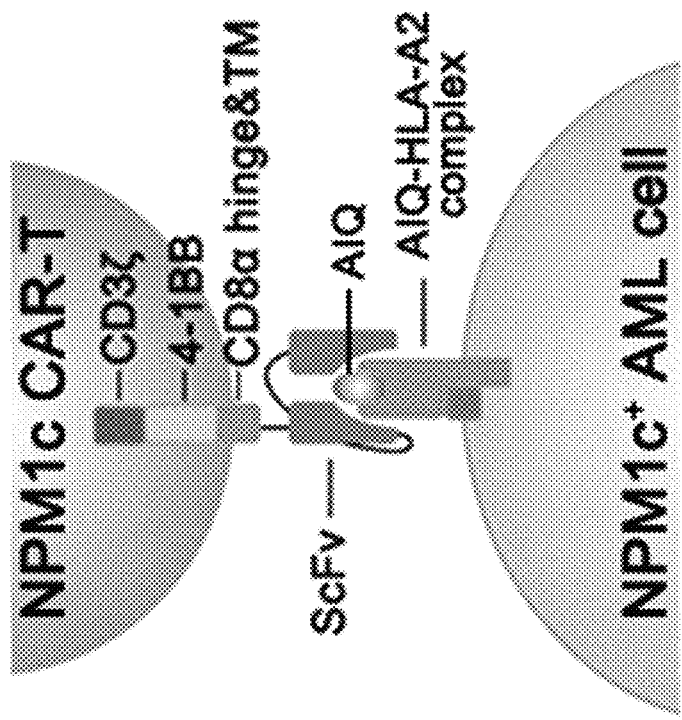
Figure 3C:
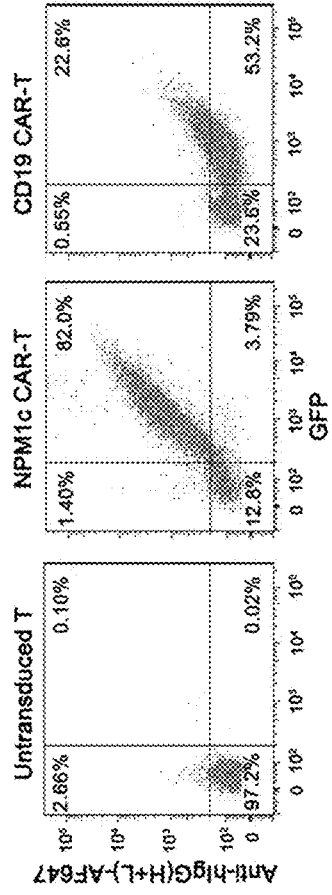
Figure 3D:
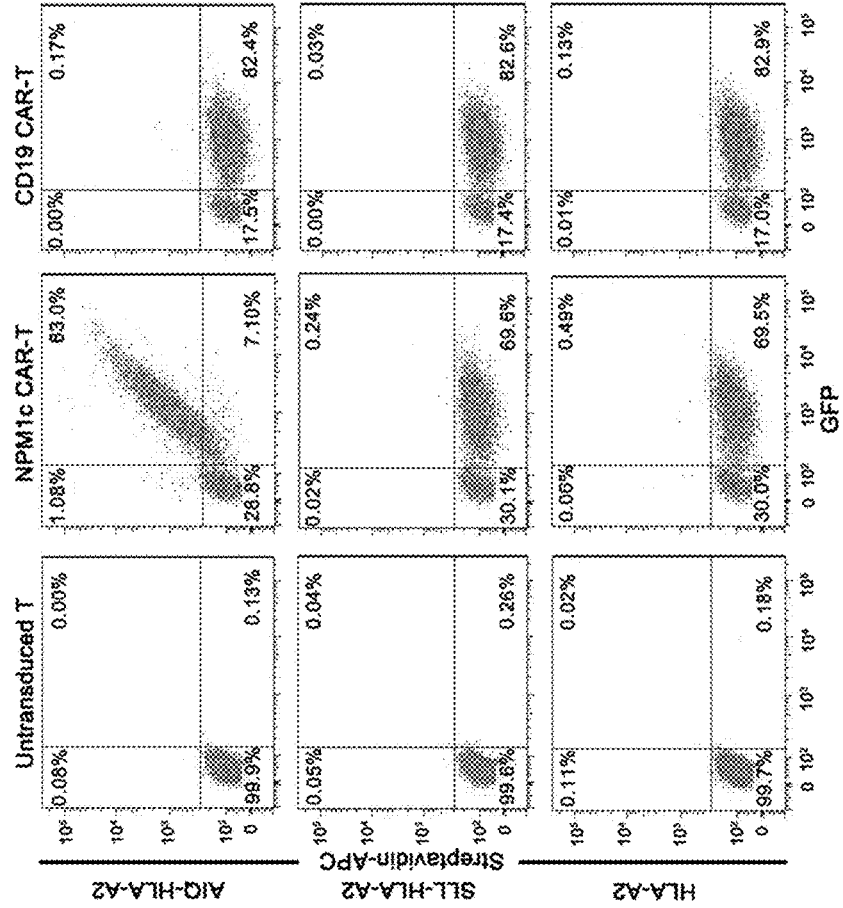

To construct NPM1c CAR, the YG1 scFv was cloned in-frame into a CAR backbone containing a CD8a hinge and transmembrane (TM) domain, a 4-1BB co-stimulatory domain and a CD3ζ activation domain, followed by self-cleavage P2A and EGFP (FIG. 3A and FIG. 3B, and the Sequences section, below). As a control, the same structural backbone was used for expressing CAR specific for CD19 (CD19 CAR). Human CD8+ T cells were purified from donor peripheral blood mononuclear cells (PBMCs), activated with anti-CD3ζ and anti-CD28 for four days and then either not transduced or transduced with lentiviruses expressing NPM1c CAR or CD19 CAR. Four days later, transduced T cells were isolated by sorting for GFP+ cells and expanded for another ten days. The resulting T cells were analyzed for GFP and CAR expression by staining with AF647 labeled anti-human IgG heavy and light chain antibody that recognizes scFv. As shown in FIG. 3C, T cells transduced with NPM1c CAR-expressing lentiviruses were positive for both GFP and scFv, whereas T cells transduced with CD19 CAR-expressing lentiviruses were positive for GFP but only weakly positive for scFv. The latter is probably because CD19 scFv is humanized from mouse sequences (see U.S. Patent Pub. No. 2014/0271635 A1). To determine if the resulting NPM1c CAR-T cells specifically recognize AIQ-HLA-A2 complex, CAR-T cells were incubated with biotinylated AIQ-HLA-A2, SLL-HLA-A2 or HLA-A2 followed by streptavidin-APC staining. GFP NPM1c CAR-T cells were specifically bound to AIQ-HLA-A2 complex, but not to SLL-HLA-A2 or HLA-A2 (FIG. 3D), while both untransduced T cells and CD19 CART cells did not show binding to any of the three complexes. These results confirm the specificity of NPM1c-CAR-T cells (with the YG1 scFv) to AIQ-HLA-A2 complex.

Example 4: Specific Killing of Human AML Cells by NPM1c CAR-T Cells In Vitro

Figure 4A:
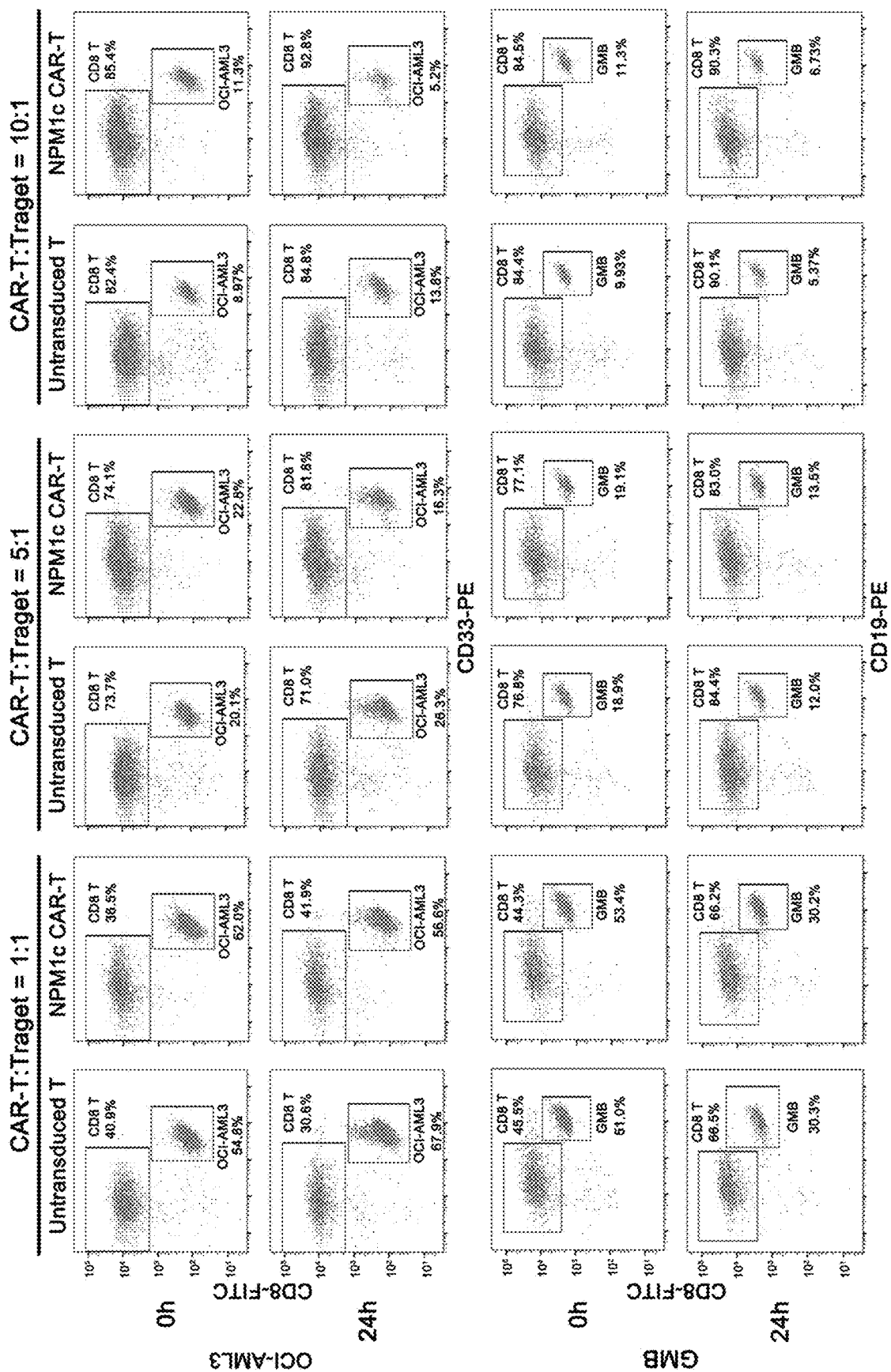

To investigate the potency and specificity of NPM1c CAR-T cells, untransduced T cells and NPM1c CAR-T cells (with the YG1 scFv) were co-cultured with OCI-AML3, GMB and PC-3 tumor cells at different effector:target (E:T) ratio for 24 hrs. The relative proportions of T cells and tumor cells were quantified by flow cytometry staining for CD8 plus CD33 (for OCI-AML3), CD19 (for GMB), or mCherry (for PC-3). As shown in FIG. 4A and FIG. 4B, NPM1c CAR-T cells killed HLA-A2$^+$ NPM1c OCI-AML3 cells in a dose-dependent manner, but did not kill HLA-A2$^+$ NPM1c$^-$ GMB cells or HLA-A2$^-$ NPM1c$^-$ PC-3 cells regardless of the E:T ratio. Consistently, a significantly higher percentage of NPM1c CAR-T cells expressed IFN-γ as compared to untransduced T cells when co-cultured with OCI-AML3 cells as compared to GMB or PC-3 cells (FIG. 4C, see bars on the left panel, where the left set of shaded bars correspond to NPM1c CAR-T cells and the right set of shaded bars correspond to untransduced T cells). Similarly, a significantly higher percentage of NPM1c CAR-T cells expressed IL-2 as compared to untransduced T cells when co-cultured with OCI-AML3 cells but percentage was much low (<2%) (FIG. 4C, see bars on the right panel, where the left set of shaded bars correspond to NPM1c CAR-T cells and the right set of shaded bars correspond to untransduced T cells). These results show that NPM1c CAR-T cells can specifically kill HLA-A2$^+$ NPM1c$^+$ AML cells in vitro. The very small proportion of NPM1c CAR-T cells (<2%) expressing IL-2 when co-cultured with OCI-AML3 target cells may be due to low density of NPM1c peptide-HLA-A2 complex present on the surface of OCI-AML3 cells. Supporting this possibility, Watanabe et al. showed that the target antigen density that is required to induce T cell cytokine production was much higher than that required to stimulate CAR-mediated lysis: CD20-specific CAR-T cells could lyse target cells with the lowest density of CD20 (~200 molecules/cell), but cytokine production required a higher density of CD20 (5,000 molecules/cell) (Watanabe et al., *J IMMUNOL* 194: 911 (2015)). Recently, Walker et al. investigated antigen density required to activate CAR-T cells using Nalm6 cells and found that CAR T cells could lyse target cells with the lowest CD20 expression and induce IFN-γ production with moderate antigen density, but a significantly higher threshold of CD20 density was required for IL-2 production as compared to IFN-γ production (Id.). Although the density of AIQ-HLA-A2 on OCI-AML3 cells is not known, the density of peptide-MHC I complex on the cancer cells usually ranges from 100 to a few thousand molecules (Dubrovsky et al., *ONCOIMMUNOLOGY* 5: e1049803 (2016)), which is sufficient to trigger cytolytic activity of CAR-T cells, but may not be enough to trigger CAR-T cell to produce cytokines (Watanabe et al., *FRONT IMMUNOL* 9: 2486 (2018)). In this respect, the risk of cytokine release syndrome may potentially be lower using CAR-T cells targeting peptide-MHC complexes than, e.g., highly expressed TAAs.

Figure 4D:
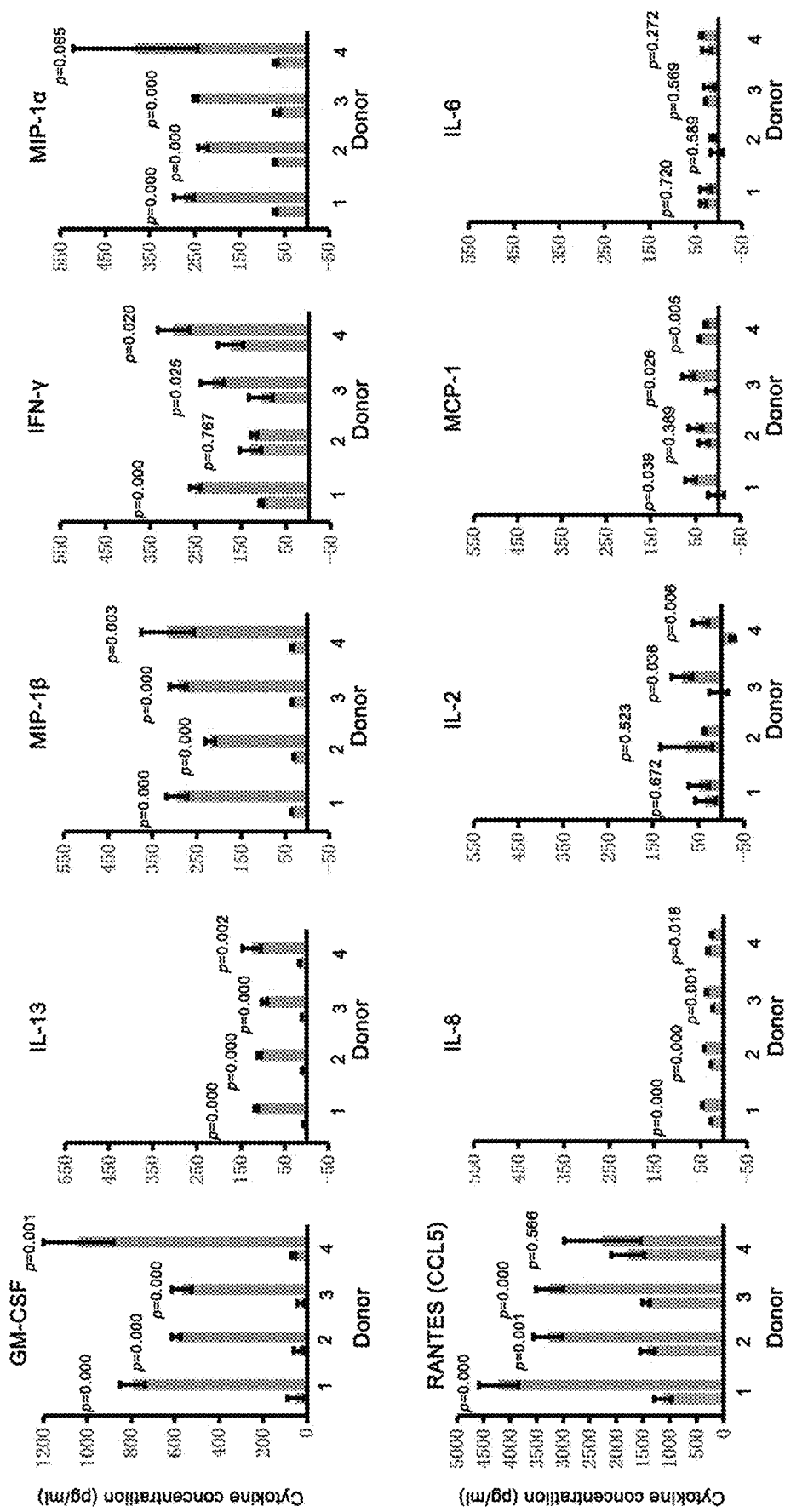

To assess the release of a broader range of cytokines by NPM1c CAR-T cells after stimulation with target cells, Quantibody Human Cytokine Array was used to quantitatively measure the secretion of 20 human cytokines and chemokines in supernatants from co-culture of NPM1c CAR-T cells (with the YG1 scFv) or untransduced T cells that were prepared from four healthy donors, with OCI-AML3 target cells. Significantly increased secretion of GM-CSF (4 out of 4 donors), IL-13 (4 out of 4 donors), MIP-1β (4 out of 4 donors), IL-8 (4 out of 4 donors), IFN-γ (3 out of 4 donors), MIP-1α (3 out of 4 donors), RANTES (3 out of 4 donors), IL-2 (2 out of 4 donors), MCP-1 (2 out of 4 donors) was found in supernatants from NPM1c CAR-T cells compared with untransduced T cells (FIG. 4D).

To assess whether NPM1c$^+$HLA-A2$^+$ target cells stimulate the proliferation of NPM1c CAR-T cells, NPM1c CAR-T cells (with the YG1 scFv) or untransduced T cells were co-cultured with OCI-AML3 cells for 5 days, and T cell number and Ki-67 expression were quantified by flow cytometry. The absolute number of NPM1c CAR-T cells was significantly higher than that of untransduced T cells as determined by flow cytometry using precision count beads (FIG. 4E). The increased expression of Ki-67 was observed in NPM1c CAR-T cells as compared to untransduced T cells as determined by mean fluorescence intensity (MFI) of intracellular Ki-67 staining (FIG. 4F). These results indicate the ability of NPM1c CAR-T cells to proliferate in response to NPM1c$^+$HLA-A2$^+$ target cells.

To further verify the specificity of NPM1c CAR-T cells in targeting NPM1c$^+$HLA-A2$^+$ AML cells, HLA-A2$^+$ OCI-AML2 cells and HLA-A2$^-$ PC-3 cells were transduced with lentivirus to stably express NPM1c (data not shown). Following exogenous NPM1c expression, HLA-A2$^+$ OCI-AML2 cells were stained positive for YG1 scFv-Fc (data not shown) and killed by NPM1c CAR-T cells (with the YG1 scFv) in an E:T ratio-dependent manner (FIG. 4G). However, NPM1c-expressing HLA-A2$^-$ PC-3 cells were not stained by YG1 scFv-Fc (data not shown) and were not killed by NPM1c CAR-T cells (with the YG1 scFv) at any E:T ratio as compared to untransduced T cells (FIG. 4H).

Figure 4I:
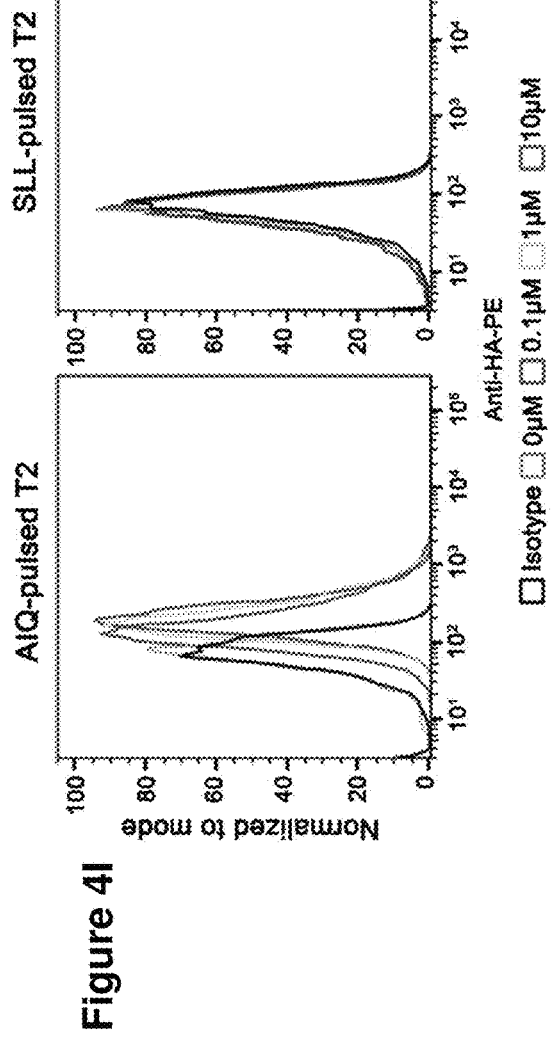
Figure 4J:
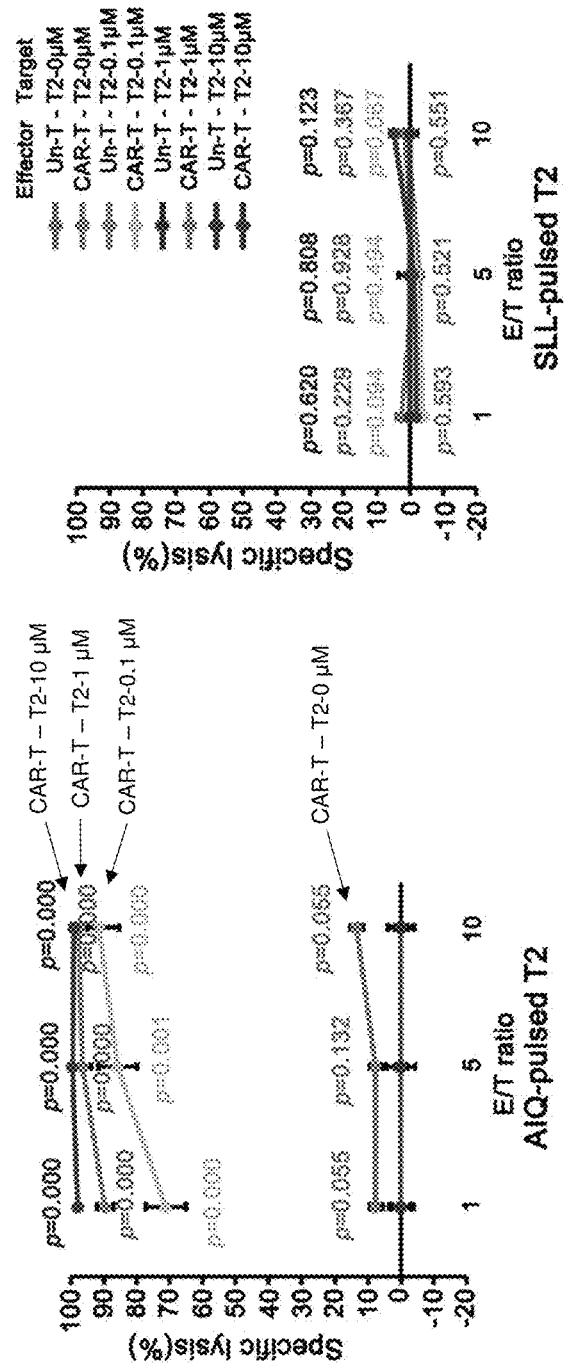

Additionally, T2 cells were loaded with different peptides to demonstrate antigen specificity of NPM1c CAR-T cells. T2 cells are HLA-A2$^+$ but deficient in transporter associated with antigen processing (TAP). Therefore, many of the HLA-A2 molecules on the T2 cell surface are not loaded with endogenous peptides, but can be loaded with exogenous peptides (see e.g., Hosken, N., et al., *SCIENCE* 248:367 (1990); Bossi, G. et al., *ONCOIMMUNOLOGY* 2:e26840 (2013)). T2 cells were pulsed with different concentrations of NPM1c peptide (AIQ) or NY-ESO-1 peptide (SLL) ranging from 0.1 μM to 1 μM to 10 μM. T2 cells pulsed with AIQ peptide but not SLL peptide were stained by YG1 scFv-Fc (FIG. 4I). Consistently, NPM1c CAR-T (with the YG1 scFv) killed AIQ-pulsed T2 cells in a peptide concentration-dependent manner but not SLL-pulsed T2 cells (FIG. 4J). These results further support the specificity of NPM1c CAR-T cell recognition and killing of target cells with NPM1c-HLA-A2 complex on the cell surface.

Example 5: NPM1c CAR-T Therapy Reduces Leukemia Burden and Prolongs Survival

Figure 5A:
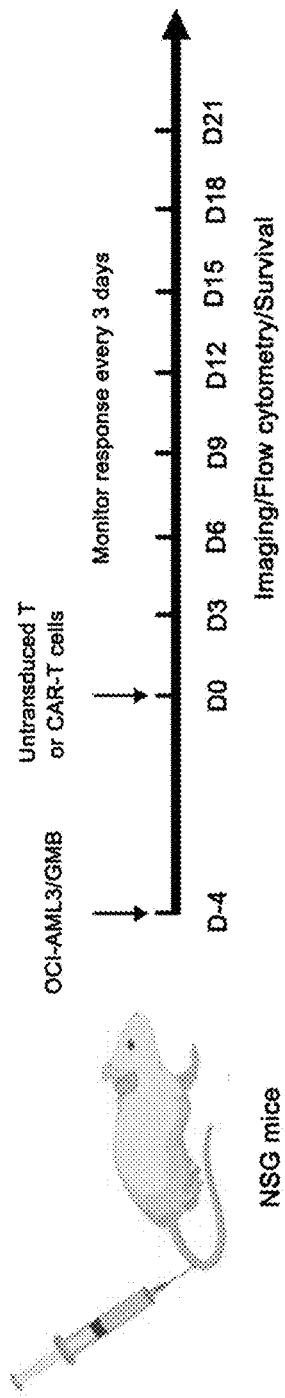
Figure 5C:
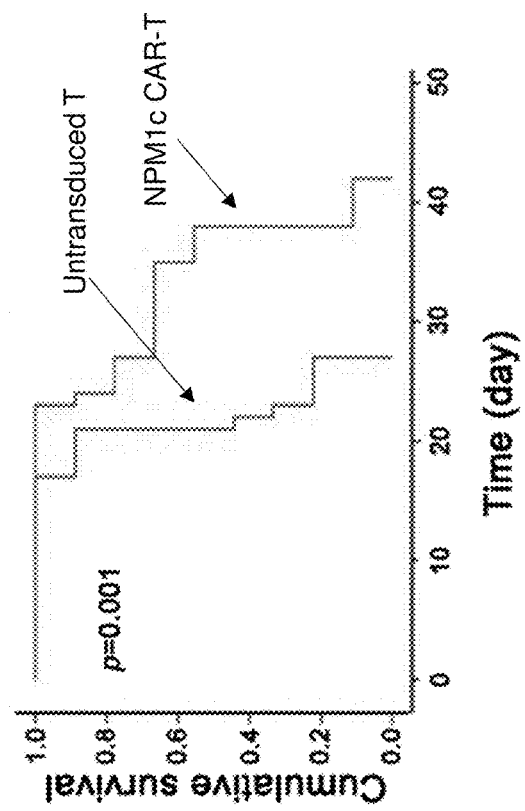
Figure 5B:
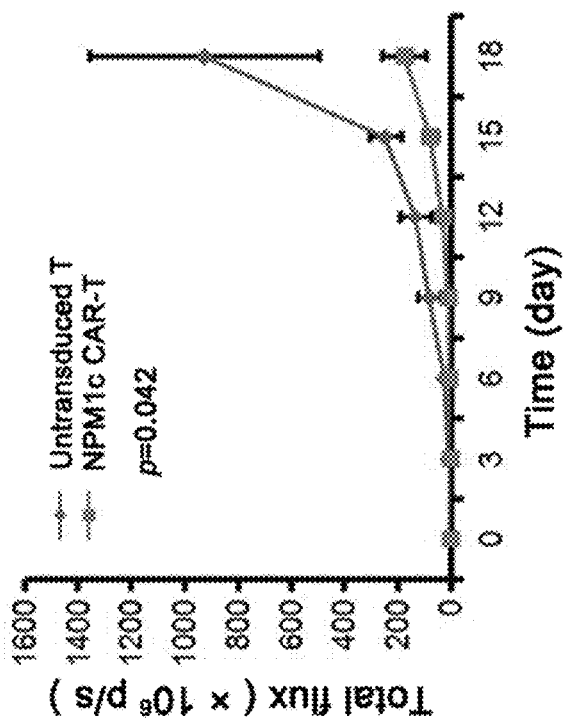
Figure 5D:
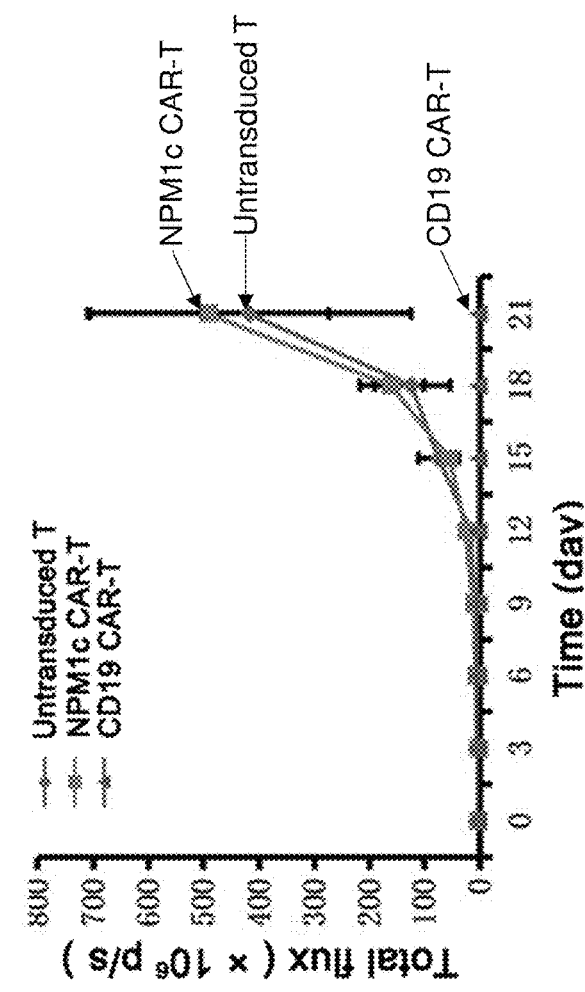
Figure 5E:
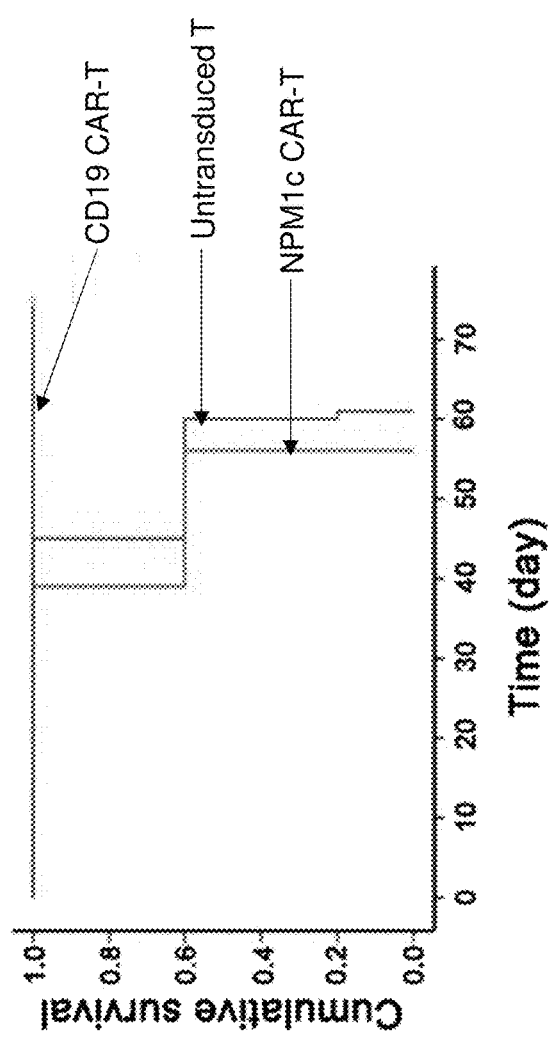

To test anti-tumor activity of NPM1c CAR-T cells in vivo, NSG mice were injected intravenously with luciferase-expressing OCI-AML3 AML tumor cells (1×10$^6$ per mouse, FIG. 5A). After confirmation of engraftment by bioluminescence imaging (BLI) 4 days post injection, mice were given a single injection of CAR-T or control untransduced T cells (1×10$^7$ cells per mouse) intravenously. Leukemia burden was monitored every three days using BLI. Mice treated with NPM1c CAR-T cells (with the YG1 scFv) showed significant reduction of leukemia burden and resulted in prolonged survival as compared to mice treated with untransduced T cells (FIG. 5B and FIG. 5C). To test the specificity of NPM1c CAR-T cell killing in vivo, NSG mice were injected with luciferase-expressing human HLA-A2$^+$ CD19$^+$ GMB cells (Leskov et al., *ONCOGENE* 32: 1066 (2013); Pallasch et al., CELL 156: 590 (2014)). Tumor-bearing mice were given a single dose of NPM1c CAR-T cells (with the YG1 scFv), untransduced T cells or CD19 CAR-T cells. Compared to untransduced T cells, NPM1c CAR-T cells did not reduce lymphoma burden or prolonged survival, whereas CD19 CAR-T cells greatly reduced lymphoma burden and prolonged survival (FIG. 5D and FIG. 5E). These results show that NMP1c CAR-T cells are capable of killing AML that are HLA-A2$^+$ and NPM1c$^+$ in vivo, but not HLA-A2$^+$ lymphoma cells without NPM1c mutation, demonstrating exquisite specificity.

OCI-AML2 cells have a similar background as OCI-AML3 cells but express wildtype NPM1 protein (see, e.g., van der Lee, D. I. et al., *J CLIN INVEST* 129 774 (2019)). As a negative control for NPM1c CAR-T cell specificity, NSG mice were injected with luciferase-expressing OCI-AML2 cells (1×10$^6$ per mouse) and followed by a single injection of NPM1c CAR-T (with the YG1 scFv) or control untransduced T cells (1×10$^7$ cells per mouse) intravenously four days later. As shown in FIG. 5F, NPM1c CAR-T cells effectively reduced OCI-AML3 leukemia burden compared to PBS control or untransduced T cells. But NPM1c CAR-T cells did not reduce OCI-AML2 leukemia burden in NSG mice nor prolonged the survival of the treated mice as compared to untransduced T cells (FIGS. 5G-5H). These results further support that NPM1c CAR-T cells specifically kill NPM1c-positive AML cells but not NPM1c-negative AML cells.

Figure 6A:
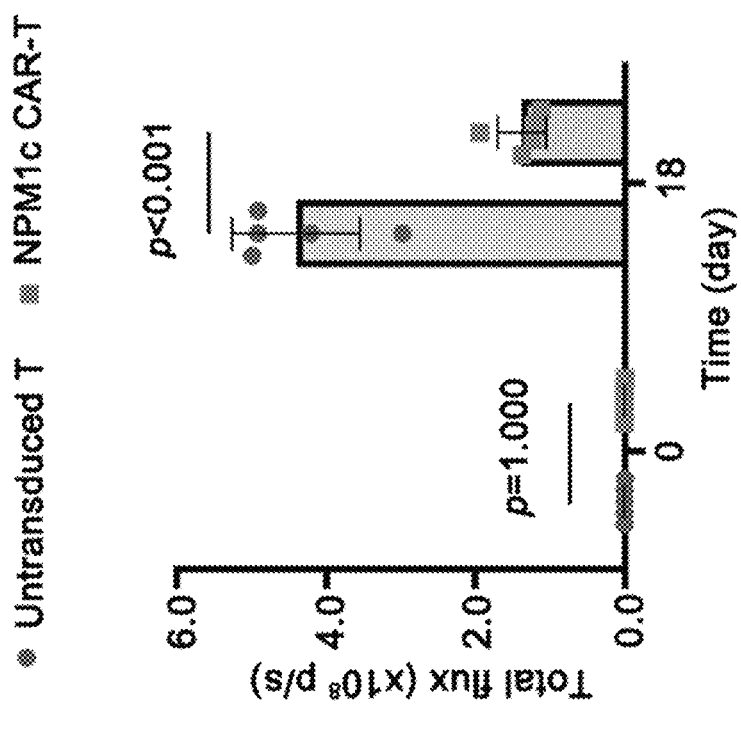
FIGS. 6A-6I show that NPM1c CAR-T cells (with YG1 scFv) reduce leukemia burden in blood, spleen, bone marrow and liver.
Figure 6B:
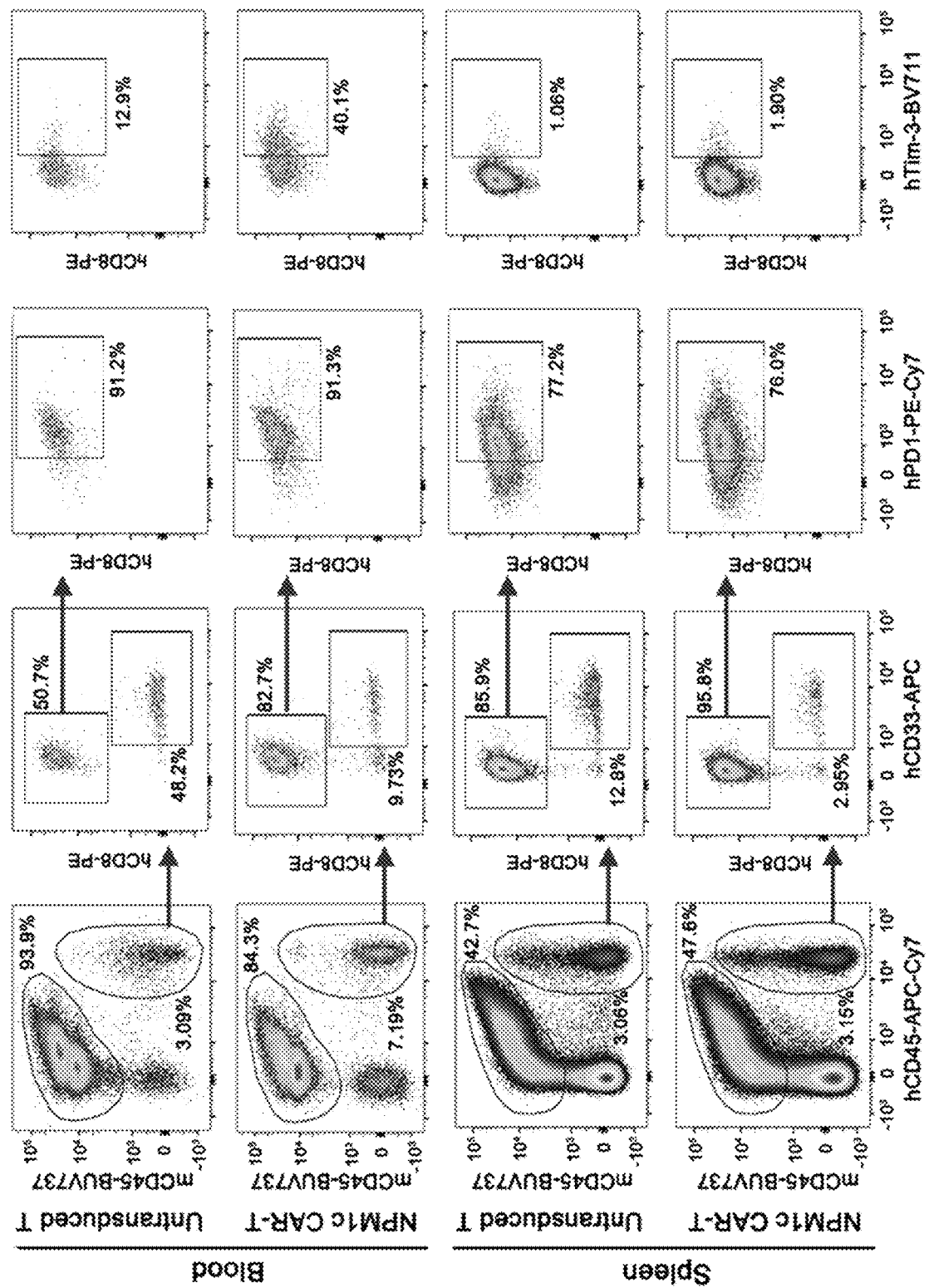
Figure 6C:
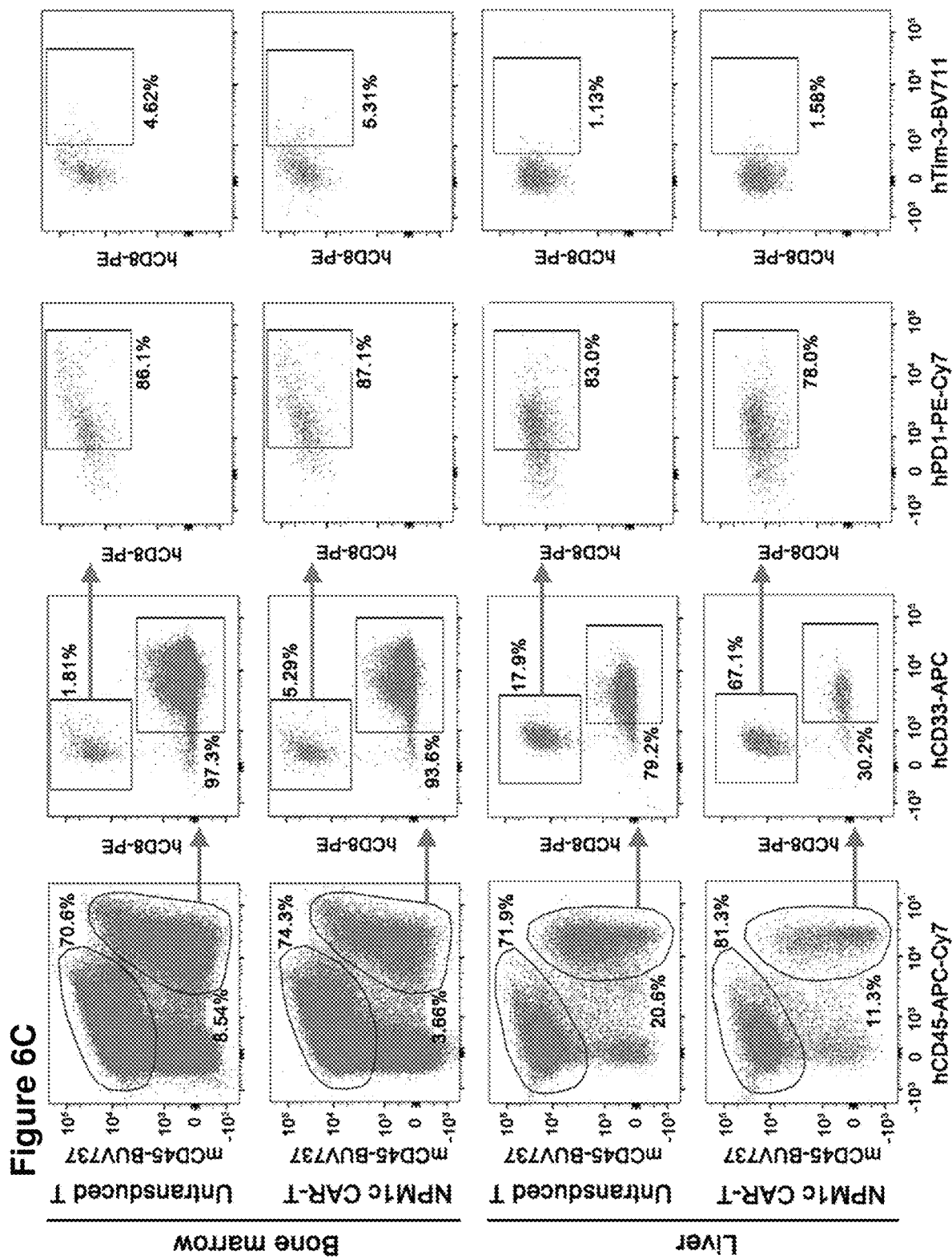
Figure 6E:
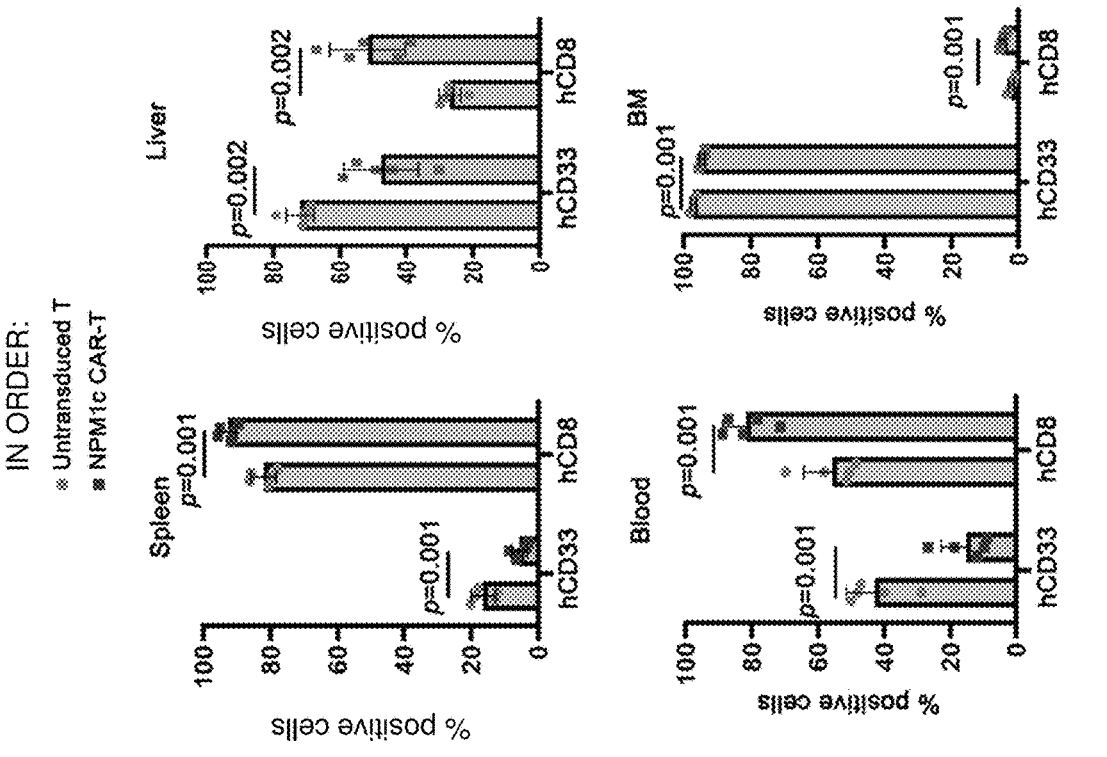
Figure 6D:
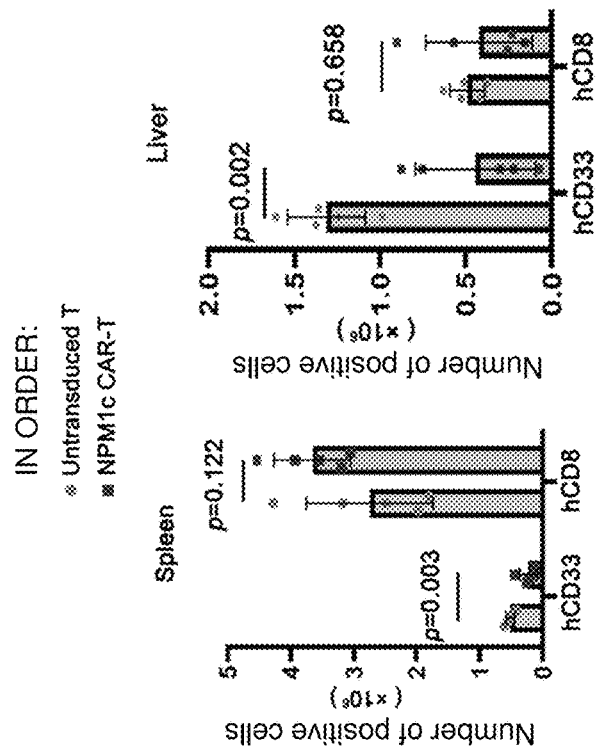
Figure 6F:
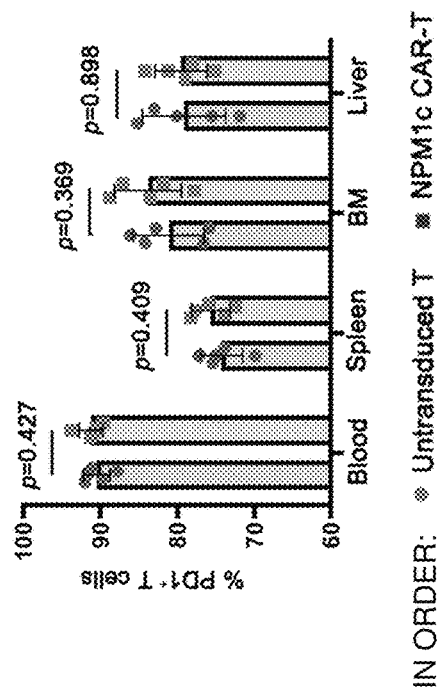
Figure 6G:
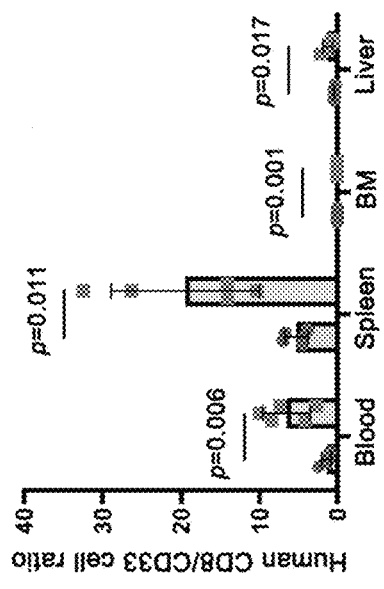
Figure 6H:
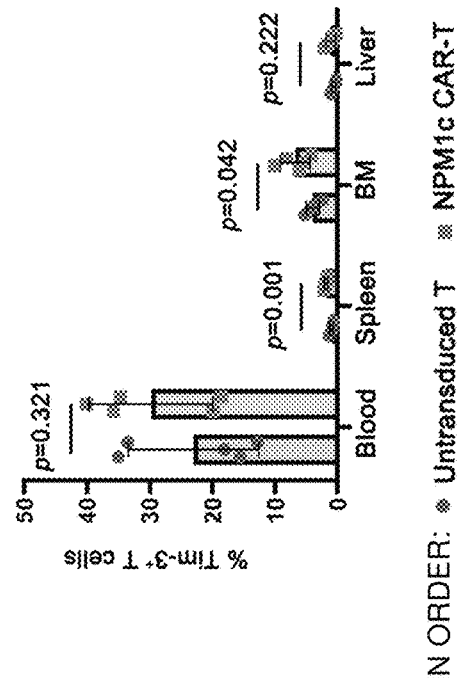

Example 6: NPM1c CAR-T Therapy Reduces Leukemic Cell Number in Different Tissues To examine anti-leukemia activity of NPM1c CAR-T cells, CAR-T cells and leukemia cells in different tissues were analyzed by flow cytometry 18 days post CAR-T cell transfer. As shown in FIG. 6A, leukemia burden was similar on the day of T cell transfer (day 4 after OCI-AML3 injection), but by 18 days post T cell transfer, leukemia burden was significantly lower in mice that received NPM1c CAR-T cells (with the YG1 scFv) than mice that received untransduced T cells. On day 18, blood, spleen, bone marrow and liver were harvested and single cell suspensions were prepared and stained for mouse CD45 (mCD45), human CD45 (hCD45), hCD8, hCD33, hPD-1 and hTim-3. As shown in FIGS. 6B-6C, hCD45$^+$ cells consisted of hCD8$^+$ T cells and hCD33$^+$ leukemic cells. The numbers and percentages of hCD33$^+$ leukemic cells were significantly lower in all four tissues in mice treated with NPM1c CAR-T cells (with the YG1 scFv) than those treated with untransduced T cells (FIG. 6D and FIG. 6E). Consistently, there were higher percentages of hCD8$^+$ T cells in all four tissues in mice treated with NPM1c CAR-T cells (with the YG1 scFv) than those treated with untransduced T cells. Furthermore, the ratio of hCD8$^+$ T cells over hCD33$^+$ leukemic cells was significantly higher in all tissues in mice treated with NPM1c CAR-T cells (with the YG1 scFv) than mice given untransduced T cells (FIG. 6F). Human CD8$^+$ T cells were also analyzed for PD-1 and Tim-3 expression (FIG. 6C). Although the percentages of hCD8$^+$ T cells that expressed PD-1 varied significantly among blood, spleen, bone marrow and liver, there was no significant difference in the same tissue between mice given untransduced T cells or NPM1c CAR-T cells (FIG. 6G). Interestingly, percentages of T cells that expressed Tim-3 were significantly higher in the spleen and bone marrow of mice given NPM1c CAR-T cells, but the percentages were low (<5%) (FIG. 6H). These results are consistent with the results based on bioluminescence imaging analysis of leukemic burden in FIGS. 5B and 6A.

Figure 6I:
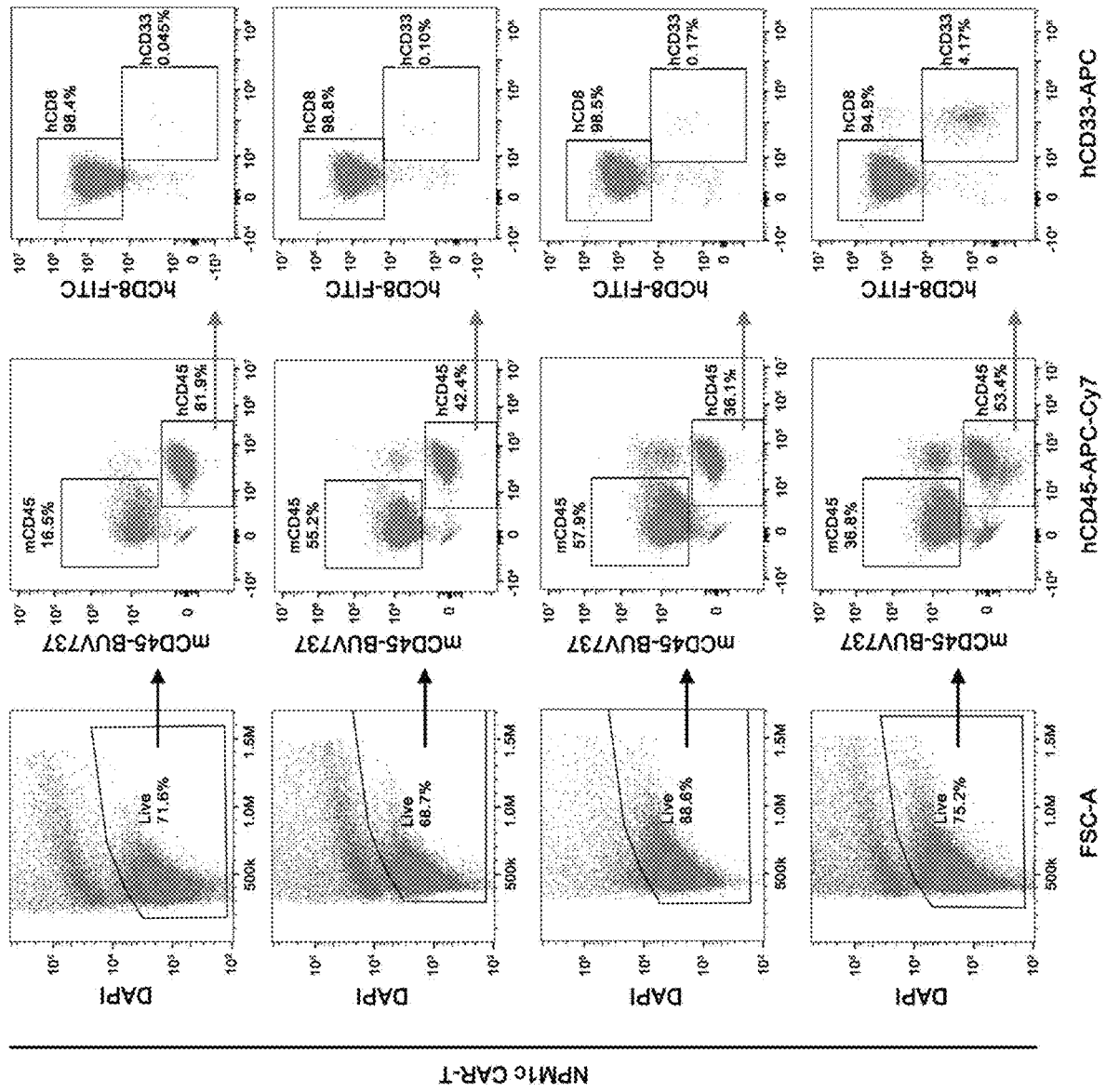

The leukemia burden in the bone marrow from surviving mice 30 days after injection with NPM1c CAR-T cells (with the YG1 scFv) or untransduced T cells or PBS was further analyzed (mice are those represented in FIG. 5F and described in Example 5). OCI-AML3 leukemia cells were almost completely absent in the bone marrow of three of the four NPM1c CAR-T-treated mice (FIG. 6I), whereas a large population of human T cells was detected in the bone marrow. In contrast, a large number of leukemia cells were detected in the bone marrow from one surviving mouse (the other mice died within 30 days) treated with untransduced T cells and two surviving mice (the other mice died within 30 days) treated with PBS (FIG. 6I). Therefore, NPM1c CAR-T cells appears capable of expanding and killing OCI-AML3 cells in the bone marrow and significantly control the disease progression.

Figure 7A:
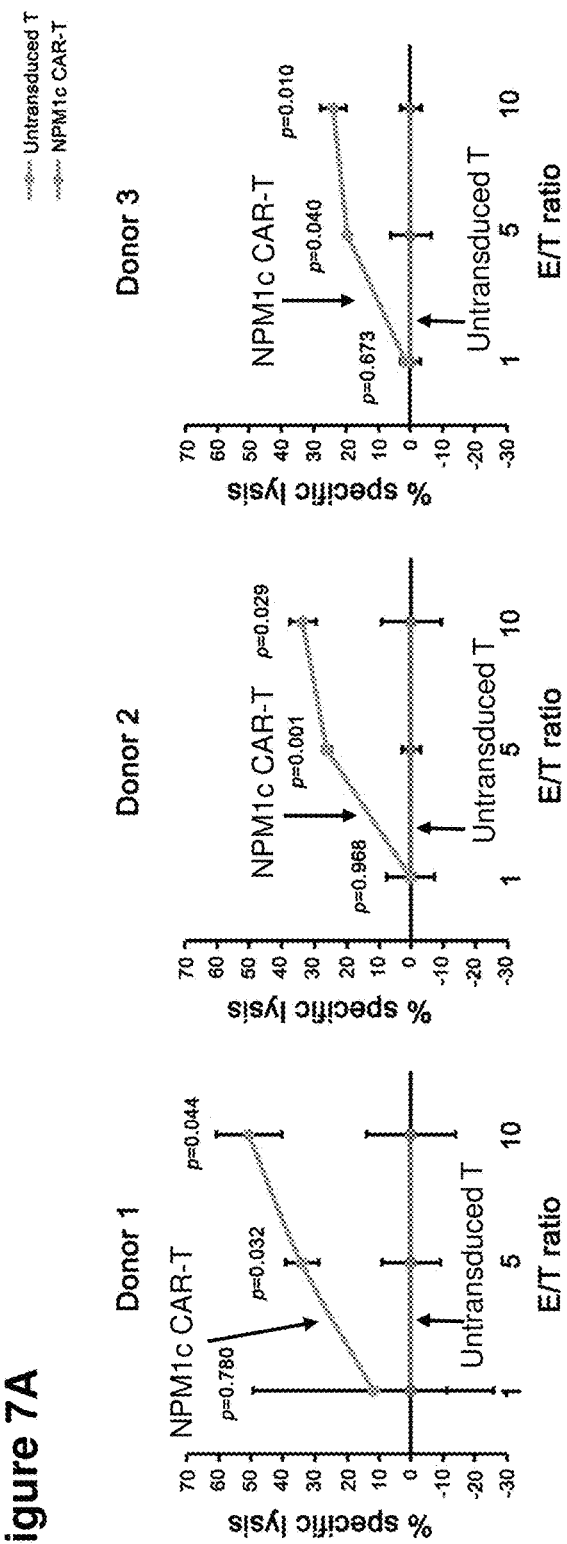
FIGS. 7A-7G show that NMP1c CAR-T cells (with YG1 scFv) effectively kill primary human AML blasts in vitro and in vivo but do not exhibit cytotoxicity towards normal human HLA-A2$^+$ CD34$^+$ hematopoietic stem/progenitor cells (HSPCs).
Figure 7B:
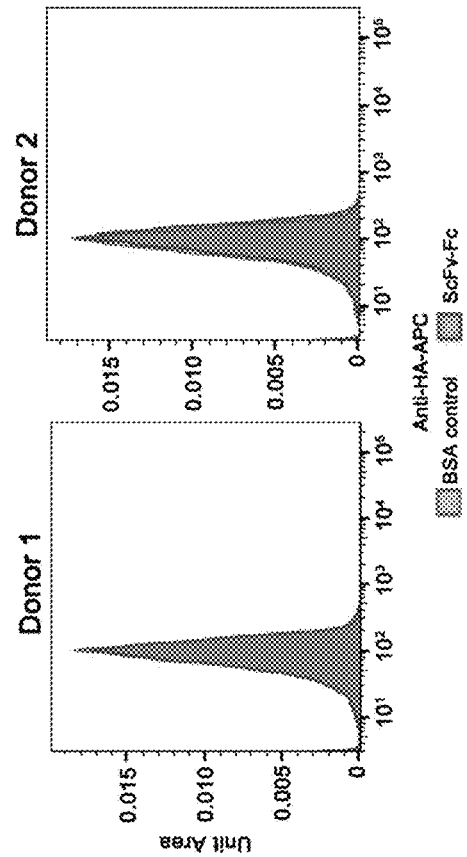
Figure 7C:
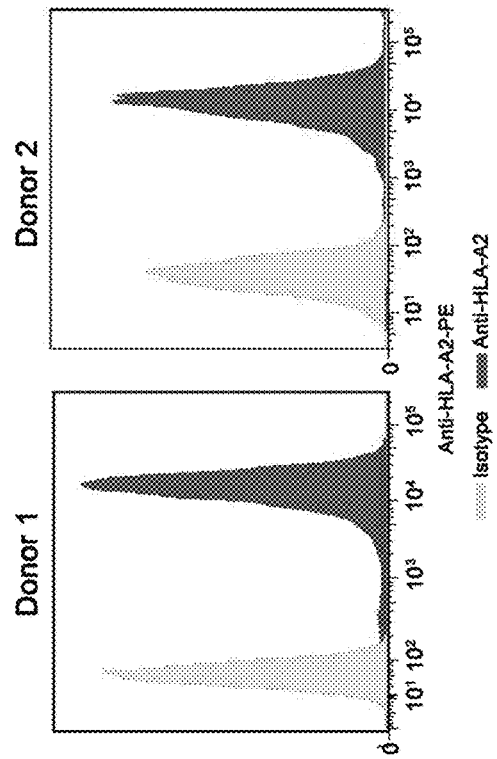
Figure 7D:
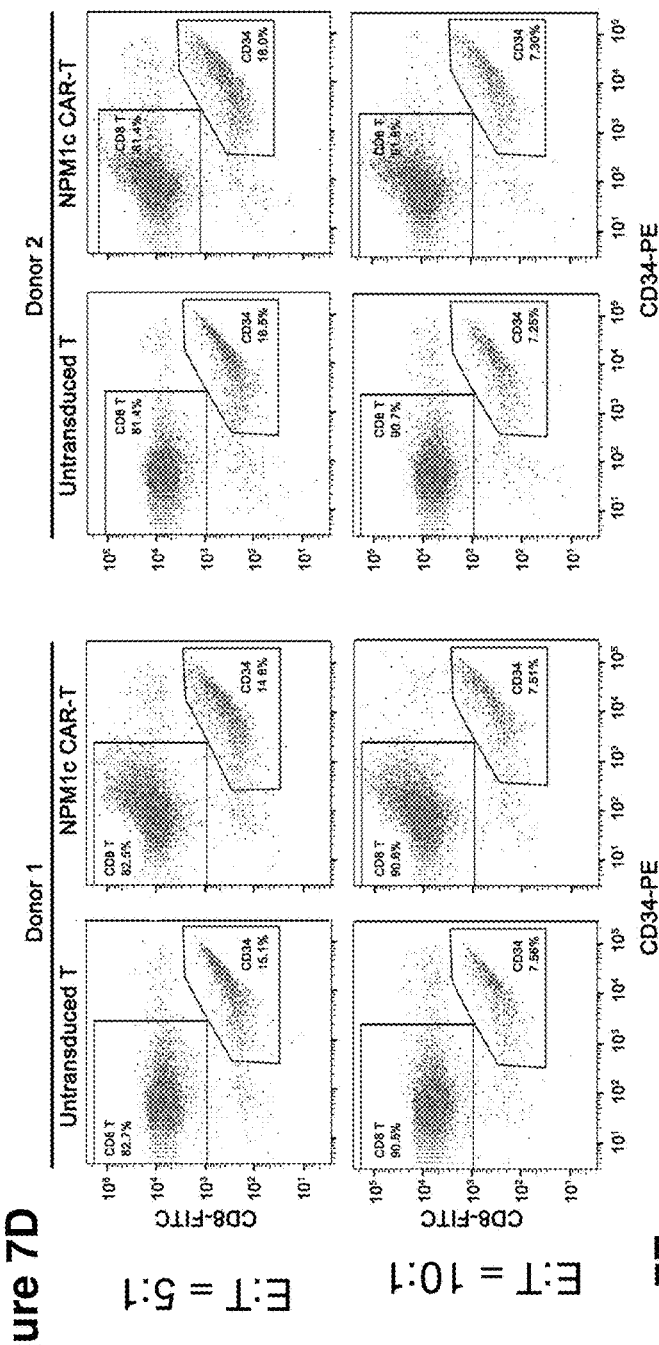
Figure 7E:
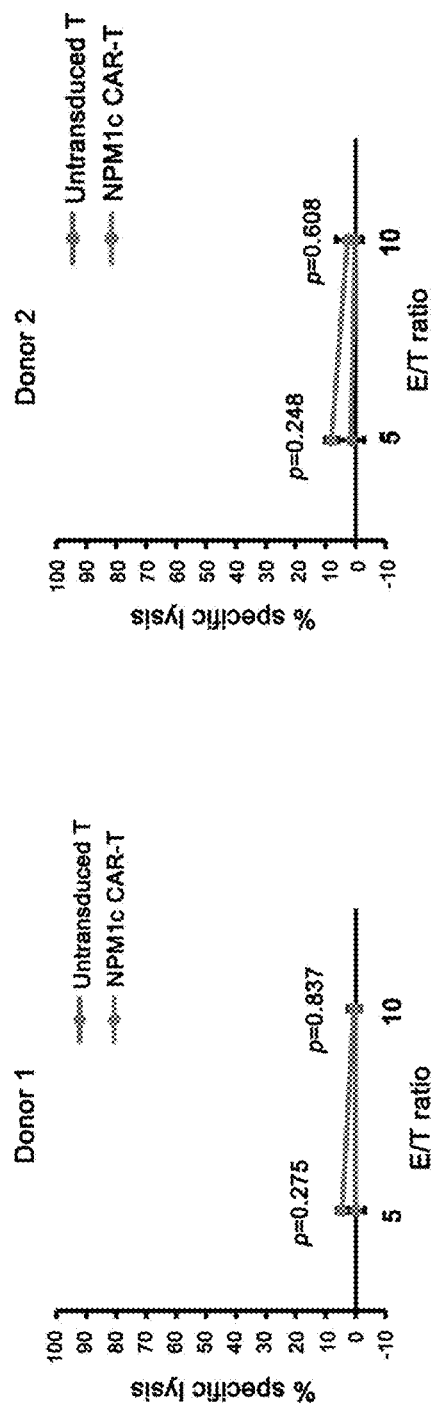

Example 7: NMP1c CAR-T Cells Effectively Kill Primary Human AML Blasts In Vitro and In Vivo It was further evaluated if NPM1c CAR-T cells kill NPM1c$^+$HLA-A2$^+$ primary AML blasts. NPM1c$^+$HLA-A2$^+$ primary AML blasts from three different donors were incubated with NPM1c CAR-T cells (with the YG1 scFv) at different E:T ratios and the number of AML blasts was quantified 24 hours later by flow cytometry with precision count beads. As shown in FIG. 7A, all three primary AML samples were effectively killed by NPM1c CAR-T cells in an E:T ratio-dependent manner although killing activities were variable between samples. In contrast, human HLA-A2$^+$ CD34$^+$ hematopoietic stem/progenitor cells (HSPCs) from two different donors were not stained by YG1 scFv-Fc (FIG. 7B and FIG. 7C), and were not killed by NPM1c CAR-T cells as compared with untransduced T cells (FIG. 7D and FIG. 7E).

Figure 7F:
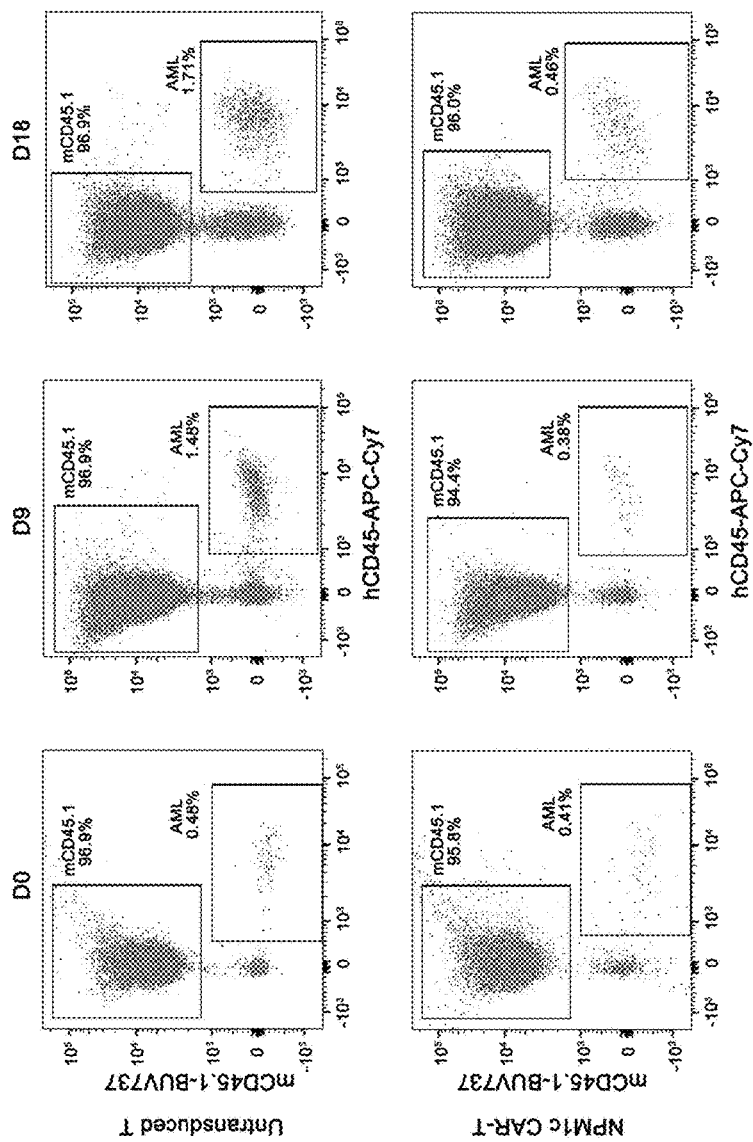
Figure 7G:
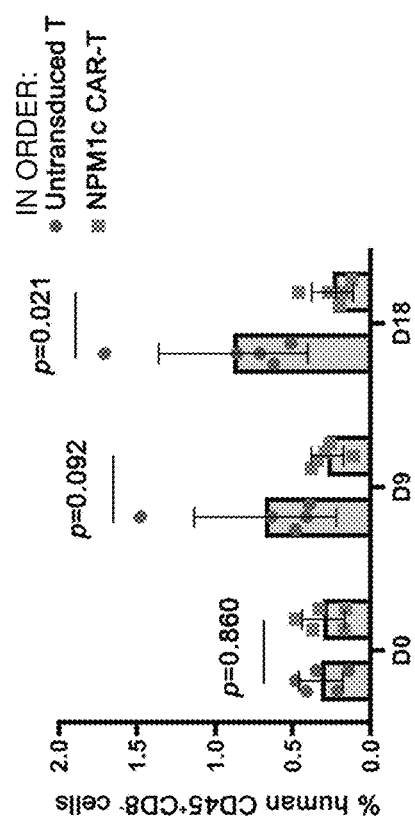

To assess the efficacy of NPM1c CAR-T therapy in patient-derived xenografts, NSGS mice were injected with HLA-A2$^+$ NPM1c+ human primary AML blasts. To improve engraftment efficiency of human primary AML, NSGS mice were hydrodynamically injected with 100 μg DNA plasmids encoding human IL-3 and GM-CSF 24 hours before primary AML injection, as previously described (see, e.g., Chen, Q et al (2009) *PNAS* 106:21783). AML burden was quantified in the peripheral blood by tail vein bleeding and flow cytometry assaying for human CD45$^+$ CD8$^-$ cells. AML blasts were detected in the blood 2 weeks after injection (FIG. 7F) and the mice were injected with NPM1c CAR-T cells (with the YG1 scFv) or untransduced T cells. The level of AML blasts in the blood was monitored every 9 days. As shown in FIG. 7F and FIG. 7G, the level of AML blasts was reduced in mice treated with NPM1c CAR-T cells as compared with untransduced T cells at both 9 and 18 days after T cell injection. The difference became significant by day 18. These results show that NPM1c CAR-T cells were also effective in killing primary HLA-A2$^+$ NPM1c$^+$ AML blasts in a patient-derived xenograft model.

REFERENCES

[1] Coulie, P. G., Van den Eynde, B. J., van der Bruggen, P. & Boon, T., Tumour antigens recognized by T lymphocytes: at the core of cancer immunotherapy. *NAT REV CANCER* 14 135 (2014).

[2] Srivastava, S. & Riddell, S. R., Chimeric Antigen Receptor T Cell Therapy: Challenges to Bench-to-Bedside Efficacy. *J IMMUNOL* 200 459 (2018).

[3] Blankenstein, T., Leisegang, M., Uckert, W. & Schreiber, H., Targeting cancer-specific mutations by T cell receptor gene therapy. *CURR OPIN IMMUNOL* 33 112 (2015).

4 Schumacher, T. N. & Schreiber, R. D., Neoantigens in cancer immunotherapy. *SCIENCE* 348 69 (2015).

5 van der Lee, D. I. et al., Mutated nucleophosmin 1 as immunotherapy target in acute myeloid leukemia. *J CLIN INVEST* 129 774 (2019).

6 Verdegaal, E. M. et al., Neoantigen landscape dynamics during human melanoma-T cell interactions. *NATURE* 536 91 (2016).

7 Blankenstein, T., Leisegang, M., Uckert, W. & Schreiber, H., Targeting cancer-specific mutations by T cell receptor gene therapy. *CURR OPIN IMMUNOL* 33 112 (2015).

8 Thomas, D. & Majeti, R., Biology and relevance of human acute myeloid leukemia stem cells. *BLOOD* 129 1577 (2017).

9 Dombret, H. & Gardin, C., An update of current treatments for adult acute myeloid leukemia. *BLOOD* 127 53 (2016).

10 Dohner, H., Weisdorf, D. J. & Bloomfield, C. D., Acute Myeloid Leukemia. *N Engl J Med* 373 1136 (2015).

11 Ossenkoppele, G. J., Janssen, J. J. & van de Loosdrecht, A. A., Risk factors for relapse after allogeneic transplantation in acute myeloid leukemia. *HAEMATOLOGICA* 101 20 (2016).

12 Ley, T. J. et al., Genomic and epigenomic landscapes of adult de novo acute myeloid leukemia. *N Engl J Med* 368 2059 (2013).

13 Alexandrov, L. B. et al., Signatures of mutational processes in human cancer. *NATURE* 500 415 (2013).

14 Kandoth, C. et al., Mutational landscape and significance across 12 major cancer types. *NATURE* 502 333 (2013).

15 Papaemmanuil, E. et al., Genomic Classification and Prognosis in Acute Myeloid Leukemia. *N Engl J Med* 374 2209 (2016).

16 Falini, B. et al., Cytoplasmic nucleophosmin in acute myelogenous leukemia with a normal karyotype. *N Engl J Med* 352 254 (2005).

17 Greiner, J. et al., Mutated regions of nucleophosmin 1 elicit both CD4(+) and CD8(+) T-cell responses in patients with acute myeloid leukemia. *BLOOD* 120 1282 (2012).

18 Greiner, J. et al., Immune responses against the mutated region of cytoplasmatic NPM1 might contribute to the favorable clinical outcome of AML patients with NPM1 mutations (NPM1mut). *BLOOD* 122 1087 (2013).

19 Chao, G. et al., Isolating and engineering human antibodies using yeast surface display. *NAT PROTOC* 1 755 (2006).

20 Choo, J. A., Liu, J., Toh, X., Grotenbreg, G. M. & Ren, E. C., The immunodominant influenza A virus M158-66 cytotoxic T lymphocyte epitope exhibits degenerate class I major histocompatibility complex restriction in humans. *J VIROL* 88 10613 (2014).

21 Van Deventer, J. A., Kelly, R. L., Rajan, S., Wittrup, K. D. & Sidhu, S. S., A switchable yeast display/secretion system. *PROTEIN ENG DES SEL* 28 317 (2015).

22 Quentmeier, H. et al., Cell line OCI/AML3 bears exon-12 NPM gene mutation-A and cytoplasmic expression of nucleophosmin. *LEUKEMIA* 19 1760 (2005).

23 Lorente, E., Garcia, R. & Lopez, D., Allele-dependent processing pathways generate the endogenous human leukocyte antigen (HLA) class I peptide repertoire in transporters associated with antigen processing (TAP)-deficient cells. *J BIOL CHEM* 286 38054 (2011).

24 Leskov, I. et al., Rapidgeneration of human B-cell lymphomas via combined expression of Myc and Bcl2 and their use as a preclinical model for biological therapies. *ONCOGENE* 32 1066 (2013).

25 Matsueda, S. et al., Identification of prostate-specific G-protein coupled receptor as a tumor antigen recognized by CD8(+) T cells for cancer immunotherapy. *PLOS ONE* 7 e45756 (2012).

26 Jennifer, B., Carl, H. J., Andreas, L, Marcela, M., John, S., Treatment of cancer using humanized anti-CD19 chimeric antigen receptor: U S, 20140271635A1[P]. 2014-09-18.

27 Pallasch, C. P. et al., Sensitizing protective tumor microenvironments to antibody-mediated therapy. *CELL* 156 590 (2014).

28 Shah, N. N. & Fry, T. J., Mechanisms of resistance to CAR T cell therapy. *NAT REV CLIN ONCOL* 16 372 (2019).

29 Salmikangas, P., Kinsella, N. & Chamberlain, P., Chimeric Antigen Receptor T-Cells (CAR T-Cells) for Cancer Immunotherapy—Moving Target for Industry? *Pharm Res* 35 152 (2018).

30 Brudno, J. N. & Kochenderfer, J. N., Recent advances in CAR T-cell toxicity: Mechanisms, manifestations and management. *BLOOD REV* 34 45 (2019).

31 Gill, S. et al., Preclinical targeting of human acute myeloid leukemia and myeloablation using chimeric antigen receptor-modified T cells. *BLOOD* 123 2343 (2014).

32 Kenderian, S. S. et al., CD33-specific chimeric antigen receptor T cells exhibit potent preclinical activity against human acute myeloid leukemia. *LEUKEMIA* 29 1637 (2015).

33 Uhlen, M. et al., Proteomics. Tissue-based map of the human proteome. *SCIENCE* 347 1260419 (2015).

34 Watanabe, K. et al., Target antigen density governs the efficacy of anti-CD20-CD28-CD3 zeta chimeric antigen receptor-modified effector CD8+ T cells. *J IMMUNOL* 194 911 (2015).

35 Dubrovsky, L. et al., T cell receptor mimic antibodies for cancer therapy. *ONCOIMMUNOLOGY* 5 e1049803 (2016).

36 Watanabe, K., Kuramitsu, S., Posey, A. J. & June, C. H., Expanding the Therapeutic Window for CAR T Cell Therapy in Solid Tumors: The Knowns and Unknowns of CAR T Cell Biology. *FRONT IMMUNOL* 9 2486 (2018).

37 Zhang, J. & Wang, L., The Emerging World of TCR-T Cell Trials Against Cancer: A Systematic Review. *Technol Cancer Res Treat* 18 1078098716 (2019).

38 Morris, E. C. & Stauss, H. J., Optimizing T-cell receptor gene therapy for hematologic malignancies. *BLOOD* 127 3305 (2016).

39 Amir, A. L. et al., PRAME-specific Allo-HLA-restricted T cells with potent antitumor reactivity useful for therapeutic T-cell receptor gene transfer. *CLIN CANCER RES* 17 5615 (2011).

40 Provasi, E. et al., Editing T cell specificity towards leukemia by zinc finger nucleases and lentiviral gene transfer. *NAT MED* 18 807 (2012).

41 Bendle, G. M. et al., Lethalgraft-versus-host disease in mouse models of T cell receptor gene therapy. *NAT MED* 16 565, 1p (2010).

42 van Loenen, M. M. et al., Mixed T cell receptor dimers harbor potentially harmful neoreactivity. *Proc Natl Acad Sci USA* 107 10972 (2010).

43 Vivier, E. et al., Innate or adaptive immunity? The example of natural killer cells. *SCIENCE* 331 44 (2011).

44 Shah, N. N. & Fry, T. J., Mechanisms of resistance to CAR T cell therapy. *NAT REV CLIN ONCOL* 16 372 (2019).

45 Hermanson, D. L. et al., Induced Pluripotent Stem Cell-Derived Natural Killer Cells for Treatment of Ovarian Cancer. *STEM CELLS* 34 93 (2016).

46 Li, Y., Hermanson, D. L., Moriarity, B. S. & Kaufman, D. S., Human iPSC-Derived Natural Killer Cells Engineered with Chimeric Antigen Receptors Enhance Anti-tumor Activity. *CELL STEM CELL* 23 181 (2018).

APPENDIX 1

Example of steps for selection of specific anti-AIQDLCLAV:HLA-A2 antibodies (based on, without being bound by any theory, Example 1):
The 1st Round Selection:
Selection of yeast population that is positively binding to biotinalyted AIQ-HLA-A2 antigen by magnetic sorting (MACS).
The 2nd Round of Selection:
To exclude the sorted yeast cells that could bind to other peptide-HLA-A2 complex antigens, using control peptide (SLL)-HLA-A2 complex to stain yeast cells sorted from the 1st step and collecting the yeast cells that fail to bind to SLL-HLA-A2 antigen, by magnetic sorting.
The 3rd Round of Selection:
The 1st and 2nd round of selections may roughly enrich for yeast cells that can bind to AIQ-HLA-A2 complex, from up to 1×1010 yeast cells. As shown in FIG. 1B #1, after 2 rounds of MACS sorting, there was only 3.64% cells that were double-positively stained for AIQ-HAL-A2 complex antigen and scFv expression. Accordingly, in 3rd round selection, these 3.64% of double-positive yeast cells can be sorted by flow cytometry sorting.
The 4rd Round of Selection:
As shown in FIG. 1B #2, the 3rd selection could further enrich yeast population (41.4%) that are double-positively stained for AIQ-HAL-A2 complex antigen and scFv expression. Accordingly, in 4th round selection, these 41.4% of double-positive yeast cells can be further sorted by flow cytometry sorting.
The 5th Round of Selection:
As shown in FIG. 1C #1-#4, the 4th selection could further enrich yeast population (45.1%) that are double-positively stained for AIQ-HAL-A2 complex antigen and scFv expression. However, there was a small fraction of yeast cells that were double-positively stained for GIL-HAL-A2 or SLL-HLA-A2 complex and scFv expression. Accordingly, in 5th round selection, to further exclude the yeast cells that could bind to other peptide-HLA-A2 complex antigen, SLL-HLA-A2 complex can be used to stain yeast cells that sorted at the 4th round selection, and sorted the yeast cells that were scFv-positive but negatively stained for SLL-HLA-A2 antigen can be sorted (FIG. 1B #3).
The 6th Round of Selection:
As shown in FIG. 1C #7-9, the 5th selection could further enrich yeast population (55.8%) that are double-positively stained for AIQ-HAL-A2 complex antigen and scFv expression, and decrease the percentage of yeast cells that positively bound to control peptide GIL or SLL-HLA-A2 complex. Unexpectedly, the inventors found that most of the yeast cells that were positively stained for AIQ-HLA-A2, were also positively stained for HLA-A2 protein (28.1%, FIG. 1C #6). In 6th selection, the yeast population with high-affinity binding to AIQ-HLA-A2 complex can be isolated (FIG. 1B #4).
The 7th Round of Selection:
As shown in FIG. 1C #14, the 6th selection enriched yeast population (74.9%) with high-affinity binding to AIQ-HAL-A2 complex antigen; however, it also enriched yeast population (76.7%) with high-affinity binding to HAL-A2 antigen, which indicated that almost all of the sorted yeast cells were able to bind to HLA-A2 alone. Accordingly, in 7th round of selection, yeast cells (~0.5%) that negatively bound to HLA-A2 antigen can be sorted. After 7th round of selection, inventors found that the yeast population that was positively stained for AIQ-HLA-A2 were enriched (22.8%, FIG. 1C #19) while the percentage of that positively stained for HLA-A2 alone was decreased (12.1%, FIG. 1C #16).
The 8th Round of Selection:
To further enrich yeast population that was positively stained for AIQ-HLA-A2 complex, AIQ-HLA-A2 staining-positive yeast cells can be further sorted in 8th selection, as shown in FIG. 1B #6. After this selection, up to 69.5% of yeast cells with high-affinity binding to AIQ-HLA-A2 complex were enriched (FIG. 1C #24), but there still were half of these yeast cells (31.3%, FIG. 1C #21) that positively bound to HLA-A2 antigen alone.
The 9th Round of Selection:
To further exclude yeast population that was able to bind to HLA-A2 antigen alone, the yeast cells that were negatively stained for HLA-A2 antigen alone can be further sorted (FIG. 1B #7). After this selection, yeast cells with high-affinity binding to AIQ-HLA-A2 complex were highly enriched (60.6%, FIG. 1C #29), and only 2.87% of yeast cells (FIG. 1C #26) bound to HLA-A2 antigen alone.

SEQUENCES

| SEQ ID NO: | Description | Sequence |
|---|---|---|
| 1 | Leukemia-specific neoantigen epitope of NPM1c | AIQDLCLAV |
| 2 | YG1 scFv amino acid sequence | DIQMTQSPSSLSASVGDRVTITCRASQSISSYLNWYQQKPGKAPKL LIYAASSLQSGVPSRFSGSGSGTDFTLTISSLQPEDFATYYCQQSY STPLTFGQGTKVEIKSGILGTTAASGSSGGSSGAEVQLVESGGGL VQPGGSLRLSCAASGFTFSSYAMSWVRQAPGKGLEWVSAISGSGGS TYYADSVKGRFTISRDNSKNTLYLQMNSLRAEDTAVYYCARLGYPT TTLLPFDYWGQGTLVTVSS |
| 3 | YG1 scFv VL amino acid sequence | DIQMIQSPSSLSASVGDRVTITCRASQSISSYLNWYQQKPGKAPKL LIYAASSLQSGVPSRFSGSGSGTDFTLTISSLQPEDFATYYCQQSY STPLTFGQGTKVEIKSGILGITAA |

-continued

| SEQ ID NO: | Description | Sequence |
|---|---|---|
| 4 | YG1 scFv linker amino acid sequence | SGSSGGSSSG |
| 5 | YG1 scFv VH amino acid sequence | AEVQLVESGGGLVQPGGSLRLSCAASGFTFSSYAMSWVRQAPGKGL EWVSAISGSGGSTYYADSVKGRFTISRDNSKNTLYLQMNSLRAEDT AVYYCARLGYPTTTLLPFDYWGQGTLVTVSS |
| 6 | YG1 scFv VL CDR1 amino acid sequence (IMGT) | QSISSY |
| 7 | YG1 scFv VL CDR2 amino acid sequence (IMGT) | AAS |
| 8 | YG1 scFv VL CDR3 amino acid sequence (IMGT) | QQSYSTPLT |
| 9 | YG1 scFv VH CDR1 amino acid sequence (IMGT) | GFTFSSYA |
| 10 | YG1 scFv VH CDR2 amino acid sequence (IMGT) | ISGSGGST |
| 11 | YG1 scFv VH CDR3 amino acid sequence (IMGT) | ARLGYPTTTLLPFDY |
| 12 | YG1 scFv nucleic acid sequence | GACATCCAGATGACCCAGTCTCCATCCTCCCTGTCTGCATCTGTAG GAGACAGAGTCACCATCACTTGCCGGGCAAGTCAGAGCATTAGCAG CTATTTAAATTGGTATCAGCAGAAACCAGGGAAAGCCCCTAAGCTC CTGATCTATGCTGCATCCAGTTTGCAAAGTGGGGTCCCATCAAGGT TCAGTGGCAGTGGATCTGGGACAGATTTCACTCTCACCATCAGCAG TCTGCAACCTGAAGATTTTGCAACTTACTACTGTCAACAGAGTTAC AGTACCCCGCTCACGTTCGGCCAAGGGACCAAGGTGGAAATCAAAT CCGGAATTCTAGGTACTACTGCCGCTAGTGGTAGTAGTGGTGGCAG TAGCAGTGGTGCCGAGGTGCAGCTGGTGGAGTCTGGGGGAGGCTTG GTACAGCCTGGGGGGTCCCTGAGACTCTCCTGTGCAGCCTCTGGAT TCACCTTTAGCAGCTATGCCATGAGCTGGGTCCGCCAGGCTCCAGG GAAGGGGCTGGAGTGGGTCTCAGCTATTAGTGGTAGTGGTGGTAGC ACATACTACGCAGACTCCGTGAAGGGCCGGTTCACCATCTCCAGAG ACAATTCCAAGAACACGCTGTATCTGCAAATGAACAGCCTGAGAGC CGAGGACACGGCCGTGTATTACTGTGCGAGGCTGGGTTACCCTACT ACTACCCTACTACCCTTTGATTACTGGGGCCAAGGTACCCTGGTCA CTGTCTCCAGT |
| 13 | YG1 scFv VL nucleic acid sequence | GACATCCAGATGACCCAGTCTCCATCCTCCCTGTCTGCATCTGTAG GAGACAGAGTCACCATCACTTGCCGGGCAAGTCAGAGCATTAGCAG CTATTTAAATTGGTATCAGCAGAAACCAGGGAAAGCCCCTAAGCTC CTGATCTATGCTGCATCCAGTTTGCAAAGTGGGGTCCCATCAAGGT TCAGTGGCAGTGGATCTGGGACAGATTTCACTCTCACCATCAGCAG TCTGCAACCTGAAGATTTTGCAACTTACTACTGTCAACAGAGTTAC AGTACCCCGCTCACGTTCGGCCAAGGGACCAAGGTGGAAATCAAAT CCGGAATTCTAGGTACTACTGCCGCT |
| 14 | YG1 scFv linker nucleic acid sequence | AGTGGTAGTAGTGGTGGCAGTAGCAGTGGT |
| 15 | YG1 scFv VH nucleic acid sequence | GCCGAGGTGCAGCTGGTGGAGTCTGGGGGAGGCTTGGTACAGCCTG GGGGGTCCCTGAGACTCTCCTGTGCAGCCTCTGGATTCACCTTTAG CAGCTATGCCATGAGCTGGGTCCGCCAGGCTCCAGGGAAGGGGCTG GAGTGGGTCTCAGCTATTAGTGGTAGTGGTGGTAGCACATACTACG |

-continued

| SEQ ID NO: | Description | Sequence |
|---|---|---|
| | | CAGACTCCGTGAAGGGCCGGTTCACCATCTCCAGAGACAATTCCAA GAACACGCTGTATCTGCAAATGAACAGCCTGAGAGCCGAGGACACG GCCGTGTATTACTGTGCGAGGCTGGGTTACCCTACTACTACCCTAC TACCCTTTGATTACTGGGGCCAAGGTACCCTGGTCACTGTCTCCAG T |
| 16 | YG1 scFv VL CDR1 nucleic acid sequence (IMGT) | CAGAGCATTAGCAGCTAT |
| 17 | YG1 scFv VL CDR2 nucleic acid sequence (IMGT) | GCTGCATCC |
| 18 | YG1 scFv VL CDR3 nucleic acid sequence (IMGT) | CAACAGAGTTACAGTACCCCGCTCACG |
| 19 | YG1 scFv VH CDR1 nucleic acid sequence (IMGT) | GGATTCACCTTTAGCAGCTATGCC |
| 20 | YG1 scFv VH CDR2 nucleic acid sequence (IMGT) | ATTAGTGGTAGTGGTGGTAGCACA |
| 21 | YG1 scFv VH CDR3 nucleic acid sequence (IMGT) | GCGAGGCTGGGTTACCCTACTACTACCCTACTACCCTTTGATTAC |
| 22 | NPM1c CAR amino acid sequence (with YG1 scFv) | MALPVTALLLPLALLLHAARPDIQMTQSPSSLSASVGDRVTITCRA SQSISSYLNWYQQKPGKAPKLLIYAASSLQSGVPSRFSGSGSGTDF TLTISSLQPEDFATYYCQQSYSTPLTFGQGTKVEIKSGILGTTAAS GSSGGSSSGAEVQLVESGGGLVQPGGSLRLSCAASGFTFSSYAMSW VRQAPGKGLEWVSAISGSGGSTYYADSVKGRFTISRDNSKNTLYLQ MNSLRAEDTAVYYCARLGYPTTTLLPFDYWGQGTLVTVSSTTTPAP RPPTPAPTIASQPLSLRPEACRPAAGGAVHTRGLDFACDIYIWAPL AGTCGVLLLSLVITLYCKRGRKKLLYIFKQPFMRPVQTTQEEDGCS CRFPEEEEGGCELRVKFSRSADAPAYKQGQNQLYNELNLGRREEYD VLDKRRGRDPEMGGKPRRKNPQEGLYNELQKDKMAEAYSEIGMKGE RRRGKGHDGLYQGLSTATKDTYDALHMQALPPRATNFSLLKQAGDV EENPGPMVSKGEELFTGVVPILVELDGDVNGHKFSVSGEGEGDATY GKLTLKFICTTGKLPVPWPTLVTTLTYGVQCFSRYPDHMKQHDFFK SAMPEGYVQERTIFFKDDGNYKTRAEVKFEGDTLVNRIELKGIDFK EDGNILGHKLEYNYNSHNVYIMADKQKNGIKVNFKIRHNIEDGSVQ LADHYQQNTPIGDGPVLLPDNHYLSTQSALSKDPNEKRDHMVLLEF VTAAGITLGMDELYK |
| 23 | Amino acid sequence of the leading sequence in the NPM1c CAR | MALPVTALLLPLALLLHAARP |
| 24 | Amino acid sequence of the YG1 scFv in the NPM1c CAR | DIQMTQSPSSLSASVGDRVTITCRASQSISSYLNWYQQKPGKAPKL LIYAASSLQSGVPSRFSGSGSGTDFTLTISSLQPEDFATYYCQQSY STPLTFGQGTKVEIKSGILGTTAASGSSGGSSSGAEVQLVESGGGL VQPGGSLRLSCAASGFTFSSYAMSWVRQAPGKGLEWVSAISGSGGS TYYADSVKGRFTISRDNSKNTLYLQMNSLRAEDTAVYYCARLGYPT TTLLPFDYWGQGTLVTVSS |
| 25 | Amino acid sequence of the CD8 hinge and transmembrane regions in the NPM1c CAR | TTTPAPRPPTPAPTIASQPLSLRPEACRPAAGGAVHTRGLDFACDI YIWAPLAGTCGVLLLSLVITLYC |

| SEQ ID NO: | Description | Sequence |
|---|---|---|
| 26 | Amino acid sequence of the 4-1BB signaling domain in the NPM1c CAR | KRGRKKLLYIFKQPFMRPVQTTQEEDGCSCRFPEEEEGGCEL |
| 27 | Amino acid sequence of the CD3-zeta signaling domain in the NPM1c CAR | RVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| 28 | Amino acid sequence of the P2A self-cleaving peptide in the NPM1c CAR | ATNFSLLKQAGDVEENPGP |
| 29 | Amino acid sequence of the EGFP region in the NPM1c CAR | MVSKGEELFTGVVPILVELDGDVNGHKFSVSGEGEGDATYGKLTLKFICTTGKLPVPWPTLVTTLTYGVQCFSRYPDHMKQHDFFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSALSKDPNEKRDHMVLLEFVTAAGITLGMDELYK |
| 30 | NPM1c CAR nucleic acid sequence (with YG1 scFv) | ATGGCCCTCCCTGTCACCGCCCTGCTGCTTCCGCTGGCTCTTCTGCTCCACGCCGCTCGGCCCGACATCCAGATGACCCAGTCTCCATCCTCCCTGTCTGCATCTGTAGGAGACAGAGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCAACAGAGTTACAGTACCCCGCTCACGTTCGGCCAAGGGACCAAGGTGGAAATCAAATCCGGAATTCTAGGTACTACTGCCGCTAGTGGTAGTAGTGGTGGCAGTAGCAGTGGTGCCGAGGTGCAGCTGGTGGAGTCTGGGGGAGGCTTGGTACAGCCTGGGGGGTCCCTGAGACTCTCCTGTGCAGCCTCTGGATTCACCTTTAGCAGCTATGCCATGAGCTGGGTCCGCCAGGCTCCAGGGAAGGGGCTGGAGTGGGTCTCAGCTATTAGTGGTAGTGGTGGTAGCACATACTACGCAGACTCCGTGAAGGGCCGGTTCACCATCTCCAGAGACAATTCCAAGAACACGCTGTATCTGCAAATGAACAGCCTGAGAGCCGAGGACACGGCCGTGTATTACTGTGCGAGGCTGGGGTTACCCTACTACTACCCTACTACCCTTTGATTACTGGGGCCAAGGTACCCTGGTCACTGTCTCCAGTACCACTACCCCAGCACCGAGGCCACCCACCCCGGCTCCTACCATCGCCTCCCAGCCTCTGTCCCTGCGTCCGGAGGCATGTAGACCCGCAGCTGGTGGGGCCGTGCATACCCGGGGTCTTGACTTCGCCTGCGATATCTACATTTGGGCCCCTCTGGCTGGTACTTGCGGGGTCCTGCTGCTTTCACTCGTGATCACTCTTTACTGTAAGCGCGGTCGGAAGAAGCTGCTGTACATCTTTAAGCAACCCTTCATGAGGCCTGTGCAGACTACTCAAGAGGAGGACGGCTGTTCATGCCGGTTCCCAGAGGAGGAGGAAGGCGGCTGCGAACTGCGCGTGAAATTCAGCCGCAGCGCAGATGCTCCAGCCTACAAGCAGGGGCAGAACCAGCTCTACAACGAACTCAATCTTGGTCGGAGAGAGGAGTACGACGTGCTGGACAAGCGGAGAGGACGGGACCCAGAAATGGGCGGGAAGCCGCGCAGAAAGAATCCCCAAGAGGGCCTGTACAACGAGCTCCAAAAGGATAAGATGGCAGAAGCCTATAGCGAGATTGGTATGAAAGGGGAACGCAGAAGAGGCAAAGGCCACGACGGACTGTACCAGGGACTCAGCACCGCCACCAAGGACACCTATGACGCTCTTCACATGCAGGCCCTGCCGCCTCGGGGATCCGGCGCAACAAACTTCTCTCTGCTGAAACAAGCCGGAGATGTCGAAGAGAATCCTGGACCGATGGTGAGCAAGGGCGAGGAGCTGTTCACCGGGGTGGTGCCCATCCTGGTCGAGCTGGACGGCGACGTAAACGGCCACAAGTTCAGCGTGTCCGGCGAGGGCGAGGGCGATGCCACCTACGGCAAGCTGACCCTGAAGTTCATCTGCACCACCGGCAAGCTGCCCGTGCCCTGGCCCACCCTCGTGACCACCCTGACCTACGGCGTGCAGTGCTTCAGCCGCTACCCCGACCACATGAAGCAGCACGACTTCTTCAAGTCCGCCATGCCCGAAGGCTACGTCCAGGAGCGCACCATCTTCTTCAAGGACGACGGCAACTACAAGACCCGCGCCGAGGTGAAGTTCGAGGGCGACACCCTGGTGAACCGCATCGAGCTGAAGGGCATCGACTTCAAGGAGGACGGCAACATCCTGGGGCACAAGCTGGAGTACAACTACAACAGCCACAACGTCTATATCATGGCCGACAAGCAGAAGAA |

| SEQ ID NO: | Description | Sequence |
|---|---|---|
| | | CGGCATCAAGGTGAACTTCAAGATCCGCCACAACATCGAGGACGGC<br>AGCGTGCAGCTCGCCGACCACTACCAGCAGAACACCCCCATCGGCG<br>ACGGCCCCGTGCTGCTGCCCGACAACCACTACCTGAGCACCCAGTC<br>CGCCCTGAGCAAAGACCCCAACGAGAAGCGCGATCACATGGTCCTG<br>CTGGAGTTCGTGACCGCCGCCGGGATCACTCTCGGCATGGACGAGC<br>TGTACAAGTGA |
| 31 | Nucleic acid sequence of the leading sequence in the NPM1c CAR | ATGGCCCTCCCTGTCACCGCCCTGCTGCTTCCGCTGGCTCTTCTGC<br>TCCACGCCGCTCGGCCC |
| 32 | Nucleic acid sequence of the YG1 scFv in the NPM1c CAR | GACATCCAGATGACCCAGTCTCCATCCTCCCTGTCTGCATCTGTAG<br>GAGACAGAGTCACCATCACTTGCCGGGCAAGTCAGAGCATTAGCAG<br>CTATTTAAATTGGTATCAGCAGAAACCAGGGAAAGCCCCTAAGCTC<br>CTGATCTATGCTGCATCCAGTTTGCAAAGTGGGGTCCCATCAAGGT<br>TCAGTGGCAGTGGATCTGGGACAGATTTCACTCTCACCATCAGCAG<br>TCTGCAACCTGAAGATTTTGCAACTTACTACTGTCAACAGAGTTAC<br>AGTACCCCGCTCACGTTCGGCCAAGGGACCAAGGTGGAAATCAAAT<br>CCGGAATTCTAGGTACTACTGCCGCTAGTGGTAGTAGTGGTGGCAG<br>TAGCAGTGGTGCCGAGGTGCAGCTGGTGGAGTCTGGGGGAGGCTTG<br>GTACAGCCTGGGGGGTCCCTGAGACTCTCCTGTGCAGCCTCTGGAT<br>TCACCTTTAGCAGCTATGCCATGAGCTGGGTCCGCCAGGCTCCAGG<br>GAAGGGGCTGGAGTGGGTCTCAGCTATTAGTGGTAGTGGTGGTAGC<br>ACATACTACGCAGACTCCGTGAAGGGCCGGTTCACCATCTCCAGAG<br>ACAATTCCAAGAACACGCTGTATCTGCAAATGAACAGCCTGAGAGC<br>CGAGGACACGGCCGTGTATTACTGTGCGAGGCTGGGTTACCCTACT<br>ACTACCCTACTACCCTTTGATTACTGGGGCCAAGGTACCCTGGTCA<br>CTGTCTCCAGT |
| 33 | Nucleic acid sequence of the CD8 hinge and transmembrane regions in the NPM1c CAR | ACCACTACCCCAGCACCGAGGCCACCCACCCCGGCTCCTACCATCG<br>CCTCCCAGCCTCTGTCCCTGCGTCCGGAGGCATGTAGACCCGCAGC<br>TGGTGGGGCCGTGCATACCCGGGGTCTTGACTTCGCCTGCGATATC<br>TACATTTGGGCCCCTCTGGCTGGTACTTGCGGGGTCCTGCTGCTTT<br>CACTCGTGATCACTCTTTACTGT |
| 34 | Nucleic acid sequence of the 4-1BB signaling domain in the NPM1c CAR | AAGCGCGGTCGGAAGAAGCTGCTGTACATCTTTAAGCAACCCTTCA<br>TGAGGCCTGTGCAGACTACTCAAGAGGAGGACGGCTGTTCATGCCG<br>GTTCCCAGAGGAGGAGGAAGGCGGCTGCGAACTG |
| 35 | Nucleic acid sequence of the CD3-zeta signaling domain in the NPM1c CAR | CGCGTGAAATTCAGCCGCAGCGCAGATGCTCCAGCCTACAAGCAGG<br>GGCAGAACCAGCTCTACAACGAACTCAATCTTGGTCGGAGAGAGGA<br>GTACGACGTGCTGGACAAGCGGAGAGGACGGGACCCAGAAATGGGC<br>GGGAAGCCGCGCAGAAGAATCCCCAAGAGGGCCTGTACAACCAGGA<br>TCCAAAAGGATAAGATGGCAGAAGCCTATAGCGAGATTGGTATGAA<br>AGGGGAACGCAGAAGAGGCAAAGGCCACGACGGACTGTACCAGGGA<br>CTCAGCACCGCCACCAAGGACACCTATGACGCTCTTCACATGCAGG<br>CCCTGCCGCCTCGG |
| 36 | Nucleic acid sequence of the P2A self-cleaving peptide in the NPM1c CAR | GCAACAAACTTCTCTCTGCTGAAACAAGCCGGAGATGTCGAAGAGA<br>ATCCTGGACCG |
| 37 | Nucleic acid sequence of the EGFP region in the NPM1c CAR | ATGGTGAGCAAGGGCGAGGAGCTGTTCACCGGGGTGGTGCCCATCC<br>TGGTCGAGCTGGACGGCGACGTAAACGGCCACAAGTTCAGCGTGTC<br>CGGCGAGGGCGAGGGCGATGCCACCTACGGCAAGCTGACCCTGAAG<br>TTCATCTGCACCACCGGCAAGCTGCCCGTGCCCTGGCCCACCCTCG<br>TGACCACCCTGACCTACGGCGTGCAGTGCTTCAGCCGCTACCCCGA<br>CCACATGAAGCAGCACGACTTCTTCAAGTCCGCCATGCCCGAAGGC<br>TACGTCCAGGAGCGCACCATCTTCTTCAAGGACGACGGCAACTACA<br>AGACCCGCGCCGAGGTGAAGTTCGAGGGCGACACCCTGGTGAACCG<br>CATCGAGCTGAAGGGCATCGACTTCAAGGAGGACGGCAACATCCTG<br>GGGCACAAGCTGGAGTACAACTACAACAGCCACAACGTCTATATCA<br>TGGCCGACAAGCAGAAGAACGGCATCAAGGTGAACTTCAAGATCCG<br>CCACAACATCGAGGACGGCAGCGTGCAGCTCGCCGACCACTACCAG |

| SEQ ID NO: | Description | Sequence |
|---|---|---|
| | | CAGAACACCCCCATCGGCGACGGCCCCGTGCTGCTGCCCGACAACC<br>ACTACCTGAGCACCCAGTCCGCCCTGAGCAAAGACCCCAACGAGAA<br>GCGCGATCACATGGTCCTGCTGGAGTTCGTGACCGCCGCCGGGATC<br>ACTCTCGGCATGGACGAGCTGTACAAGTGA |
| 38 | Human IgG1 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPELLGGPSVFLFPPKPKDTLMISR<br>TPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPGK |
| 39 | Human IgG4 (terminal K absent) | ASTKGPSVFPLAPCSRSTSESTAALGCLVKDYFPEPVTVSWNSGAL<br>TSGVHTFPAVLQSSGLYSLSSVVTVPSSSLGTKTYTCNVDHKPSNT<br>KVDKRVESKYGPPCPSCPAPEFLGGPSVFLFPPKPKDTLMISRTPE<br>VTCVVVDVSQEDPEVQFNWYVDGVEVHNAKTKPREEQFNSTYRVVS<br>VLTVLHQDWLNGKEYKCKVSNKGLPSSIEKTISKAKGQPREPQVYT<br>LPPSQEEMTKNQVSLTCLVKGFYPSDIAVEWESNGQPENNYKTTPP<br>VLDSDGSFFLYSRLTVDKSRWQEGNVFSCSVMHEALHNHYTQKSLS<br>LSLG- |
| 40 | Human IgG4 single mutant (S228P) (terminal K absent) | ASTKGPSVFPLAPCSRSTSESTAALGCLVKDYFPEPVTVSWNSGAL<br>TSGVHTFPAVLQSSGLYSLSSVVTVPSSSLGTKTYTCNVDHKPSNT<br>KVDKRVESKYGPPCPPCPAPEFLGGPSVFLFPPKPKDTLMISRTPE<br>VTCVVVDVSQEDPEVQFNWYVDGVEVHNAKTKPREEQFNSTYRVVS<br>VLTVLHQDWLNGKEYKCKVSNKGLPSSIEKTISKAKGQPREPQVYT<br>LPPSQEEMTKNQVSLTCLVKGFYPSDIAVEWESNGQPENNYKTTPP<br>VLDSDGSFFLYSRLTVDKSRWQEGNVFSCSVMHEALHNHYTQKSLS<br>LSLG- |
| 41 | Human IgG4 double mutant (S228P) (L235E) (terminal K absent) | ASTKGPSVFPLAPCSRSTSESTAALGCLVKDYFPEPVTVSWNSGAL<br>TSGVHTFPAVLQSSGLYSLSSVVTVPSSSLGTKTYTCNVDHKPSNT<br>KVDKRVESKYGPPCPPCPAPEFEGGPSVFLFPPKPKDTLMISRTPE<br>VTCVVVDVSQEDPEVQFNWYVDGVEVHNAKTKPREEQFNSTYRVVS<br>VLTVLHQDWLNGKEYKCKVSNKGLPSSIEKTISKAKGQPREPQVYT<br>LPPSQEEMTKNQVSLTCLVKGFYPSDIAVEWESNGQPENNYKTTPP<br>VLDSDGSFFLYSRLTVDKSRWQEGNVFSCSVMHEALHNHYTQKSLS<br>LSLG- |
| 42 | Human IgG4 double mutant (S228P) (L235A) (terminal K absent) | ASTKGPSVFPLAPCSRSTSESTAALGCLVKDYFPEPVTVSWNSGAL<br>TSGVHTFPAVLQSSGLYSLSSVVTVPSSSLGTKTYTCNVDHKPSNT<br>KVDKRVESKYGPPCPPCPAPEFAGGPSVFLFPPKPKDTLMISRTPE<br>VTCVVVDVSQEDPEVQFNWYVDGVEVHNAKTKPREEQFNSTYRVVS<br>VLTVLHQDWLNGKEYKCKVSNKGLPSSIEKTISKAKGQPREPQVYT<br>LPPSQEEMTKNQVSLTCLVKGFYPSDIAVEWESNGQPENNYKTTPP<br>VLDSDGSFFLYSRLTVDKSRWQEGNVFSCSVMHEALHNHYTQKSLS<br>LSLG- |
| 43 | CD20 amino acid sequence | MTTPRNSVNGTFPAEPMKGPIAMQSGPKPLFRRMSSLVGPTQSFFM<br>RESKTLGAVQIMNGLFHIALGGLLMIPAGIYAPICVTVWYPLWGGI<br>MYIISGSLLAATEKNSRKCLVKGKMIMNSLSLFAAISGMILSIMDI<br>LNIKISHFLKMESLNFIRAHTPYINIYNCEPANPSEKNSPSTQYCY<br>SIQSLFLGILSVMLIFAFFQELVIAGIVENEWKRTCSRPKSNIVLL<br>SAEEKKEQTIEIKEEVVGLTETSSQPKNEEDIEIIPIQEEEEEETE<br>TNFPEPPQDQESSPIENDSSP |
| 44 | FLAG | DYKDDDDK |
| 45 | polyhistidine (6-His) | HHHHHH |
| 46 | hemagglutinin (HA) | YPYDVPDYA |
| 47 | HCDR1.1 (anti-CD3) amino acid sequence | GYTFTRYTMH |
| 48 | HCDR1.2 (anti-CD3) amino acid sequence | RYTMH |

-continued

| SEQ ID NO: | Description | Sequence |
|---|---|---|
| 49 | HCDR2 (anti-CD3) amino acid sequence | YINPSRGYTNYNQKFKD |
| 50 | HCDR3 (anti-CD3) amino acid sequence | YYDDHYCLDY |
| 51 | LCDR1 (anti-CD3) amino acid sequence | RASSSVSYMN |
| 52 | LCDR2 (anti-CD3) amino acid sequence | DTSKVAS |
| 53 | LCDR3 (anti-CD3) amino acid sequence | QQWSSNPLT |
| 54 | Human wild type nucleophosmin (amino acid sequence - Accession # NM_002520) | MEDSMDMDMSPLRPQNYLFGCELKADKDYHFKVDNDENEHQLSLRTVSLGAGAKDELHIVEAEAMNYEGSPIKVTLATLKMSVQPTVSLGGFEITPPVVLRLKCGSGPVHISGQHLVAVEEDAESEDEEEEDVKLLSISGKRSAPGGGSKVPQKKVKLAADEDDDDDEEDDDEDDDDDFDDEEAEEKAPVKKSIRDTPAKNAQKSNQNGKDSKPSSTPRSKGQESFKKQEKTPKTPKGPSSVEDIKAKMQASIEKGGSLPKVEAKFINYVKNCFRMTDQEAIQDLWQWRKSL |
| 55 | C-terminus of human wild type nucleophosmin (amino acid sequence) | MTDQEAIQDLWQWRKSL |
| 56 | Human nucleophosmin encoded by mutant NPM1c gene (amino acid sequence) | MEDSMDMDMSPLRPQNYLFGCELKADKDYHFKVDNDENEHQLSLRTVSLGAGAKDELHIVEAEAMNYEGSPIKVTLATLKMSVQPTVSLGGFEITPPVVLRLKCGSGPVHISGQHLVAVEEDAESEDEEEEDVKLLSISGKRSAPGGGSKVPQKKVKLAADEDDDDDEEDDDEDDDDDFDDEEAEEKAPVKKSIRDTPAKNAQKSNQNGKDSKPSSTPRSKGQESFKKQEKTPKTPKGPSSVEDIKAKMQASIEKGGSLPKVEAKFINYVKNCFRMTDQEAIQDLCLAVEEVSLRK |
| 57 | C-terminus of human nucleophosmin encoded by mutant NPM1c gene (amino acid sequence) | MTDQEAIQDLCLAVEEVSLRK |
| 58 | Linker | (Gly4Ser)1 |
| 59 | Linker | (Gly4Ser)2 |
| 60 | Linker | (Gly4Ser)3 |
| 61 | Linker | (Gly4Ser)4 |
| 62 | NY-ESO-1 neoepitope (SLL) | SLLMWITQC |
| 63 | influenza virus M1 protein neoepitope (GIL) | GILGFVFTL |
| 64 | Forward primer | GTCAGTAATTGCGGTTCTCACC |
| 65 | Reverse primer | GTACAGTGGGAACAAAGTCG |

-continued

| SEQ ID NO: | Description | Sequence |
|---|---|---|
| 66 | Forward primer | CCGGGGTAGAACCTAAAAGTTCCG |
| 67 | Reverse primer | TTTGTTCTGCACGCGTGGATC |
| 68 | Forward primer | GGGTAATTAATCAGCGAAGCGATG |
| 69 | Forward primer | GTTAGGCCAGCTTGGCACTTGATGT |
| 70 | Reverse primer | AGGCACAATCAGCATTGGTAGCTG |
| 71 | NPM1c neoepitope | AIQDLCVAV |
| 72 | NPM1c neoepitope | CLAVEEVSL |
| 73 | NPM1c neoepitope | VEEVSLRK |
| 74 | NPM1c neoepitope | AVEEVSLR |
| 75 | NPM1c neoepitope | AVEEVSLRK |
| 76 | NPM1c neoepitope | CLAVEEVSLRK |
| 77 | AIQ $X_1$ substitution | VIQDLCLAV |
| 78 | AIQ $X_1$ substitution | LIQDLCLAV |
| 79 | AIQ $X_1$ substitution | IIQDLCLAV |
| 80 | AIQ $X_3$ substitution | AINDLCLAV |
| 81 | AIQ $X_4$ substitution | AIQELCLAV |
| 82 | AIQ $X_5$ substitution | AIQDICLAV |
| 83 | AIQ $X_5$ substitution | AIQDVCLAV |
| 84 | AIQ $X_5$ substitution | AIQDMCLAV |
| 85 | AIQ $X_5$ substitution | AIQDACLAV |
| 86 | AIQ $X_5$ substitution | AIQDFCLAV |
| 87 | AIQ $X_6$ substitution | AIQDLSLAV |
| 88 | AIQ $X_6$ substitution | AIQDLALAV |
| 89 | AIQ $X_7$ substitution | AIQDLCIAV |
| 90 | AIQ $X_7$ substitution | AIQDLCVAV |
| 91 | AIQ $X_7$ substitution | AIQDLCMAV |

SEQUENCES

| SEQ ID NO: | Description | Sequence |
|---|---|---|
| 92 | AIQ $X_7$ substitution | AIQDLCAAV |
| 93 | AIQ $X_7$ substitution | AIQDLCFAV |
| 94 | AIQ $X_8$ substitution | AIQDLCLVV |
| 95 | AIQ $X_8$ substitution | AIQDLCLLV |
| 96 | AIQ $X_8$ substitution | AIQDLCLIV |

INCORPORATION BY REFERENCE

The disclosures of all references such as patents, patent applications, and publications that are cited herein are hereby incorporated by reference herein in their entireties.

---

What is claimed is:

1. An antibody, or antigen binding fragment thereof, that specifically binds to an antigen comprising an NPM1c neoepitope in complex with a class I major histocompatibility complex (MHC class I) protein, wherein the antibody, or antigen binding fragment comprises:
   (a) a heavy chain variable region (VH), wherein the VH comprises VH complementarity determining region (CDR)1, VH CDR2 and VH CDR3, wherein the VH CDR1 has the amino acid sequence GFTFSSYA (SEQ ID NO:9), the VH CDR2 has the amino acid sequence ISGSGGST (SEQ ID NO:10), and the VH CDR3 has the amino acid sequence ARLGYPTTTLLPFDY (SEQ ID NO:11); and
   (b) a light chain variable region (VL), wherein the VL comprises VL complementarity determining region (CDR)1, VL CDR2 and VL CDR3, wherein the VL CDR1 has the amino acid sequence QSISSY (SEQ ID NO:6), the VL CDR2 has the amino acid sequence AAS (SEQ ID NO:7), and the VL CDR3 has the amino acid sequence QQSYSTPLT (SEQ ID NO:8).

2. The antibody, or antigen binding fragment thereof, of claim 1, which does not bind to, or substantially does not bind to: (a) the MHC class I protein alone, and/or (b) a control peptide in complex with the WIC class I protein, wherein the control peptide is an NY-ESO-1 epitope or influenza virus M1 epitope.

3. The antibody, or antigen binding fragment thereof, of claim 1, wherein the NPM1c neoepitope comprises the amino acid sequence selected from: AIQDLCLAV (SEQ ID NO:1).

4. The antibody, or antigen binding fragment thereof, of claim 1, wherein the neoepitope is 7, 8, 9, 10, 11, or 12 amino acid residues in length.

5. The antibody, or antigen binding fragment thereof, of claim 1, wherein the MEW class I protein is an HLA-A*02 protein or is encoded by the HLA-A*02 allele group.

6. The antibody, or antigen binding fragment thereof, of claim 1, wherein the VH comprises an amino acid sequence of SEQ ID NO:5.

7. The antibody, or antigen binding fragment thereof, of claim 1, wherein the VL comprises an amino acid sequence of SEQ ID NO:3.

8. The antibody, or antigen binding fragment thereof, of claim 1, which is a human antibody or antigen binding fragment, a humanized antibody or antigen binding fragment or a chimeric antibody or antigen binding fragment.

9. The antibody, or antigen binding fragment thereof, of claim 1, wherein the MEW class I protein is encoded by the HLA-A*02:01 allele.

10. The antibody, or antigen binding fragment thereof, of claim 1, wherein the VH comprises the amino acid sequence of SEQ ID NO:5 and the VL comprises the amino acid sequence of SEQ ID NO:3.

11. The antibody, or antigen binding fragment thereof, of claim 1, which is a single chain Fv (scFv), an Fv fragment, a Fab fragment, a Fab' fragment, a F(ab')$_2$ fragment, or a single chain antibody molecule.

12. The antibody, or antigen binding fragment thereof, of claim 11, which is an scFv.

13. The antibody, or antigen binding fragment thereof, of claim 12, wherein the scFv comprises a linker.

14. The antibody, or antigen binding fragment thereof, of claim 13, wherein the linker is a peptide linker.

15. The antibody, or antigen binding fragment thereof, of claim 14, wherein the peptide linker is a Gly-Ser.

16. The antibody, or antigen binding fragment thereof, of claim 15, wherein the Gly-Ser linker is selected from the group consisting of (Gly4Ser) (SEQ ID NO:58), (Gly4Ser)2 (SEQ ID NO:59), (Gly4Ser)3 (SEQ ID NO:60), and (Gly4Ser)4 (SEQ ID NO:61).

17. The antibody, or antigen binding fragment thereof, of claim 15, wherein the Gly-Ser linker comprises the amino acid sequence SGSSGGSSSG (SEQ ID NO:4).

18. The antibody, or antigen binding fragment thereof, of claim 12, wherein the scFv comprises the amino acid sequence of SEQ ID NO:2.

19. The antibody, or antigen binding fragment thereof, of claim 18, wherein the scFv has an amino acid sequence of SEQ ID NO:2.

20. The antibody, or antigen binding fragment thereof, of claim 12, wherein the scFv is a human scFv.

21. The antibody, or antigen binding fragment thereof, of claim 1, which is an antibody selected from the group consisting of an IgG1, an IgG2, an IgG3, an IgG4, an IgM, an IgA1, an IgA2, an IgD, and an IgE antibody isotypes.

22. The antibody, or antigen binding fragment thereof, of claim 21, wherein the antibody is an IgG1 isotype or IgG4 isotype.

23. The antibody, or antigen binding fragment thereof, of claim 22, wherein the antibody comprises a wild type IgG1 heavy chain constant region or wild type IgG4 heavy chain constant region.

24. The antibody, or antigen binding fragment thereof, of claim 22, wherein the antibody comprises a mutant IgG1 heavy chain constant region or mutant IgG4 heavy chain constant region.

25. The antibody, or antigen binding fragment thereof, of claim 24, wherein the antibody comprises a mutant IgG4 heavy chain constant region, wherein the mutant IgG4 heavy chain constant region comprises any one of the following substitutions: S228P, L235E, L235A, or a combination thereof, according to EU numbering.

26. The antibody, or antigen binding fragment thereof, of claim 25, wherein the antibody comprises an Fc domain comprising at least one mutation.

27. The antibody, or antigen binding fragment thereof, of claim 1, wherein the antibody or antigen binding fragment thereof is purified.

28. The antibody, or antigen binding fragment thereof, of claim 1, wherein the antigen is on the surface of a cancer cell.

29. The antibody, or antigen binding fragment thereof, of claim 28, wherein the cancer is Acute Myeloid Leukemia (AML).

30. The antibody, or antigen binding fragment thereof, of claim 1 which is a bispecific antibody, or antigen binding fragment thereof, which further specifically binds to a second antigen on an immune effector cell.

31. The antibody, or antigen binding fragment thereof, of claim 30, wherein the second antigen is CD3.

32. The antibody, or antigen binding fragment thereof, of claim 31, wherein the CD3 is a human CD3 expressed on T cells.

33. The antibody, or antigen binding fragment thereof, of claim 30, wherein the second antigen is NKp46.

34. The antibody, or antigen binding fragment thereof, of claim 33, wherein the NKp46 is a human NKp46 expressed on NK cells.

35. The antibody, or antigen binding fragment thereof, of claim 30, wherein the second antigen is CD16A.

36. The antibody, or antigen binding fragment thereof, of claim 35, wherein the CD16A is a human CD16A expressed on NK-cells.

37. The antibody, or antigen binding fragment thereof, of claim 30, wherein the second antigen is CD40, CD47, 4-1BB, TGF-β, LAG-3, PD-1, TIM-3, CTLA-4, OX40, NKp30, NKG2A, NKG2D or DNAM-1.

38. An isolated nucleic acid, wherein the nucleic acid comprises a nucleic acid sequence encoding the antibody, or antigen binding fragment thereof, according to claim 1.

39. The isolated nucleic acid of claim 38, which comprises the nucleotide sequence of SEQ ID NO:12.

40. An expression vector comprising the nucleic acid of claim 38.

41. A cell transformed with the expression vector of claim 40.

42. A method for producing an antibody, or an antigen binding fragment thereof, that specifically binds to an antigen comprising an NPM1c neoepitope in complex with a class I major histocompatibility complex (MHC class I) protein, the method comprising maintaining the cell of claim 41 under conditions permitting expression of the antibody, or antigen binding fragment thereof.

43. The method of claim 42, further comprising purifying the antibody, or antigen binding fragment thereof.

44. A chimeric antigen receptor (CAR) polypeptide comprising an intracellular domain, a transmembrane domain and an extracellular binding domain, wherein the extracellular binding domain comprises the antibody, or antigen binding fragment thereof, of claim 1.

45. The CAR polypeptide of claim 44, wherein
the transmembrane domain comprises the transmembrane domain of CD3-zeta, CD8, CD28, NKG2D, CD16, NKp44 or NKp46.

46. The CAR polypeptide of claim 44, wherein the intracellular domain comprises one or more costimulatory domains of one or more costimulatory molecules selected from the group consisting of: CD27, CD28, 4-1BB, OX40, CD30, CD40, PD-1, ICOS, 2B4, DAP10, CD137 and DAP12.

47. The CAR polypeptide of claim 44, wherein the intracellular domain comprises a CD3-zeta signaling domain and a 4-1BB costimulatory domain; wherein the transmembrane domain comprises a CD8 transmembrane domain, and wherein the CAR polypeptide further comprises a CD8 hinge region.

48. The CAR polypeptide of claim 44, wherein the intracellular domain comprises a CD3-zeta signaling domain comprising the amino acid sequence of SEQ ID NO: 27, and a 4-1BB costimulatory domain comprising the amino acid sequence of SEQ ID NO: 26; wherein the CAR polypeptide comprises a CD8 transmembrane domain and a CD8 hinge region, wherein the CD8 transmembrane domain and the CD8 hinge region comprise the amino acid sequence of SEQ ID NO: 25; and wherein the CAR polypeptide further comprises a leading sequence comprising the amino acid sequence set forth in SEQ ID NO: 23.

49. The CAR polypeptide of claim 44, wherein the extracellular binding domain is an scFv comprising the amino acid sequence of SEQ ID NO:24.

50. The CAR polypeptide of claim 44, which comprises the amino acid sequence set forth in SEQ ID NO: 22.

51. The CAR polypeptide of claim 44, wherein the CAR polypeptide further comprises a self-cleaving peptide sequence and a cytokine, wherein cleavage of the self-cleaving peptide releases the cytokine.

52. The CAR polypeptide of claim 51, wherein the cytokine is IL-12, IL-7, IL-13, IL-15, TNF-α, IFN-γ, or CCL19.

53. An isolated nucleic acid encoding the CAR polypeptide of claim 44.

54. The isolated nucleic acid of claim 53, which comprises the nucleotide sequence of SEQ ID NO:30.

55. An expression vector comprising the isolated nucleic acid of claim 53, wherein the expression vector is a viral expression vector or a non-viral expression vector.

56. The expression vector of claim 55, wherein the expression vector is a viral expression vector, and wherein the viral expression vector is a lentiviral expression vector.

57. A cell transformed with the expression vector of claim 55.

58. A method for producing the cell of claim 57, wherein the method comprises:
   (i) purifying a cell from peripheral blood mononuclear cells (PBMC),
   (ii) optionally, activating the cell with an anti-CD3 antibody or an antigen binding fragment thereof and/or an anti-CD28 antibody or an antigen-binding fragment thereof,
   (iii) transducing the cell with the expression vector,
   (iv) isolating the cell expressing the CAR polypeptide, and
   (v) optionally, expanding the isolated cell.

59. A cell expressing the CAR polypeptide of claim 44.

60. The cell of claim 59, wherein the cell is an immune effector cell, wherein expression of the CAR polypeptide targets the immune effector cell to a cancer cell expressing an antigen comprising an NPM1c neoepitope in complex with a class I major histocompatibility complex (MEW class I) protein.

61. The cell of claim 60, wherein the MHC Class I protein is an HLA-A*02 protein or is encoded by the HLA-A*02 allele group.

62. The cell of claim 60, wherein the immune effector cell does not substantially target and/or induce killing of a cancer cell expressing wild type NPM1.

63. The cell of claim 60, wherein the cancer cell is an acute myeloid leukemia (AML) cell.

64. The cell of claim 59, wherein the cell is a T cell.

65. The cell of claim 64 wherein the T cell is a human CD8$^+$ T cell.

66. The cell of claim 59, wherein the cell is a Natural Killer (NK) cell.

67. The cell of claim 59, wherein the cell is a macrophage.

68. A method for producing the cell of claim 59, wherein the method comprises:
   (i) inducing a pluripotent stem cell (iPSC) to differentiate into an immune effector cell,
   (ii) transducing the immune effector cell with the expression vector of claim 55,
   (iii) isolating the immune effector cell expressing the CAR polypeptide, and
   (iv) optionally, expanding the isolated immune effector cell.

69. The method of claim 68, wherein the immune effector cell is a NK cell.

70. The method of claim 68, wherein the immune effector cell is a macrophage.

71. A pharmaceutical composition, comprising the cell of claim 59, and a pharmaceutically acceptable carrier.

72. A method of treating acute myeloid leukemia (AML) in a subject in need thereof, the method comprising administering the pharmaceutical composition of claim 71, in an amount sufficient to treat AML.

73. The method of claim 72, wherein the AML is a relapsed AML or a refractory AML.

74. A method of treating a cancer in a subject in need thereof, wherein the cell surface of cells comprising the cancer displays an NPM1c neoepitope in complex with a class I major histocompatibility complex (MHC class I) protein, the method comprising administering to the subject the antibody, or antigen binding fragment thereof, of claim 1, in an amount sufficient to treat the cancer.

75. The method of claim 74, wherein the cancer is acute myeloid leukemia (AML).

76. The method of claim 74, wherein the method of treating cancer is a method of reducing cancer burden or a method of increasing survival in the subject.

77. The method of claim 74, wherein the administering is intravenous, intrathecal, intraosseous, or into the spinal cord.

78. The method of claim 74, wherein the method further comprises administering one or more additional therapeutic agents or procedures.

79. The method of claim 78, wherein the additional therapeutic agent is an inhibitor of an immune checkpoint molecule; wherein the immune checkpoint molecule is TIM-3, PD-1, PD-L1 or CTLA-4; wherein the inhibitor is an immune checkpoint molecule antibody.

80. The method of claim 74, wherein the subject is a human.

81. A kit comprising: (i) the antibody, or antigen binding fragment thereof, of claim 1, (ii) optionally, one or more additional therapeutic agents, and (iii) instructions for use in treating cancer in a subject.

82. A pharmaceutical composition comprising a therapeutically effective amount of an antibody, or antigen binding fragment thereof, that specifically binds to a n antigen comprising an NPM1c neoepitope in complex with a class I major histocompatibility complex (MHC class I) protein, and a pharmaceutically acceptable carrier, wherein the antibody, or antigen binding fragment comprises:
   (a) a heavy chain variable region (VH), wherein the VH comprises VH complementarity determining region (CDR)1, VH CDR2 and VH CDR3, wherein the VH CDR1 has the amino acid sequence GFTFSSYA (SEQ ID NO:9), the VH CDR2 has the amino acid sequence ISGSGGST (SEQ ID NO:10), and the VH CDR3 has the amino acid sequence ARLGYPTTTLLPFDY (SEQ ID NO:11); and
   (b) a light chain variable region (VL), wherein the VL comprises VL complementarity determining region (CDR)1, VL CDR2 and VL CDR3, wherein the VL CDR1 has the amino acid sequence QSISSY (SEQ ID NO:6), the VL CDR2 has the amino acid sequence AAS (SEQ ID NO:7), and the VL CDR3 has the amino acid sequence QQSYSTPLT (SEQ ID NO:8).

* * * * *